US008435770B2

(12) United States Patent
Hogsett et al.

(10) Patent No.: US 8,435,770 B2
(45) Date of Patent: May 7, 2013

(54) GENE KNOCKOUT MESOPHILIC AND THERMOPHILIC ORGANISMS, AND METHODS OF USE THEREOF

(75) Inventors: David Anthony Hogsett, Grantham, NH (US); Vineet Badriphrajad Rajgarhia, Lebanon, NH (US)

(73) Assignee: Mascoma Corporation, Lebanon, NH (US)

( * ) Notice: Subject to any disclaimer, the term of this patent is extended or adjusted under 35 U.S.C. 154(b) by 452 days.

(21) Appl. No.: 12/599,458

(22) PCT Filed: May 9, 2008

(86) PCT No.: PCT/US2008/063237

§ 371 (c)(1), (2), (4) Date: Jun. 30, 2010

(87) PCT Pub. No.: WO2008/141174

PCT Pub. Date: Nov. 20, 2008

(65) Prior Publication Data

US 2010/0297721 A1 Nov. 25, 2010

Related U.S. Application Data

(60) Provisional application No. 60/916,978, filed on May 9, 2007.

(51) Int. Cl.

| | |
|---|---|
| ***C12P 7/06*** | (2006.01) |
| ***C12N 1/20*** | (2006.01) |
| ***C12N 15/00*** | (2006.01) |
| ***C07H 21/04*** | (2006.01) |

(52) U.S. Cl.

USPC ..................... 435/161; 435/252.3; 435/320.1; 536/23.2

(58) Field of Classification Search .................. 435/161, 435/252.31, 320.1; 536/23.1, 23.2

See application file for complete search history.

(56) References Cited

U.S. PATENT DOCUMENTS

| | | | |
|---|---|---|---|
| 2003/0165859 | A1 | 9/2003 | Nazarenko et al. |
| 2004/0126848 | A1 | 7/2004 | Dicosimo et al. |
| 2006/0105348 | A1 | 5/2006 | Lee et al. |

FOREIGN PATENT DOCUMENTS

| | | | |
|---|---|---|---|
| WO | WO-01/49865 | A1 | 7/2001 |
| WO | WO-01/85966 | A2 | 11/2001 |
| WO | WO-02/29030 | A2 | 4/2002 |
| WO | WO-2006/099615 | A2 | 9/2006 |
| WO | WO-2006/117536 | A1 | 11/2006 |
| WO | WO-2006/131734 | A1 | 12/2006 |
| WO | WO-2007/027828 | A2 | 3/2007 |
| WO | WO-2007/039753 | A1 | 4/2007 |
| WO | WO-2007/130984 | A2 | 11/2007 |
| WO | WO-2008/032007 | A1 | 3/2008 |
| WO | WO-2008/038019 | A2 | 4/2008 |

OTHER PUBLICATIONS

Ozcengiz et al. [Journal of Industrial Microbiology & Biotechnology, (1998), 21(3), 145-149.*

International Search Report for PCT/US2008/063237, dated Mar. 12, 2009.

Desai, S. G., et al.; "Cloning of L-lactate dehydrogenase and elimination of lactic acid production via gene knockout in *Thermoanaerobacterium saccharolyticum* JW/SL-YS485;" Applied Microbiology and Biotechnology vol. 65, No. 5, pp. 600-605 (Mar. 6, 2004).

Lynd, et al.; "Consolidated bioprocessing of cellulosic biomass: an update," Current Opinion in Biotechnology vol. 16, No. 5, pp. 577-583 (Oct. 1, 2005).

Lynd, L. R., et al; "Microbial Cellulose Utilization: Fundamentals and Biotechnology," Microbiology and Molecular Biology Reviews, vol. 66, No. 3, pp. 506-577 (Sep. 1, 2002).

Mai, Volker, et al.; "Advances in Development of a Genetic System for *Thermoanaerobacterium* spp.: Expression of Genes Encoding Hydrolytic Enzymes, Development of a Second Shuttle Vector, and Integration of Genes into the Chromosome;" Applied and Environmental Microbiology, vol. 66, No. 11, pp. 4817-4821 (Nov. 1, 2000).

Mai, Volker, et al.; "Transformation of *Thermoanaerobacterium* sp. strain JW/SL-Y5485 with plasmid pIKM1 conferring kanamycin resistance," FEMS Microbiology Letters, vol. 148, pp. 163-167 (Jan. 1, 1997).

Shaw, Joe, et al.; "End-product pathways in the xylose fermenting bacterium, *Thermoanerobacterium saccharolyticum*," Enzyme and Microbial Technology, vol. 42, No. 6, pp. 453-458 (Jan. 19, 2008).

Shaw, A. J., et al.; "Metabolic engineering of a thermophilic bacterium to produce ethanol at high yield," PNAS, vol. 105, No. 37, pp. 13769-13774 (Sep. 16, 2008).

Supplementary European Search Report in EP 08 76 9395 dated Jan. 25, 2010.

* cited by examiner

*Primary Examiner* — Tekchand Saidha

(74) *Attorney, Agent, or Firm* — Foley Hoag LLP

(57) ABSTRACT

One aspect of the invention relates to a genetically modified thermophilic or mesophilic microorganism, wherein a first native gene is partially, substantially, or completely deleted, silenced, inactivated, or down-regulated, which first native gene encodes a first native enzyme involved in the metabolic production of an organic acid or a salt thereof, thereby increasing the native ability of said thermophilic or mesophilic microorganism to produce ethanol as a fermentation product. In certain embodiments, the aforementioned microorganism further comprises a first non-native gene, which first non-native gene encodes a first non-native enzyme involved in the metabolic production of ethanol. Another aspect of the invention relates to a process for converting lignocellulosic biomass to ethanol, comprising contacting lignocellulosic biomass with a genetically modified thermophilic or mesophilic microorganism.

19 Claims, 70 Drawing Sheets

16 Apr 2007 Alignment Results

Reference molecule: Clostridium thermocelluffi, Region 1 to 1509
Number of sequences to align: 7
Total length of aligned sequences with gaps: 1767 bps Alignment: Global DNA alignment against reference molecule
Parameters: Scoring matrix: Linear (Mismatch 2, OpenGap 4, ExtGap 1)

| Sequence | Start | End | #Match | NonMatch | %Match |
|---|---|---|---|---|---|
| Clostridium thermocellum | 1 | 1509 | | | |
| Clostridium cellulolyticum | 1 | 1642 | 1372 | 274 | 83 |
| Thermoanaerobacterium sacc | 1 | 1552 | 1286 | 278 | 82 |
| C. stercorarium | 1 | 1519 | 1374 | 155 | 89 |
| C. stercorarium II | 1 | 1500 | 1339 | 194 | 87 |
| Caldicellulosiruptor krist | 1 | 1508 | 1250 | 300 | 80 |
| C. phytofermentans | 1 | 1371 | 1115 | 403 | 73 |

Fig. 6-1

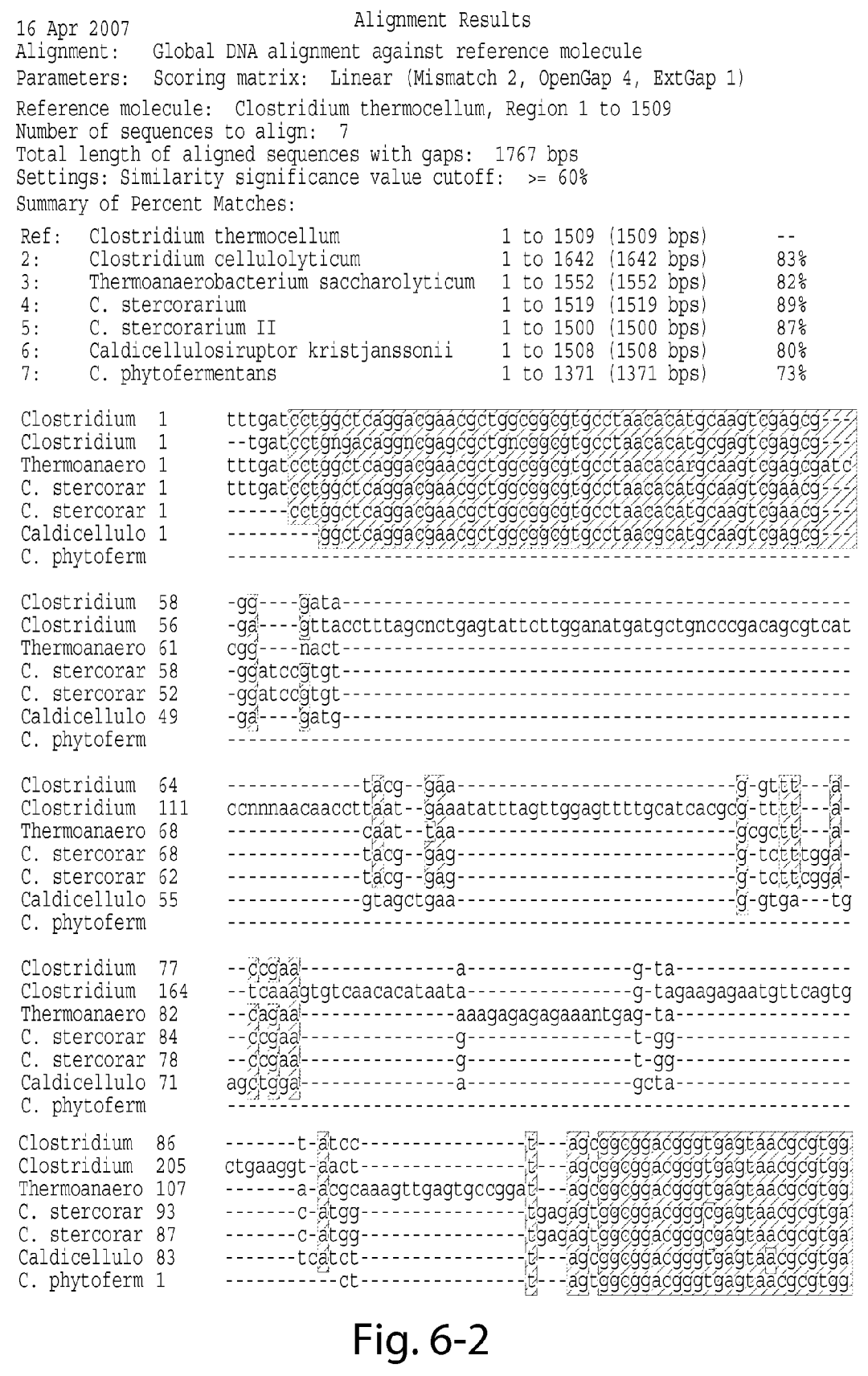

```
16 Apr 2007                    Alignment Results
Alignment:   Global DNA alignment against reference molecule
Parameters:  Scoring matrix:  Linear (Mismatch 2, OpenGap 4, ExtGap 1)
Reference molecule:  Clostridium thermocellum, Region 1 to 1509
Number of sequences to align:  7
Total length of aligned sequences with gaps:  1767 bps
Settings: Similarity significance value cutoff:  >= 60%
Summary of Percent Matches:

Ref:   Clostridium thermocellum            1 to 1509  (1509 bps)     --
2:     Clostridium cellulolyticum          1 to 1642  (1642 bps)     83%
3:     Thermoanaerobacterium saccharolyticum 1 to 1552 (1552 bps)    82%
4:     C. stercorarium                     1 to 1519  (1519 bps)     89%
5:     C. stercorarium II                  1 to 1500  (1500 bps)     87%
6:     Caldicellulosiruptor kristjanssonii 1 to 1508  (1508 bps)     80%
7:     C. phytofermentans                  1 to 1371  (1371 bps)     73%

Clostridium  1     tttgatcctggctcaggacgaacgctggcggcgtgcctaacacatgcaagtcgagcg---
Clostridium  1     --tgatcctgngacaggncgagcgctgncggcgtgcctaacacatgcgagtcgagcg---
Thermoanaero 1     tttgatcctggctcaggacgaacgctggcggcgtgcctaacacargcaagtcgagcgatc
C. stercorar 1     tttgatcctggctcaggacgaacgctggcggcgtgcctaacacatgcaagtcgaacg---
C. stercorar 1     ------cctggctcaggacgaacgctggcggcgtgcctaacacatgcaagtcgaacg---
Caldicellulo 1     ---------ggctcaggacgaacgctggcggcgtgcctaacgcatgcaagtcgagcg---
C. phytoferm       ------------------------------------------------------------

Clostridium  58    -gg----gata-------------------------------------------------
Clostridium  56    -ga----gttacctttagcnctgagtattcttgganatgatgctgncccgacagcgtcat
Thermoanaero 61    cgg----nact-------------------------------------------------
C. stercorar 58    -ggatccgtgt-------------------------------------------------
C. stercorar 52    -ggatccgtgt-------------------------------------------------
Caldicellulo 49    -ga----gatg-------------------------------------------------
C. phytoferm       ------------------------------------------------------------

Clostridium  64    -------------tacg--gaa---------------------------g-gttt---a-
Clostridium  111   ccnnnaacaaccttaat--gaaatatttagttggagttttgcatcacgcg-tttt---a-
Thermoanaero 68    -------------caat--taa---------------------------gcgctt---a-
C. stercorar 68    -------------tacg--gag---------------------------g-tctttgga-
C. stercorar 62    -------------tacg--gag---------------------------g-tcttcgga-
Caldicellulo 55    -------------gtagctgaa---------------------------g-gtga---tg
C. phytoferm       ------------------------------------------------------------

Clostridium  77    --ccgaa---------------a----------------g-ta-----------------
Clostridium  164   --tcaaagtgtcaacacataata----------------g-tagaagagaatgttcagtg
Thermoanaero 82    --cagaa---------------aaagagagagaaantgag-ta-----------------
C. stercorar 84    --ccgaa---------------g----------------t-gg-----------------
C. stercorar 78    --ccgaa---------------g----------------t-gg-----------------
Caldicellulo 71    agctgga---------------a----------------gcta-----------------
C. phytoferm       ------------------------------------------------------------

Clostridium  86    -------t-atcc----------------t---agcggcggacgggtgagtaacgcgtgg
Clostridium  205   ctgaaggt-aact----------------t---agcggcggacgggtgagtaacgcgtgg
Thermoanaero 107   -------a-acgcaaagttgagtgccggat---agcggcggacgggtgagtaacgcgtgg
C. stercorar 93    -------c-atgg----------------tgagagtggcggacgggcgagtaacgcgtga
C. stercorar 87    -------c-atgg----------------tgagagtggcggacgggcgagtaacgcgtga
Caldicellulo 83    -------tcatct----------------t---agcggcggacgggtgagtaacgcgtga
C. phytoferm 1     -----------ct----------------t---agtggcggacgggtgagtaacgcgtgg
```

Fig. 6-2

```
Clostridium  119   gtaacctacctcatacaggggggataacacagggaaacctgtgctaataccgcata-----
Clostridium  245   gcaacctgcctgttacaggggggataacacagggaaacttgtgctaataccgcata-----
Thermoanaero 156   acaatctaccctgtagtttgggataacacctcgaaagggggtgctaataccggata-----
C. stercorar 129   gcaacctgccctatgctggggggataacaccgggaaaccggtgctaataccgcata-----
C. stercorar 123   gcaacctgccctatgctggggggataacaccgggaaaccggtgctaataccgcata-----
Caldicellulo 117   gcaacctaccctcagcacggggataacagctcgaaagggctgctaataccgcatgggacc
C. phytoferm 31    gtaacctgcctcatacaggggggataacagtcggaaacgattgctaataccgcata-----

Clostridium  174   a-----cggg-----gcg-----gcatcgtcctgttatcaaaggaga------------a
Clostridium  300   a-----caca-----acgaagaagcatttcnttgttgtcaaaggagc------------a
Thermoanaero 211   a-----tgtcaagaagtg-----gcatcactttttgaagaaaggaga------------a
C. stercorar 184   agaccacagt-----gac-----gcat-gtacagtggt-aaagctg--------------
C. stercorar 178   agaccacagt-----gac-----gcatgtcacagtggtaaaagctg--------------
Caldicellulo 177   a-----cggc-----atc-----gcatggtgctgtggtgaaagggtagccgnagaggcta
C. phytoferm 86    a-----tata-----gcgaaaccgcatgatttgctatcaaat-att------------a

Clostridium  207   atccggtatgagatgggcccgcgtccgattagctagttggtgaggtaacggctcaccaag
Clostridium  338   atccggtgacagatgggcccgcgtccaattagctagttggtgatgtaacggatcaccaag
Thermoanaero 249   atccgctataggatgagtccgcgtcccattagctagttggcggggtaaaagcccaccaag
C. stercorar 218   aggcggcataggatgggctcgcggtccattagctagttggtagggtaacggcctaccaag
C. stercorar 214   aggcggcataggatgggctcgcgtccgattagctagttggtagggtaacggcctaccaag
Caldicellulo 222   tnccggctggggatgggctcgcggcccatcagctagttggtgcggtaacggcctaccaag
C. phytoferm 123   at-aggtatgagatgggcccgcgtctgattagctagttggtggggtaatggcctaccaag

Clostridium  267   gcgacgatcggtagccgaactgagaggttggtcggccacattgggactgagacacggccc
Clostridium  398   gcgacgattggtagccgaactgagaggttgatcggccacattgggnctgagacacggccc
Thermoanaero 309   gcgacgatgggtagccggcctgagagggtgaacgnccacactggaactgagacacggtcc
C. stercorar 278   gcgacgatcggtagccggactgagaggttggccggccgcattgggactgagacacggccc
C. stercorar 274   gcgacgatcggtagccggactgagaggttggccggccgcattgggactgagacacggccc
Caldicellulo 282   gcgacgacgggtagccggcctgagagggtgtacggccacagtgggactgagacacggccc
C. phytoferm 182   gcgacgatcagtagccggcttgagagagtgaccggccacattgggactgagacacggcnn

Clostridium  327   agactcctacgggaggcagcagtggggaatattgcgcaatgggggaaaccctgacgcagc
Clostridium  458   agactcctacgggaggcagcagtggggaatattgcacaatgggggaaaccctgatgcagc
Thermoanaero 369   agactcctacgggaggcagcagtggggaatattgttcaatgggggaaaccctgacgcagc
C. stercorar 338   agactcctacgggaggcagcagtggggaatattgcgcaatgggggaaaccctgacgcagc
C. stercorar 334   agactcctacgggaggcagcagtggggaatattgcgcaatgggggaaaccctgacgcagc
Caldicellulo 342   acactcctacgggaggcagcagcggggaatcttgcgcaatgggcgaaagcctgacgcagc
C. phytoferm 242   nnactnctncgggaggcagcagtggggaatattgggcaatgggggaaaccngatccagc

Clostridium  387   aacgccgcgtgaaggaagaaggccttcgggttgtaaacttctttgattggggacgaagga
Clostridium  518   aacgccgcgtgaaggatgaaggttttcggattgtaaacttctttagtcagggacgaagaa
Thermoanaero 429   gacgccgcgtgagcgaagaaggccttcgggtcgtaaagctcaatagtatgg---gaagat
C. stercorar 398   gacgccgcgtggaggaagaaggcctttgggttgtaaactcctttgatcggggacgaag--
C. stercorar 394   gacgccgcgtggaggaagaaggcctttgggttgtaaactcctttgatcggggacgaag--
Caldicellulo 402   gacnccgcgtgagggaagaagccccttcggggtgtaaacctctttggacgggga-gaagtg
C. phytoferm 302   gacgccgcgtgagtgaagaagtatttcggtatgtaaagctctatcagcagg---gaagat

Clostridium  447   agtgacggtacccaaagaacaagccacggctaactacgtgccagcagccgcggtaatacg
Clostridium  578   aatgacggtacctgaagaataagccacggctaactacgtgccagcagccgcggtaatacg
Thermoanaero 486   agtgacggtaccatacga--aagccccggctaactacgtgccagcagccgcggtaatacg
C. stercorar 456   -atgacggtacccgaagaacaagccacggctaactacgtgccagcagccgcggtaatacg
C. stercorar 452   -atgacggtacccgaagaacaagccacggctaactacgtgccagcagccgcggtaatacg
Caldicellulo 461   gaagatagtacccgtttaaaaagccacggctaactacgtgccagcagccgcggtaatacg
C. phytoferm 359   aatgacagtacctgactaagaagccccggctaactacgtgccagcagccgcggtnatacg
```

Fig. 6-3

```
Clostridium  507   taggtggcgagcgttgtccggaattactgggtgtaaagggcgcgtaggcggga-tg-c-a
Clostridium  638   taggtggcaagcgttgtccggaattactgggtgtaaagggcgtgtaggcgggaatg-t-a
Therrnoanaero544   taggggcgagcgttgtccggaattactgggcgtaaagagcacgtaggcggctgta-a-a
C. stercorar 515   taggtggcgagcgttgtccggaattactgggtgtaaagggcgtgtaggcgggg-tg-cca
C. stercorar 511   taggtggcgagcgttgtccggaattactgggtgtaaagggcgtgtaggcgggg-tg-cca
Caldicellulo 521   taggtggcgagcgttgtccggaattactgggcgtaaagggtgcgtaggcggcc-tg-gta
C. phytoferm 419   tannnnnnnagcgttatccggatttactgggtgtaaagggagcgtaggtggta-ggtc-a

Clostridium  564   agtcagatgtgaaattccggggcttaaccccggggctgcatctgaaactgtatctcttga
Clostridium  696   agtcagatgtgaaatcccagggcttaaccctggagctgcatctgaaactatgtttcttga
Thermoanaero 602   agtcagatgtgaaaaacctgggctcaaccgagggtgtgcatctgaaactaaacagcttga
C. stercorar 573   agtcaggtgtgaaataccggggcttaacctcgggggtgcatctgaaactggtgctcttga
C. stercorar 569   agtcaggtgtgaaataccggggcttaacctcgggggtgcatctgaaactggtgctcttga
Caldicellulo 579   agttgagcgtgaaattttgggctcaacccaaaaggagcgctcaagactgccgggcttga
C. phytoferm 477   agtcagatgtgaaagnccagggctcaaccctggnnctgcatttgaaactggctnactaga

Clostridium  624   gtgctggagaggaaagcggaattcctagtgtagcggtgaaatgcgtagatattaggagga
Clostridium  756   gtgccggagaggaaagcggaattcctagtgtagcggtgaaatgcgtagatattaggagga
Thermoanaero 662   gtcaaggagaggagagcggaattcctggtgtagcggtgaaatgcgtagagatcaggaaga
C. stercorar 633   gtgccggagaggaaagcggaattcccagtgtagcggtgaaatgcgtagatattgggagga
C. stercorar 629   gtgccggagaggaaagcggaattcccagtgtagcggtgaaatgcgtagatattgggagga
Caldicellulo 639   gtgcgggagaggacggcggaattcccggtgtagcggtgaaatgcgtagatatcgggagga
C. phytoferm 537   gtgcaggagaggtaagtggaattcctagtgtagcggtgaaatgcgtagatantaggagga

Clostridium  684   acaccagtggcgaaggcggctttctggacagtaactgacgctgaggcgcgaaagcgtggg
Clostridium  816   acaccagtggcgaaggcggctttctggacggtaactgacgctgaggcgcgaaagcgtggg
Thermoanaero 722   ataccagtggcgaaagcggctctctggacttgaactgacgctgaggtgcgaaagcgtggg
C. stercorar 693   acaccagtggcgaaggcggctttctggacggtaactgacgctgaggcgcgaaagcgtggg
C. stercorar 689   acaccagtggcgaaggcggctttctggacggtaactgacgctgaggcgcgaaagcgtggg
Caldicellulo 699   acaccagtggcgaaggcggccgtctggaccgtaactgacgctgaggcacgaaagcgtggg
C. phytoferm 597   acaccagtggcgaaggcggcnnactggactgtaactgacactgaggctcgnnngcgtggg

Clostridium  744   gagcaaacaggattagataccctggtagtccacgccgtaaacgatggatactaggtgtag
Clostridium  876   gagcaaacaggattagataccctggtagtccacgctgtaaacgatggatactaggtgtag
Thermoanaero 782   gagcaaacaggattagataccctggtagtccacgccgtaaacgatggatactaggtgtgg
C. stercorar 753   gagcaaacaggattagataccctggtagtccacgctgtaaacgatggatactaggtgtag
C. stercorar 749   gagcaaacaggattagataccctggtagtccacgctgtaaacgatggatactaggtgtag
Caldicellulo 759   gagcaaacaggattagataccctggtagtccacgctgtaaacgatggatgctaggtgt-g
C. phytoferm 657   gagcaaacaggattagatnccctggtagtncacgccgtaaacgatgaatactagctgttc

Clostridium  804   gaggtatcg-accccttctgtgccggagttaacacaataagtatcccacctggggagtac
Clostridium  936   gaggtatcg-accccttctgtgccggagttaacacaataagtatcccacctggggagtac
Thermoanaero 842   gtg----aa-gcatcatccgtgccggagttaacgcaataagtatcccacctggggagtac
C. stercorar 813   gaggtatcg-accccttctgtgccgtagttaacacaataagtatcccacctggggagtac
c. stercorar 809   gaggtatcg-accccttctgtgccgtagttaacacaataagtatcccacctggggagtac
Caldicellulo 818   ggggagaag-aactcttccgtgccgtagttaacacaataagcatcccgcctggggagtac
C. phytoferm 717   ggggtcnnacagggcttcggtggcgcacgtaacgcaataagtattccacctggggngtac

Clostridium  863   ggccgcaaggttgaaactcaaaggaattgacgggggcccgcacaagcagtggagtatgtg
Clostridium  995   ggccgcaaggttgaaactcaaaggaattgacgggggcccgcacaagcagtggagtatgtg
Thermoanaero 897   ggccgcaaggttgaaactcaaaggaattgacgggggcccgcacaagcagcggagcatgtg
C. stercorar 872   ggccgcaaggctgaaactcaaaggaattgacgggggcccgcacaagcagtggagcatgtg
C. stercorar 868   ggccgcaaggctgaaactcaaaggaattgacgggggcccgcacaagcagtggagcatgtg
Caldicellulo 877   ggtcgcaaggttgaaactcaaaggaattgacgggggcccgcacaagcggtggagcatgtg
C. phytoferm 777   gttcgcaagaatgaaactcaaaggaattgacggggannngcacaagcggtggagcatgtg
```

Fig. 6-4

```
Clostridium  923   gtttaattcgaagcaacgcgaagaaccttaccagggcttgacatccctctgacagctcta
Clostridium  1055  gtttaattcgaagcaacgcgaagaaccttaccaaggcttgacatatagcggaatncggca
Thermoanaero 957   gtttaattcgaagcaacgcgaagaaccttaccagggcttgacatc-cacagaatcaggta
C. stercorar 932   gtttaattcgaagcaacgcgaagaaccttaccagggcttgacatcccccctgacggatgta
C. stercorar 928   gtttaattcgaagcaacgcgaagaaccttaccagggcttgacatcccccctgacggatgta
Caldicellulo 937   gtttaattcgaagcaacgcgaagaaccttaccagggcttgacatgcc---gggaaccctg
C. phytoferm 837   gtttaattcgaannaacgcgaagaaccttaccaagtcttgacatccctctgacaaccgag

Clostridium  983   gagatag--g----gct-tccttcg----gg------gcaga-----g----g-agacag
Clostridium  1115  gagatgt--c----gtagtccttcg----gg------actgc-----t----atacacag
Thermoanaero 1016  gaaataccag----agt-gcctcga----aa------gagga-----gctgtg-agacag
C. stercorar 992   gagatac--a----tct-t-ctccgcaagga------gcagg-----g----g-agacag
C. stercorar 988   gagatac--a----tct-t-ctccgcaagga------gcagg-----g----g-agacag
Caldicellulo 994   ccgaaag--gcggggt-gcctgct----tgttaagagcaggagcccg----g-acacag
C. phytoferm 897   taacgtc--g----gnn-ttcttcg----gg------ncaga-----g----g-ngacag

Clostridium  1016  gtggtgcatggttgtcgtcagctcgtgtcgtgagatgttgggttaagtcccgcaacgagc
Clostridium  1150  gtggtgcatggttgtcgtcagctcgtgtcgtgagatgttgggttaagtcccgcaacgagc
Thermoanaero 1055  gtggtgcatggttgtcgtcagctcgtgtcgtgagatgttgggttaagtcccgcaacgagc
C. stereorar 1028  gtggtgcatggtgcagctcagctcgtgtcgtgagatgttgggttaagtcccgcaacgagc
C. stercorar 1024  gtggtgcatggttgtcgtcagctcgtgtcgtgagatgttgggttaagtcccgcaacgagc
Caldicellulo 1042  gtggtgcatggttgtcgtcagctcgtgtcgtgagatgttgggttaagtcccgcaacgagc
C. phytoferm 930   gtggtgcatggttgtcgtcagctcgtgtcgtgagatgttgggttaagtcccgcaacgagc

Clostridium  1076  gcaacccttgtcgttagttgccagcacgttaaggtgggcactctagcgagactgccggcg
Clostridium  1210  gcaacccctgttgctagttg--ataacattaagatgatcactctagcgagactgccggtg
Thermoanaero 1115  gcaacccctgttggtagttaccag--cgtaaagacggggactctaccgagactgccgtgg
C. stercorar 1088  gcaacccttgtcgttagttgccagcag--taagatgggcactctaacgagactgccggcg
C. stercorar 1084  gcaacccttgtcgttagttgccagcag--taagatgggcactctaacgagactgccggcg
Caldicellulo 1102  gcaacccctgcccttagttgccagcggtttagccgggcactctaaggggactgccgccg
C. phytoferm 990   gcaacccctatctttagtagccagca-gttcggctgnncactctagagagactgccaggg

Clostridium  1136  acaagtcggaggaaggtggggacgacgtcaaatcatcatgccccttatgtcctgggctac
Clostridium  1268  acaaatcggaggaaggtggggacgacgtcaaatcatcatgccccttatgtcttgggctac
Thermoanaero 1173  agaacacggaggaaggcggggatgacgtcaaatcatcatgcccttatgccctgggctac
C. stercorar 1146  agaagtcggaggaaggtggggatgacgtcaaatcatcatgccccttatgtcctgggctac
C. stercorar 1142  agaagtcggaggaaggtggggatgacgtcaaatcatcatgccccttatgtcctgggctac
Caldicellulo 1162  atgaggcggaggaaggtggggatgacgtcaaatcatcatgccccttatgccctgggctac
C. phytoferm 1049  ataacctggaggaaggcggggatgacgtnnaatcatcatgccccnnatgatttgggctac

Clostridium  1196  acacgtactacaatggctgctacaaagggaagcgataccgcgaggtggagcaaatcccca
Clostridium  1328  acacgtactacaatggctataacagagggaagctaagctgcaaagtggagcaaatcccca
Thermoanaero 1233  acacgtgctacaatggcctgaacagagggcagcgaaggagcgatccggagcgaatcccag
C. stercorar 1206  acacgtgctacaatggcgactacagagggaagcaaatccggcaggaggagcaaatcccga
C. stercorar 1202  acacgtgctacaatggcgactacagagggaagcaaatccgcgaggaggagcaaatcccga
Caldicellulo 1222  acacgtgctacaatgggtgctacagagggcggcgaaggcgcgagccggagcgaatcccaa
C. phytoferm 1109  acacgtgctacaatggtgactacaaagagaagcaagcctgcnnggggagcaaatctcaa

Clostridium  1256  aaa-gcag-tcccagttcggattgcaggctgaaactcgcctgcatgaagtcggaattgct
Clostridium  1388  aaa-atag-tcccagttcagatggtgggctgcaacccgcccacatgaagtcggaattgct
Thermoanaero 1293  aaa-acaggtcccagttcagattgcaggctgcaacccgcctgcatgaagacggagttgct
C. stereorar 1266  aag-gtcg-tcccagttcggattgcaggctcgaactcgcctgcatgaagccggaattgct
C. stercorar 1262  aag-gtcg-tcccagttcggattgcaggctgcaactcgcctgcatgaagccggaattgct
Caldicellulo 1282  aaaagcac-ccccagttcggattgcaggctgcaactcgcctgcatgaagtcggaatcgct
C. phytoferm 1169  aaa-ggtcatcccagttcggattgtactctgcaactcgagtacatgaagctggaatcgct
```

Fig. 6-5

```
Clostridium  1314   agtaatggcaggtcagcatactgccgtgaatacgttcccgggccttgtacacaccgcccg
Clostridium  1446   agtaatggtaggtcagtatactgtcgtgaatacgttcccgggccttgtacacaccgcccg
Thermoanaero 1352   agtaatcgcggatcagcatgccgcggtgaatacgttcccgggccttgtacacaccgcccg
C. stercorar 1324   agtaatggcaggtcagcatactgccgtgaatacgttcccgggccttgtacacaccgcccg
C. stercorar 1320   agtaatggcaggtcagcatactgccgtgaatacgttcccgggccttgtacacaccgcccg
Caldicellulo 1341   agtaatcgcggatcagcatgccgcggtgaatacgttcccgggccttgtacacaccgcccg
C. phytoferm 1228   agtaatcgcgaatcagaatgtcgcggtgaatacgttcccgggtcttgtacacaccgyycg

Clostridium  1374   tcacaccatgagagtctgcaacacccgaagtc-a-tagtc-t-aaccgcaaggagggcgc
Clostridium  1506   tcacaccatgagagtctgcaacacccgaagtcga-tagtc-t-aaccgcaaggaggacgt
Thermoanaero 1412   tcacaccacgagagtttacaacacccgaagtc-a-gtgacct-aaccgcaaggaggagc
C. stercorar 1384   tcacaccatgagagctggcaacacccgaagcc-g-tagcc-t-aaccgagaggggggcgc
C. stercorar 1380   tcacaccatgagagctggcaacacccgaagcc-ggtagcc-t-aaccgagaggggggcgc
Caldicellulo 1401   tcacaccatgagagtcagcaacacctgaagac-a-cagga-t-atctg-----------
C. phytoferm 1288   tcactccatgggagtaggtaacgcccgaagtc-a-gtgac-cyaaccgtaaggagggagc

Clostridium  1430   tgccgaaggtggggcagatgattggggtgaagtcgtaaca---aggtagccgtatcggaa
Clostridium  1563   cgccgaaggtggggccgatgattggtgtgaagtcgtaaca---aggtagccgtatcggaa
Thermoanaero 1469   tgccgaaggtggggtaaatgattggggtgaagtcgtaaca---aggtagccgtatcggaa
C. stercorar 1440   cgtcgaaggtggggcaggtgattggggtgaagtcgtaaca---aggtagccgtatcggaa
C. stercorar 1437   cgtcgaaggtggggcacccgaagccggt---agcctaaccgagaggggggcgccgccgaa
Caldicellulo 1445   tgttgaaggtggggctgatgattggggtgaagtcgtaaca---aggtagccgtacgggaa
C. phytoferm 1345   tgccgaaggcgggatctataactgggg---------------------------------

Clostridium  1487   ggtgcggctggatcacctccttt----
Clostridium  1620   ggtgcggctggatcacctccttt----
Therrnoanaero1526   ggtgcggctggatcacctcctttccct
c. stercorar 1497   ggtgcggctggatcacctccttt----
C. stercorar 1494   ggtgggg--------------------
Caldicellulo 1502   cgtgcgg--------------------
C. phytoferm        ---------------------------
```

Fig. 6-6

| Figure 13A | Figure 13B |
| --- | --- |
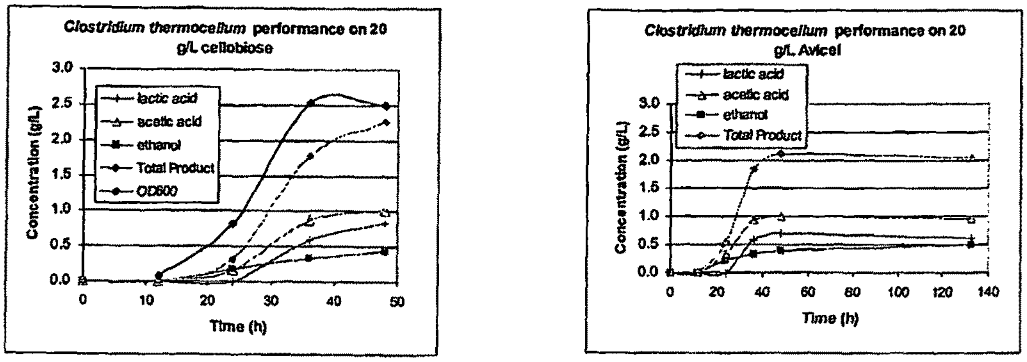

| Figure 14A | Figure14B |
| --- | --- |
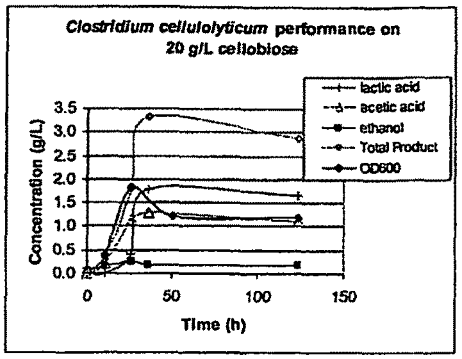
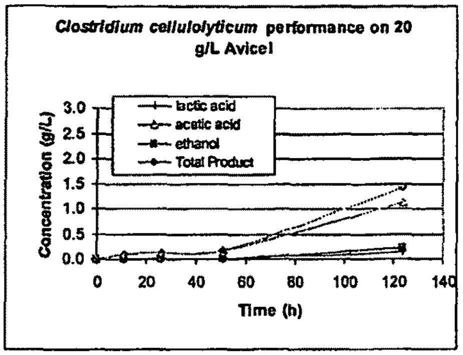

| Figure 15A | Figure 15B |
| --- | --- |
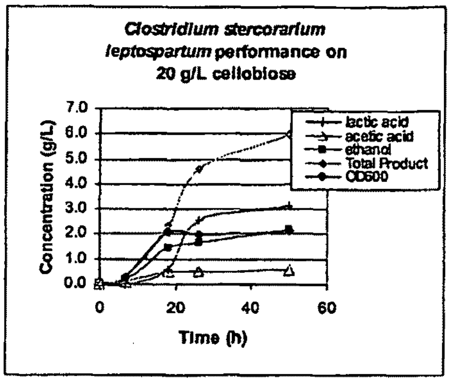
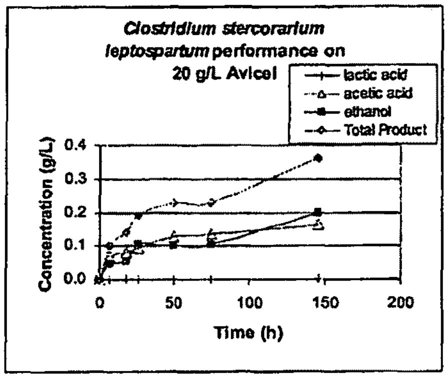

| Figure 16A | Figure 16B |
|---|---|
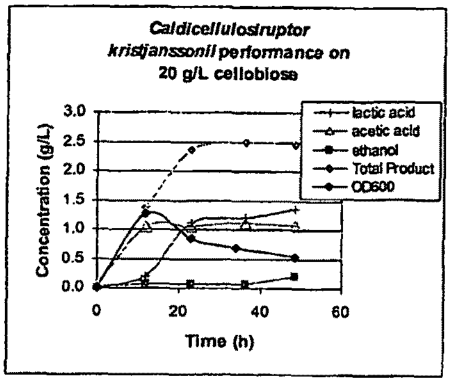
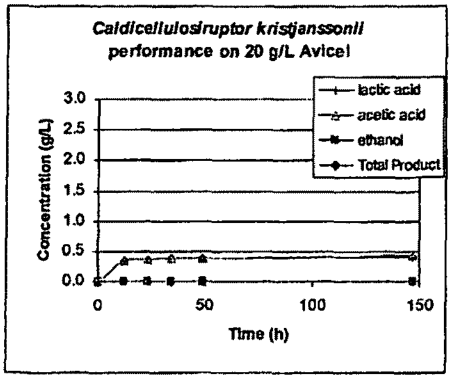

| Figure 17A | Figure 17B |
|---|---|
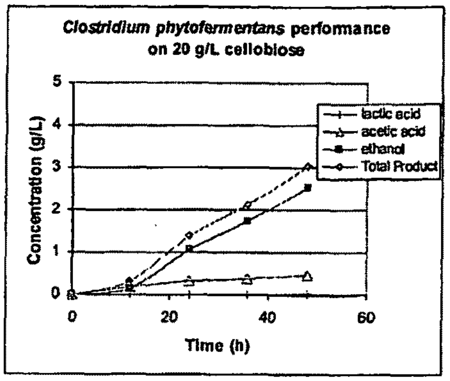
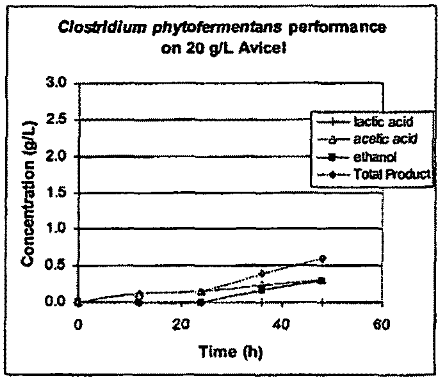

ldh 2262 region for single cross over knockout

C. cellulolyticum ldh 2262 double cross over KO fragment

C. phytofermentens ack double cross over KO fragment
2676 bp

C. phytofermentens ldh 1389 single cross over fragment

C. phytpfermentens double crossover ko fragment 2732 bp

Percent identity of 16S sequence to T. saccharolyticum JW/SL-YS485:
Thermoanaerobacterium saccharolyticum B6A-RI - 99.0%
Thermoanaerobacter sp. strain 59 - 95.7%
Thermoanaerobacter pseudoethanolicus 39E - 83.7%

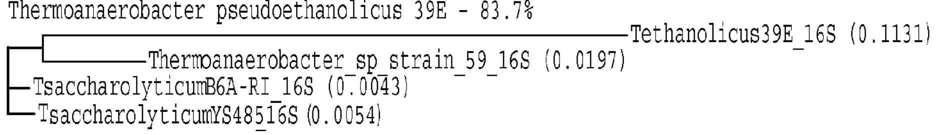

```
                                         1                                                50
                 Tethanolicus39E_16S   (1) ------CCTGGCTCAGGACGAACGCTGGCGGCGTGCCTAACACATGCAAG
Thermoanaerobacter_sp_strain_59_16S   (1) --------------------------------------------------
          TsaccharolyticumB6A-RI_16S   (1) TTTGATCCTGGCTCAGGACGAACGCTGGCGGCGTGCCTAACACATGCAAG
           TsaccharolyticumYS485_16S   (1) TTTGATCCTGGCTCAGGACGAACGCTGGCGGCGTGCCTAACACATGCAAG
                           Consensus   (1) TTTGATCCTGGCTCAGGACGAACGCTGGCGGCGTGCCTAACACATGCAAG
                                         51                                              100
                 Tethanolicus39E_16S  (45) TCGAGCGGTCCGGC-----------------------------AGCCAA-
Thermoanaerobacter_sp_strain_59_16S   (1) ----------------------------CTACACATGCAGTCGAGCGAA-
          TsaccharolyticumB6A-RI_16S  (51) TCGAGCGATCCGGNACTCAATTAAGCGCTTACAGAAAAAGA-GAGAGAAA
           TsaccharolyticumYS485_16S  (51) TCGAGCGATCCGGCACTCAACTAAGCGCTTACAGAAAAAGA-GAGAGAAA
                           Consensus  (51) TCGAGCGATCCGGCACTCAA TAAGCGCTTACAGAAAAAGA GAGCGAAA
                                         101                                             150
                 Tethanolicus39E_16S  (65) ----------CTTANGNCGGACCCGGATAGCGGCGGACGGGTGAGTAAC
Thermoanaerobacter_sp_strain_59_16S  (22) GGGAGTA----CTACGGTACGAACT---TAGCGGCGGACGGGTGAGTAAC
          TsaccharolyticumB6A-RI_16S (100) NTGAGTAAACGCAAAGTTGAGTCCCGGATAGCGGCGGACGGGTGAGTAAC
           TsaccharolyticumYS485_16S (100) ATGAGTAAACGCAAAGTTGAGTCCCGGATAGCGGCGGACGGGTGAGTAAC
                           Consensus (101)  TGAGTAAACGCTAAGTTGAGTGCCGGATAGCGGCGGACGGGTGAGTAAC
                                         151                                             200
                 Tethanolicus39E_16S (105) GCGTGGGCAACCTACCCTTAAGACCGGGATAACACCTCGAAAGGGGTGCT
Thermoanaerobacter_sp_strain_59_16S  (65) GCGTGGACAATCTACCCTGTAGACCGGGATAACACCTCGAAAGGGGTGCT
          TsaccharolyticumB6A-RI_16S (150) GCGTGGACAATCTACCCTGTAGTTTGGGATAACACCTCGAAAGGGGTGCT
           TsaccharolyticumYS485_16S (150) GCGTGGACAATCTACCCTGTAGTTTGGGATAACACCTCGAAAGGGGTGCT
                           Consensus (151) GCGTGGACAATCTACCCTGTAGTTTGGGATAACACCTCGAAAGGGGTGCT
                                         201                                             250
                 Tethanolicus39E_16S (155) AATACTGGATAAGCTCCTTGTACGGCATGGTATGAGGACGAAGGTAGCGG
Thermoanaerobacter_sp_strain_59_16S (115) AATACCGGATAATGTCGACAAGCGGCATCGCTTTTTGAAGAAAGGAGAG-
          TsaccharolyticumB6A-RI_16S (200) AATACCGGATAATGTCAAGAAGTGGCATCACTTTTTGAAGAAAGGAGA--
           TsaccharolyticumYS485_16S (200) AATACCGGATAATGTCAAGAAGTGGCATCACTTTTTGAAGAAAGGAGA--
                           Consensus (201) AATACCGGATAATGTCAAGAAGTGGCATCGCTTTTTGAAGAAAGGAGAG
                                         251                                             300
                 Tethanolicus39E_16S (205) GACTACCGCTTAAGGATGGGCCCGCGTCCCATCAGCTAGTTGGTA-GGGT
Thermoanaerobacter_sp_strain_59_16S (164) -AAT-CCGCTATAGGACGAGTCCGCGTCCCATTAGCTAGTTGGCGAGGGT
          TsaccharolyticumB6A-RI_16S (248) -AAT-CCGCTATAGGATGAGTCCGCGTCCCATTAGCTAGTTGGCG-GGGT
           TsaccharolyticumYS485_16S (248) -AAT-CCGCTATAGGATGAGTCCGCGTCCCATTAGCTAGTTGGCG-GGGT
                           Consensus (251)  AAT CCGCTATAGGATGAGTCCGCGTCCCATTAGCTAGTTGGCG GGGT
```

Fig. 30-1

| | | |
|---|---|---|
| | | 301 350 |
| Tethanolicus39E_16S | (254) | AACGGCCTACCAAGGCGACGACGGGTAGCCGGCCTGAGAGGGTGGTCGGC |
| Thermoanaerobacter_sp_strain_59_16S | (212) | AAAAGCCCACCAAGGCGACGATGGGTAGCCGGCCTGAGAGGGTGAACGGC |
| TsaccharolyticumB6A-RI_16S | (295) | AAAAGCCCACCAAGGCGACGATGGGTAGCCGGCCTGAGAGGGTGAACGNC |
| TsaccharolyticumYS485_16S | (295) | AAAAGCCCACCAAGGCGACGATGGGTAGCCGGCCTGAGAGGGTGAACGGC |
| Consensus | (301) | AAAAGCCCACCAAGGCGACGATGGGTAGCCGGCCTGAGAGGGTGAACGGC |
| | | 351 400 |
| Tethanolicus39E_16S | (304) | CACACTGGGACTGAGACACGGCCCAGACTCCTACGGGAGGCAGCAGTGGG |
| Thermoanaerobacter_sp_strain_59_16S | (262) | CACACTGGAACTGAGACACGGTCCAGACTCCTACGGGAGGCAGCAGTGGG |
| TsaccharolyticumB6A-RI_16S | (345) | CACACTGGAACTGAGACACGGTCCAGACTCCTACGGGAGGCAGCAGTGGG |
| TsaccharolyticumYS485_16S | (345) | CACACTGGAACTGAGACACGGTCCAGACTCCTACGGGAGGCAGCAGTGGG |
| Consensus | (351) | CACACTGGAACTGAGACACGGTCCAGACTCCTACGGGAGGCAGCAGTGGG |
| | | 401 450 |
| Tethanolicus39E_16S | (354) | GAATCTTGCGCAATGGGCGAAAGCCTGACGCAGCGACGCCGCGTGAGCGA |
| Thermoanaerobacter_sp_strain_59_16S | (312) | GAATATTGTGCAATGGGGGAAACCCTGACACAGCGACGCCGCGTGAGTGA |
| TsaccharolyticumB6A-RI_16S | (395) | GAATATTGTTCAATGGGGGAAACCCTGACACAGCGACGCCGCGTGAGCGA |
| TsaccharolyticumYS485_16S | (395) | GAATATTGTGCAATGGGGGAAACCCTGACACAGCGACGCCGCGTGAGCGA |
| Consensus | (401) | GAATATTGTGCAATGGGGGAAACCCTGACACAGCGACGCCGCGTGAGCGA |
| | | 451 500 |
| Tethanolicus39E_16S | (404) | GGAAGGCCTTCGGGTCGTAAAGCTCGATAGTGTGGGAAGAAGGGA-TGAC |
| Thermoanaerobacter_sp_strain_59_16S | (362) | AGAAGGCCTTCGGGTCGTAAAGCTCAATAGTATGGGAAGAAAGAAATGAC |
| TsaccharolyticumB6A-RI_16S | (445) | AGAAGGCCTTCGGGTCGTAAAGCTCAATAGTATGGGAAGATAG---TGAC |
| TsaccharolyticumYS485_16S | (445) | AGAAGGCCTTCGGGTCGTAAAGCTCAATAGTATGGGAAGATAG---TGAC |
| Consensus | (451) | AGAAGGCCTTCGGGTCGTAAAGCTCAATAGTATGGGAAGATAG A TGAC |
| | | 501 550 |
| Tethanolicus39E_16S | (453) | GGTACCACACGAAAGCCCCGGCTAACTACGTGCCAGCAGCCTCGGTAAGA |
| Thermoanaerobacter_sp_strain_59_16S | (412) | GGTACCATACGAAAGCCCCGGCTAACTACGTGCCAGCAGCCGCGGTAATA |
| TsaccharolyticumB6A-RI_16S | (492) | GGTACCATACGAAAGCCCCGGCTAACTACGTGCCAGCAGCCGCGGTAATA |
| TsaccharolyticumYS485_16S | (492) | GGTACCATACGAAAGCCCCGGGCTACTACGTGCCAGCAGCCGCGGTAATA |
| Consensus | (501) | GGTACCATACGAAAGCCCCGGCTAACTACGTGCCAGCAGCCGCGGTAATA |
| | | 551 600 |
| Tethanolicus39E_16S | (503) | CGTAGGGGGCGAGCGTTGTCCGGAATTACTGGGCGTAAAGGGCGCGTAGG |
| Thermoanaerobacter_sp_strain_59_16S | (462) | CGTAGGGGGCGAGCGTTGTCCGGAATTACTGGGCGTAAAGAGCACGTAGG |
| TsaccharolyticumB6A-RI_16S | (542) | CGTAGGGGGCGAGCGTTGTCCGGAATTACTGGGCGTAAAGAGCACGTAGG |
| TsaccharolyticumYS485_16S | (542) | CGTAGGGGGCGAGCGTTGTCCGGAATTACTGGGCGTAAAGAGCACGTAGG |
| Consensus | (551) | CGTAGGGGGCGAGCGTTGTCCGGAATTACTGGGCGTAAAGAGCACGTAGG |
| | | 601 650 |
| Tethanolicus39E_16S | (553) | CGGCCGTTCAAGTCAGGTGTAAAATACCCGGGCTCAACCCCGGGATAGCA |
| Thermoanaerobacter_sp_strain_59_16S | (512) | CGGCTATAAAAGTCAGATGTGAAAAACCTGGGCTCAACCGAGGGTATGCA |
| TsaccharolyticumB6A-RI_16S | (592) | CGGCTGTAAAAGTCAGATGTGAAAAACCTGGGCTCAACCGAGGGTGTGCA |
| TsaccharolyticumYS485_16S | (592) | CGGCTGTAAAAGTCAGATGTGAAAAACCTGGGCTCAACCGAGGGTGTGCA |
| Consensus | (601) | CGGCTGTAAAAGTCAGATGTGAAAAACCTGGGCTCAACCGAGGGTGTGCA |

Fig. 30-2

```
                                          651                                              700
              Tethanolicus39E_16S   (603) CTTGAAACTGGGCGGCTAGAGGGCAGGAGAGGCGAGTGGAATTCCCGGTG
Thermoanaerobacter_sp_strain_59_16S (562) TCTGAAACTAAATAGCTTGAGTCAAGGAGAGGAGAGCGGAATTCCTGGTG
       TsaccharolyticumB6A-RI_16S   (642) TCTGAAACTAAACAGCTTGAGTCAAGGAGAGGAGAGCGGAATTCCTGGTG
        TsaccharolyticumYS485_16S   (642) TCTGAAACTAAACAGCTTGAGTCAAGGAGAGGAGAGCGGAATTCCTGGTG
                        Consensus   (651) TCTGAAACTAAACAGCTTGAGTCAAGGAGAGGAGAGCGGAATTCCTGGTG
                                          701                                              750
              Tethanolicus39E_16S   (653) TAGCGGTGAAATGCGTAGATATCGGGAGGAATACCAGTGGCGAAGGCGAC
Thermoanaerobacter_sp_strain_59_16S (612) TAGCGGTGAAATGCGTAGAGATCAGGAAGAATACCAGTGGCGAAAGCGGC
       TsaccharolyticumB6A-RI_16S   (692) TAGCGGTGAAATGCGTAGAGATCAGGAAGAATACCAGTGGCGAAAGCGGC
        TsaccharolyticumYS485_16S   (692) TAGCGGTGAAATGCGTAGAGATCAGGAAGAATACCAGTGGCGAAAGCGGC
                        Consensus   (701) TAGCGGTGAAATGCGTAGAGATCAGGAAGAATACCAGTGGCGAAAGCGGC
                                          751                                              800
              Tethanolicus39E_16S   (703) TCTCTGGACTGACCCTGACGCTGAGGCGCGAAAGCGTGGGGAGCAAACAG
Thermoanaerobacter_sp_strain_59_16S (662) TCTCTGGACTTGAACTGACGCTGAGGTGCGAAAGCGTGGGGAGCAAACAG
       TsaccharolyticumB6A-RI_16S   (742) TCTCTGGACTTGAACTGACGCTGAGGTGCGAAAGCGTGGGGAGCAAACAG
        TsaccharolyticumYS485_16S   (742) TCTCTGGACTTGAACTGACGCTGAGGTGCGAAAGCGTGGGGAGCAAACAG
                        Consensus   (751) TCTCTGGACTTGAACTGACGCTGAGGTGCGAAAGCGTGGGGAGCAAACAG
                                          801                                              850
              Tethanolicus39E_16S   (753) GATTAGATACCCTGGTAGTCCACGCCGTAAACGATGGGTACTAGGTGTGG
Thermoanaerobacter_sp_strain_59_16S (712) GATTAGATACCCTGGTAGTCCACGCCGTAAACGATGGATACTAGGTGTGG
       TsaccharolyticumB6A-RI_16S   (792) GATTAGATACCCTGGTAGTCCACGCCGTAAACGATGGATACTAGGTGTGG
        TsaccharolyticumYS485_16S   (792) GATTAGATACCCTGGTAGTCCACGCCGTAAACGATGGATACTAGGTGTGG
                        Consensus   (801) GATTAGATACCCTGGTAGTCCACGCCGTAAACGATGGATACTAGGTGTGG
                                          851                                              900
              Tethanolicus39E_16S   (803) GATGCGGAAGCATTCCGTGCCGTAGTTAACGCAATAAGTACCCCGCCTGG
Thermoanaerobacter_sp_strain_59_16S (762) G-TTAGATATAAT-CCGTGCCGGAGTTAACGCAATAAGTATCCCGCCTGG
       TsaccharolyticumB6A-RI_16S   (842) G-TGAAGCATCAT-CCGTGCCGGAGTTAACGCAATAAGTATCCCGCCTGG
        TsaccharolyticumYS485_16S   (842) G-TGAAGCATCAT-CCGTGCCGGAGTTAACGCAATAAGTATCCCGCCTGG
                        Consensus   (851) G TGAGGCATCAT CCGTGCCGGAGTTAACGCAATAAGTATCCCGCCTGG
                                          901                                              950
              Tethanolicus39E_16S   (853) GGAGTACGGCCGCAAGGTTGAAACTCAAAGGAATTGACGGGGGCCCGCAC
Thermoanaerobacter_sp_strain_59_16S (810) GGAGTACGGCCGCAAGGTTGAAACTCAAAGGAATTGACGGGGGCCCGCAC
       TsaccharolyticumB6A-RI_16S   (890) GGAGTACGGCCGCAAGGTTGAAACTCAAAGGAATTGACGGGGGCCCGCAC
        TsaccharolyticumYS485_16S   (890) GGAGTACGGCCGCAAGGTTGAAACTCAAAGGAATTGACGGGGGCCCGCAC
                        Consensus   (901) GGAGTACGGCCGCAAGGTTGAAACTCAAAGGAATTGACGGGGGCCCGCAC
                                          951                                             1000
              Tethanolicus39E_16S   (903) AAGCGGTGGAGCATGTGGTTTAATTCGAAGCAACGCGAAGAACCTTACCA
Thermoanaerobacter_sp_strain_59_16S (860) AAGCAGCGGAGCATGTGGTTTAATTCGAAGCAACGCGAAGAACCTTACCA
       TsaccharolyticumB6A-RI_16S   (940) AAGCAGCGGAGCATGTGGTTTAATTCGAAGCAACGCGAAGAACCTTACCA
        TsaccharolyticumYS485_16S   (940) AAGCAGCGGAGCATGTGGTTTAATTCGAAGCAACGCGAAGAACCTTACCA
                        Consensus   (951) AAGCAGCGGAGCATGTGGTTTAATTCGAAGCAACGCGAAGAACCTTACCA
```

Fig. 30-3

```
                                          1001                                              1050
             Tethanolicus39E_16S   (953)  GGGCTTGACATCCAGGTAGTAGCCAGCCGAAAGGTCAGCGACCTTACCTT
Thermoanaerobacter_sp_strain_59_16S (910)  GGGCTTGACATCCAC--AGAATCCAGTAGAAATAGTTGAGTGCCTCG---
       TsaccharolyticumB6A-RI_16S  (990)  GGGCTTGACATCCAC--AGAATCAGGTAGAAATACCAGAGTGCCTCG---
        TsaccharolyticumYS485_16S  (990)  GGGCTTGACATCCAC--AGAATCTGGTAGAAATACCGGAGTGCCTCG---
                        Consensus (1001)  GGGCTTGACATCCAC  AGAATCGGGTAGAAATACCAGAGTGCCTCG
                                          1051                                              1100
             Tethanolicus39E_16S  (1003)  AAAGGTCAGGAGCCTGCACAGGTGGTGCATGGTTGTCGTCAGCTCGTGTC
Thermoanaerobacter_sp_strain_59_16S (955)  TAAGAGCAGCTGTGAG-ACAGGTGGTGCATGGTTGTCGTCAGCTCGTGTC
       TsaccharolyticumB6A-RI_16S (1035)  AAAGAGCAGCTGTGAG-ACAGGTGGTGCATGGTTGTCGTCAGCTCGTGTC
        TsaccharolyticumYS485_16S (1035)  AAAGAGCAGCTGTGAG-ACAGGTGGTGCATGGTTGTCGTCAGCTCGTGTC
                        Consensus (1051)  AAAGAGGAGCTGTGAG ACAGGTGGTGCATGGTTGTCGTCAGCTCGTGTC
                                          1101                                              1150
             Tethanolicus39E_16S  (1053)  GTGAGATGTTGGGTTAAGTCCCGCAACGAGCGCAACCCCTGCCTCTAGTT
Thermoanaerobacter_sp_strain_59_16S (1004) GTGAGATGTTGGGTTAAGTCCCGCAACGAGCGCAACCCCTGTTGGTAGTT
       TsaccharolyticumB6A-RI_16S (1084)  GTGAGATGTTGGGTTAAGTCCCGCAACGAGCGCAACCCCTGTTGGTAGTT
        TsaccharolyticumYS485_16S (1084)  GTGAGATGTTGGGTTAAGTCCCGCAACGAGCGCAACCCCTGTTGGTAGTT
                        Consensus (1101)  GTGAGATGTTGGGTTAAGTCCCGCAACGAGCGCAACCCCTGTTGGTAGTT
                                          1151                                              1200
             Tethanolicus39E_16S  (1103)  GCCAGCCGGTGAAGCCGGGCACGCTAGAGGGACTGCCGTGGACAACACGG
Thermoanaerobacter_sp_strain_59_16S (1054) ACCAGCG--TAAAGACGGGCACTCTACCGAGACTGCCGTGGATAACACGG
       TsaccharolyticumB6A-RI_16S (1134)  ACCAGCG--TAAAGACGGGCACTCTACCGAGACTGCCGTGGAGAACACGG
        TsaccharolyticumYS485_16S (1134)  ACCAGCG--TAAAGACGGGCACTCTACCGAGACTGCCGTGGAGAACACGG
                        Consensus (1151)  ACCAGCG  TAAAGACGGGGACTCTACCGAGACTGCCGTGGAGAACACGG
                                          1201                                              1250
             Tethanolicus39E_16S  (1153)  AGGAAGCTGGGGATGACGTCAAATCATCATGCCCTATATGCCCTGGCCCA
Thermoanaerobacter_sp_strain_59_16S (1102) AGGAAGGCGGGGATGACGTCAAATCATCATGCCCTTTATGCCCTGGGCTA
       TsaccharolyticumB6A-RI_16S (1182)  AGGAAGGCGGGGATGACGTCAAATCATCATGCCCTTTATGCCCTGGGCTA
        TsaccharolyticumYS485_16S (1182)  AGGAAGGCGGGGATGACGTCAAATCATCATGCCCTTTATGCCCTGGGCTA
                        Consensus (1201)  AGGAAGGCGGGGATGACGTCAAATCATCATGCCCTTTATGCCCTGGGCTA
                                          1251                                              1300
             Tethanolicus39E_16S  (1203)  CACACGTGCTACAATGGCCGGTACAGAGGGAAGCGAAGCCGCGAGGTGGA
Thermoanaerobacter_sp_strain_59_16S (1152) CACACGTGCTACAATGGCCTGAACAGAGGGCAGCGAAGGAGCGATCCGGA
       TsaccharolyticumB6A-RI_16S (1232)  CACACGTGCTACAATGGCCTGAACAGAGGGCAGCGAAGGAGCGATCCGGA
        TsaccharolyticumYS485_16S (1232)  CACACGTGCTACAATGGCCTGAACAGAGGGCAGCGAAGGAGCGATCCGGA
                        Consensus (1251)  CACACGTGCTACAATGGCCTGAACAGAGGGCAGCGAAGGAGCGATCCGGA
                                          1301                                              1350
             Tethanolicus39E_16S  (1253)  GCGAAACCCAAAAAGCCGGTCCAAGTTCGGATTGCAGGCTGCAACTCGCC
Thermoanaerobacter_sp_strain_59_16S (1202) GCGAATCCCAGAAAACAGGTCCCAGTTCAGATTGCAGGCTGCAACCCGCC
       TsaccharolyticumB6A-RI_16S (1282)  GCGAATCCCAGAAAACAGGTCCCAGTTCAGATTGCAGGCTGCAACCCGCC
        TsaccharolyticumYS485_16S (1282)  GCGAATCCCAGAAAACAGGTCCCAGTTCAGATTGCAGGCTGCAACCCGCC
                        Consensus (1301)  GCGAATCCCAGAAAACAGGTCCCAGTTCAGATTGCAGGCTGCAACCCGCC
```

Fig. 30-4

```
                                            1351                                             1400
          Tethanolicus39E_16S     (1303)  TGCATGAAGTCGGAATCGCTAGTAATCGCGGATCAGCATGCCGCGGTGAA
Thermoanaerobacter_sp_strain_59_16S (1252)  TGCATGAAGACGGAGTTGCTAGTAATCGCGGATCAGCATGCCGCGGTGAA
      TsaccharolyticumB6A-RI_16S  (1332)  TGCATGAAGACGGAGTTGCTAGTAATCGCGGATCAGCATGCCGCGGTGAA
       TsaccharolyticumYS485_16S  (1332)  TGCATGAAGACGGAGTTGCTAGTAATCGCGGATCAGCATGCCGCGGTGAA
                       Consensus  (1351)  TGCATGAAGACGGAGTTGCTAGTAATCGCGGATCAGCATGCCGCGGTGAA
                                            1401                                             1450
          Tethanolicus39E_16S     (1353)  TACGTT-CCCGGGCCTTGTACACACCGCCCGTCACACCACGAGAGTCTGC
Thermoanaerobacter_sp_strain_59_16S (1302)  TACGTT-CCCGGGCCTTGTACACACCGCCCGTCACACCACGAGAGTTTAC
      TsaccharolyticumB6A-RI_16S  (1382)  TACGTT-CCCGGGCCTTGTACACACCGCCCGTCACACCACGAGAGTTTAC
       TsaccharolyticumYS485_16S  (1382)  TACGTTTCCCGGGCCTTGTACACACCGCCCGTCACACCACGAGAGTTTAC
                       Consensus  (1401)  TACGTT CCCGGGCCTTGTACACACCGCCCGTCACACCACGAGAGTTTAC
                                            1451                                             1500
          Tethanolicus39E_16S     (1402)  AACACCCGAAG-CCGTGACCCAACCGNAAGGAGGGAGCCGTCGAAGGTGG
Thermoanaerobacter_sp_strain_59_16S (1351)  AACACCCGAAGTCAGTGACCTAACCGCAAGGGAGGAGCTGCCGAA-----
      TsaccharolyticumB6A-RI_16S  (1431)  AACACCCGAAGTCAGTGACCTAACCGCAAGGGAGGAGCTGCCGAAGGTGG
       TsaccharolyticumYS485_16S  (1432)  AACACCCGAAGTCAGTGACCTAACCGAAAGGAAGGAGCTGCCGAAGGTGG
                       Consensus  (1451)  AACACCCGAAGTCAGTGACCTAACCGCAAGGGAGGAGCTGCCGAAGGTGG
                                            1501                                             1550
          Tethanolicus39E_16S     (1451)  GGCAGATGATTGGGGTGAAGTCGTAACAAGGTAGCCGTATCGGAAGGTGC
Thermoanaerobacter_sp_strain_59_16S (1396)  --------------------------------------------------
      TsaccharolyticumB6A-RI_16S  (1481)  GGTAAATGATTGGGGTGAAGTCGTAACAAGGTAGCCGTATCGGAAGGTGC
       TsaccharolyticumYS485_16S  (1482)  GGTAAATGATTGGGGTGAAGTCGTAACAAGGTAGCCGTATCGGAAGGTGC
                       Consensus  (1501)  GGTAAATGATTGGGGTGAAGTCGTAACAAGGTAGCCGTATCGGAAGGTGC
                                            1551            1572
          Tethanolicus39E_16S     (1501)  GGCTGGATCACCTCC-------
Thermoanaerobacter_sp_strain_59_16S (1396)  ----------------------
      TsaccharolyticumB6A-RI_16S  (1531)  GGCTGGATCACCTCCTTTCCCT
       TsaccharolyticumYS485_16S  (1532)  GGCTGGATCACCTCCTTTCTAA
                       Consensus  (1551)  GGCTGGATCACCTCCTTTC
```

Fig. 30-5

| | | |
|---|---|---|
| | | 1 50 |
| Thermoanaerobacter_sp._strain_59_pta | (1) | GTGTATACAATATATTTCTTCTTTTTAGTAAGAGGAATGTATAAAAATAA |
| Tpsuedoethanolicus_pta | (1) | -------------------------------------------------- |
| Tsaccharolyticum_B6A-RI_pta | (1) | GTGTATACAATATATTTCTTCTTTTTAGTAAGAGGAATGTATAAAAATAA |
| Tsaccharolyticum_YS485_pta | (1) | GTGTATACAATATATTTCTTC---TTAGTAAGAGGAATGTATAAAAATAA |
| Consensus | (1) | GTGTATACAATATATTTCTTCTTTTTAGTAAGAGGAATGTATAAAAATAA |
| | | 51 100 |
| Thermoanaerobacter_sp._strain_59_pta | (51) | ATATTTTAAAGGAAGGGACGATCTTATGAGCATTATTCAAAACATCATTG |
| Tpsuedoethanolicus_pta | (1) | -------------------------ATGGCAGTAATGGATAGTATCATAC |
| Tsaccharolyticum_B6A-RI_pta | (51) | ATATTTTAAAGGAAGGGATGATCTTATGAGCATTATTCAGAACATCATTG |
| Tsaccharolyticum_YS485_pta | (48) | ATATTTTAAAGGAAGGGACGATCTTATGAGCATTATTCAAAACATCATTG |
| Consensus | (51) | ATATTTTAAAGGAAGGGACGATCTTATGAGCATTATTCAAAACATCATTG |
| | | 101 150 |
| Thermoanaerobacter_sp._strain_59_pta | (101) | AAAAAGCTAAAAGTGATAAAAAGAAAATTGTTCTGCCGGAAGGTGCAGAA |
| Tpsuedoethanolicus_pta | (26) | AAAAGGCTAAAGCTAATAAAAAAAGGATTGTGCTTCCTGAGGGAAGTGAA |
| Tsaccharolyticum_B6A-RI_pta | (101) | AAAAAGCTAAAAGCGATAAAAAGAAAATTGTTCTGCCAGAAGGTGCAGAA |
| Tsaccharolyticum_YS485_pta | (98) | AAAAAGCTAAAAGCGATAAAAAGAAAATTGTTCTGCCAGAAGGTGCAGAA |
| Consensus | (101) | AAAAAGCTAAAAGTGATAAAAAGAAAATTGTTCTGCCAGAAGGTGCAGAA |
| | | 151 200 |
| Thermoanaerobacter_sp._strain_59_pta | (151) | CCCAGAACATTAAAAGCTGCTGAAATAGTTTTAAAAGAAGGAATTGCAGA |
| Tpsuedoethanolicus_pta | (76) | GCTCGAACTTTAAAAGCTGCTGAAAAGGTTATTAAAGAAGGTATTGCTGA |
| Tsaccharolyticum_B6A-RI_pta | (151) | CCCAGGACATTAAAAGCTGCTGAAATAGTTTTAAAAGAAGGAATTGCAGA |
| Tsaccharolyticum_YS485_pta | (148) | CCCAGGACATTAAAAGCTGCTGAAATAGTTTTAAAAGAAGGGATTGCAGA |
| Consensus | (151) | CCCAGGACATTAAAAGCTGCTGAAATAGTTTTAAAAGAAGGAATTGCAGA |
| | | 201 250 |
| Thermoanaerobacter_sp._strain_59_pta | (201) | TTTGGTGCTTCTTGGAAATGAAGATGAGATAAGAAATGCTGCAAAAGACT |
| Tpsuedoethanolicus_pta | (126) | TGTAGTTTTATTAGGGAAGGAAGAAGAAATAAAAGAAAAAGCAAAGGGAT |
| Tsaccharolyticum_B6A-RI_pta | (201) | TTTGGTGCTTCTTGGAAATGAAGATGAGATAAGAAATGCAGCAAAAGACT |
| Tsaccharolyticum_YS485_pta | (198) | TTTAGTGCTTCTTGGAAATGAAGATGAGATAAGAAATGCTGCAAAAGACT |
| Consensus | (201) | TTTGGTGCTTCTTGGAAATGAAGATGAGATAAGAAATGCTGCAAAAGACT |
| | | 251 300 |
| Thermoanaerobacter_sp._strain_59_pta | (251) | TGGACATATCTAAAGCTGAAATCATTGATCCTGTAAAATCTGAAATGTTT |
| Tpsuedoethanolicus_pta | (176) | TGGATATCTCGAAAGCAGAAATTATAGACCCTGAAAAGTCGCCTCTTTTA |
| Tsaccharolyticum_B6A-RI_pta | (251) | TGGACATATCCAAAGCTGAAATAATTGACCCTGTAAAATCTGAAATGTTT |
| Tsaccharolyticum_YS485_pta | (248) | TGGACATATCCAAAGCTGAAATCATTGACCCTGTAAAGTCTGAAATGTTT |
| Consensus | (251) | TGGACATATCCAAAGCTGAAATCATTGACCCTGTAAAGTCTGAAATGTTT |
| | | 301 350 |
| Thermoanaerobacter_sp._strain_59_pta | (301) | GATAGGTATGCTAATGATTTTTATGAGTTAAGGAAGAGCAAAGGAATCAC |
| Tpsuedoethanolicus_pta | (226) | CAAAAATATGCTGAAGAATATTATAATTTGAGAAAAACCAAAGGAGTTAC |
| Tsaccharolyticum_B6A-RI_pta | (301) | GATAGGTATGCTAATGATTTTTACGAATTAAGAAACAGCAAGGGAATCAC |
| Tsaccharolyticum_YS485_pta | (298) | GATAGGTATGCTAATGATTTCTATGAGTTAAGGAACAACAAAGGAATCAC |
| Consensus | (301) | GATAGGTATGCTAATGATTTTTATGAGTTAAGGAAGAGCAAAGGAATCAC |

Fig. 31-1

| | | 351 … 400 |
|---|---|---|
| Thermoanaerobacter_sp._strain_59_pta | (351) | GTTGGAAAAAGCCAGAGAAACAATCAAGGATAATATCTATTTTGGATGTA |
| Tpsuedoethanolicus_pta | (276) | AGAAGAACAGGCATATCAAATTATGAAAGACCCTATGTACTATGGGTGCA |
| Tsaccharolyticum_B6A-RI_pta | (351) | ATTGGAAAAAGCCAGAGAAACAATCAAGGATAATATCTATTTTGGATGTA |
| Tsaccharolyticum_YS485_pta | (348) | GTTGGAAAAAGCCAGAGAAACAATCAAGGATAATATCTATTTTGGATGTA |
| Consensus | (351) | GTTGGAAAAAGCCAGAGAAACAATCAAGGATAATATCTATTTTGGATGTA |

| | | 401 … 450 |
|---|---|---|
| Thermoanaerobacter_sp._strain_59_pta | (401) | TGATGGTTAAAGAAGGTTATGCTGATGGATTGGTATCTGGCGCTATTCAT |
| Tpsuedoethanolicus_pta | (326) | TGATGGTCAAATTAGACCGATGTTGATGGTATGGTATCTGGGCGATTCAC |
| Tsaccharolyticum_B6A-RI_pta | (401) | TGATGGTTAAAGAAGGTTATGCTGATGGATTAGTATCTGGCGCTATTCAT |
| Tsaccharolyticum_YS485_pta | (398) | TGATGGTTAAAGAAGGTTATGCTGATGGATTGGTATCTGGCGCTATTCAT |
| Consensus | (401) | TGATGGTTAAAGAAGGTTATGCTGATGGATTGGTATCTGGCGCTATTCAT |

| | | 451 … 500 |
|---|---|---|
| Thermoanaerobacter_sp._strain_59_pta | (451) | GCTACTGCAGATTTATTAAGACCTGCATTTCAGATAATTAAAACGGCTCC |
| Tpsuedoethanolicus_pta | (376) | GCTACTGCTGATGTTTTCAGACCGGCTTTTCAAATTGTAAAAACTGCTGC |
| Tsaccharolyticum_B6A-RI_pta | (451) | GCTACTGCAGATTTATTAAGACCTGCATTTCAGATAATTAAAACAGCTCC |
| Tsaccharolyticum_YS485_pta | (448) | GCTACTGCAGATTTATTAAGACCTGCATTTCAGATAATTAAAACGGCTCC |
| Consensus | (451) | GCTACTGCAGATTTATTAAGACCTGCATTTCAGATAATTAAAACGGCTCC |

| | | 501 … 550 |
|---|---|---|
| Thermoanaerobacter_sp._strain_59_pta | (501) | AGGAGCAAAGATAGTATCAAGCTTTTTTATAATGGAAGTGCCTAATTGTG |
| Tpsuedoethanolicus_pta | (426) | AGGTGTCAAAGTAGTATCCAGCGCCTTTATAATGGAAGTACCTAATTGTA |
| Tsaccharolyticum_B6A-RI_pta | (501) | AGGAGCAAAGATAGTATCAAGCTTTTTTATAATGGAAGTGCCTAATTGTG |
| Tsaccharolyticum_YS485_pta | (498) | AGGAGCAAAGATAGTATCAAGCTTTTTTATAATGGAAGTGCCTAATTGTG |
| Consensus | (501) | AGGAGCAAAGATAGTATCAAGCTTTTTTATAATGGAAGTGCCTAATTGTG |

| | | 551 … 600 |
|---|---|---|
| Thermoanaerobacter_sp._strain_59_pta | (551) | AATATGGTGAAAATGGTGTATTCTTGTTTGCTGATTGCGCGGTCAACCCA |
| Tpsuedoethanolicus_pta | (476) | CTTATGGAAGCCGATGGAGTATTTATTTTTGCTGATTGTGCAATAAATCCT |
| Tsaccharolyticum_B6A-RI_pta | (551) | AATATGGTGAAAATGGCGTATTCTTGTTTGCTGATTGTGCGGTCAATCCA |
| Tsaccharolyticum_YS485_pta | (548) | AATATGGTGAAAATGGTGTATTCTTGTTTGCTGATTGTGCGGTCAACCCA |
| Consensus | (551) | AATATGGTGAAAATGGTGTATTCTTGTTTGCTGATTGTGCGGTCAATCCA |

| | | 601 … 650 |
|---|---|---|
| Thermoanaerobacter_sp._strain_59_pta | (601) | TCGCCTAATGCAGAAGAACTTGCTTCTATTGCTGTACAATCTGCTAATAC |
| Tpsuedoethanolicus_pta | (526) | AATCCTAATGAAGAGGAATTAGCAGCAATTGCCATTGCTTCTGCCCATAC |
| Tsaccharolyticum_B6A-RI_pta | (601) | TCACCTAATGCAGAAGAACTTGCTTCTATTGCTGTACAATCTGCTAATAC |
| Tsaccharolyticum_YS485_pta | (598) | TCGCCTAATGCAGAAGAACTTGCTTCTATTGCCGTACAATCTGCTAATAC |
| Consensus | (601) | TCGCCTAATGCAGAAGAACTTGCTTCTATTGCTGTACAATCTGCTAATAC |

| | | 651 … 700 |
|---|---|---|
| Thermoanaerobacter_sp._strain_59_pta | (651) | TGCAAA-GAATTTGTTGGGCTTTGAACCAAAAGTTGCTATGCTATCATTT |
| Tpsuedoethanolicus_pta | (576) | TGCAAAAGTCCTTGCTGGAATT-GAGCCTAGAATTGCTATGCTGTCATTT |
| Tsaccharolyticum_B6A-RI_pta | (651) | TGCAAA-GAATTTGTTGGGTTTTGAACCAAAAGTTGCCATGCTATCATTT |
| Tsaccharolyticum_YS485_pta | (648) | TGCAAA-GAATTTGTTGGGCTTTGAACCAAAAGTTGCCATGCTATCATTT |
| Consensus | (651) | TGCAAA GAATTTGTTGGGCTTTGAACCAAAAGTTGCTATGCTATCATTT |

Fig. 31-2

```
                                          701                                            750
Thermoanaerobacter_sp._strain_59_pta  (700) TCCACAAAAGGTAGTGCATCACATGAATTAGTAGATAAAGTAAGAAAAGC
             Tpsuedoethanolicus_pta  (625) TCTACTAAAGGAAGTGCAAACCATGAATTAGTAGATAAGGTGAAAAATGC
        Tsaccharolyticum_B6A-RI_pta  (700) TCCACAAAAGGTAGTGCATCACATGAATTAGTAGACAAGGTAAGAAAAGC
         Tsaccharolyticum_YS485_pta  (697) TCTACAAAAGGTAGTGCATCACATGAATTAGTAGATAAAGTAAGAAAAGC
                          Consensus  (701) TCTACAAAAGGTAGTGCATCACATGAATTAGTAGATAAGGTAAGAAAAGC
                                          751                                            800
Thermoanaerobacter_sp._strain_59_pta  (750) GACAGAAATAGCAAAAGAATTGATGCCAGATGTTGCTA-TCGACGGTGAA
             Tpsuedoethanolicus_pta  (675) GACTAAAATCGCAAAAGAATTGGCGCCTGAT-TTGCTAATTGATGGTGAG
        Tsaccharolyticum_B6A-RI_pta  (750) GACAGAGATAGCAAAGGATTTGATGCCAGATGTTGCTA-TCGATGGTGAA
         Tsaccharolyticum_YS485_pta  (747) GACAGAGATAGCAAAAGAATTGATGCCAGATGTTGCTA-TCGACGGTGAA
                          Consensus  (751) GACAGAGATAGCAAAAGAATTGATGCCAGATGTTGCTA TCGATGGTGAA
                                          801                                            850
Thermoanaerobacter_sp._strain_59_pta  (799) TTGCAATTGGATGCTGCTCTTGTCAAAGAAGTTGCAGAGCTAAAAGCGCC
             Tpsuedoethanolicus_pta  (724) CTTCAATTAGATGCTGCGATTGTCAAAGAAGTAGGAGAGTTAAAGGCTCC
        Tsaccharolyticum_B6A-RI_pta  (799) TTGCAACTGGATGCTGCTATTGTTAAACAAGTTGCAGAGCTAAAAGCACC
         Tsaccharolyticum_YS485_pta  (796) TTGCAATTGGATGCTGCTCTTGTTAAAGAAGTTGCAGAGCTAAAAGCGCC
                          Consensus  (801) TTGCAATTGGATGCTGCTCTTGTTAAAGAAGTTGCAGAGCTAAAAGCGCC
                                          851                                            900
Thermoanaerobacter_sp._strain_59_pta  (849) AGGAAGCAAAGTTGCGGGATGTGCAAATGTGCTTATATTCCCTGATTTAC
             Tpsuedoethanolicus_pta  (774) AGGAAGTCCTGTAGCGGGGAATGCAAATGTGCTTATTTTCCCAGATTTGC
        Tsaccharolyticum_B6A-RI_pta  (849) GGGAAGCAAAGTTGCGGGATGTGCAAATGTGCTTATATTCCCTGACTTAC
         Tsaccharolyticum_YS485_pta  (846) GGGAAGCAAAGTTGCGGGATGTGCAAATGTGCTTATATTCCCTGATTTAC
                          Consensus  (851) GGGAAGCAAAGTTGCGGGATGTGCAAATGTGCTTATATTCCCTGATTTAC
                                          901                                            950
Thermoanaerobacter_sp._strain_59_pta  (899) AAGCTGGTAATATAGGATATAAGCTTGTACAGAGATTAGCTA--GCAAAT
             Tpsuedoethanolicus_pta  (824) AAGCCGGAAACATTGGATATAAGCTAGTGCAAAGACTTGCTAAAGCTAAT
        Tsaccharolyticum_B6A-RI_pta  (899) AAGCTGGTAATATAGGATATAAGCTTGTACAGAGATTAGCTAAGGCAAAT
         Tsaccharolyticum_YS485_pta  (896) AAGCTGGTAATATAGGATATAAGCTTGTACAGAGGTTAGCTAAGGCAAAT
                          Consensus  (901) AAGCTGGTAATATAGGATATAAGCTTGTACAGAGATTAGCTAAGGCAAAT
                                          951                                           1000
Thermoanaerobacter_sp._strain_59_pta  (947) GCAATTGGACCTATAACACA-GGAATGGGTGCACCGGTTAATGATTTATC
             Tpsuedoethanolicus_pta  (874) GCTATCGGACCAATTTCTCAAGGTCTTGCAAAACCTATCAATGACTTGTC
        Tsaccharolyticum_B6A-RI_pta  (949) GCAATTGGACCGATAACGCAAGGAATGGGTGCACCAGTTAATGATTTATC
         Tsaccharolyticum_YS485_pta  (946) GCAATTGGACCTATAACACAAGGAATGGGTGCACCGGTTAATGATTTATC
                          Consensus  (951) GCAATTGGACCTATAACACAAGGAATGGGTGCACCGGTTAATGATTTATC
                                          1001                                          1050
Thermoanaerobacter_sp._strain_59_pta  (996) AAGAGGATGCAGCTATAGAGATATTGTTGACGTAATAGCAC--ACAGCTG
             Tpsuedoethanolicus_pta  (924) AAGAGGTTGTAGTGTAGAAGATATTGTTAATGTTATAGCAATAACTTGTG
        Tsaccharolyticum_B6A-RI_pta  (999) AAGAGGATGCAGCTATAAAGATATTGTTGACGTAATAGCGACAACAGCTG
         Tsaccharolyticum_YS485_pta  (996) AAGAGGATGCAGCTATAGAGATATTGTTGACGTAATAGCAACAACAGCTG
                          Consensus (1001) AAGAGGATGCAGCTATAGAGATATTGTTGACGTAATAGCAACAACAGCTG
```

Fig. 31-3

```
                                         1051                                              1100
Thermoanaerobacter_sp._strain_59_pta  (1044) TACAGGCTCA----------------------------------------
            Tpsuedoethanolicus_pta   (974) TACAAGCTCAAGGGGTGCAAAAATAACTTTGAGCAGGCAGCGATTATGAA
      Tsaccharolyticum_B6A-RI_pta  (1049) TGCAGGCTCAA---------------------------------------
       Tsaccharolyticum_YS485_pta  (1046) TGCAGGCTCAA---------------------------------------
                        Consensus  (1051) TGCAGGCTCAA
                                         1101                                              1150
Thermoanaerobacter_sp._strain_59_pta  (1054) --------------------------------------------------
            Tpsuedoethanolicus_pta  (1024) AATTTTAGTCATGAACTGTGGAAGCTCGTCATTAAAAGTATCAATTGTTA
      Tsaccharolyticum_B6A-RI_pta  (1060) --------------------------------------------------
       Tsaccharolyticum_YS485_pta  (1057) --------------------------------------------------
                        Consensus  (1101)
                                         1151                                              1200
Thermoanaerobacter_sp._strain_59_pta  (1054) --------------------------------------------------
            Tpsuedoethanolicus_pta  (1074) GATATGGATAATGGGAAAGTGCTAGCGAAAGGATTGGCGGAAAGGATAGG
      Tsaccharolyticum_B6A-RI_pta  (1060) --------------------------------------------------
       Tsaccharolyticum_YS485_pta  (1057) --------------------------------------------------
                        Consensus  (1151)
                                         1201                                              1250
Thermoanaerobacter_sp._strain_59_pta  (1054) --------------------------------------------------
            Tpsuedoethanolicus_pta  (1124) TATCAATGATTCTCTTTTAACTCATCAAGTAGAGGGCAAAGATAAAATAA
      Tsaccharolyticum_B6A-RI_pta  (1060) --------------------------------------------------
       Tsaccharolyticum_YS485_pta  (1057) --------------------------------------------------
                        Consensus  (1201)

                                         1251                  1273
Thermoanaerobacter_sp._strain_59_pta  (1054) -----------------------
            Tpsuedoethanolicus_pta  (1174) AAATACAAAAAGATATGAAAAAT
      Tsaccharolyticum_B6A-RI_pta  (1060) -----------------------
       Tsaccharolyticum_YS485_pta  (1057) -----------------------
                        Consensus  (1251)
```

Fig. 31-4

```
                                              1                                                50
Thermoanaerobacter_sp._strain_59_ack    (1)   --------------------------------------------------
             Tpsuedoethanclicus_ack     (1)   GCTAATGCTATCGGACCAATTTCTCAAGGTCTTGCAAAACCTATCAATGA
        Tsaccharolyticum_B6A-RI_ack     (1)   --------------------------------------------------
          Tsaccharolyticum_YS485_ack    (1)   --------------------------------------------------
                          Consensus     (1)
                                              51                                              100
Thermoanaerobacter_sp._strain_59_ack    (1)   --------------------------------------------------
             Tpsuedoethanclicus_ack    (51)   CTTGTCAAGAGGTTGTAGTGTAGAAGATATTGTTAATGTTATAGCAATAA
        Tsaccharolyticum_B6A-RI_ack     (1)   --------------------------------------------------
          Tsaccharolyticum_YS485_ack    (1)   --------------------------------------------------
                          Consensus    (51)
                                              101                                             150
Thermoanaerobacter_sp._strain_59_ack    (1)   --------------------------------------------------
             Tpsuedoethanclicus_ack   (101)   CTTGTGTACAAGCTCAAGGGGTGCAAAAATAACTTTGAGGAGGCAGCGAT
        Tsaccharolyticum_B6A-RI_ack     (1)   ------------------------------------------ATGAAAAC
          Tsaccharolyticum_YS485_ack    (1)   ------------------------------------------ATGAAAAT
                          Consensus   (101)                                             ATGAAAAT
                                              151                                             200
Thermoanaerobacter_sp._strain_59_ack    (1)   --------------------------------------------------
             Tpsuedoethanclicus_ack   (151)   TATGAAAATTTTAGTCATGAACTGTGGAAGCTCGTCATTAAAAGTATCAA
        Tsaccharolyticum_B6A-RI_ack     (9)   TATGAAAATTCTGGTTATTAATTGTGGAAGTTCTTCACTAAAA-TATCAA
          Tsaccharolyticum_YS485_ack    (9)   TATGAAAATACTGGTTATTAATTGCGGAAGTTCTTCGCTAAAA-TATCAA
                          Consensus   (151)   TATGAAAATTCTGGTTATTAATTGTGGAAGTTCTTCACTAAAA TATCAA
                                              201                                             250
Thermoanaerobacter_sp._strain_59_ack    (1)   --------------------------------------------------
             Tpsuedoethanclicus_ack   (201)   TTGTTAGATATGGATAATGGCAAAGTGCTAGGCAAACGATTGGCGGAAAG
        Tsaccharolyticum_B6A-RI_ack    (58)   TTCATTGAATCAATTGATGGAAATGTCCTGGCAAAAGGCCTTGCTGAAAG
          Tsaccharolyticum_YS485_ack   (58)   CTGATTGAATCAACTGATGGAAATGTCTTGGCAAAAGGCCTTGCTGAAAG
                          Consensus   (201)   T TGATTGAATCAA TGATGGAAATGTGCTGGCAAAAGG CCTTGCTGAAAG
                                              251                                             300
Thermoanaerobacter_sp._strain_59_ack    (1)   ---------------------------------ATGCTAACGG---AGAAA
             Tpsuedoethanclicus_ack   (251)   GATACGGTATCAATGATTCTCTTTTAACTCATCAAGTACACGGCAAAGATA
        Tsaccharolyticum_B6A-RI_ack   (108)   AATCGGCATAAATGATTCCCTGTTGACGCATAATGCTAACGG---AGAAA
          Tsaccharolyticum_YS485_ack  (108)   AATCGGCATAAATGATTCCATGTTGACACATAATGCTAACGG---AGAAA
                          Consensus   (251)   AATCGGCATAAATGATTCCCTGTTGAC CATAATGCTAACGG   AGAAA
                                              301                                             350
Thermoanaerobacter_sp._strain_59_ack   (16)   AA-TCAAGATAAAAAAAGACATGAAAGATCACAAAGACGCAATAAAATTG
             Tpsuedoethanclicus_ack   (301)   AAATAAAAATACAAAAAGATATGAAAAATCATAAAGAAGCTATACAAATT
        Tsaccharolyticum_B6A-RI_ack   (155)   AAATCAAGATAAAAAAAGACATGAAAGATCACAAAGACGCAATAAAATTG
          Tsaccharolyticum_YS485_ack  (155)   AAATCAAGATAAAAAAAGACATGAAAGATCACAAAGACGCAATAAAATTG
                          Consensus   (301)   AAATCAAGATAAAAAAAGACATGAAAGATCACAAAGACGCAATAAAATTG
```

Fig. 32-1

| | | 351 … 400 |
|---|---|---|
| Thermoanaerobacter_sp._strain_59_ack | (65) | - TTTTAGATGCTTTGGTAAGCAGTGACTACGGCGTTATAAAGGATATGTC |
| Tpsuedoethanolicus_ack | (351) | GTTTTAGACGCTTTAGTAGATAAAGAAATCGGAAATATTAAAAGATATGAA |
| Tsaccharolyticum_B6A-RI_ack | (205) | GTTTTAGATGCTTTGGTAAGTAGCGACTACGGCGTTATAAAGGATATGTC |
| Tsaccharolyticum_YS485_ack | (205) | GTTTTAGATGCTTTGGTAAACAGTGACTACGGCGTTATAAAAGATATGTC |
| Consensus | (351) | GTTTTAGATGCTTTGGTAAGTAGTGACTACGGCGTTATAAAGGATATGTC |

| | | 401 … 450 |
|---|---|---|
| Thermoanaerobacter_sp._strain_59_ack | (114) | TGAGATAGATGCTGTAGGACATAGAGTTGTTCACGGAGGAGAATCTTTTA |
| Tpsuedoethanolicus_ack | (401) | A GAAATAGATGCAGTAGGACATAGAGTTGTGCACGGGGGAGAGTTTTTTA |
| Tsaccharolyticum_B6A-RI_ack | (255) | TGAGATAGATGCTGTAGGACATAGAGTTGTTCATCGAGGAGAGTCTTTTA |
| Tsaccharolyticum_YS485_ack | (255) | TGAGATAGATGCTGTAGGACATAGAGTTGTTCACGGAGGAGAATCTTTTA |
| Consensus | (401) | TGAGATAGATGCTGTAGGACATAGAGTTGTTCACGGAGGAGAGTCTTTTA |

| | | 451 … 500 |
|---|---|---|
| Thermoanaerobacter_sp._strain_59_ack | (164) | CATCATCAGTTCTCATAAATGATGATGTGTTAAAAGCGATAACAGATTGC |
| Tpsuedoethanolicus_ack | (451) | CTCATTCCCTATTGATTGACGATGAGGTAATCAAAAAATTAGAAGCATGT |
| Tsaccharolyticum_B6A-RI_ack | (305) | CATCATCAGTTCTTATAAATGATGAAGTGTTAAACGGCATAACAGATTGT |
| Tsaccharolyticum_YS485_ack | (305) | CATCATCAGTTCTCATAAATGATGAAGTGTTAAAAGCGATAACAGATTGC |
| Consensus | (451) | CATCATCAGTTCTCATAAATGATGAAGTGTTAAAAGCGATAACAGATTGT |

| | | 501 … 550 |
|---|---|---|
| Thermoanaerobacter_sp._strain_59_ack | (214) | ATAGAATTAGCTCCACTGCACAATCCTGCCAATATAGAAGGAATTAAAGC |
| Tpsuedoethanolicus_ack | (501) | ATTGACCTTGCACCTTTGCACAATCCTGCTAATATTGAGGGAATAAAAGC |
| Tsaccharolyticum_B6A-RI_ack | (355) | ATAGAATTAGCTCCACTGCATAATCCTGCTAATATAGAAGGAATTAAAGC |
| Tsaccharolyticum_YS485_ack | (355) | ATAGAATTAGCTCCAGTGCACAATCCTGCTAATATAGAAGGAATTAAAGC |
| Consensus | (501) | ATAGAATTAGCTCCACTGCACAATCCTGCTAATATAGAAGGAATTAAAGC |

| | | 551 … 600 |
|---|---|---|
| Thermoanaerobacter_sp._strain_59_ack | (264) | TTGCCAGCAAATCATGCCAAACGTTCCAATGGTGGCGGTATTTGATACAG |
| Tpsuedoethanolicus_ack | (551) | TTGTCGGCAGATAATGCCAGGGGTGCCAATGGTAGCAGTTTTTGATACGG |
| Tsaccharolyticum_B6A-RI_ack | (405) | TTGCCAGCAAATCATGCCAAACGTTCCAATGGTGGCGGTATTTGATACAG |
| Tsaccharolyticum_YS485_ack | (405) | TTGCCAGCAAATCATGCCAAACGTTCCAATGGTGGCGGTATTTGATACAG |
| Consensus | (551) | TTGCCAGCAAATCATGCCAAACGTTCCAATGGTGGCGGTATTTGATACAG |

| | | 601 … 650 |
|---|---|---|
| Thermoanaerobacter_sp._strain_59_ack | (314) | CCTTTCATCAGACAATGCCTGATTATGCATATCTTTATCCAATACCTTAT |
| Tpsuedoethanolicus_ack | (601) | CTTTCCATCAAACAATGCCAGATTATGCGTATATTTATCCCATTCCTTAT |
| Tsaccharolyticum_B6A-RI_ack | (455) | CCTTTCATCAAACAATGCCTGATTATGCATATCTTTATCCAATACCTTAT |
| Tsaccharolyticum_YS485_ack | (455) | CCTTTCATCAGACAATGCCTGATTATGCATATCTTTATCCAATACCTTAT |
| Consensus | (601) | CCTTTCATCAGACAATGCCTGATTATGCATATCTTTATCCAATACCTTAT |

| | | 651 … 700 |
|---|---|---|
| Thermoanaerobacter_sp._strain_59_ack | (364) | GAATACTACACAAAGTACAGGATCAGAAGATATGGATTTCATGGCACATC |
| Tpsuedoethanolicus_ack | (651) | GAATACTACGAAAAATATAGAATAACAAGATATGGATTCCATGGCACTTC |
| Tsaccharolyticum_B6A-RI_ack | (505) | GAGTACTACACAAAGTACAGGATCAGAAGATATGGATTTCATGGCACGTC |
| Tsaccharolyticum_YS485_ack | (505) | GAATACTACACAAAGTACAGGATTAGAAGATATGGATTTCATGGCACATC |
| Consensus | (651) | GAATACTACACAAAGTACAGGATCAGAAGATATGGATTTCATGGCACATC |

Fig. 32-2

| | | |
|---|---|---|
| | | 701 750 |
| Thermoanaerobacter_sp._strain_59_ack | (414) | GCATAAATATGTTTCAAATAGGGCTGCAGAGATTTTAAATAAACCTATTG |
| Tpsuedoethanolicus_ack | (701) | TCATAAATATGTATCTTTAAGAGCTGCTGAAATATTAAAGAGGCCTATTG |
| Tsaccharolyticum_B6A-RI_ack | (555) | GCATAAATATGTTTCAAGTAGGGCTGCAGAGATTTTGAATAAACCTATTG |
| Tsaccharolyticum_YS485_ack | (555) | GCATAAATATGTTTCAAATAGGGCTGCAGAGATTTTGAATAAACCTATTG |
| Consensus | (701) | GCATAAATATGTTTCAAATAGGGCTGCAGAGATTTTGAATAAACCTATTG |
| | | 751 800 |
| Thermoanaerobacter_sp._strain_59_ack | (464) | AAGATTTGAAAATCATAACTTGTCATCTTGGAAATGGCTCCAGCATTGCT |
| Tpsuedoethanolicus_ack | (751) | AAGACTTAAAAATTATTACTTCCCATTTAGCCAATGGCTCTAGTATTGCT |
| Tsaccharolyticum_B6A-RI_ack | (605) | AAGATTTGAAAATCATAACTTGTCATCTTGGAAATGGCTCCAGTATTGCT |
| Tsaccharolyticum_YS485_ack | (605) | AAGATTTGAAAATCATAACTTGTCATCTTGGAAATGGCTCCAGCATTGCT |
| Consensus | (751) | AAGATTTGAAAATCATAACTTGTCATCTTGGAAATGGCTCCAGTATTGCT |
| | | 801 850 |
| Thermoanaerobacter_sp._strain_59_ack | (514) | GCTGTCAAATATGGTAAATCAATTGACACAAGCATGGATTTACACCATT |
| Tpsuedoethanolicus_ack | (801) | GCGGTTAAAGGCGGTAAGTCGATAGATACAAGTATGGATTTACTCCATT |
| Tsaccharolyticum_B6A-RI_ack | (655) | GCCGTCAAATATGGTAAATCAATTGACACAAGCATGGATTTACACCATT |
| Tsaccharolyticum_YS485_ack | (655) | GCTGTCAAATATGGTAAATCAATTGACACAAGCATGGATTTACACCATT |
| Consensus | (801) | GCTGTCAAATATGGTAAATCAATTGACACAAGCATGGATTTACACCATT |
| | | 851 900 |
| Thermoanaerobacter_sp._strain_59_ack | (564) | AGAAGGTTTGGCTATGGGTACACGATCTGGAAGCATAGACCCATCCATTA |
| Tpsuedoethanolicus_ack | (851) | AGAAGGGCTGGCTATGGGTACAAGGTCCGGAAATGTTGATCCTTCAATTA |
| Tsaccharolyticum_B6A-RI_ack | (705) | AGAAGGTTTGGCTATGGGTACACGATCTGGAAGTATAGACCCATCCATCA |
| Tsaccharolyticum_YS485_ack | (705) | AGAAGGTTTGGCTATGGGTACACGATCTGGAAGCATAGACCCATCCATCA |
| Consensus | (851) | AGAAGGTTTGGCTATGGGTACACGATCTGGAAGTATAGACCCATCCATTA |
| | | 901 950 |
| Thermoanaerobacter_sp._strain_59_ack | (614) | TTTCGTATCTTATGGAAAAAGAAAATATAAGCGCTGAAGAAGTAGTAAAT |
| Tpsuedoethanolicus_ack | (901) | TAACTTTCTTAATGGAAAAAGAAGGATTGACTGCAGAACAGGTTATAGAT |
| Tsaccharolyticum_B6A-RI_ack | (755) | TTTCTTATCTTATGGAAAAAGAAAATATAAGTGCTGAAGAGGTAGTAAAT |
| Tsaccharolyticum_YS485_ack | (755) | TTTCGTATCTTATGGAAAAAGAAAATATAAGCGCTGAAGAAGTAGTAAAT |
| Consensus | (901) | TTTCTTATCTTATGGAAAAAGAAAATATAAGTGCTGAAGAGGTAGTAAAT |
| | | 951 1000 |
| Thermoanaerobacter_sp._strain_59_ack | (664) | ATATTAAATAAAAAATCTGGTGTTTACGGTATTTCAGGAATAAGCAGCGA |
| Tpsuedoethanolicus_ack | (951) | ATACTTAATAAGAAATCAGGTGTATACGGAATTTCAGGAATAAGTAATGA |
| Tsaccharolyticum_B6A-RI_ack | (805) | ATATTAAATAAAAAATCTGGTGTTTACGGTATTTCGGGAATAAGCAGCGA |
| Tsaccharolyticum_YS485_ack | (805) | ATATTAAATAAAAAATCTGGTGTTTACGGTATTTCAGGAATAAGCAGCGA |
| Consensus | (951) | ATATTAAATAAAAAATCTGGTGTTTACGGTATTTCAGGAATAAGCAGCGA |
| | | 1001 1050 |
| Thermoanaerobacter_sp._strain_59_ack | (714) | TTTTAGAGACTTAGAAGATGCCGCCTTTAAAAATGGAGATGAAAGAGCTC |
| Tpsuedoethanolicus_ack | (1001) | CTTTAGAGATATAGAAAATGCAGCTTTTAAAGAAGGGCATAAAAGCGCTA |
| Tsaccharolyticum_B6A-RI_ack | (855) | TTTTAGAGATTTAGAAGATGCTGCCTTTAAAAATGGAGATGAAAGAGCTC |
| Tsaccharolyticum_YS485_ack | (855) | TTTTAGAGACTTAGAAGATGCCGCCTTTAAAAATGGAGATGAAAGAGCTC |
| Consensus | (1001) | TTTTAGAGATTTAGAAGATGCCGCCTTTAAAAATGGAGATGAAAGAGCTC |

Fig. 32-3

```
                                                1051                                              1100
Thermoanaerobacter_sp._strain_59_ack     (764)  AGTTGGCTTTAAATGTGTTTGCATATCCAGTAAAGAAGATGATTGGCGCT
         Tpsuedoethanolicus_ack         (1051)  TGTTGGCATTAAAAGTTTTCGCTTATACGGTGAAAAAGACAATAGGTTCT
    Tsaccharolyticum_B6A-RI_ack          (905)  AGTTGGCCTTAAATGTGTTTGCATATCCAGTAAAGAAGACGATTGGACCT
     Tsaccharolyticum_YS485_ack          (905)  AGTTGGCTTTAAATGTGTTTGCATATCCAGTAAAGAAGACGATTGGCGCT
                      Consensus         (1051)  AGTTGGCTTTAAATGTGTTTGCATATCGAGTAAAGAAGACGATTGGCGCT
                                                1101                                              1150
Thermoanaerobacter_sp._strain_59_ack     (814)  TATGCAGCAGCTATGGGAGGCGTCGATGCCATTGTATTTACAGCAGGTGT
         Tpsuedoethanolicus_ack         (1101)  TATACAGCTGCTATGGGTGGCGTTGATCTAATTGTGTTTACTGCTGGAGT
    Tsaccharolyticum_B6A-RI_ack          (955)  TATGCAGCAGCTATGGGAGGCGTTGATGTCATTGTATTTACGGCAGGTGT
     Tsaccharolyticum_YS485_ack          (955)  TATGCAGCAGCTATGGGAGGCGTCGATGTCATTGTATTTACAGCAGGTGT
                      Consensus         (1101)  TATGCAGCAGCTATGGGAGGCGTTGATGTCATTGTATTTACAGCAGGTGT
                                                1151                                              1200
Thermoanaerobacter_sp._strain_59_ack     (864)  TGGTGAAAATGGTCCTGAGATACGAGAATTTATACTTGATGGATTAGAGT
         Tpsuedoethanolicus_ack         (1151)  TGGAGAAAATGGACCAGAAATGAGAGAGTTTATTTTAGAGGATCTAGAGT
    Tsaccharolyticum_B6A-RI_ack         (1005)  TGGTGAAAATGGGCCTGAGATAAGAGAATTTATACTTGATGGATTCGAGT
     Tsaccharolyticum_YS485_ack         (1005)  TGGTGAAAATGGTCCTGAGATACGAGAATTTATACTTGATGGATTAGAGT
                      Consensus         (1151)  TGGTGAAAATGGTCCTGAGATACGAGAATTTATACTTGATGGATTAGAGT
                                                1201                                              1250
Thermoanaerobacter_sp._strain_59_ack     (914)  TCTTAGGGTTCAGCTTGGATAAAGAAAAAAATAAAGTCAGAGGAAAAGAA
         Tpsuedoethanolicus_ack         (1201)  TTTTAGGCTTTAAACTGGACAAAGAGAAGAATAAGGTAAGAGGAAAAGAG
    Tsaccharolyticum_B6A-RI_ack         (1055)  TCTTAGGGTTCAGCTTGGATAAAGAAAAAAATAAAGTCAGAGGAAAGGAA
     Tsaccharolyticum_YS485_ack         (1055)  TTTTAGGGTTCAGCTTGGATAAAGAAAAAAATAAAGTCAGAGGAAAAGAA
                      Consensus         (1201)  TTTTAGGGTTCAGCTTGGATAAAGAAAAAAATAAAGTCAGAGGAAAAGAA
                                                1251                                              1300
Thermoanaerobacter_sp._strain_59_ack     (964)  ACTATTATATCTACGCCGAATTCAAAAGTTAGCGTGATGGTTGTGCCCAC
         Tpsuedoethanolicus_ack         (1251) GAA ATTATATCTACAGAAGATTCAAAAGTTAAAGTTATGGTTATTCCTAC
    Tsaccharolyticum_B6A-RI_ack         (1105)  ACTATTATATCTACGCCAAATTCAAAAATTAGCGTGATGGTTGTGCCGAC
     Tsaccharolyticum_YS485_ack         (1105)  ACTATTATATCTACGCCGAATTCAAAAGTTAGCGTGATGGTTGTGCCTAC
                      Consensus         (1251)  ACTATTATATCTACGCCGAATTCAAAAGTTAGCGTGATGGTTGTGCCTAC
                                                1301                                              1350
Thermoanaerobacter_sp._strain_59_ack    (1014)  TAATGAAGAATACATGATTGCTAAAGATACTGAAAAGATTGTAAAGAGTA
         Tpsuedoethanolicus_ack         (1301) A AATGAAGAATATATGATTGCTAAAGATACTGAAAAATTGGTAAAAGGTT
    Tsaccharolyticum_B6A-RI_ack         (1155)  TAATGAAGAATATATGATTGCTAAAGATACTGAAAACATTGTAAACAGTA
     Tsaccharolyticum_YS485_ack         (1155)  TAATGAAGAATACATGATTGCTAAAGATACTGAAAAGATTGTAAAGAGTA
                      Consensus         (1301)  TAATGAAGAATATATGATTGCTAAAGATACTGAAAAGATTGTAAAGAGTA
                                                1351
Thermoanaerobacter_sp._strain_59_ack    (1064)  TAAAA---
         Tpsuedoethanolicus_ack         (1351)  TAAAGTAG
    Tsaccharolyticum_B6A-RI_ack         (1205)  TAAAA---
     Tsaccharolyticum_YS485_ack         (1205)  TAAAA---
                      Consensus         (1351)  TAAAA
```

Fig. 32-4

```
                                           1                                                50
Thermoanaerobacter_sp._strain59    (1)  ATGAGTAAAGTGGCCATAATAGGTTCAGGATTTGTAGGTGCTACATCTGC
       Tpseudoethanolicus_39E      (1)  ATGAACAAATATGTATAATAGGTTCTGGATTTGTCGGTGCTACTACTGGC
        Tsaccharolyticum_B6ARI     (1)  --------------------------------------------------
        Tsaccharolyticum_YS485     (1)  ATGAGCAAGTAGCAATAATAGGATCTGGTTTTGTAGGTGCAACATCGCC
                      Consensus    (1)  ATGAGCAAAGTAGC ATAATAGGTTCTGGATTTGTAGGTGCTACATCTGC
                                           51                                               100
Thermoanaerobacter_sp._strain59   (51)  ATTTACATTGGCTCTAAGTGGGACTGTGACAGACATTGTTTAGTAGATT
       Tpseudoethanolicus_39E     (51)  ATACACACTGGCTTTGAGTGGGATTGCCAAAACTATTGTATTAATAGATA
        Tsaccharolyticum_B6ARI     (1)  --------------------------------------------------
        Tsaccharolyticum_YS485    (51)  ATTTACGCTGGCATTAAGTGGGACTGTGACAGATATCGTGCTGGTGGATT
                      Consensus   (51)  ATTTACACTGGCTTTAAGTGGGACTGTGACAGATATTGT TTAGTAGATT
                                          101                                               150
Thermoanaerobacter_sp._strain59  (101)  TAAACAAGGACAAGCGGATAGGCGATGCACTGGATATTAGCCACGGTATA
       Tpseudoethanolicus_39E    (101)  TTAATAAAGACAAAGCAGAAGGCGATGCTCTTGATATAAGCCACGGGCTA
        Tsaccharolyticum_B6ARI     (1)  -------------------AGGCGATGCACTGGACATAAGCCATGGCATA
        Tsaccharolyticum_YS485   (101)  TAAACAAGGACAAGGCTATAGGCGATGCACTGGACATAAGCCATGGCATA
                      Consensus  (101)  TAAACAAGGACAAGGC ATAGGCGATGCACTGGATATAAGCCATGGCATA
                                          151                                               200
Thermoanaerobacter_sp._strain59  (151)  CCGCTTATACAGCCTGTAAATGTGTATGCTGGCGAGTACAACGATATCGA
       Tpseudoethanolicus_39E    (151)  CCGTTTATTAGTCCAGTTGAATGTACGGGGAGATTATAGTGATGTTTC
        Tsaccharolyticum_B6ARI    (32)  CCATTAATACAGCCTGTAAATGTGTATGCAGGTGAGTACAAAGATGTTGA
        Tsaccharolyticum_YS485   (151)  CCGCTAATACAGCCTGTAAATGTGTATGCAGGTGAGTACAAAGATGTGAA
                      Consensus  (151)  CCGTTTATACAGCCTGTAAATGTGTATGCAGGTGACTACAAAGATGTTGA
                                          201                                               250
Thermoanaerobacter_sp._strain59  (201)  GGGGCAGATGTAGTAGTTGTAACAGCAGGTGCCGGCTCAAAAGCCAGGAG
       Tpseudoethanolicus_39E    (201)  AGGTTCTGACATAATAATCATTACAGCGGGAGCAGCACAAAAACCGGGAG
        Tsaccharolyticum_B6ARI    (82)  AGGGCGCAGATAATAGTTGTGACAGCAGGGGCTGCTCAAAAGCCAGGTG
        Tsaccharolyticum_YS485   (201)  AGGCGCAGATGTAATAGTTGTGACAGCAGGTGCTGCTCAAAAGCCAGGAG
                      Consensus  (201)  AGGCGCAGATGTAATAGTTGTGACAGCAGGTGCTGCTCAAAAGCCAGGAG
                                          251                                               300
Thermoanaerobacter_sp._strain59  (251)  AGTCTAGGCTGGACGTTGTAAAAAGAATACATGTATATTCAAGTCCATG
       Tpseudoethanolicus_39E    (251)  AAACCAGACTTGACTTAGTGAAGAAAATACGATGATTTTTAAAGACATA
        Tsaccharolyticum_B6ARI   (132)  AGACGAGGCTTGACGTTGTGAAGAAAAATACAGCTATATTTAAGTCCATG
        Tsaccharolyticum_YS485   (251)  AGACACGGCTTGACGTTGTAAAGAAAAATACAGGCTATTTAAGTCCATG
                      Consensus  (251)  AGAC AGGCTTGACCTTGTGAAGAAAAATACAGCTATATTTAAGTCCATG
                                          301                                               350
Thermoanaerobacter_sp._strain59  (301)  ATACCTGAACTT-TTAAAATAGAATGATAAAGCTATATACCTGATTGTAA
       Tpseudoethanolicus_39E    (301)  GTGGCAAAACTTATTAAAGTA-AATGACACAGCAATATACCTTATAGTTA
        Tsaccharolyticum_B6ARI   (182)  ATACCTGAGCTT-TTAAAGTACAATGACAAGGCTATATATTTGATCGTCA
        Tsaccharolyticum_YS485   (301)  ATACCTGAGCTT-TTAAAGTACAATGACAAGGCATATATTTGATCGTGA
                      Consensus  (301)  ATACCTGAGCTT TTAAAGTACAATGACAAGGCTATATATTTGATTGT A
```

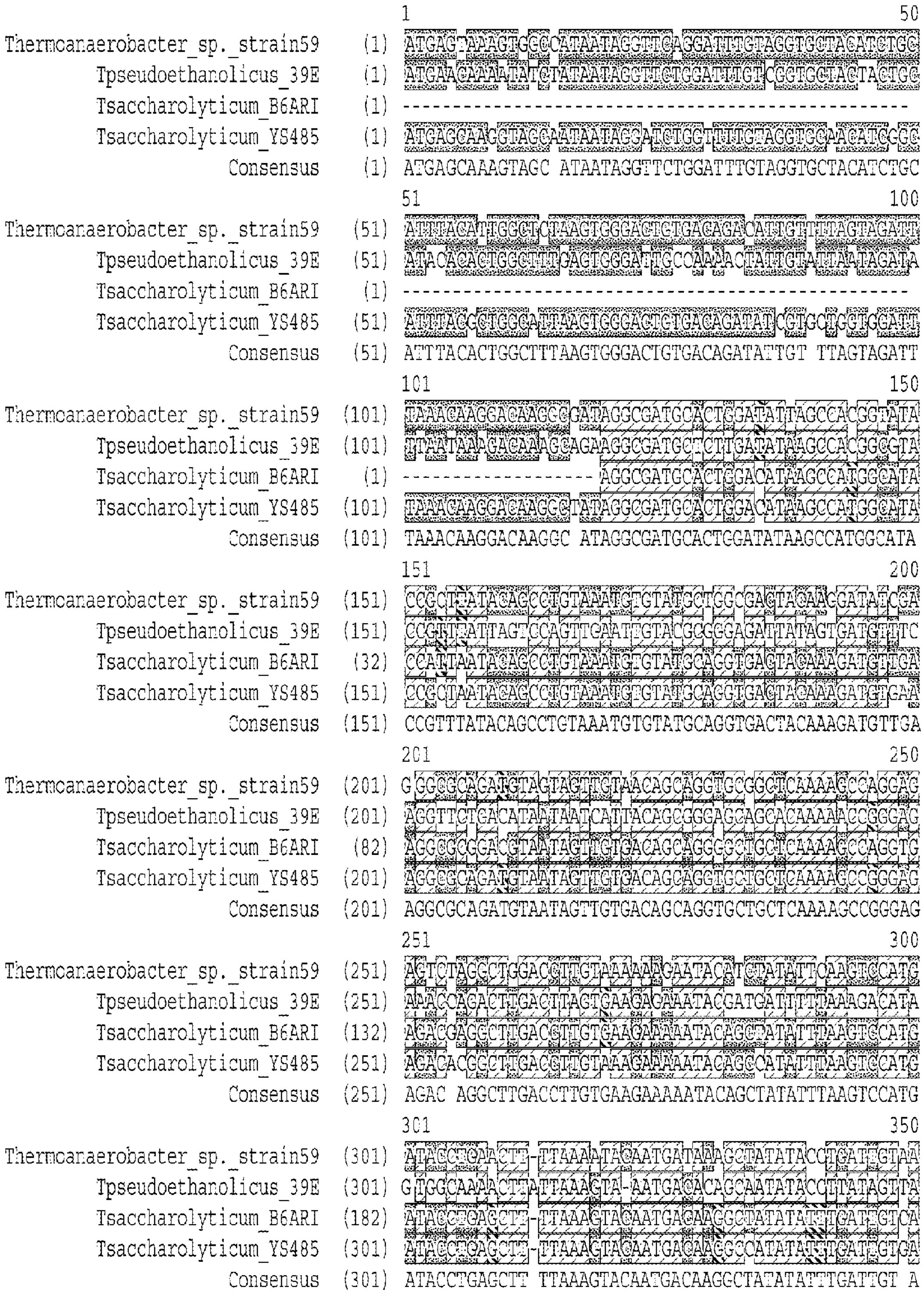

Fig. 33-1

```
                                     351                                          400
Thermoanaerobacter_sp._strain59 (350) CAAATCCTGTTGATATATTAACGTATGTTACATACAAAATAGCGAAACTT
       Tpseudoethanolicus_39E   (350) CAAATCCAGTAGATATTCTTACATACGGTTACCTATAAAATATCTGGCTTG
       Tsaccharolyticum_B6ARI   (231) CAAATCCTGTAGACATAGTGACGTACGTTACATACAAGATATCTGGACTT
       Tsaccharolyticum_YS485   (350) CAAATCCCGTAGATATAGTGACGTACGTTACATACAAGATTTCTGGACTT
                     Consensus  (351) CAAATCCTGTAGATATACTGACGTACGTTACATACAAGATATCTGGACTT
                                     401                                          450
Thermoanaerobacter_sp._strain59 (400) CCGTGGGGCGTGTATTCGGTTCAGGTACTGTCCTTGACAGTTCCCGATT
       Tpseudoethanolicus_39E   (400) CCATACGGAACAGTATTGGGGTCTGGCACAGTTCTCGACAGTGCGAGATT
       Tsaccharolyticum_B6ARI   (281) CCATGGGGCGAGTTTTCGGTTCTGGCACTGTTCTTGACAGTTCAAGGTT
       Tsaccharolyticum_YS485   (400) CCATGGGGCAGAGTTTTGGTTCTGGGACCGTTCTTGACAGCTCAAGGTT
                     Consensus  (401) CCATGGGGCAGAGTTTTCGGTTCTGGCACTGTTCTTGACAGTTCAAGGTT
                                     451                                          500
Thermoanaerobacter_sp._strain59 (450) TAGGTATCTTTTAAGTAAACATTGCAATATTGAT-CCTAGAAATGTACAT
       Tpseudoethanolicus_39E   (450) CAGATATCTTTTAAGCAAACATTGTAACATAGAT-CCGAGGAATATACAG
       Tsaccharolyticum_B6ARI   (331) TAGGTACCTTTTAAGCAGGCACTGCAATATAGATTCCAAGAAATGTCCAG
       Tsaccharolyticum_YS485   (450) TAGATACCTTTTAAGCAAGCACTGCAATATAGAT-CCGAGAAATGTCCAG
                     Consensus  (451) TAGGTATCTTTTAAGCAAGCATTGCAATATAGAT CCGAGAAATGTCCAC
                                     501                                          550
Thermoanaerobacter_sp._strain59 (499) GGAAGGATAATTGGAGAACACGGCGATACAGAATTTGCGGCGTGGAGCAT
       Tpseudoethanolicus_39E   (499) GGATATATAATTGGGGAGCATGGCGATTCTGAGCTTGCAGCTTGGAGCAT
       Tsaccharolyticum_B6ARI   (381) GGAAGGATAATCGGCGAGCATGGTGACACAGAGTTTGCAGCATGGAGCAT
       Tsaccharolyticum_YS485   (499) GGAAGGATAATCGGCGAGCATGGTGACACAGAGTTTGCAGCATGGAGCAT
                     Consensus  (501) GGAAGGATAATTGGCGAGCATGGTGATACAGAGTTTGCAGCATGGAGCAT
                                     551                                          600
Thermoanaerobacter_sp._strain59 (549) AACAAATATTTCAGGAATATCATTTAATGAGTACTGCAATTTGTGGGAG
       Tpseudoethanolicus_39E   (549) TACGAAGATAGCAGGCATACCAAGTGATAATTACTGCAATTTATGTGGAA
       Tsaccharolyticum_B6ARI   (431) AACAAAGATATCTGGAATATCATTTAATGAGTACTGCAGCATATGCGGGG
       Tsaccharolyticum_YS485   (549) AACAAAGATATCGGGTATATCATTTAATGAGTACTGCAGCATATGCGGGAC
                     Consensus  (551) AACAAACATATCAGGAATATCATTTAATGAGTACTGCAGTTTATGCGGAC
                                     601                                          650
Thermoanaerobacter_sp._strain59 (599) GAGTTTGTAATAGAAATTTCAGAAAGGAAGTGGAAGATGAAGTTGTCAAT
       Tpseudoethanolicus_39E   (599) AAGCATGTGAAAAGATTTTAGAGAGGAGATTTTAATAATGTTGTAAGA
       Tsaccharolyticum_B6ARI   (481) GGATCTGCAACACAAATTTCAGAAAGGAAGTAGAAGAACAAGTCGTAAAT
       Tsaccharolyticum_YS485   (599) GGCTCTGCAACACAAATTTCAGAAAGGAAGTAGAAGAACAAGTCGTAAAT
                     Consensus  (601) GCGTCTGTAACACAAATTTCAGAAAGGAAGTAGAAGATGAAGTTGTAAAT
                                     651                                          700
Thermoanaerobacter_sp._strain59 (649) GCCGCTTACAAAATTATTGATAAAAAGGGTGCCACGTATTACGCTGTGGC
       Tpseudoethanolicus_39E   (649) GCTGCCTATACGATAATAGAAAAAAGGGTGCCACATATTATGCGGTTGC
       Tsaccharolyticum_B6ARI   (531) GCTGCTTATAAGATAATAGACAAAAAAGGTGCTACATACTATGCTGTCGC
       Tsaccharolyticum_YS485   (649) GCTGCTTACAAGATAATAGACAAAAAAGGTGCTACATACTATGCTGTGGC
                     Consensus  (651) GCTGCTTATAAGATAATAGACAAAAAGGGTGCTACATATTATGCTGTGGC
```

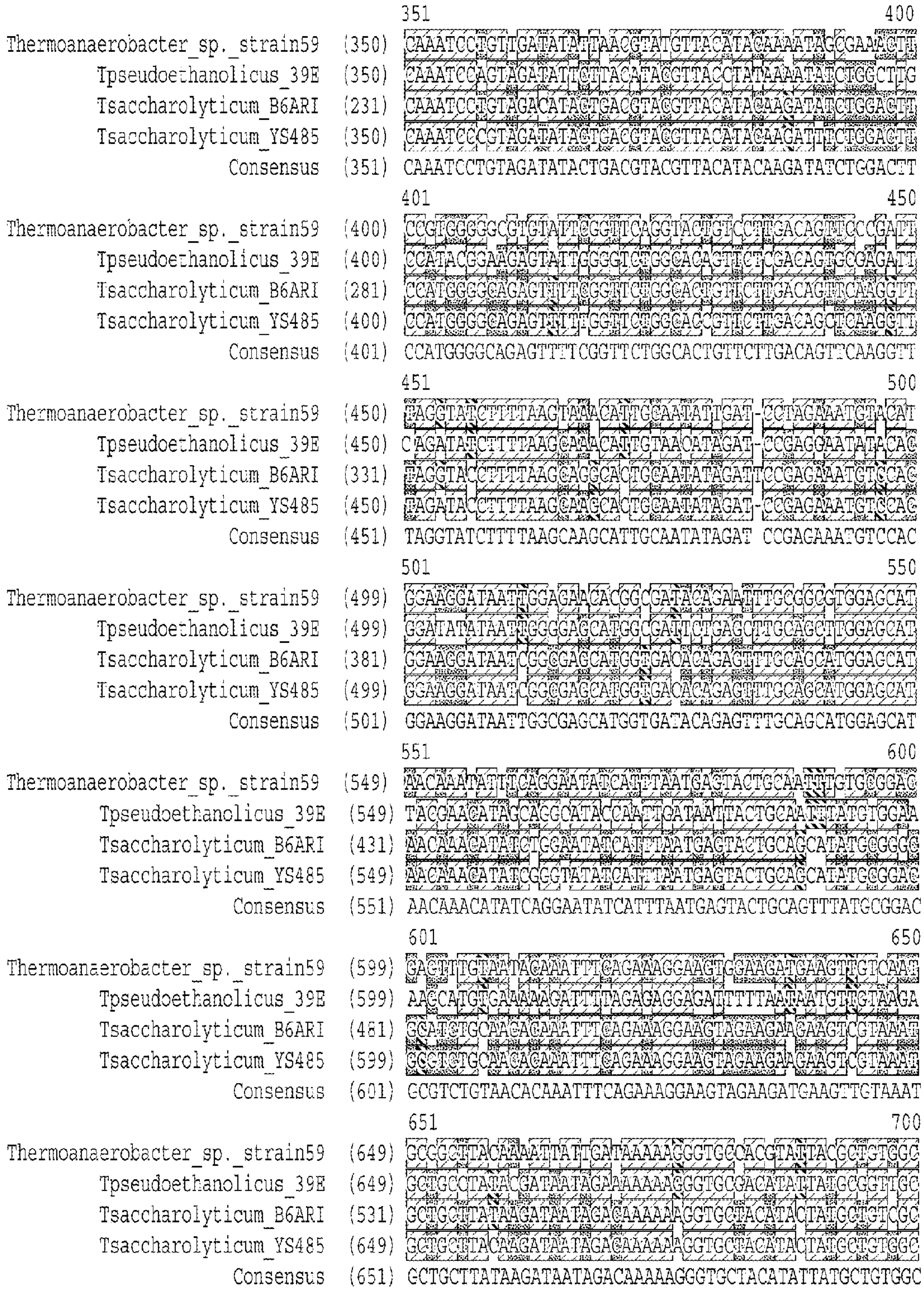

Fig. 33-2

```
                                         701                                               750
Thermoanaerobacter_sp._strain59   (699)  TGTAGCAGTAAGAAGAATAGTTGAGTGTATCATAAGGGATGAAAATTCAA
     Tpseudoethanolicus_39E       (699)  TCTCGCAGTAAGAAGAATCGTAGAAGCTATTTTCAGAGATGAAAATTCCA
     Tsaccharolyticum_B6ARI       (581)  AGTTGCAGTAAGAAGGATTGTGGAGTGCATCTTAAGAGATGAAAATTCCA
     Tsaccharolyticum_YS485       (699)  AGTTGCAGTAAGAACGATTGTGGAGTGCATCTTAAGAGATGAAAATTCCA
                  Consensus       (701)  TGTTGCAGTAAGAAGGATTGTGGAGTGTATCTTAAGAGATGAAAATTCCA
                                         751                                               800
Thermoanaerobacter_sp._strain59   (749)  TTCTTACAGTTTCATCTCCATTAAATGGTCAATACGGTGTAACAGATGTA
     Tpseudoethanolicus_39E       (749)  TTTTGACTGTGTCATCTCCGCTAACCGGCCAATATGGTGTTACAAATGTG
     Tsaccharolyticum_B6ARI       (631)  T-------------------------------------------------
     Tsaccharolyticum_YS485       (749)  TCCTCACAGTATCATCTCCATTAAATGGACAGTACGGCGTGAAAGATGTT
                  Consensus       (751)  TTCT ACAGT TCATCTCCATTAAATGG CAATACGGTGT A AGATGT
                                         801                                               850
Thermoanaerobacter_sp._strain59   (799)  TCTTTAAGCTTGCCATCAATTGTGGCCAAAAATGGTGTTGCAAGGGTTCT
     Tpseudoethanolicus_39E       (799)  CCTTTGAGCCTTCCCTCCGTTGTTGCACGAAATGGAATCGTAAATATACT
     Tsaccharolyticum_B6ARI       (632)  --------------------------------------------------
     Tsaccharolyticum_YS485       (799)  TCATTAAGCTTGCCATCTATCGTAGCCAGCAATGGCGTTGCCAGGATTTT
                  Consensus       (801)  TCTTTAAGCTTGCCATC ATTGT GGCAGAAATGG GTTGCAAGGATTCT
                                         851                                               900
Thermoanaerobacter_sp._strain59   (849)  GCATTTGCCTTTGGCTGATCACGAACTTGAGAACTTTAAACATTCGGCAA
     Tpseudoethanolicus_39E       (849)  TGAATTACCACTTTCACACGAAGAAATTGCTGCTTTTAGAAGATCAGCCG
     Tsaccharolyticum_B6ARI       (632)  --------------------------------------------------
     Tsaccharolyticum_YS485       (849)  GGACTTGCCTTTATCTGACGAAGAACTGGAGAAGTTTAGGCATTCAGCAA
                  Consensus       (851)  GGA TTGCCTTT TCTGA GAAGAAGTTGAGAAGTTTAGACATTCAGCAA
                                         901                                 938
Thermoanaerobacter_sp._strain59   (899)  GCGTTATGGCTGATGTTATAAAACACTTGGACATA---
     Tpseudoethanolicus_39E       (899)  AAGTTATCAAAAGTGTAATACAAGAGCTTGATATATAA
     Tsaccharolyticum_B6ARI       (632)  --------------------------------------
     Tsaccharolyticum_YS485       (899)  GTGTCATGGCAGATGTCATAAAACAATTAGATATA---
                  Consensus       (901)  G GTTATGGCAGATGT ATAAAACAGTT GATATA
```

Fig. 33-3

SEQUENCE LISTING

```
<160> NUMBER OF SEQ ID NOS: 92

<210> SEQ ID NO 1
<211> LENGTH: 9000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

agctttggct aacacacacg ccattccaac caatagtttt ctcggcataa agccatgctc     60

tgacgcttaa atgcactaat gccttaaaaa aacattaaag tctaacacac tagacttatt    120

tacttcgtaa ttaagtcgtt aaaccgtgtg ctctacgacc aaaagtataa aacctttaag    180

aactttcttt tttcttgtaa aaaaagaaac tagataaatc tctcatatct tttattcaat    240

aatcgcatca gattgcagta taaatttaac gatcactcat catgttcata tttatcagag    300

ctcgtgctat aattatacta attttataag gaggaaaaaa taaagagggt tataatgaac    360

gagaaaaata taaaacacag tcaaaacttt attacttcaa aacataatat agataaaata    420

atgacaaata taagattaaa tgaacatgat aatatctttg aaatcggctc aggaaaaggg    480

cattttaccc ttgaattagt acagaggtgt aatttcgtaa ctgccattga aatagaccat    540

aaattatgca aaactacaga aaataaactt gttgatcacg ataatttcca agttttaaac    600

aaggatatat tgcagtttaa atttcctaaa aaccaatcct ataaaatatt tggtaatata    660

ccttataaca taagtacgga tataatacgc aaaattgttt ttgatagtat agctgatgag    720

atttatttaa tcgtggaata cgggtttgct aaaagattat taaatacaaa acgctcattg    780

gcattatttt taatggcaga agttgatatt tctatattaa gtatggttcc aagagaatat    840

tttcatccta aacctaaagt gaatagctca cttatcagat taaatagaaa aaaatcaaga    900

atatcacaca aagataaaca gaagtataat tatttcgtta tgaaatgggt taacaaagaa    960

tacaagaaaa tatttacaaa aaatcaattt aacaattcct taaaacatgc aggaattgac   1020

gatttaaaca atattagctt tgaacaattc ttatctcttt tcaatagcta taaattattt   1080

aataagtaag ttaagggatg cataaactgc atcccttaac ttgtttttcg tgtacctatt   1140

ttttgtgaat cgattatgtc ttttgcgcat tcacttcttt tctatataaa tatgagcgaa   1200

gcgaataagc gtcggaaaag cagcaaaaag tttccttttt gctgttggag catgggggtt   1260

caggggggtgc agtatctgac gtcaatgccg agcgaaagcg agccgaaggg tagcatttac   1320

gttagataac cccctgatat gctccgacgc tttatataga aaagaagatt caactaggta   1380

aaatcttaat ataggttgag atgataaggt ttataaggaa tttgtttgtt ctaatttttc   1440

actcattttg ttctaatttc ttttaacaaa tgttcttttt tttttagaac agttatgata   1500
```

-continued

```
tagttagaat agtttaaaat aaggagtgag aaaaagatga aagaaagata tggaacagtc   1560
tataaaggct ctcagaggct catagacgaa gaaagtggag aagtcataga ggtagacaag   1620
ttataccgta aacaaacgtc tggtaacttc gtaaaggcat atatagtgca attaataagt   1680
atgttagata tgattggcgg aaaaaaactt aaaatcgtta actatatcct agataatgtc   1740
cacttaagta acaatacaat gatagctaca acaagagaaa tagcaaaagc tacaggaaca   1800
agtctacaaa cagtaataac aacacttaaa atcttagaag aaggaaatat tataaaaaga   1860
aaaactggag tattaatgtt aaaccctgaa ctactaatga gaggcgacga ccaaaaacaa   1920
aaatacctct tactcgaatt tgggaacttt gagcaagagg caaatgaaat agattgacct   1980
cccaataaca ccacgtagtt attgggaggt caatctatga aatgcgatta agcttggctg   2040
caggtcgata aacccagcga accatttgag gtgataggta agattatacc gaggtatgaa   2100
aacgagaatt ggacctttac agaattactc tatgaagcgc catatttaaa aagctaccaa   2160
gacgaagagg atgaagagga tgaggaggca gattgccttg aatatattga caatactgat   2220
aagataatat atcttttata tagaagatat cgccgtatgt aaggatttca gggggcaagg   2280
cataggcagc gcgcttatca atatatctat agaatgggca aagcataaaa acttgcatgg   2340
actaatgctt gaaacccagg acaataacct tatagcttgt aaattctatc ataattgtgg   2400
tttcaaaatc ggctccgtcg atactatgtt atacgccaac tttcaaaaca actttgaaaa   2460
agctgttttc tggtatttaa ggttttagaa tgcaaggaac agtgaattgg agttcgtctt   2520
gttataatta gcttcttggg gtatctttaa atactgtaga aaagaggaag gaaataataa   2580
atggctaaaa tgagaatatc accggaattg aaaaaactga tcgaaaaata ccgctgcgta   2640
aaagatacgg aaggaatgtc tcctgctaag gtatataagc tggtgggaga aaatgaaaac   2700
ctatatttaa aaatgacgga cagccggtat aaagggacca cctatgatgt ggaacgggaa   2760
aaggacatga tgctatggct ggaaggaaag ctgcctgttc caaaggtcct gcactttgaa   2820
cggcatgatg gctggagcaa tctgctcatg agtgaggccg atggcgtcct ttgctcggaa   2880
gagtatgaag atgaacaaag ccctgaaaag attatcgagc tgtatgcgga gtgcatcagg   2940
ctctttcact ccatcgacat atcggattgt ccctatacga atagcttaga cagccgctta   3000
gccgaattgg attacttact gaataacgat ctggccgatg tggattgcga aaactgggaa   3060
gaagacactc catttaaaga tccgcgcgag ctgtatgatt ttttaaagac ggaaaagccc   3120
gaagaggaac ttgtcttttc ccacggcgac ctgggagaca gcaacatctt tgtgaaagat   3180
ggcaaagtaa gtggctttat tgatcttggg agaagcggca gggcggacaa gtggtatgac   3240
attgccttct gcgtccggtc gatcagggag gatatcgggg aagaacagta tgtcgagcta   3300
ttttttgact tactggggat caagcctgat tgggagaaaa taaaatatta tattttactg   3360
gatgaattgt tttagtacct agatttagat gtctaaaaag ctttttagac atctaatctt   3420
ttctgaagta catccgcaac tgtccatact ctgatgtttt atatcttttc taaaagttcg   3480
ctagataggg gtcccgagcg cctacgagga atttgtatcg actctagagg atccctcagc   3540
gaagctccac tatgtttcaa aatgtcagat atatcaattt tcatcaaagt cacctcttaa   3600
aaccgacaag gactattata ctaactaata accctcatgt caagaattat atgacagatt   3660
ggcttaaata acaaaaataa ttttgtttag ttaaattcgg aatttcttct taatattatt   3720
aacatattcc acatattaat acaagaaaaa acccggcaaa aaaataaaaa aattttataa   3780
gcccgtttcc taaaaaaaca ggcttgtaaa attataacgc atcttttata agtttttac    3840
aagtcttaaa gtctcccttg caatctcaag ctcctcattt gtcgggataa ccaaagtctt   3900
```

-continued

```
tactttcgca tcgggagcac tgatatccgc ttctttgcct ttcacttcat ttttatccaa   3960
atctatttta attccgaaaa agtccatatc cttcaaaact tctcttctta tataagcatt   4020
gttttcgccg atacctgcag tgaataccac cgcatcaacg ccgttcagca ctgcaatata   4080
ttttccaata tatttcctaa caccatagca gaaaatatcc aatgccagct gcgccctgtc   4140
atctcccttt tctgcggcat cctgaacatc tctgaaatca ctgcttacac ctgaaattcc   4200
aagcacacct gatttcttgt taaggaaatt gtttatatcg ttaatattca tttttccctt   4260
ttccatcaaa taagttataa ccgcagggtc aacattgccg cttctggtac ccatgcacaa   4320
cccctgcaga ggagtaaatc ccattgaggt gtcaacggat tttccgcctt ttaccgcaca   4380
aatacttgct ccgtttccaa gatggcaggt tatcagcttc aggctctcaa taggtttgcc   4440
cagcatctga gccgccctgt gggccacata tttgtgggaa gttccgtgga atccgtattt   4500
tctcaattta tacttctcat atatctcata agggagggca taaatatatg catgctagtt   4560
caacaaacgg gattgacttt taaaaaagga ttgattctaa tgaagaaagc agacaagtaa   4620
gcctcctaaa ttcactttag ataaaaattt aggaggcata tcaaatgaac tttaataaaa   4680
ttgatttaga caattggaag agaaaagaga tatttaatca ttatttgaac caacaaacga   4740
cttttagtat aaccacagaa attgatatta gtgttttata ccgaaacata aaacaagaag   4800
gatataaatt ttaccctgca tttattttct tagtgacaag ggtgataaac tcaaatacag   4860
cttttagaac tggttacaat agcgacggag agttaggtta ttgggataag ttagagccac   4920
tttatacaat tttgatggt gtatctaaaa cattctctgg tatttggact cctgtaaaga   4980
atgacttcaa agagttttat gatttatacc tttctgatgt agagaaatat aatggttcgg   5040
ggaaattgtt tcccaaaaca cctatacctg aaaatgcttt ttctctttct attattccat   5100
ggacttcatt tactgggttt aacttaaata tcaataataa tagtaattac cttctaccca   5160
ttattacagc aggaaaattc attaataaag gtaattcaat atatttaccg ctatctttac   5220
aggtacatca ttctgtttgt gatggttatc atgcaggatt gtttatgaac tctattcagg   5280
aattgtcaga taggcctaat gactggcttt tataacctga ggttttgctc caaccagcat   5340
ctcaaaagat ttggatgcag atattgcaat ttcagaaagc tggtctgcat ccggattttc   5400
caccaagccg caatcggcat atacaaaggt tccgttatga ccatattcac agttgggtac   5460
aaccataaca aaaaaggatg atacgagttt tgtccccggg gccgtcttta atatctgcaa   5520
agccggtctc aaagtatttg cagtggaatt gacagcaccc gccaccatac catccgcttc   5580
accttttttt accatcataa ctccataata aagagggtct ttgatcgttt cccttgcggc   5640
ttctatagtc ataccttcg attttctaag ctcatacagt gtatttgcat aatcctccaa   5700
tttttcggaa tttaaggaat cctctatcat cactccttca agatcaatat cccccgccag   5760
actcttaatc tccttttcat tgcctatcag tacaaccttt gcaattccct ttttcattat   5820
catggatgcg gctttaataa ccctcagatc cgtactttcc ggcaaaacta tggtttttac   5880
gtctgatttc gccctttcaa ttatttgttc caaaaaactc ataaattctt ctcctttcat   5940
aatcccaaaa ctgttatcat aaaaactgta tttgtaatac ttataactat atattatcac   6000
caggtaataa tacctactca ctataaacag ctattttact gggttccaag caactctaat   6060
tatatacaaa atgtttttg tatacaacac cctccttatc ttttttcgg ctttagccat   6120
aaataacggc aagtaactcc aaaatacagg atatttcatg cttttagaaa ctttttatta   6180
gtcttcttaa ttattcagat tttgtggcaa ttaaactttg cagctcctcc aaatagttgt   6240
ccagctcctc ttctttaaga ttgctgagat atgacaatct gtaattttta gcctttttgg   6300
```

-continued

```
ccatctctag cgcactctcc gtcattccca aatctttcaa aacacagcta tagttatagt   6360

atgcgaattc actggccgtc gttttacaac gtcgtgactg ggaaaaccct ggcgttaccc   6420

aacttaatcg ccttgcagca catccccctt tcgccagctg gcgtaatagc gaagaggccc   6480

gcaccgatcg cccttcccaa cagttgcgca gcctgaatgg cgaatggcgc ctgatgcggt   6540

attttctcct tacgcatctg tgcggtattt cacaccgcat atggtgcact ctcagtacaa   6600

tctgctctga tgccgcatag ttaagccagc cccgacaccc gccaacaccc gctgacgcgc   6660

cctgacgggc ttgtctgctc ccggcatccg cttacagaca agctgtgacc gtctccggga   6720

gctgcatgtg tcagaggttt tcaccgtcat caccgaaacg cgcgagacga aagggcctcg   6780

tgatacgcct atttttatag gttaatgtca tgataataat ggtttcttag acgtcaggtg   6840

gcacttttcg gggaaatgtg cgcggaaccc ctatttgttt atttttctaa atacattcaa   6900

atatgtatcc gctcatgaga caataaccct gataaatgct tcaataatat tgaaaaagga   6960

agagtatgag tattcaacat ttccgtgtcg cccttattcc cttttttgcg gcattttgcc   7020

ttcctgtttt tgctcaccca gaaacgctgg tgaaagtaaa agatgctgaa gatcagttgg   7080

gtgcacgagt gggttacatc gaactggatc tcaacagcgg taagatcctt gagagttttc   7140

gccccgaaga acgttttcca atgatgagca cttttaaagt tctgctatgt ggcgcggtat   7200

tatcccgtat tgacgccggg caagagcaac tcggtcgccg catacactat tctcagaatg   7260

acttggttga gtactcacca gtcacagaaa agcatcttac ggatggcatg acagtaagag   7320

aattatgcag tgctgccata accatgagtg ataacactgc ggccaactta cttctgacaa   7380

cgatcggagg accgaaggag ctaaccgctt ttttgcacaa catgggggat catgtaactc   7440

gccttgatcg ttgggaaccg gagctgaatg aagccatacc aaacgacgag cgtgacacca   7500

cgatgcctgt agcaatggca acaacgttgc gcaaactatt aactggcgaa ctacttactc   7560

tagcttcccg gcaacaatta atagactgga tggaggcgga taaagttgca ggaccacttc   7620

tgcgctcggc ccttccggct ggctggttta ttgctgataa atctggagcc ggtgagcgtg   7680

ggtctcgcgg tatcattgca gcactggggc cagatggtaa gccctcccgt atcgtagtta   7740

tctacacgac ggggagtcag gcaactatgg atgaacgaaa tagacagatc gctgagatag   7800

gtgcctcact gattaagcat tggtaactgt cagaccaagt ttactcatat atactttaga   7860

ttgatttaaa acttcatttt taatttaaaa ggatctaggt gaagatcctt tttgataatc   7920

tcatgaccaa aatcccttaa cgtgagtttt cgttccactg agcgtcagac cccgtagaaa   7980

agatcaaagg atcttcttga gatccttttt ttctgcgcgt aatctgctgc ttgcaaacaa   8040

aaaaaccacc gctaccagcg gtggtttgtt tgccggatca agagctacca actctttttc   8100

cgaaggtaac tggcttcagc agagcgcaga taccaaatac tgtccttcta gtgtagccgt   8160

agttaggcca ccacttcaag aactctgtag caccgcctac atacctcgct ctgctaatcc   8220

tgttaccagt ggctgctgcc agtggcgata agtcgtgtct taccgggttg gactcaagac   8280

gatagttacc ggataaggcg cagcggtcgg gctgaacggg gggttcgtgc acacagccca   8340

gcttggagcg aacgacctac accgaactga gatacctaca gcgtgagcta tgagaaagcg   8400

ccacgcttcc cgaagggaga aaggcggaca ggtatccggt aagcggcagg gtcggaacag   8460

gagagcgcac gagggagctt ccagggggaa acgcctggta tctttatagt cctgtcgggt   8520

ttcgccacct ctgacttgag cgtcgatttt tgtgatgctc gtcagggggg cggagcctat   8580

ggaaaaacgc cagcaacgcg gcctttttac ggttcctggc cttttgctgg ccttttgctc   8640

acatgttctt tcctgcgtta tcccctgatt ctgtggataa ccgtattacc gcctttgagt   8700
```

gagctgatac cgctcgccgc agccgaacga ccgagcgcag cgagtcagtg agcgaggaag 8760
cggaagagcg cccaatacgc aaaccgcctc tccccgcgcg ttggccgatt cattaatgca 8820
gctggcacga caggtttccc gactggaaag cgggcagtga gcgcaacgca attaatgtga 8880
gttagctcac tcattaggca ccccaggctt tacactttat gcttccggct cgtatgttgt 8940
gtggaattgt gagcggataa caatttcaca caggaaacag ctatgaccat gattacgcca 9000

<210> SEQ ID NO 2
<211> LENGTH: 7582
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
aattctgttc tggctttaga ccatttacgc tttgggtttg ccatgcatca cacctcctcg 60
tcaccataca acaaaccttg tgtataaata aaatcttgta cacatggaag gtactcgatt 120
ttgtttttac ttaaaacaaa gctacactaa ttgtctgtaa aaaagttttt gaaaacttcc 180
agccgcggat ctatatcctc atttacgcat ttgcactcat cgttgttaag atccgctcca 240
cacttcgggc aatatccctt gcaggcctcg tcacaaacct gctttgccgg aagattcagt 300
atgatattgt ctatcattac cttttccagc tcgaggaact taccatggta cgtataaatat 360 tcctcgtcgg ttttgttact gccctcttct acaaagtttt cctttacatc aatatgcatc 420
tttgattcaa tatccttgag gcaccttgag cattttgccc tgtaatccgc ccagagttca 480
ccgtcaagtt ttataatccc tccggcattt accaaagtgc ccttaaaagt taccggtttc 540
gcaaagtcaa aatcctcagc tataaaatca ttaattttaa ttgactcact aaagtccagt 600
ctcagcgaag ctccactatg tttcaaaatg tcagatatat caattttcat caaagtcacc 660
tcttaaaacc gacaaggact attatactaa ctaataaccc tcatgtcaag aattatatga 720
cagattggct taaataacaa aaataatttt gtttagttaa attcggaatt tcttcttaat 780
attattaaca tattccacat attaatacaa gaaaaaaccc ggcaaaaaaa taaaaaaatt 840
ttataagccc gtttcctaaa aaaacaggct tgtaaaatta taacgcatct tttataagtt 900
ttttacaagt cttaaagtct cccttgcaat ctcaagctcc tcatttgtcg ggataaccaa 960
agtctttact ttcgcatcgg gagcactgat atccgcttct ttgcctttca cttcattttt 1020
atccaaatct attttaattc cgaaaaagtc catatccttc aaaacttctc ttcttatata 1080
agcattgttt tcgccgatac ctgcagtgaa taccaccgca tcaacgccgt tcagcactgc 1140
aatatatttt ccaatatatt tcctaacacc atagcagaaa atatccaatg ccagctgctg 1200
cagtaatcgc atcagattgc agtataaatt taacgatcac tcatcatgtt catatttatc 1260
agagctcgtg ctataattat actaatttta taaggaggaa aaaataaaga gggttataat 1320
gaacgagaaa aatataaaac acagtcaaaa ctttattact tcaaaacata atatagataa 1380
aataatgaca aatataagat taaatgaaca tgataatatc tttgaaatcg gctcaggaaa 1440
agggcatttt acccttgaat tagtacagag gtgtaatttc gtaactgcca ttgaaataga 1500
ccataaatta tgcaaaacta cagaaaataa acttgttgat cacgataatt tccaagtttt 1560
aaacaaggat atattgcagt ttaaatttcc taaaaaccaa tcctataaaa tatttggtaa 1620
tataccttat aacataagta cggatataat acgcaaaatt gtttttgata gtatagctga 1680
tgagatttat ttaatcgtgg aatacgggtt tgctaaaaga ttattaaata caaaacgctc 1740
attggcatta tttttaatgg cagaagttga tatttctata ttaagtatgg ttccaagaga 1800

```
atattttcat cctaaaccta aagtgaatag ctcacttatc agattaaata gaaaaaaatc   1860
aagaatatca cacaaagata aacagaagta taattatttc gttatgaaat gggttaacaa   1920
agaatacaag aaaatattta caaaaaatca atttaacaat tccttaaaac atgcaggaat   1980
tgacgattta aacaatatta gctttgaaca attcttatct cttttcaata gctataaatt   2040
atttaataag taagttaagg gatgcataaa ctgcatccct tacagctgat actttagtga   2100
tgagcttccg gtattaataa ccaaaatatt catttcaaaa actcactccc gtcttgtttt   2160
ttttaatttt cctattccta aacttcgata aacagatgtt tttattaaac gctgcgcaac   2220
accttcttca atgtccggtt ttaacagaat ttatgccttg acatattgag cctgaaccgc   2280
agtaattgcc gcaaccccga ctatatcctc ggcactgcag cctcgtgaca gatcatttac   2340
cggtcttgcc aaaccttgtg ttatcgggcc gtaagcttca gcttttgcca atctctgtgt   2400
aagcttgtat gcaatatttc cggcatcaag atccgggaaa ataagaacat tggcctttcc   2460
tgcaacactg cttccctttg ccttcgattt tgccacttcc ggaacaatgg cggcatccac   2520
ctgaagttct ccgtcaattg caaggtgggg agctttttcc tttgcaagct gtgttgcctt   2580
gattaccttt tcggtcagct cacttttggc actgccgtaa gaagaataag aaagcattgc   2640
cacctgaggt tttgctccaa ccagcatctc aaaagatttg gatgcagata ttgcaatttc   2700
agaaagctgg tctgcatccg gattttccac caagccgcaa tcggcatata caaaggttcc   2760
gttatgacca tattcacagt tgggtacaac cataacaaaa aaggatgata cgagttttgt   2820
ccccggggcc gtctttaata tctgcaaagc cggtctcaaa gtatttgcag tggaattgac   2880
agcacccgcc accataccat ccgcttcacc ttttttacc atcataactc cataataaag    2940
agggtctttg atcgtttccc ttgcggcttc tatagtcata cccttcgatt ttctaagctc   3000
atacagtgta tttgcataat cctccaattt ttcggaattt aaggaatcct ctatcatcac   3060
tccttcaaga tcaatatccc ccgccagact cttaatctcc ttttcattgc ctatcagtac   3120
aacctttgca attccctttt tcattatcat ggatgcggct ttaataaccc tcagatccgt   3180
actttccggc aaaactatgg tttttacgtc tgatttcgcc ctttcaatta tttgttccaa   3240
aaaactcata aattcttctc ctttcataat cccaaaactg ttatcataaa aactgtattt   3300
gtaatactta taactatata ttatcaccag gtaataatac ctactcacta taaacagcta   3360
ttttactggg ttccaagcaa ctctaggatc ctctagagtc gacctgcagg catgcaagct   3420
tggcgtaatc atggtcatag ctgtttcctg tgtgaaattg ttatccgctc acaattccac   3480
acaacatacg agccggaagc ataaagtgta aagcctgggg tgcctaatga gtgagctaac   3540
tcacattaat tgcgttgcgc tcactgcccg ctttccagtc gggaaacctg tcgtgccagc   3600
ccttcaaact tcccaaaggc gagccctagt gacattagaa aaccgactgt aaaaagtaca   3660
gtcggcatta tctcatatta taaaagccag tcattaggcc tatctgacaa ttcctgaata   3720
gagttcataa acaatcctgc atgataacca tcacaaacag aatgatgtac ctgtaaagat   3780
agcggtaaat atattgaatt acctttatta atgaattttc ctgctgtaat aatgggtaga   3840
aggtaattac tattattatt gatatttaag ttaaacccag taaatgaagt ccatggaata   3900
atagaaagag aaaaagcatt ttcaggtata ggtgttttgg gaaacaattt ccccgaacca   3960
ttatatttct ctacatcaga aaggtataaa tcataaaact ctttgaagtc attctttaca   4020
ggagtccaaa taccagagaa tgttttagat acaccatcaa aaattgtata aagtggctct   4080
aacttatccc aataacctaa ctctccgtcg ctattgtaac cagttctaaa agctgtattt   4140
gagtttatca cccttgtcac taagaaaata aatgcagggt aaaatttata tccttcttgt   4200
```

-continued

```
tttatgtttc ggtataaaac actaatatca atttctgtgg ttatactaaa agtcgtttgt   4260
tggttcaaat aatgattaaa tatctctttt ctcttccaat tgtctaaatc aattttatta   4320
aagttcattt gatatgcctc ctaaattttt atctaaagtg aatttaggag gcttacttgt   4380
ctgctttctt cattagaatc aatccttttt taaaagtcaa tcccgtttgt tgaactactc   4440
tttaataaaa taatttttcc gttcccaatt ccacattgca ataatagaaa atccatcttc   4500
atcggctttt tcgtcatcat ctgtatgaat caaatcgcct tcttctgtgt catcaaggtt   4560
taattttta tgtatttctt ttaacaaacc accataggag attaaccttt tacggtgtaa   4620
accttcctcc aaatcagaca aacgtttcaa attcttttct tcatcatcgg tcataaaatc   4680
cgtatccttt acaggatatt ttgcagtttc gtcaattgcc gattgtatat ccgatttata   4740
tttatttttc ggtcgaatca tttgaacttt tacatttgga tcatagtcta atttcattgc   4800
ctttttccaa aattgaatcc attgtttttg attcacgtag ttttctgtat tcttaaaata   4860
agttggttcc acacatacca atacatgcat gtgctgatta taagaattat ctttattatt   4920
tattgtcact tccgttgcac gcataaaacc aacaagattt ttattaattt ttttatattg   4980
catcattcgg cgaaatcctt gagccatatc tgacaaactc ttatttaatt cttcgccatc   5040
ataaacattt ttaactgtta atgtgagaaa caaccaacga actgttggct tttgtttaat   5100
aacttcagca acaacctttt gtgactgaat gccatgtttc attgctctcc tccagttgca   5160
cattggacaa agcctggatt tacaaaacca cactcgatac aactttcttt cgcctgtttc   5220
acgattttgt ttatactcta atatttcagc acaatctttt actctttcag ccttttttaaa   5280
ttcaagaata tgcagaagtt caaagtaatc aacattagcg attttctttt ctctccatgg   5340
tctcactttt ccactttttg tcttgtccac taaaaccctt gatttttcat ctgaataaat   5400
gctactatta ggacacataa tattaaaaga aacccccatc tatttagtta tttgtttggt   5460
cacttataac tttaacagat ggggtttttc tgtgcaacca attttaaggg ttttcaatac   5520
tttaaaacac atacatacca acacttcaac gcacctttca gcaactaaaa taaaaatgac   5580
gttatttcta tatgtatcaa gaatagaaag aactcgtttt tcgctacgct caaaacgcaa   5640
aaaaagcact cattcgagtg ctttttctta tcgctccaaa tcatgcgatt ttttcctctt   5700
tgcttttctt tgctcacgaa gttctcgatc acgctgcaaa acatcttgaa gcgaaaaagt   5760
attcttcttt tcttccgatc gctcatgctg acgcacgaaa agccctctag gcgcatagga   5820
acaactccta aatgcatgtg aggggttttc tcgtccatgt gaacagtcgc atacgcaata   5880
ttttgtttcc catactgcat taatgaatcg gccaacgcgc ggggagaggc ggtttgcgta   5940
ttgggcgctc ttccgcttcc tcgctcactg actcgctgcg ctcggtcgtt cggctgcggc   6000
gagcggtatc agctcactca aaggcggtaa tacggttatc cacagaatca ggggataacg   6060
caggaaagaa catgtgagca aaaggccagc aaaaggccag gaaccgtaaa aaggccgcgt   6120
tgctggcgtt tttccatagg ctccgccccc ctgacgagca tcacaaaaat cgacgctcaa   6180
gtcagaggtg gcgaaacccg acaggactat aaagatacca ggcgtttccc cctggaagct   6240
ccctcgtgcg ctctcctgtt ccgaccctgc cgcttaccgg atacctgtcc gcctttctcc   6300
cttcgggaag cgtggcgctt tctcatagct cacgctgtag gtatctcagt tcggtgtagg   6360
tcgttcgctc caagctgggc tgtgtgcacg aaccccccgt tcagcccgac cgctgcgcct   6420
tatccggtaa ctatcgtctt gagtccaacc cggtaagaca cgacttatcg ccactggcag   6480
cagccactgg taacaggatt agcagagcga ggtatgtagg cggtgctaca gagttcttga   6540
agtggtggcc taactacggc tacactagaa gaacagtatt tggtatctgc gctctgctga   6600
```

agccagttac cttcggaaaa agagttggta gctcttgatc cggcaaacaa accaccgctg 6660
gtagcggtgg tttttttgtt tgcaagcagc agattacgcg cagaaaaaaa ggatctcaag 6720
aagatccttt gatcttttct acggggtctg acgctcagtg gaacgaaaac tcacgttaag 6780
ggattttggt catgagatta tcaaaaagga tcttcaccta gatcctttta aattaaaaat 6840
gaagttttaa atcaatctaa agtatatatg agtaaacttg gtctgacagt taccaatgct 6900
taatcagtga ggcacctatc tcagcgatct gtctatttcg ttcatccata gttgcctgac 6960
tccccgtcgt gtagataact acgatacggg agggcttacc atctggcccc agtgctgcaa 7020
tgataccgcg agacccacgc tcaccggctc cagatttatc agcaataaac cagccagccc 7080
gatatgggaa acaaaatatt gcgtatgcga ctgttcacat ggacgagaaa acccctcaca 7140
tgcatttagg agttgttcct atgcgcctag agggcttttc gtgcgtcagc atgagcgatc 7200
ggaagaaaag aagaatactt tttcgcttca agatgttttg cagcgtgatc gagaacttcg 7260
tgagcaaaga aaagcaaaga ggaaaaaatc gcatgatttg gagcgataag aaaaagcact 7320
cgaatgagtg ctttttttgc gttttgagcg tagcgaaaaa cgagttcttt ctattcttga 7380
tacatataga aataacgtca tttttatttt agttgctgaa aggtgcgttg aagtgttggt 7440
atgtatgtga ttcaataatt tcttttactc gctcgttata gtcgatcggt tcatcattca 7500
ccaaatcata attttcatgt gaccgttctt tatcaatatc gggattcgtt ttactttccc 7560
gttctctctg attgtgaaat tg 7582

<210> SEQ ID NO 3
<211> LENGTH: 8927
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
agctttggct aacacacacg ccattccaac caatagtttt ctcggcataa agccatgctc 60
tgacgcttaa atgcactaat gccttaaaaa aacattaaag tctaacacac tagacttatt 120
tacttcgtaa ttaagtcgtt aaaccgtgtg ctctacgacc aaaagtataa aacctttaag 180
aactttcttt tttcttgtaa aaaaagaaac tagataaatc tctcatatct tttattcaat 240
aatcgcatca gattgcagta taaatttaac gatcactcat catgttcata tttatcagag 300
ctcgtgctat aattatacta attttataag gaggaaaaaa taaagagggt tataatgaac 360
gagaaaaata taaaacacag tcaaaacttt attacttcaa aacataatat agataaaata 420
atgacaaata taagattaaa tgaacatgat aatatctttg aaatcggctc aggaaaaggg 480
cattttaccc ttgaattagt acagaggtgt aatttcgtaa ctgccattga aatagaccat 540
aaattatgca aaactacaga aaataaactt gttgatcacg ataatttcca agttttaaac 600
aaggatatat tgcagtttaa atttcctaaa aaccaatcct ataaaatatt tggtaatata 660
ccttataaca taagtacgga tataatacgc aaaattgttt ttgatagtat agctgatgag 720
atttatttaa tcgtggaata cgggtttgct aaaagattat taaatacaaa acgctcattg 780
gcattatttt taatggcaga agttgatatt tctatattaa gtatggttcc aagagaatat 840
tttcatccta aacctaaagt gaatagctca cttatcagat taaatagaaa aaaatcaaga 900
atatcacaca aagataaaca gaagtataat tatttcgtta tgaaatgggt taacaaagaa 960
tacaagaaaa tatttacaaa aaatcaattt aacaattcct taaaacatgc aggaattgac 1020

-continued

```
gatttaaaca atattagctt tgaacaattc ttatctcttt tcaatagcta taaattattt   1080
aataagtaag ttaagggatg cataaactgc atcccttaac ttgtttttcg tgtacctatt   1140
ttttgtgaat cgattatgtc ttttgcgcat tcacttcttt tctatataaa tatgagcgaa   1200
gcgaataagc gtcggaaaag cagcaaaaag tttccttttt gctgttggag catgggggtt   1260
cagggggtgc agtatctgac gtcaatgccg agcgaaagcg agccgaaggg tagcatttac   1320
gttagataac cccctgatat gctccgacgc tttatataga aaagaagatt caactaggta   1380
aaatcttaat ataggttgag atgataaggt ttataaggaa tttgtttgtt ctaatttttc   1440
actcattttg ttctaatttc ttttaacaaa tgttcttttt tttttagaac agttatgata   1500
tagttagaat agtttaaaat aaggagtgag aaaaagatga aagaaagata tggaacagtc   1560
tataaaggct ctcagaggct catagacgaa gaaagtggag aagtcataga ggtagacaag   1620
ttataccgta aacaaacgtc tggtaacttc gtaaaggcat atatagtgca attaataagt   1680
atgttagata tgattggcgg aaaaaaactt aaaatcgtta actatatcct agataatgtc   1740
cacttaagta acaatacaat gatagctaca acaagagaaa tagcaaaagc tacaggaaca   1800
agtctacaaa cagtaataac aacacttaaa atcttagaag aaggaaatat tataaaaaga   1860
aaaactggag tattaatgtt aaaccctgaa ctactaatga gaggcgacga ccaaaaacaa   1920
aaatacctct tactcgaatt tgggaacttt gagcaagagg caaatgaaat agattgacct   1980
cccaataaca ccacgtagtt attgggaggt caatctatga aatgcgatta agcttggctg   2040
caggtcgata aacccagcga accatttgag gtgataggta agattatacc gaggtatgaa   2100
aacgagaatt ggacctttac agaattactc tatgaagcgc catatttaaa aagctaccaa   2160
gacgaagagg atgaagagga tgaggaggca gattgccttg aatatattga caatactgat   2220
aagataatat atcttttata tagaagatat cgccgtatgt aaggatttca gggggcaagg   2280
cataggcagc gcgcttatca atatatctat agaatgggca aagcataaaa acttgcatgg   2340
actaatgctt gaaacccagg acaataacct tatagcttgt aaattctatc ataattgtgg   2400
tttcaaaatc ggctccgtcg atactatgtt atacgccaac tttcaaaaca actttgaaaa   2460
agctgttttc tggtatttaa ggttttagaa tgcaaggaac agtgaattgg agttcgtctt   2520
gttataatta gcttcttggg gtatctttaa atactgtaga aaagaggaag gaaataataa   2580
atggctaaaa tgagaatatc accggaattg aaaaaactga tcgaaaaata ccgctgcgta   2640
aaagatacgg aaggaatgtc tcctgctaag gtatataagc tggtgggaga aaatgaaaac   2700
ctatatttaa aaatgacgga cagccggtat aaagggacca cctatgatgt ggaacgggaa   2760
aaggacatga tgctatggct ggaaggaaag ctgcctgttc caaaggtcct gcactttgaa   2820
cggcatgatg gctggagcaa tctgctcatg agtgaggccg atggcgtcct ttgctcggaa   2880
gagtatgaag atgaacaaag ccctgaaaag attatcgagc tgtatgcgga gtgcatcagg   2940
ctctttcact ccatcgacat atcggattgt ccctatacga atagcttaga cagccgctta   3000
gccgaattgg attacttact gaataacgat ctggccgatg tggattgcga aaactgggaa   3060
gaagacactc catttaaaga tccgcgcgag ctgtatgatt ttttaaagac ggaaaagccc   3120
gaagaggaac ttgtcttttc ccacggcgac ctgggagaca gcaacatctt tgtgaaagat   3180
ggcaaagtaa gtggctttat tgatcttggg agaagcggca gggcggacaa gtggtatgac   3240
attgccttct gcgtccggtc gatcagggag gatatcgggg aagaacagta tgtcgagcta   3300
tttttgact tactggggat caagcctgat tgggagaaaa taaaatatta tattttactg   3360
gatgaattgt tttagtacct agatttagat gtctaaaaag ctttttagac atctaatctt   3420
```

-continued

```
ttctgaagta catccgcaac tgtccatact ctgatgtttt atatcttttc taaaagttcg   3480
ctagataggg gtcccgagag ccccatactc atgagcagtc ttgttacagc tatgccggca   3540
gcacctgaac cgtttacaac aacttctata tcctcgattt tcttgttgac aagctttaat   3600
gcattgatca ttgctgcaac agtaacaacg gctgtaccgt gctggtcatc atggaatatt   3660
ggaatgtcac attcctcttt gagtcttctt tctatttcaa agcatctcgg agcggatata   3720
tcttcgaggt ttataccgcc aaagcttccg gagatgagct tgattgtctt tacaatttca   3780
tctacgtctt ttgatttgat acagagcgga aatgcgtcca catcaccaaa cttcttgaag   3840
agtacgcatt taccttccat aacaggcatt ccggcttcag gtcctatgtc tccgagccct   3900
aaaaccgccg taccgtcggt aataaccgct accaggttcc aacgtcttgt atattcataa   3960
gaaagattaa catctttctg aattgcaaga catggttctg caacacccgg tgtataagca   4020
agcgacaact cttccttggt tgaaacaggt accttgtgta taacctcaat tttacccttc   4080
cactcaccgt gaagccttag tgattctttt ctgtaatcca tttgattcta cctccaaatt   4140
atattattaa atatctgcga tattaatgca caattataaa ttcttaactt cgttcaatac   4200
ttttttaacc tgctccgctg agaatcttaa agcttcttct tcttcaggag tcagattaaa   4260
ttggagaact tcctgaacac cttcggaatt tacgatggat ggaaggctta ttgcaacatc   4320
ttctattcca tacatgccgt ttataacggt tcctacggtt cttattgtat tctgattctt   4380
aaggagtgtt tcaactattg tgttgattga aactgcaata ccatagtatg ttgcaccttt   4440
gttcttgata atggttgcac ccgcagtttt aacatcttca gcgatttttt tcttgtcttc   4500
ttctgtgaaa ttgcatttcg gatcatcgat atattcgttg atatttttac cggcgatatg   4560
tgtgcagctc cacaacggaa gctgtgaatc accgtgttcg cctattatgt agccgtgtac   4620
atagttcaac aaacgggatt gacttttaaa aaaggattga ttctaatgaa gaaagcagac   4680
aagtaagcct cctaaattca ctttagataa aaatttagga ggcatatcaa atgaacttta   4740
ataaaattga tttagacaat tggaagagaa aagagatatt taatcattat ttgaaccaac   4800
aaacgacttt tagtataacc acagaaattg atattagtgt tttataccga aacataaaac   4860
aagaaggata taaattttac cctgcattta ttttcttagt gacaagggtg ataaactcaa   4920
atacagcttt tagaactggt tacaatagcg acggagagtt aggttattgg gataagttag   4980
agccacttta tacaattttt gatggtgtat ctaaaacatt ctctggtatt tggactcctg   5040
taaagaatga cttcaaagag ttttatgatt tatacctttc tgatgtagag aaatataatg   5100
gttcggggaa attgtttccc aaaacaccta tacctgaaaa tgctttttct ctttctatta   5160
ttccatggac ttcatttact gggtttaact taaatatcaa taataatagt aattaccttc   5220
tacccattat tacagcagga aaattcatta ataaaggtaa ttcaatatat ttaccgctat   5280
ctttacaggt acatcattct gtttgtgatg gttatcatgc aggattgttt atgaactcta   5340
ttcaggaatt gtcagatagg cctaatgact ggcttttata atgtacattt attggtaaca   5400
ttgtcttttg ggtttttctt tcttatatcc gttcttgccg ccgcggtttc ggaaaaattt   5460
gaaatattgc ttgtttccct tcttttgttg gtacttttga taccttatat tgcccattat   5520
tacaaactgg agaacggagt tcagaggctt tatgagcttt ataacaaaat tgatgaaaaa   5580
tgtgtaagga aaaacaagac cgcctgagtt ctcacccaga cggtcggtat tggcagtttc   5640
actttcgtta gtcgatgttt ttcatgccgg caaagaaatt attttcttgc aagaaccttt   5700
ttcagttttg caaatcttgg aagaccatct tcgataggag gtcttgattc tccctgaatt   5760
aacggaagag catacttaat aaagtcttct gtaaggcctg ctccgtcagg tttaatccat   5820
```

-continued

```
tccaacggaa ctttcttctc agtatttgca acttcactga ggttcagaag cttgatattg   5880
cacttgtatt caggaccttc cgctctttca aaagcaacca tgtagtctgt tttcccttca   5940
acggcatatt gtacggctgc ctgtcctgca agataagctt catttacgtc ggtaagagaa   6000
gctacgtgag ctgcgcatct ttggagaagg ctgaattcaa tgccgcgaac ctttgcgccg   6060
gtcttctctt taacaatgtt agccagtgtt gaagcaagac cgcccaactg tgcatgtcca   6120
aaggagtctt ttgttttcgc aaggtctgaa ccgtattcgg aaatatattt tccgtttttg   6180
tctttgatac cttcagatac ggctacaata acctttccgt tttctttgta gattcttgtc   6240
acatcttcaa caaatttgtc tatgtcaaag gaaagctcgg gtaccgagct cgaattcact   6300
ggccgtcgtt ttacaacgtc gtgactggga aaaccctggc gttacccaac ttaatcgcct   6360
tgcagcacat ccccctttcg ccagctggcg taatagcgaa gaggcccgca ccgatcgccc   6420
ttcccaacag ttgcgcagcc tgaatggcga atggcgcctg atgcggtatt ttctccttac   6480
gcatctgtgc ggtatttcac accgcatatg gtgcactctc agtacaatct gctctgatgc   6540
cgcatagtta agccagcccc gacacccgcc aacacccgct gacgcgccct gacgggcttg   6600
tctgctcccg gcatccgctt acagacaagc tgtgaccgtc tccgggagct gcatgtgtca   6660
gaggttttca ccgtcatcac cgaaacgcgc gagacgaaag ggcctcgtga tacgcctatt   6720
tttataggtt aatgtcatga taataatggt ttcttagacg tcaggtggca cttttcgggg   6780
aaatgtgcgc ggaaccccta tttgtttatt tttctaaata cattcaaata tgtatccgct   6840
catgagacaa taaccctgat aaatgcttca ataatattga aaaaggaaga gtatgagtat   6900
tcaacatttc cgtgtcgccc ttattccctt ttttgcggca ttttgccttc ctgtttttgc   6960
tcacccagaa acgctggtga aagtaaaaga tgctgaagat cagttgggtg cacgagtggg   7020
ttacatcgaa ctggatctca acagcggtaa gatccttgag agttttcgcc ccgaagaacg   7080
ttttccaatg atgagcactt ttaaagttct gctatgtggc gcggtattat cccgtattga   7140
cgccgggcaa gagcaactcg gtcgccgcat acactattct cagaatgact tggttgagta   7200
ctcaccagtc acagaaaagc atcttacgga tggcatgaca gtaagagaat tatgcagtgc   7260
tgccataacc atgagtgata acactgcggc caacttactt ctgacaacga tcggaggacc   7320
gaaggagcta accgcttttt tgcacaacat gggggatcat gtaactcgcc ttgatcgttg   7380
ggaaccggag ctgaatgaag ccataccaaa cgacgagcgt gacaccacga tgcctgtagc   7440
aatggcaaca acgttgcgca aactattaac tggcgaacta cttactctag cttcccggca   7500
acaattaata gactggatgg aggcggataa agttgcagga ccacttctgc gctcggccct   7560
tccggctggc tggtttattg ctgataaatc tggagccggt gagcgtgggt ctcgcggtat   7620
cattgcagca ctggggccag atggtaagcc ctcccgtatc gtagttatct acacgacggg   7680
gagtcaggca actatggatg aacgaaatag acagatcgct gagataggtg cctcactgat   7740
taagcattgg taactgtcag accaagttta ctcatatata ctttagattg atttaaaact   7800
tcatttttaa tttaaaagga tctaggtgaa gatccttttt gataatctca tgaccaaaat   7860
cccttaacgt gagttttcgt tccactgagc gtcagacccc gtagaaaaga tcaaaggatc   7920
ttcttgagat cctttttttc tgcgcgtaat ctgctgcttg caaacaaaaa aaccaccgct   7980
accagcggtg gtttgtttgc cggatcaaga gctaccaact ctttttccga aggtaactgg   8040
cttcagcaga gcgcagatac caaatactgt ccttctagtg tagccgtagt taggccacca   8100
cttcaagaac tctgtagcac cgcctacata cctcgctctg ctaatcctgt taccagtggc   8160
tgctgccagt ggcgataagt cgtgtcttac cgggttggac tcaagacgat agttaccgga   8220
```

-continued

```
taaggcgcag cggtcgggct gaacgggggg ttcgtgcaca cagcccagct tggagcgaac   8280

gacctacacc gaactgagat acctacagcg tgagctatga gaaagcgcca cgcttcccga   8340

agggagaaag gcggacaggt atccggtaag cggcagggtc ggaacaggag agcgcacgag   8400

ggagcttcca gggggaaacg cctggtatct ttatagtcct gtcgggtttc gccacctctg   8460

acttgagcgt cgatttttgt gatgctcgtc aggggggcgg agcctatgga aaaacgccag   8520

caacgcggcc tttttacggt tcctggcctt ttgctggcct tttgctcaca tgttctttcc   8580

tgcgttatcc cctgattctg tggataaccg tattaccgcc tttgagtgag ctgataccgc   8640

tcgccgcagc cgaacgaccg agcgcagcga gtcagtgagc gaggaagcgg aagagcgccc   8700

aatacgcaaa ccgcctctcc ccgcgcgttg gccgattcat taatgcagct ggcacgacag   8760

gtttcccgac tggaaagcgg gcagtgagcg caacgcaatt aatgtgagtt agctcactca   8820

ttaggcaccc caggctttac actttatgct tccggctcgt atgttgtgtg gaattgtgag   8880

cggataacaa tttcacacag gaaacagcta tgaccatgat tacgcca                 8927
```

```
<210> SEQ ID NO 4
<211> LENGTH: 7114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
```

```
aattcagccc catactcatg agcagtcttg ttacagctat gccggcagca cctgaaccgt     60

ttacaacaac ttctatatcc tcgattttct tgttgacaag ctttaatgca ttgatcattg    120

ctgcaacagt aacaacggct gtaccgtgct ggtcatcatg gaatattgga atgtcacatt    180

cctctttgag tcttctttct atttcaaagc atctcggagc ggatatatct tcgaggttta    240

taccgccaaa gcttccggag atgagcttga ttgtctttac aatttcatct acgtcttttg    300

atttgataca gagcggaaat gcgtccacat caccaaactt cttgaagagt acgcatttac    360

cttccataac aggcattccg gcttcaggtc ctatgtctcc gagccctaaa accgccgtac    420

cgtcggtaat aaccgctacc aggttccaac gtcttgtata ttcataagaa agattaacat    480

ctttctgaat tgcaagacat ggttctgcaa cacccggtgt ataagcaagc gacaactctt    540

ccttggttga aacaggtacc ttgtgtataa cctcaatttt acccttccac tcaccgtgaa    600

gccttagtga ttcttttctg taatccattt gattctacct ccaaattata ttattaaata    660

tctgcgatat taatgcacaa ttataaattc ttaacttcgt tcaatacttt tttaacctgc    720

tccgctgaga atcttaaagc ttcttcttct tcaggagtca gattaaattg gagaacttcc    780

tgaacacctt cggaatttac gatggatgga aggcttattg caacatcttc tattccatac    840

atgccgttta taacggttcc tacggttctt attgtattct gattcttaag gagtgtttca    900

actattgtgt tgattgaaac tgcaatacca tagtatgttg caccctttgtt cttgataatg   960

gttgcacccg cagttttaac atcttcagcg atttttttct tgtcttcttc tgtgaaattg   1020

catttcggat catcgattaa tcgcatcaga ttgcagtata aatttaacga tcactcatca   1080

tgttcatatt tatcagagct cgtgctataa ttatactaat tttataagga ggaaaaaata   1140

aagagggtta taatgaacga gaaaaatata aaacacagtc aaaactttat tacttcaaaa   1200

cataatatag ataaaataat gacaaatata agattaaatg aacatgataa tatctttgaa   1260

atcggctcag gaaaagggca ttttaccctt gaattagtac agaggtgtaa tttcgtaact   1320

gccattgaaa tagaccataa attatgcaaa actacagaaa ataaacttgt tgatcacgat   1380
```

```
aatttccaag ttttaaacaa ggatatattg cagtttaaat ttcctaaaaa ccaatcctat   1440
aaaatatttg gtaatatacc ttataacata agtacggata taatacgcaa aattgttttt   1500
gatagtatag ctgatgagat ttatttaatc gtggaatacg ggtttgctaa aagattatta   1560
aatacaaaac gctcattggc attattttta atggcagaag ttgatatttc tatattaagt   1620
atggttccaa gagaatattt tcatcctaaa cctaaagtga atagctcact tatcagatta   1680
aatagaaaaa aatcaagaat atcacacaaa gataaacaga agtataatta tttcgttatg   1740
aaatgggtta acaaagaata caagaaaata tttacaaaaa atcaatttaa caattcctta   1800
aaacatgcag gaattgacga tttaaacaat attagctttg aacaattctt atctcttttc   1860
aatagctata aattatttaa taagtaagtt aagggatgca taaactgcat cccttaatcg   1920
atgagaacaa gttcatttgc ggtttgccgc aaagccattg tgaaggctgc agacgcacct   1980
acaaaaccag caccaatgat tgcaactttt gacctacttt ttaccatttc cataccattc   2040
ctttcaatta cccagtatat ttaacggtta gttcgtttat aaatttgaga ttaattcttt   2100
aaattttaac tgtgaacccg gttcacaggt attatcatta atttcagtat atgtgtttaa   2160
taaaaattag tgaaaatttg caactgcaag catttaaaat tgtaaacgat aaataaatcc   2220
aggcaacaaa tttcccccat tttaaatagc ccagttaaac acattgataa cattttaaca   2280
ttattttata tctgcgtcca taactgaaaa agggaaatcc attactttat gaaatcaaat   2340
tttgaagtta tcaagaaatt atgacgattt tctccgtggc atgcaagatt tcgcgatatt   2400
tcattcgttt atattaattt tttatgaaaa ctgcggtttg ggctgacaat tgcgatggaa   2460
gtttcaatta gactttttgt caaatattat gtataataat attatctata ataatgtatg   2520
aaaaaattgt cctaagatgg aagacggggg tggtttcata tatggttaaa tatctgaaga   2580
ggcaggaaga gttggtagaa gaagctctct caaaggataa ctgttctgac tgggaaagtt   2640
tgagaaatta tcataagtcc caaattgaat ttttgcagca tgagagactt gtacatttat   2700
tggtaacatt gtcttttggg tttttctttc ttatatccgt tcttgccgcc gcggtttcgg   2760
aaaaatttga aatattgctt gtttcccttc ttttgttggt acttttgata ccttatattg   2820
cccattatta caaactggag aacggagttc agaggcttta tgagctttat aacaaaattg   2880
atgaaaaatg tgtaaggaaa aacaagaccg cctgagtgga tcctctagag tcgacctgca   2940
ggcatgcaag cttggcgtaa tcatggtcat agctgtttcc tgtgtgaaat tgttatccgc   3000
tcacaattcc acacaacata cgagccggaa gcataaagtg taaagcctgg ggtgcctaat   3060
gagtgagcta actcacatta attgcgttgc gctcactgcc cgctttccag tcgggaaacc   3120
tgtcgtgcca gcccttcaaa cttcccaaag gcgagcccta gtgacattag aaaaccgact   3180
gtaaaaagta cagtcggcat tatctcatat tataaaagcc agtcattagg cctatctgac   3240
aattcctgaa tagagttcat aaacaatcct gcatgataac catcacaaac agaatgatgt   3300
acctgtaaag atagcggtaa atatattgaa ttacctttat taatgaattt tcctgctgta   3360
ataatgggta gaaggtaatt actattatta ttgatattta agttaaaccc agtaaatgaa   3420
gtccatggaa taatagaaag agaaaaagca ttttcaggta taggtgtttt gggaaacaat   3480
ttccccgaac cattatattt ctctacatca gaaaggtata aatcataaaa ctctttgaag   3540
tcattcttta caggagtcca aataccagag aatgttttag atacaccatc aaaaattgta   3600
taaagtggct ctaacttatc ccaataacct aactctccgt cgctattgta accagttcta   3660
aaagctgtat ttgagtttat cacccttgtc actaagaaaa taaatgcagg gtaaaattta   3720
tatccttctt gttttatgtt tcggtataaa acactaatat caatttctgt ggttatacta   3780
```

-continued aaagtcgttt gttggttcaa ataatgatta aatatctctt ttctcttcca attgtctaaa 3840
tcaattttat taaagttcat ttgatatgcc tcctaaattt ttatctaaag tgaatttagg 3900
aggcttactt gtctgctttc ttcattagaa tcaatccttt tttaaaagtc aatcccgttt 3960
gttgaactac tctttaataa aataattttt ccgttcccaa ttccacattg caataataga 4020
aaatccatct tcatcggctt tttcgtcatc atctgtatga atcaaatcgc cttcttctgt 4080
gtcatcaagg tttaattttt tatgtatttc ttttaacaaa ccaccatagg agattaacct 4140
tttacggtgt aaaccttcct ccaaatcaga caaacgtttc aaattctttt cttcatcatc 4200
ggtcataaaa tccgtatcct ttacaggata ttttgcagtt tcgtcaattg ccgattgtat 4260
atccgattta tatttatttt tcggtcgaat catttgaact tttacatttg gatcatagtc 4320
taatttcatt gcctttttcc aaaattgaat ccattgtttt tgattcacgt agttttctgt 4380
attcttaaaa taagttggtt ccacacatac caatacatgc atgtgctgat tataagaatt 4440
atctttatta tttattgtca cttccgttgc acgcataaaa ccaacaagat ttttattaat 4500
tttttatat tgcatcattc ggcgaaatcc ttgagccata tctgacaaac tcttatttaa 4560
ttcttcgcca tcataaacat ttttaactgt taatgtgaga aacaaccaac gaactgttgg 4620
cttttgttta ataacttcag caacaacctt ttgtgactga atgccatgtt tcattgctct 4680
cctccagttg cacattggac aaagcctgga tttacaaaac cacactcgat acaactttct 4740
ttcgcctgtt tcacgatttt gtttatactc taatatttca gcacaatctt ttactctttc 4800
agccttttta aattcaagaa tatgcagaag ttcaaagtaa tcaacattag cgattttctt 4860
ttctctccat ggtctcactt ttccactttt tgtcttgtcc actaaaaccc ttgatttttc 4920
atctgaataa atgctactat taggacacat aatattaaaa gaaacccccca tctatttagt 4980
tatttgtttg gtcacttata actttaacag atggggtttt tctgtgcaac caattttaag 5040
ggttttcaat actttaaaac acatacatac caacacttca acgcaccttt cagcaactaa 5100
aataaaaatg acgttatttc tatatgtatc aagaatagaa agaactcgtt tttcgctacg 5160
ctcaaaacgc aaaaaaagca ctcattcgag tgctttttct tatcgctcca aatcatgcga 5220
tttttcctc tttgcttttc tttgctcacg aagttctcga tcacgctgca aaacatcttg 5280
aagcgaaaaa gtattcttct tttcttccga tcgctcatgc tgacgcacga aaagccctct 5340
aggcgcatag gaacaactcc taaatgcatg tgaggggttt tctcgtccat gtgaacagtc 5400
gcatacgcaa tattttgttt cccatactgc attaatgaat cggccaacgc gcggggagag 5460
gcggtttgcg tattgggcgc tcttccgctt cctcgctcac tgactcgctg cgctcggtcg 5520
ttcggctgcg gcgagcggta tcagctcact caaaggcggt aatacggtta tccacagaat 5580
caggggataa cgcaggaaag aacatgtgag caaaaggcca gcaaaaggcc aggaaccgta 5640
aaaaggccgc gttgctggcg tttttccata ggctccgccc ccctgacgag catcacaaaa 5700
atcgacgctc aagtcagagg tggcgaaacc cgacaggact ataaagatac caggcgtttc 5760
cccctggaag ctccctcgtg cgctctcctg ttccgaccct gccgcttacc ggatacctgt 5820
ccgcctttct cccttcggga agcgtggcgc tttctcatag ctcacgctgt aggtatctca 5880
gttcggtgta ggtcgttcgc tccaagctgg gctgtgtgca cgaacccccc gttcagcccg 5940
accgctgcgc cttatccggt aactatcgtc ttgagtccaa cccggtaaga cacgacttat 6000
cgccactggc agcagccact ggtaacagga ttagcagagc gaggtatgta ggcggtgcta 6060
cagagttctt gaagtggtgg cctaactacg gctacactag aagaacagta tttggtatct 6120
gcgctctgct gaagccagtt accttcggaa aaagagttgg tagctcttga tccggcaaac 6180
aaaccaccgc tggtagcggt ggtttttttg tttgcaagca gcagattacg cgcagaaaaa 6240
aaggatctca agaagatcct ttgatctttt ctacggggtc tgacgctcag tggaacgaaa 6300
actcacgtta agggattttg gtcatgagat tatcaaaaag gatcttcacc tagatccttt 6360
taaattaaaa atgaagtttt aaatcaatct aaagtatata tgagtaaact tggtctgaca 6420
gttaccaatg cttaatcagt gaggcaccta tctcagcgat ctgtctattt cgttcatcca 6480
tagttgcctg actccccgtc gtgtagataa ctacgatacg ggagggctta ccatctggcc 6540
ccagtgctgc aatgataccg cgagacccac gctcaccggc tccagattta tcagcaataa 6600
accagccagc ccgatatggg aaacaaaata ttgcgtatgc gactgttcac atggacgaga 6660
aaacccctca catgcattta ggagttgttc ctatgcgcct agagggcttt tcgtgcgtca 6720
gcatgagcga tcggaagaaa agaagaatac tttttcgctt caagatgttt tgcagcgtga 6780
tcgagaactt cgtgagcaaa gaaaagcaaa gaggaaaaaa tcgcatgatt tggagcgata 6840
agaaaaagca ctcgaatgag tgcttttttt gcgttttgag cgtagcgaaa aacgagttct 6900
ttctattctt gatacatata gaaataacgt catttttatt ttagttgctg aaaggtgcgt 6960
tgaagtgttg gtatgtatgt gattcaataa tttcttttac tcgctcgtta tagtcgatcg 7020
gttcatcatt caccaaatca taattttcat gtgaccgttc tttatcaata tcgggattcg 7080
ttttactttc ccgttctctc tgattgtgaa attg 7114

<210> SEQ ID NO 5
<211> LENGTH: 3932
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5
gacgaaaggg cctcgtgata cgcctatttt tataggttaa tgtcatgata ataatggttt 60
cttagacgtc aggtggcact tttcggggaa atgtgcgcgg aacccctatt tgtttatttt 120
tctaaataca ttcaaatatg tatccgctca tgagacaata accctgataa atgcttcaat 180
aatattgaaa aaggaagagt atgagtattc aacatttccg tgtcgccctt attccctttt 240
ttgcggcatt ttgccttcct gtttttgctc acccagaaac gctggtgaaa gtaaaagatg 300
ctgaagatca gttgggtgca cgagtgggtt acatcgaact ggatctcaac agcggtaaga 360
tccttgagag ttttcgcccc gaagaacgtt ttccaatgat gagcactttt aaagttctgc 420
tatgtggcgc ggtattatcc cgtattgacg ccgggcaaga gcaactcggt cgccgcatac 480
actattctca gaatgacttg gttgagtact caccagtcac agaaaagcat cttacggatg 540
gcatgacagt aagagaatta tgcagtgctg ccataaccat gagtgataac actgcggcca 600
acttacttct gacaacgatc ggaggaccga aggagctaac cgcttttttg cacaacatgg 660
gggatcatgt aactcgcctt gatcgttggg aaccggagct gaatgaagcc ataccaaacg 720
acgagcgtga caccacgatg cctgtagcaa tggcaacaac gttgcgcaaa ctattaactg 780
gcgaactact tactctagct tcccggcaac aattaataga ctggatggag gcggataaag 840
ttgcaggacc acttctgcgc tcggcccttc cggctggctg gtttattgct gataaatctg 900
gagccggtga gcgtgggtct cgcggtatca ttgcagcact ggggccagat ggtaagccct 960
cccgtatcgt agttatctac acgacgggga gtcaggcaac tatggatgaa cgaaatagac 1020
agatcgctga gataggtgcc tcactgatta agcattggta actgtcagac caagtttact 1080

-continued

```
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt gtagttggtg caggctttgt aggttccacc acagcttata   2280
cattgatgct cagcggactt atatctgaaa ttgtactgat agacataaat gcaaaaaaag   2340
ccgacggaga agtcatggac ttaaatcacg gcatgccttt tgtaaggccc gttgaaattt   2400
atcgtggtga ctacaaagac tgtgccggat ccgacatagt aatcattacc gccggtgcca   2460
accaaaaaga aggcgaaacg agaatagatc ttagttcaac aaacgggatt gacttttaaa   2520
aaaggattga ttctaatgaa gaaagcagac aagtaagcct cctaaattca ctttagataa   2580
aaatttagga ggcatatcaa atgaacttta ataaaattga tttagacaat tggaagagaa   2640
aagagatatt taatcattat ttgaaccaac aaacgacttt tagtataacc acagaaattg   2700
atattagtgt tttataccga aacataaaac aagaaggata taaattttac cctgcattta   2760
ttttcttagt gacaagggtg ataaactcaa atacagcttt tagaactggt tacaatagcg   2820
acggagagtt aggttattgg gataagttag agccacttta tacaattttt gatggtgtat   2880
ctaaaacatt ctctggtatt tggactcctg taaagaatga cttcaaagag ttttatgatt   2940
tatacctttc tgatgtagag aaatataatg gttcggggaa attgtttccc aaaacaccta   3000
tacctgaaaa tgctttttct ctttctatta ttccatggac ttcatttact gggtttaact   3060
taaatatcaa taataatagt aattaccttc tacccattat tacagcagga aaattcatta   3120
ataaaggtaa ttcaatatat ttaccgctat ctttacaggt acatcattct gtttgtgatg   3180
gttatcatgc aggattgttt atgaactcta ttcaggaatt gtcagatagg cctaatgact   3240
ggcttttata atgtacatgc ttatattatt ggcgaacacg gtgacaccga agttgcggcc   3300
tggagtcttg caaatattgc gggaattccc atggatcgct actgtgacga atgccatcag   3360
tgcgaggagc agatttcccg gaataaaata tatgaaagtg ttaaaaaatgc agcttatgaa   3420
atcatcagga acaaaggtgc aacctattat gccgtagccc ttgccgtaag aagaatcgtt   3480
```

gaagccattg tactgcaggt cgactctaga ggatccccgg gtaccgagct cgaattcact 3540
ggccgtcgtt ttacaacgtc gtgactggga aaaccctggc gttacccaac ttaatcgcct 3600
tgcagcacat ccccctttcg ccagctggcg taatagcgaa gaggcccgca ccgatcgccc 3660
ttcccaacag ttgcgcagcc tgaatggcga atggcgcctg atgcggtatt ttctccttac 3720
gcatctgtgc ggtatttcac accgcatatg gtgcactctc agtacaatct gctctgatgc 3780
cgcatagtta agccagcccc gacacccgcc aacacccgct gacgcgccct gacgggcttg 3840
tctgctcccg gcatccgctt acagacaagc tgtgaccgtc tccgggagct gcatgtgtca 3900
gaggttttca ccgtcatcac cgaaacgcgc ga 3932

<210> SEQ ID NO 6
<211> LENGTH: 1320
<212> TYPE: DNA
<213> ORGANISM: Thermoanaerobacterium saccharolyticum

<400> SEQUENCE: 6
atgaataaat attttgagaa cgtatctaaa ataaaatatg aaggaccaaa atcaaataat 60
ccttattcct ttaaatttta caatccagag gaagtaatcg atggcaagac gatggaggag 120
catctccgct tttctatagc ttattggcac acttttactg ctgatggaac agatcaattt 180
ggcaaggcta ctatgcaaag accatggaac cactacacag atcctatgga tatagcgaaa 240
cgaagggtag aagcagcatt tgagtttttt gataagataa atgcaccttt cttctgcttc 300
catgataggg atattgcccc tgaaggagat actcttagag agacaaacaa aaacttagat 360
acaatagttg ctatgataaa ggattactta aagaccagca agacaaaagt tttgtggggt 420
accgcaaatc ttttctccaa tccgagattt gtacatggtg catcaacatc ctgcaatgct 480
gacgtttttg catattctgc agcgcaagtc aaaaaagccc ttgagattac taaggagctt 540
ggccgcgaaa actacgtatt ttggggtgga agagaagggt acgagacgct tctcaataca 600
gatatggagt tagagcttga taactttgca agatttttgc acatggctgt tgactatgca 660
aaggaaatcg gctttgaagg tcagttcttg attgagccga agccaaagga gcctacaaaa 720
catcaatacg actttgacgt ggcaaatgta ttggcattct tgagaaaata cgaccttgac 780
aaatatttca aagtaaatat cgaagcaaac catgcgacat tggcattcca cgacttccaa 840
catgagctaa gatacgccag aataaacggt gtattaggat caattgacgc aaatacaggc 900
gacatgcttt tgggatggga tacggaccag ttccctacag atatacgcat gacaacgctt 960
gctatgtatg aagtcataaa gatgggtgga tttgacaaag gtggccttaa ctttgatgca 1020
aaagtaagac gtgcttcatt tgagccagaa gatcttttct taggtcacat agcaggaatg 1080
gatgcttttg caaaaggctt taaagttgct tacaagcttg tgaaagatgg cgtatttgac 1140
aagttcatcg aagaaagata cgcaagctac aaagaaggca ttggcgctga tattgtaagc 1200
ggtaaagctg acttcaagag ccttgaaaag tatgcattag agcacagcca gattgtaaac 1260
aaatcaggca gacaagagct attagaatca atcctaaatc agtatttgtt tgcagaataa 1320

<210> SEQ ID NO 7
<211> LENGTH: 1566
<212> TYPE: DNA
<213> ORGANISM: Thermoanaerobacterium saccharolyticum

<400> SEQUENCE: 7
atgagggcgg cttcatgctt cattaaagct gccctcaaca aaaatcatgg aggtaaatgt 60
atgtattttt tagggataga tttagggaca tcatcagtta agataatact gatgaatgaa 120

-continued

```
agcggcaatg tggtatcaag cgtttcaaaa gaatatcctg tgtactatcc agagccaggc     180

tgggctgagc aaaatccaga agattggtgg aatggcacaa gggatggaat aagagagatt     240

attgcgaaaa gcggcgtaaa tggcgatgaa ataaagggtg ttggcttaag cgggcagatg     300

catggactgg tgcttttaga caaagacaat aacgttttaa cgccagccat actttggtgt     360

gaccagagga cacaggaaga atgcgactac atcacagaga aaataggaaa agaaggcctt     420

ttgaagtaca cagggaataa agcattgaca ggttttactg caccaaagat attatgggta     480

aagaagcacc ttaaagacgt atatgaaaga atcgctcata tccttttgcc aaaagattat     540

ataaggttta aattgacagg tgagtacgct acagaagttt cagatgcatc aggtacactt     600

cttttcgatg tggaaaatag aagatggtca aaggaaatga tagacatatt tgaaataccg     660

gaaaaagccc ttcctaagtg ctacgaatca acagatgtca cagggtatgt caccaaagag     720

gcagcagatt tgacagggct tcatgaaggg actattgtcg taggcggtgg tggtgaccaa     780

gccagcggcg ctgtaggcac tggcacggtg aaaagcggca tagtgtccat cgcattagga     840

acttcaggcg tcgtatttgc atcacaggac aagtacgcag cagatgatga gcttaggctt     900

cactcattct gccatgcaaa cggcaaatgg catgtgatgg gtgtcatgct ttcggctgca     960

tcatgtctta aatggtgggt agatgatgta aataattaca agaccgatgt tatgacattt    1020

gatggactct tagaagaagc agagaaggtg aagccaggca gtgatggatt gatattcttg    1080

ccatacctga tgggtgaaag gacccccttac agcgatcctt atgcgagagg cagctttgta   1140

ggtttaacaa ttacacacaa tagaagccac atgacaagat ctatattaga aggcgtcgca    1200

tttggactta gggattcgct ggagcttata aaggctttaa atatacctgt aaatgaagcc    1260

agggtaagtg gtggtggtgc taaaagcagg ctttggaggc aaatacttgc cgatgtattc    1320

aatgtaagga tagacatgat aaatgctaca gaaggacctt catttggtgc agcaataatg    1380

gcgtctgtgg gatatggcct ttacaaaaat gtagatgatg catgcaatag tttaataaaa    1440

gttacagaca gcgtatatcc aatcaaagaa aacgtcgaaa agtacaacaa actgtatcca    1500

atctacgtga gcttgtattc aaggcttaaa ggcgcctttg aagaaattgg gaagttggat    1560

ttgtaa                                                               1566
```

<210> SEQ ID NO 8
<211> LENGTH: 1407
<212> TYPE: DNA
<213> ORGANISM: Thermoanaerobacterium saccharolyticum

<400> SEQUENCE: 8

```
atgattattg tgtacaaaga tgaaaagccc aggataggtt ttttgggtat tatgcaggag      60

ttatacgatg atatgttgcc tggtattact gaaaggcaag agatgtatgc acaacaggtt     120

ataggtagat taggtgatgt tgctgatttt tatttcccag gtgctgcaaa aaacagaaat     180

gatatagaaa ggatagttaa ggaattcaac gataaagatc ttgacggaat aatgatcgtg     240

atgctgacat acggaccagc cacaaatctt gtgaatgctt taagaaacaa taggcttccg     300

attatgctgg cgaatataca gccagaaagc actgtgacag acgattggga tatgggggac     360

ttgacctaca accaaggtgt tcatggtgca caggatactt caaatattat tctgagaatg     420

ggcataactt gtcctgttat aacagaagat tggcattctg atgaatttaa agattttgtg     480

aatgattggg caaaaactgt aaagacagta aaagctttga ggaatatgaa gatagcacaa     540

tttggaagaa tgcatggtat gtatgacata atgggtgatg atgcagcttt tacaagaaaa     600

ttggggccgc aaataaacca ggagtacatt ggccaagttt ttagatatat ggaagaagct     660
```

-continued

```
acaaatgaag aaattgacaa agtgatagag gaaaacaaga agaactttta tatagatcct     720

aaattaagtg atgagagcca cagatatgct gcaaggcttc aaataggatt taagaaattg     780

cttgaggaga aagggtactc tggctttagt gctcactttg atgtgtttaa aggcgatgga     840

agatttaagc agatacacat gatggcagca tcaaacttga tggcagaagg atatggctat     900

gcggcagagg gcgatgtagt tacggcaagc ctggtggcag caggtcatgt tttgataggc     960

aatgcacact ttaccgagat gtatgcgatg gattttaaga gagattcaat tttgatgagc    1020

cacatgggag agggcaattg gaagatagcc agaaaagata gacctataaa attagtcgat    1080

cgagagcttg gcataggaaa gcttgataat cctccaacag tggtgtttat ggctcaacca    1140

ggcattgcga cattggcatc attagtgtct ttagaaggcg aaaaatatag acttgttgtt    1200

tcaaagggag aaattttaga tacagaagaa gcgaaaaata tagagatgcc gtatttccat    1260

tttagacctg aaaacggagt tagggcttgt ctaaatggct ggcttaaaaa tggtggtaca    1320

catcatcagt gcttgacatt aggtgatgct actaaaagat ggaagctttt atgcgaatta    1380

ttagatatcg agtatgttga agtgtaa                                         1407
```

<210> SEQ ID NO 9
<211> LENGTH: 642
<212> TYPE: DNA
<213> ORGANISM: Thermoanaerobacterium saccharolyticum

<400> SEQUENCE: 9

```
atgttagaga acctaaaaca acgtgtatat aaaatgaaca tgatgcttcc taaaaacaat      60

ttagtcacaa tgacaagcgg caatgtcagc ggaagagatc ctgagacaaa tcttgtagtc     120

ataaagccca gcggagtttt gtacgatgaa atgacgccag atgatatggt agtcgtggat     180

ttggatggca atgtggttga gggtaagcta aaaccatctg tcgatactgc tacacatctt     240

tacgtctaca ggcatagaaa tgatgtaaac ggcattgtcc atacacactc accgtatgct     300

acaagttttg ccgcacttgg ccggtcaatt ccggtctatc ttacagctat tgcagacgag     360

tttggatgcg caattcctgt agggccttat gccaaaattg gcggggaaga gataggaaaa     420

gccatcgtag attatatagg tgagagtcct gcaatactta tgaaaaatca cggcgttttt     480

accattggca attcacctga agcagcctta aaagctgctg ttatggtaga agatacagct     540

aagacggtgc acttatcact gcttttaggc acacctgatg taataccaga tgaagaagta     600

aaaagagccc atgaaagata tcttacaaaa tacggtcaat ga                        642
```

<210> SEQ ID NO 10
<211> LENGTH: 1320
<212> TYPE: DNA
<213> ORGANISM: Clostridium cellulolyticum

<400> SEQUENCE: 10

```
atgtcagaag tatttagcgg tatttcaaac attaaatttg aaggaagcgg gtcagataat      60

ccattagctt ttaagtacta tgaccctaag gcagttatcg gcggaaagac aatggaagaa     120

catctgagat tcgcagttgc ctactggcat acttttgcag caccaggtgc tgacatgttc     180

ggtgcaggat catatgtaag accttggaat acaatgtccg atcctctgga aattgcaaaa     240

tacaaagttg aagcaaactt tgaattcatt gaaaagctgg gagcaccttt cttcgctttc     300

catgacaggg atattgctcc tgaaggcgac acactcgctg aaacaaataa aaaccttgat     360

acaatagttt cagtaattaa agatagaatg aaatccagtc cggtaaagtt attatgggga     420

actacaaatg ctttcggaaa cccaagattt atgcatggtg catcaacttc gccaaacgct     480
```

-continued

```
gacatatttg cgtatgcagc agctcaggtt aaaaaggcaa tggaaatcac aaaggaatta    540
ggcggagaaa actatgtatt ctggggtggt agagaaggtt atgaaactct cttgaataca    600
gacatgaagc tggaacttga taatttagca agattcttga agatggctgt tgactatgct    660
aaggaaatcg gttttgacgg acaattccta atcgaaccaa agccaaaaga accaactaag    720
caccaatatg attttgatac agctacagtt atcggcttcc tgaagacata tggattagac    780
ccatacttca agatgaatat cgaagctaac catgctacat tagcaggaca cacattccaa    840
catgagcttg ctatgtgcag aatcaacgac atgcttggaa gtattgatgc taaccaaggt    900
gatgtaatgc tcggatggga tacagaccaa ttcccaacga acctatatga tgcaacacta    960
gcaatggtgg aagtattaaa ggccggcgga ttgaaaaagg gaggtttgaa cttcgactca   1020
aaagttagaa gaggatcatt cgaaccatca gacttgttct atggacatat tgcaggtatg   1080
gatacttttg caaagggtct tatcatagca aataagatcg ttgaggacgg taagtttgat   1140
gcatttgttg ctgacagata ctcaagctac acaaatggta tcggaaaaga tattgttgaa   1200
ggaaaagttg gctttaagga attggagcaa tatgcactta ctgcaaagat tcagaacaag   1260
tctggacgtc aggaaatgct ggaagctttg ttaaaccagt atatcctcga aacaaaataa   1320
```

<210> SEQ ID NO 11
<211> LENGTH: 1608
<212> TYPE: DNA
<213> ORGANISM: Clostridium cellulolyticum

<400> SEQUENCE: 11

```
atgaagcatg aactaaatga cgggagaaat gctattctaa atggaaagac agcaattggg     60
attgaactcg gatcaactag aataaaaacg gtattgatag gtgcagacaa tgcacctatc    120
gcatccggta gtcatgactg ggaaaacagc tatatcaata atatttggac ttacagcttg    180
gaagatatct ggaaaggcgt acagagcagc tatcaggaaa tggttaaaga tgttagggac    240
aaattcggag taagtctaaa gacaaccgga gcaataggtt ttagcggaat gatgcacggt    300
tatatggttt ttgataagga aggtaatctt ctgactcatt tcagaacatg gcgtaacact    360
ataactgcac aggcttccga ggaactaacc aagttgttta attatcctat tcctcaaagg    420
tggagcattg cccatcttta ccaagccata ctgaacaatg aagagcatgt atccaatatc    480
gattttatga ctacattggc cggatttata cactggaagt tgacaggaga aaaagttctt    540
ggtgtcggag aggcatcagg tgttttccca atagatttag atactaagga ttttaattca    600
agtatgatta atcagtttaa tgaggctacc accaatcgaa atttttcatg gaagcttcaa    660
aatattcttc caaaagtttt ggtttcgggt actgaagcag gtaggctgac agaagaaggt    720
gcaaagcttc ttgatgttac cggggagctt caggcgggta ttccttttg tcccccctgag    780
ggagatgcgg gaaccggtat ggttgcaact aacagcgttg ctgtccgtac aggcaatgtg    840
tctgccggga cttctgtttt tgctatggtt gttctcgaaa aggaattatc caaagtgtat    900
tcggaaattg acctggtgac tacacctgac gcaaatcttg tggctatggt tcattcaaat    960
aattgtacat cggactatga cgcatggatg ggtatatttg ctgaggcagt taagaccttg   1020
ggctttgacg tgaaaaaacc acagctatat gataccctgc tgggagccgc acttcaaggt   1080
gaccctgatt gcggagggtt gcttgcgtac ggttatattt caggtgagca tattacccat   1140
tttgaagaag gtcgcccgat ggttgttcgt tcatcaaaca gcaaattcaa cctggccaac   1200
tttatcaggg tcaatttgtt tacatctctt ggagccttga agaccggttt ggatattctt   1260
tttcaaaagg aagctgttaa agtggacggt attaccggac acggcggttt ctttaagacg   1320
```

aaggaagtag gacagaagat tatggcggct gcctttaatg tccctgtatc tgttatgaag 1380
actgcgggtg aaggcggtgc atggggtatt gccctacttg cttcgtatat gattaatagg 1440
gaaagctcac agtccttgga ggatttttctt aaacaaaatg tgtttgggga aagccaaggt 1500
gagactgtac agccagattc gaaggatgtt gacggtttca acgagtttat gaaaaggtac 1560
acaaagggac tgggtattga aagggctgcg ataaacttct tgaactga 1608

<210> SEQ ID NO 12
<211> LENGTH: 1380
<212> TYPE: DNA
<213> ORGANISM: Clostridium cellulolyticum

<400> SEQUENCE: 12
atgataacca aacaaaaacc aagaatcgga tttttgggcc taatgcaggg attgtatgac 60
gaatcacagc cggaactgcc gaaaatgcag gaggcatttg ccagagaagt ggttgaacaa 120
ttaaaagatg tggcagatat tgattttccc ggtccagcaa aagaaagaga agatatagaa 180
agatatgtaa aatatttcaa tgataaagag tacgatggaa taatgatagt aaatctgttg 240
tacagtccgg gaaatcgttt aatacaggct atgaagaata ataatctgcc aatattgctg 300
gctaatattc aaccacttcc cgatgttaca tcaaactggg attggatttt gtgcacaact 360
aatcagggaa ttcatggaat acaggataca agtaatgttc tcatgcgttg tggtattaaa 420
ccggctatta taacagatga ttggaaggct gaatccttta aagcctactt tgaagattgg 480
gcattggctg ccaacacgca taacagacta aaaaagacaa aggttgcgat tttcggccgt 540
atgcacaata tgggtgacat acttggtgat gatgcggcat tgtgcagaaa atttggtgta 600
gaggcaaacc atgtaacaat cggtccggtt tattacaaca tggaaggatt gtcagataaa 660
gaagtagatg cccagattga ggaagataaa aagaatttta aaattgatcc taatcttcct 720
gaagaaagtc atcggtatgc tgcacgtatg caattagcct ttgaaaaatt ccttaatgat 780
aacggttatg aaggtttttc acagttcttc aacatataca aggaagacgg caggttcaaa 840
caaataccga tattggcagg ctccagtctc cttgcaaaag gttatggtta ttcggcggaa 900
ggtgatacaa atgtacttct catgactgtg atcggtcaca tgatgatagg ggatcctcat 960
tttactgaga tgtactccct ggactttggt aaggattcag caatgctaag ccatatggga 1020
gaaggcaact ggaaggttgc aaggaaggat cgcggagtga cactgattga caggcctctt 1080
gatattggtg gtcttggtaa tcctccgaca ccaaagttca acgtagaacc aggaacagct 1140
acccttgttt ccctcgttgc agtagaagga gaaaaatacc aactaattgt atcaaagggt 1200
actatccttg atactgagga cttgccagat gttcctatga accatgcttt tttcagaccg 1260
gattccggca tcaaaaaggc tatggacgaa tggttagcta atggtggtac acatcacgaa 1320
gtactattcc tgggtgattt tagaagacgt tttgaattat tatgtaaatt cttgacataa 1380

<210> SEQ ID NO 13
<211> LENGTH: 690
<212> TYPE: DNA
<213> ORGANISM: Clostridium cellulolyticum

<400> SEQUENCE: 13
atgttggaac aactaaaaca agcggtgttg gaagccaatc tagagctgcc tgaaaaagga 60
cttgtaacat atacatgggg aaatgtaagc ggtatcgaca gagaaagcag acttattgca 120
attaaaccca gtggtgttga gtataatgtt atgacagctg atgatattgt attaatcgac 180
cttacaggta aagtggtgga aggaaaattg aagccgtctt ctgatgcacc aacacatgta 240

-continued

```
gctctgtata atgcatttcc tgatatagga ggtgtaacac acacccattc caggtgggca    300

actgcttttg cacaggctgg tatggggatt cctgcttacg ggactactca tgcggattac    360

ttttatggtg aaatcccatg tactcgggaa atgacaaagg atgagattga gtccgattat    420

gaagcaaata ccggaacggt gataatagag acttttaaag atttaaatcc taactatatc    480

cctgccgtac ttgtaaaaaa tcatgcacct tttacatggg gaaaaagtgc agcggaatcg    540

gttcataatt ctgttgtttt agaagaagta gctatgatgg ctattcagtg cagacaactg    600

aacccaaatg taactcccat gccgcaggtg ctgctagaca agcattttat gaggaagcac    660

ggcccgaaag cttattacgg acaaaaataa                                      690
```

<210> SEQ ID NO 14
<211> LENGTH: 1317
<212> TYPE: DNA
<213> ORGANISM: Clostridium phytofermentans

<400> SEQUENCE: 14

```
atgaaaaatt actttccaaa tgttccagaa gtaaaatacg aaggcccaaa ttcaacgaat     60

ccatttgctt ttaaatatta tgacgcaaat aaagttgtag cgggtaaaac aatgaaagag    120

cactgtcgtt ttgcattatc ttggtggcat actctttgtg caggtggtgc tgatccattc    180

ggtgtaacaa ctatggatag aacctacgga aatatcacag atccaatgga acttgctaag    240

gcaaaagttg acgctggttt cgaattaatg actaaattag gaattgaatt cttctgtttc    300

catgacgcag atattgctcc agaaggtgat acttttgaag agtcaaagaa gaatcttttt    360

gaaatcgttg attacatcaa agagaagatg gatcagactg gtatcaagtt attatggggt    420

actgctaata actttagtca tccaagattt atgcatggtg cttccacatc ttgcaacgca    480

gacgtatttg catatgctgc tgctaagatt aagaatgcat tagatgcaac aattaaatta    540

ggcggtaaag gttatgtatt ctggggtggt cgtgaaggtt atgaaacact tcttaataca    600

gatttaggac ttgagcttga taatatggct agacttatga agatggctgt agagtatggc    660

cgtgcaaatg gttttgatgg cgacttctat attgagccaa agccaaagga accaaccaag    720

catcaatatg attttgatac agcaaccgta cttgctttcc ttcgcaaata tggcttagaa    780

aaagatttca agatgaacat tgaagcaaac catgctactc ttgcaggtca tacctttgaa    840

catgaacttg caatggctag agttaatggt gcatttggtt ctgtagatgc aaaccagggt    900

gatccaaacc ttggatggga tacggatcaa ttcccaactg atgttcatag tgcaactctt    960

gcaatgcttg aagtacttaa ggctggtgga ttcactaacg gcggacttaa ctttgatgca   1020

aaggtaagac gtggttcctt cgaatttgat gatattgcat acggttatat tgcaggaatg   1080

gatacttttg cacttggttt aattaaggct gctgagatta tcgacgatgg tagaatcgca   1140

aaatttgtag atgatcgtta tgcaagctat aaaacaggaa ttggtaaagc aattgtggat   1200

ggaactacat ctcttgaaga attagagcag tatgttttaa cacatagtga accagtaatg   1260

cagagtggtc gtcaggaagt tcttgaaaca atcgtaaata atattttatt tagataa      1317
```

<210> SEQ ID NO 15
<211> LENGTH: 1599
<212> TYPE: DNA
<213> ORGANISM: Clostridium phytofermentans

<400> SEQUENCE: 15

```
atgggcatgg agcattttaa agatgcgatt cttacgggta aaacaacact tggaattgag     60

cttggttcca ctagaataaa agctgtttta gtaaatgaag aaaacgaacc aattgcgtca    120
```

-continued

```
ggaagccatg attgggaaaa tcaatatatt gataatgtat ggacttacaa tctggatgat    180

atctggaggg gcgttcagaa tagttatgga caaatgacaa gtgatgttaa gaataagtac    240

ggagtagaac ttacaacaat tggagccatt ggttttagtg gaatgatgca tggctatatg    300

gcttttgacg aaagtggaga gttacttgta ccatttcgta cctggagaaa tacaataaca    360

ggaccagcat ccgagcagtt gaccaatgta tttcagtatc aaattccaca acgttggagt    420

attgcccatc tatatcaagc tatcttaaat ggggaatccc acgtgaaaaa tattagattc    480

ctgacaacat tggcaggata tattcactgg aagctaacag gagaaaaagt attaggagtc    540

ggagaagcat ctggaatgtt tccaatcgat ataaatacga aagattttaa taaatcaatg    600

ttagctcagt ttaatgaact ggttgcttcg aatgactatt catggaaaat agaagatatt    660

ctaccgaaag tactagttgc aggagagtct gctggagtat taaccgaaga aggagtaaaa    720

cttcttgatg tttcaggtaa attaaaagca ggaattcctc tttgtccgcc ggaaggagat    780

gctggaactg gtatggtagc aaccaacagc gtagcaaaga gaactggtaa tgtatctgct    840

ggtacttctg tatttgcaat ggctgtatta gaaaaagagc tttcaaaagt ttacgaagaa    900

attgaccttg tgacgactcc aagcggagat cttgtggcta tggtgcactg caataactgt    960

acttctgatt tgaatgcgtg ggtttctatc tttaaagaat ttgcttcggc aatgggcatg   1020

gaagctgata tgtcaaagat attctcaacg ctatacaata aggcgttaga aggcaatgca   1080

gagtgtggag gcttactcgc atacaattat ttttccggtg aacatataac acactttgaa   1140

gaaggccgcc cattgtttgt aagaactcca gagagtaagt ttaaccttgc gaatttcatg   1200

agagttcatc tattcacagc acttggtgct ttaaagatag gtcttgatat cctattaaaa   1260

caagaatcag tacaattgga tgagattttt ggtcatggtg gattatttaa gacgaaagat   1320

gtcggacaaa aaattatggc tggtgcaatc aatgttcctg tttctgtgat ggagactgcc   1380

ggagaaggcg gagcatgggg aatcgcaatc ttggcttctt atatgatttc taaggaagaa   1440

ggtcagtcct tagatgagta tctttctaaa catgtattcc aaggaaagac aggtagcaag   1500

atgcagccgg atccaaggga tgtagaaggt tttgaacagt ttatcaaacg atatattgac   1560

ggacttgaaa ttgagcgtaa agcagtggag atattataa                          1599
```

<210> SEQ ID NO 16
<211> LENGTH: 240
<212> TYPE: DNA
<213> ORGANISM: Clostridium thermocellum

<400> SEQUENCE: 16

```
actttgccaa cggtacaagg gaagttgcaa gagcggttgc cgagtccgga gcaatttcaa     60

taatcggagg cggagattct gccgcagcta tagaacagct tggttttgcc gataagatta    120

cccacatttc aaccggaggc ggcgcgtctt tggagtttct tgaaggaaaa gtattgccgg    180

gaattgatgt attaatggat aaataaggag agaagaggtc atgagtagaa aagttattgc    240
```

<210> SEQ ID NO 17
<211> LENGTH: 420
<212> TYPE: DNA
<213> ORGANISM: Clostridium thermocellum

<400> SEQUENCE: 17

```
aattactgta tctctctggc attgccaggt tttaataaag attaaaatta ttgactagaa     60

ataaaaaaat tgtccataat attaatggac aaaaaaacaa agaattacat caaaggaaga    120

taaaaatact ttgttaaaaa attaattatt ttttatctaa actattgaaa atgaaaataa    180
```

-continued

```
aataatataa aatgaatcat agtgcaagag atacttgcca gaggatgaat attttactgc    240

attcatgctt tatggcagct aatagaggca ttaaattaaa ttttaattta caataggagg    300

cgatattaat ggcagtaaaa attggtatca acggttttgg acgtatcggt cgtcttgtgt    360

tcagggccag tctcaacaac ccgaacgttg aggttgtagg tataaacgac ccatttattg    420


<210> SEQ ID NO 18
<211> LENGTH: 300
<212> TYPE: DNA
<213> ORGANISM: Clostridium thermocellum

<400> SEQUENCE: 18

ctgccccatt aaaagctcgg ttccaaccgc taatatctcc gcattcatat tgaaagaccc     60

cttaaattta aactttttgt aacttattat atcaattagt gttataaaat aaaagggaaa    120

aagaattaaa atcaaaggtt tcaagagcag ccgtatcacc cgtaaaagtt tcagccgatt    180

caacctttt acacataaaa ctttcaaaaa ttgatgactt acaattatca agtaggatat    240

aatattacta atgctaaaca gttattgata aaggaggaag gaatatgaac aataacaaag    300


<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

ggcggaattc cttggtctga caatcgatgc                                      30


<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

ggcggaattc tatcagttat tacccacttt tcg                                  33


<210> SEQ ID NO 21
<211> LENGTH: 674
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

gaattctgcg acagaatagg gattgacaat tcctttataa agcaatcaag gggttcagaa     60

gaggctgtta ttttgaataa agagctaaag aatcacaaag atgcaataga ggctgttatt    120

tctgcactga ctgacgataa tatgggcgtt ataaaaaaca tgtccgaaat atcagcagtg    180

ggacacagaa tagtacacgg cggtgaaaaa ttcaacagtt ctgtagttat agatgaaaac    240

gttatgaatg cagtaagaga gtgtatagac gttgcaccgc ttcataatcc gccgaatatt    300

ataggtatag aggcttgcca gcagattatg cccaatatac ctatggtagc tgtatttgat    360

accactttcc acagctccat gcctgattat gcataccttt acgcattgcc atatgaactt    420

tatgaaaagt acggtataag aaaatatggt ttccacggaa catcacacaa atatgttgca    480

gaaagagctt ctgcaatgct tgataagtct ttgaacgaat taaagataat tacatgccat    540
```

```
cttgggaacg gttcaagtat ttgtgctgtt aacaagggta aatcaattga tacttccatg    600

ggctttacac ctttgcaggg acttgcaatg ggtacaagaa gcggtacaat agaccctgaa    660

gttgttacga attc                                                      674
```

<210> SEQ ID NO 22
<211> LENGTH: 951
<212> TYPE: DNA
<213> ORGANISM: Clostridium thermocellum

<400> SEQUENCE: 22

```
atgaaaaata aatctataaa taaaatagta attgtaggta cgggttttgt cggttcaaca     60

actgcctata ctttaatggt cagcggacta gtttccgaga ttgtacttat tgaccgtaac    120

acaagcaaag ccgaaggaga ggcaatggat atgaatcacg gtatgccctt tgtaagacct    180

gtcagaatat acaaaggtga ttatcctgat tgcaaaggtg ctgatattgt tgtaataaca    240

ggtggagcaa accagaagcc cggtgaaacc agaattgacc ttgtaaataa aaatactgaa    300

gtttttaaag acattgttgg aaatatcatt aaatacaata cagactgtat tttacttgtt    360

gttacaaacc cggttgatat cttaacctat gtaacataca aattatccgg atttcccaaa    420

aacagagtta taggctccgg aacagttctt gatactgcac gtttcaaata tatgcttggt    480

gaacacatgg gagttgaccc aagaaacgtt catgcttata taatcggtga acatggagat    540

acagaggtac ctacatggag tctggcatcc atagccggga taccgatgga tgcttattgc    600

aaggaatgta aatcctgtga tgctgaaaac tttaagagtg aaacttttga caaagtaaaa    660

aatgcagctt atgaaattat tgatagaaaa aatgcaacct actacgccgt tgctcttgca    720

gtaagaagaa ttgtagaggc tatcgttcgt aatgaaaact ccatattgac ggtatcaagc    780

ctattcgaag gagaatacgg cctcaatgac atatgtctca gtattcccag ccaggtaaat    840

tcggagggtg tttcaaggat tttgaatatt cctctgagca gtgaggaaac aggtttactt    900

aataaatctg cccaggcctt gaaacaggtt atcagtgggc tgaatttata a             951
```

<210> SEQ ID NO 23
<211> LENGTH: 933
<212> TYPE: DNA
<213> ORGANISM: Clostridium thermocellum

<400> SEQUENCE: 23

```
atgggtttta aagttgcgat cataggagca ggatttgttg gagcatcagc tgcgtatgcg     60

atgtctataa acaacttggt ttctgaattg gtattaattg atgtaaataa agagaaggct    120

tatggtgaag cacttgatat cagccatggc ttatcattct caggaaatat gacagtttat    180

tccggcgact attctgatgt taaggattgt gatgttatag ttgtaactgc aggggcagca    240

agaaaaccgg gagaaactcg tttggacctt gctaaaaaga atactatgat catgaagagc    300

atagttactg atataatgaa gtactacaat aagggtgtta ttgtaagtgt atcaaatcct    360

gttgatgtat tggcatatat gacacaaaag tggtcaggat tgcctgcaaa taaagttata    420

ggatcaggaa cagttcttga cagtgcaaga ctgagaactc atatcagtca ggcattggat    480

gtagacattg ctaacgttca cggttatatt gttggtgaac atggtgattc tcagttgcca    540

ttatggagtg caacacatat agcaggagta caatttgacg actatgtaaa agctactggc    600

ttaaatgttg ataaggaagc tcttttcaat gaagttaagg tagcaggtgc aactattatt    660

aagaacaagg gagcaactta ctacggtata gctctttcaa ttaacagaat agttgaatca    720

atcctgaagg acttcaatac tattatgcct gttggtacag ttcttgacgg acagtacgga    780
```

ttaaaggatg ttttattaaa cgttcctacg atagttggcg gaaacggagc tgaaaaagtt 840
cttgaagtga acattacaga tgcagaatta caacttttga agcattcagc tgaacaggtt 900
agggcagtta ttaacgaagt taaagacata taa 933

<210> SEQ ID NO 24
<211> LENGTH: 2830
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24
gacgcataca ggttgtaaca cccatttccc ttagcttttc gggagatgaa taaaacaaac 60
tttccgggtc ctttaccaca ccgcccacat aaagagctat gccgcatgaa agaaacgata 120
tgttatcatt tttttcgtaa actgttattt ccgaacccgg ataaagcttt accatattat 180
taactgctgc cgtccctgca tgtgtacacc ctataaccac tattttcata tacatcctcc 240
tttgtttgct tgtaaatata tcccatatat accacctaaa tatattttat aaacaaattc 300
ggtatatcat tcttttggta aataaaaagt acatccgata ttagaatgta cctaaaaaaa 360
attattattt tattgtatat gctttatctg ttttcattat atggtttgct atccattcta 420
cggtaaaatc aagtaattcc attaagtact gatcctgatc cttgtctatc ctgctataat 480
ccgtattact gattttctca ataaaatcat ggtgttcaac tttgtgggag agaagcttgc 540
gatatcctat gctatgcatg tattcttctt cataggtaaa atgaaagaca gtgtaatctt 600
ttagttccgt aattagccgt acaatttcat catatttgtc tgtaataagc tgatttttcg 660
tggcctcata aatttccgaa gcaatctgga atagtttctt atgctgttcg tcgatttttct 720 caattccaag aataaattcg tctctccatt ctatcatatg gaccctccta aattgtaatg 780
tataccaaga ttatacatac ttcctagaat ataaacaata caaggataaa attttaatat 840
cgtataccta cataaatgac taacttaaag ctctctaaaa cttctttttt attatttcta 900
tactactaaa atcaaaaata ttctctaaag tatttctaca aatgttgttt ttgcaacaaa 960
gtagtatact tttgcaccca gaatgttttg ttataactta caaattaggg gtatatttat 1020
agtaaatact aaatggaaga gtaggatatt gattatgaac gagaaaaata taaaacacag 1080
tcaaaacttt attacttcaa aacataatat agataaaata atgacaaata taagattaaa 1140
tgaacatgat aatatctttg aaatcggctc aggaaaaggg cattttaccc ttgaattagt 1200
acagaggtgt aatttcgtaa ctgccattga aatagaccat aaattatgca aaactacaga 1260
aaataaactt gttgatcacg ataatttcca agttttaaac aaggatatat tgcagtttaa 1320
atttcctaaa aaccaatcct ataaaatatt tggtaatata ccttataaca taagtacgga 1380
tataatacgc aaaattgttt ttgatagtat agctgatgag atttatttaa tcgtggaata 1440
cgggtttgct aaaagattat taaatacaaa acgctcattg gcattatttt taatggcaga 1500
agttgatatt tctatattaa gtatggttcc aagagaatat tttcatccta aacctaaagt 1560
gaatagctca cttatcagat taaatagaaa aaaatcaaga atatcacaca aagataaaca 1620
gaagtataat tatttcgtta tgaaatgggt taacaaagaa tacaagaaaa tatttacaaa 1680
aaatcaattt aacaattcct taaaacatgc aggaattgac gatttaaaca atattagctt 1740
tgaacaattc ttatctcttt tcaatagcta taaattattt aataagatcc cctttacttc 1800
ggatgcatgc cgcaggcagg catccgaagt agtttctcca ttatacaagt attctcttga 1860
gtacgtcgtc gcttctcagc agctgctttg ctttttccct gttttccggc acatggagat 1920
aagtgtatct gttaggctta atagtgtgtg ccatgtcaat tgccttttcg aagtcatctg 1980
ccttcatttt taaggtttcc acaaaattga taaaacccgt atcagtcaga aattttacta 2040
cccgctgata tctgtgttct tgaaccctgc tcataagata ggttgcaatc ccaacctgaa 2100
ttccatgaag ctgaggtgtc tccagcagct tatctaaagc atgagatatt agatgctcac 2160
taccgctggc tggagcactg ctgtctgcta tctgcatggc aattccgctc attgtcagag 2220
agtctaccat ttcctttaaa aagaagtttt ctgtaacctg tgtgtagggc atccttacaa 2280
tactgtttac tgacttttta gcaatcattg cagcaaaatc gtcaaccttt gccgcattgt 2340
tcctttcttc aaaataccag tcatacacag ccgtaatttt ggatattatg tctccgagac 2400
ctgaataaat aaatttcata ggtgcatttt ttaatacatc taaatccact aatattccaa 2460
atggcatcga ggcatgtacg gaagtacgcc tgccatttat aatcaaagag cagcctgagc 2520
tggaaaaacc atcgtttgag gttgatgtag gtatactgat aaaaggaagc ttgtttaaaa 2580
aagctatata tttggctgca tcaagcacct ttcctcctcc tactccgacc actgcatcgg 2640
ttttggaggg aatagtaaaa gccttgagca taagattttc aagctttatg tcatcatagt 2700
cgtaagtttc aagtactgca agagattttc ttgactttat ggaatccaga atcttttcac 2760
caaataagtc acgtattccc tctccaaaaa gtactacaac attactaatt cctgcccttt 2820
caatatgtgc 2830

<210> SEQ ID NO 25
<211> LENGTH: 572
<212> TYPE: DNA
<213> ORGANISM: Clostridium thermocellum

<400> SEQUENCE: 25
ccaaggtgac aaacgataac ttttgagtta tttacatcta agccagcaag cgtggttgct 60
cttttagaaa catagctgtg acttgttccg tggaaaccat atcttcttac cttatattta 120
tcatagtact caaatggaat accataaagg taagcttctt ttggcattgt ctgatggaat 180
gcagtatcaa aaacagctac cattggtaca tttggcataa ttgatttaca agcgttgata 240
ccaataaggt ttgctgggtt gtgtaaaggt gcaagatcat tacactcttc aattgcattt 300
aagacttcat cattgattac tacggaatga gcaaatttct caccaccatg tactactcta 360
tgtccaacag cgttgatttc atctaaggac ttaatcacac cataattttc attcataaga 420
gcagcgatta catttttaat agcaacctca tggtttggaa gtgcatcctc aagaactacc 480
ttctcaccgt cagctgactt gtgagtaaga cggccatcaa taccgattct ttcacaaaga 540
cctactgcta atgcttgctc tgtcacagag tc 572

<210> SEQ ID NO 26
<211> LENGTH: 2676
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
ctgagtgcaa tgtaaaaaag gatgcctcaa gtattcttga aacatcctta tattatacta 60
caaaatcata aagtaaatta ctcagctgta gcaatgatct ctttttttgtt gtaagatcca 120 caagctttac aaactctatg aggcatcata agtgcaccac acttgctgca tttcactaag 180
tttggagcag tcatcttcca gtttgcacga cgactatctc ttctagcttt ggaatgttta 240

-continued

```
ttctttggac aaatagctcc cattgattac acctccttaa acttgttaaa aatatctcgg    300
atagcagaca ttcttgggtc tagttctgta cggtcacacc cgcactctcc ttcatttagg    360
ttagcaccgc agaccttgca gattccttta cagtcttctt tgcacagaac cttcattggg    420
aaaccaatca agacttcttc atagataagt ttatctacgt ctaaatcata tccggaaaca    480
aaatttgttt catctaaatc ctcggtacgc tgttcctctg ttttcgatac atcaatctct    540
gtagccacgt cgatgtcttg ttggatggtt tcttccttca aacaacgatc gcaaggaacg    600
gctaacgcta atttcgtttt tgcttccacc agaatttttc ggccacctag attagttaat    660
ctaagtttaa ccggttcttt ataggtaata gaataaccga caccatttaa ttcgaatata    720
tcaaattcaa tcggtgcagt gtattctttg agaccattag gaacattcat gacttcagac    780
atttgtatca gcataagtaa ctcctgtcta aaaaaacgca taatgtaagc gcccaaaaat    840
tcacactgtt agtattataa acgcttaaaa taggtttgtc aactcctaac tgttaaaaat    900
gtcagaattg tgtaaccata ttttctcttc attatcgttc ttcccttatt aaataattta    960
tagctattga aaagagataa gaattgttca aagctaatat tgtttaaatc gtcaattcct   1020
gcatgtttta aggaattgtt aaattgattt tttgtaaata ttttcttgta ttctttgtta   1080
acccatttca taacgaaata attatacttc tgtttatctt tgtgtgatat tcttgatttt   1140
tttctattta atctgataag tgagctattc actttaggtt taggatgaaa atattctctt   1200
ggaaccatac ttaatataga aatatcaact tctgccatta aaaataatgc caatgagcgt   1260
tttgtattta ataatctttt agcaaacccg tattccacga ttaaataaat ctcatcagct   1320
atactatcaa aaacaatttt gcgtattata tccgtactta tgttataagg tatattacca   1380
aatattttat aggattggtt tttaggaaat ttaaactgca atatatcctt gtttaaaact   1440
tggaaattat cgtgatcaac aagtttattt tctgtagttt tgcataattt atggtctatt   1500
tcaatggcag ttacgaaatt acacctctgt actaattcaa gggtaaaatg cccttttcct   1560
gagccgattt caaagatatt atcatgttca tttaatctta tatttgtcat tattttatct   1620
atattatgtt ttgaagtaat aaagttttga ctgtgtttta tatttttctc gttcattgta   1680
tttctcctta taatgttctt aaattcattt atcacggggc aacttaatat atccgaaata   1740
tagttcttct atatcgttcc cccagtataa tgattattat actatttaat cttcaactta   1800
acaattggag tttccagtta agaaataata atttaatgcc aaagcggata ttcgcaatcc   1860
gcttacgcta cttgctcata acctcaacag gcaatgaagc taagttaatt atttactctg   1920
tgcctgaaca gcagtgattg caacaacacc aacgatatca tcagaagaac aacctcttga   1980
taaatcattt actggagctg caataccctg agttaatggt ccataagctt ctgcctttgc   2040
aagacgctgt gttaacttat atccaatgtt accagcatca aggtctggga agattaatac   2100
gttagctttt ccagcaatat cactaccagg agcttttgaa gcacctacac taggaacgat   2160
tgctgcatct aactggaact cgccgtcgat cttatattct gggtataatt catttgcaat   2220
cttagttgct tctacaacct tatcaacatc tgcatgcttt gcgcttccct ttgttgaatg   2280
agaaagcata gctacgatag gttcagagcc aactaattgt tcaaaactct tcgctgtgga   2340
accagcgatt gctgctaact cttcagcatt tggattctga tttaaaccag catcagagaa   2400
aaggaaagtt ccatttgcgc ccatatcaca attaggtact accattacga agaaagcaga   2460
aactaactta gtatttggag cagtttttaa aatctgaaga catggtctta aggtatctgc   2520
tgtagagtga caagcaccag atactaaacc atctgcatcg cccatcttaa ccatcattac   2580
accgtatgta atgtagtctg ttgttaaaag ctcttttgct ttttcagggg tcatgccttt   2640
```

-continued tgcctgtcta agttctacaa gcttgttaat gtaagc 2676

<210> SEQ ID NO 27
<211> LENGTH: 978
<212> TYPE: DNA
<213> ORGANISM: Clostridium thermocellum

<400> SEQUENCE: 27
atggcgatta caataaaccg aagtaaagtt attgttgtgg gtgcaggttt agttggtact 60
tcaacggcgt ttagtctaat tacgcaaagt gtttgtgatg aggttatgtt gatagatatc 120
aatcgtgcta aggcgcatgg ggaagtaatg gatttgtgtc atagtatcga gtatttaaat 180
cgaaatgttt tggtaacgga aggagattat acagactgta aggacgctga tattgttgta 240
ataactgcag ggcctccgcc aaaaccagga cagtcgcggc ttgatactct tgggttatcc 300
gcagatattg tgagcacgat tgtggaacct gtcatgaaga gtgggttcaa tggaatattc 360
ttagtcgtga cgaatccggt ggattcgatt gctcaatatg tttatcaatt atcggggctt 420
ccaaagcaac aagttcttgg aactggaaca gcgattgact ctgcaagatt aaaacacttt 480
attggagata ttttacatgt agatcctaga agcatacagg cttatacgat gggagagcat 540
ggagattctc aaatgtgtcc ttggtcgctt gttacggttg gcggtaaaaa tattatggac 600
atcgtacggg ataacaaaga gtattccgat attgacttta atgaaatctt atataaggtt 660
accagggtag gttttgatat tttatcagtg aagggtacta cttgttatgg aatagcgtca 720
gcagctgtgg ggattataaa agcaattctt tatgatgaga attccatcct tccggtctct 780
accttattgg agggggaata tggtgagttt gatgtatatg caggggtacc atgcattcta 840
aatcgtttcg gcgtgaagga tgtagtggaa gtaaatatga cagaagtaga gttaaatcaa 900
ttccgagcct ctgttcacgt tgtgagggaa gctattgaaa acttaaaaga cagagataaa 960
aaggcattat ttttataa 978

<210> SEQ ID NO 28
<211> LENGTH: 960
<212> TYPE: DNA
<213> ORGANISM: Clostridium thermocellum

<400> SEQUENCE: 28
ttatgatagc gtcaatgcat actgaaaatt ttctttcatt gttctacaag aagcatcgaa 60
ttttcccttt tcttcaggtg tcaaatttag ctcaatgatt tcttctacac catgaattcc 120
aagtaccgta ggaacagatg catagacatc atgctggcca tactcaccat ttaagagagt 180
agatactggt aataccttct tctcatctga gaaaatggct cgtgtaacct cagctagtga 240
tgcaccaata ccaaattccg ttgagccttt tccagttagg atatgccatc cccctgctct 300
agcttcatca gaaagcttag aaagatcaat ctgcccatat ttttcaggtt tttccttgat 360
tagttccaaa attggttttc cagctataga taccgttgac catgcaacca tctggctttc 420
tccgtgttct ccaagaacaa atccatagat tgatttttga tcaatttcaa cagcatctgc 480
aattgctctt ctaagtctgg cagagtctag taccgtactt gttgaaataa ttttattgga 540
tgagtactga agtaaatgct gtaaataatg tgttattaca tctgctggat ttgaaatgct 600
aacaatcata ccatcaaaac ctgaattttt gatatgccaa gctacctctt taataattag 660
agcagtattc gtaagggtac tcattcttgt ttcaccctta tttttatctg gattggttcc 720
tactgcaatc accatgagat ctgcatcagc tgcatcacta taatcacccg attttacctt 780
aactctgtgt ggtaggtata ctgtagcatc gtagatatcc agtgcttgtg ctttcgcttt 840
ttctctatca atatcaataa agataatttc ttctgcaagc ccctgctctg ccagtgcata 900
tccagcatga gatcctacgt gacctgctcc gataataatg acttttcttg gttttgccat 960

<210> SEQ ID NO 29
<211> LENGTH: 2732
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29
tggaatctca ctatgcacca atgtggtact aaattatatc tttatctatg gaaaattagg 60
ttttccgcga atggagatag agggagctgc cattgctact ttaatttgta gaattcttga 120
gagtatttta gttgttattt atatgtataa gggtgagaag gtacttaaga tgagactttc 180
ttatattttt aagagatcta aacagtattt tcgctctttg gctcgttata gtgcgccagt 240
gcttatgagt gaggttaact gggggcttgg gattgctgtt cagtctgcaa tcattgggcg 300
tatgggtgtt agttttctta cagccgccag cttcattaat gtagtacaac agttagccgg 360
aatcattctg attggtattg gtgtgggttc gagcattata atagggaatt tgattggtga 420
gggaaaagag catgaggcga gaatgctagc caataagtta atacgtatca gtatgatact 480
cggaggaatt gttgcttttg cagtaatctt actacgtcca atcgctccta actttattga 540
ggcgtctaag gaaacagcgg atttaattcg tcagatgcta tttgtttcgg cttacctctt 600
attcttccaa gccttatctg tattaactat ggccggaata ttacgtggtg caggggatac 660
cctttactgt gcaacctttg atgttttgac cttatgggta ctaaaacttg gaggaggttt 720
gcttgcaacc atagtacttc atcttccacc tgtatgggtt tactttatct taagtagcga 780
tgagtgtgtt aaagcgctat ttacggtacc gcgggtctta aagggacgtt ggattcatga 840
tacaacactg cattaagatt tcatatgtcc agatattttt gcacagtagc ataattacta 900
gagcttattc ctataatatt cataggtttt gatggtccat tttacgttac gatagcatat 960
attacatcaa aaccaattct atataagatg aggttatagt atgaacgaga aaaatataaa 1020
acacagtcaa aactttatta cttcaaaaca taatatagat aaaataatga caaatataag 1080
attaaatgaa catgataata tctttgaaat cggctcagga aaagggcatt ttacccttga 1140
attagtacag aggtgtaatt tcgtaactgc cattgaaata gaccataaat tatgcaaaac 1200
tacagaaaat aaacttgttg atcacgataa tttccaagtt ttaaacaagg atatattgca 1260
gtttaaattt cctaaaaacc aatcctataa aatatttggt aatatacctt ataacataag 1320
tacggatata atacgcaaaa ttgtttttga tagtatagct gatgagattt atttaatcgt 1380
ggaatacggg tttgctaaaa gattattaaa tacaaaacgc tcattggcat tatttttaat 1440
ggcagaagtt gatatttcta tattaagtat ggttccaaga gaatattttc atcctaaacc 1500
taaagtgaat agctcactta tcagattaaa tagaaaaaaa tcaagaatat cacacaaaga 1560
taaacagaag tataattatt tcgttatgaa atgggttaac aaagaataca agaaaatatt 1620
tacaaaaaat caatttaaca attccttaaa acatgcagga attgacgatt taaacaatat 1680
tagctttgaa caattcttat ctcttttcaa tagctataaa ttatttaata agaagtaata 1740
ggaaataata ctcgaattat tctgcaatct gttctaaaaa ataaaattaa gaaattacta 1800
tagcaagcca ggttaaaatt actagcttgc tatttttgtg catttagtac agttttgatt 1860
attaaagaat aaatttaata actattttgc aataagttat tgactatttc acaagttagt 1920
gttactatac aagtatgaaa taaagataca taaaaaaata aataatatga aacataaatt 1980
catgacatgc ggaatagaat gaaagaatat tatgtcggtt cctaatacta aatggatata 2040
acaatctatt gaaacactta tggggtgtaa gtgtggagag aatttctaaa gcgccaaaag 2100
actctacata tgaaattcta aagcttcaca cgggaataat ctaatttatg tatcttatta 2160
tcataattca ggaaggtagt gtgaaaatat aaaaattagt tttcctgttt cattcaggca 2220
gtagcatttc ttaaacaaat ttgctatgca ttgggtgtta tctgaaaaac aaaaagcaat 2280
tttctcacaa cttatttctg aacaacaatg gtattaaaaa tttggaggag gattttacta 2340
tgaaaaaaac ggtaacatta ctgttggttc tgaccatggt ggtaagctta tttgcagcat 2400
gtggtaagaa aaatggatca agcgaaaccg gcacaaaaga tcctgtggca acaagcggtg 2460
caaaagaacc tgacaaacaa gatccaggca ataaagagcc tgaaaaacaa gaccctgtta 2520
aaatcaagat ttattactct gataatgcaa ccttaccatt taaagaagat tggttagtta 2580
taaaggaagc tgagaagaga tttaatgttg atttcgattt cgaagtaatt ccaattgcag 2640
attatcaaac aaaagtttct ttaacattaa atacaggaaa taacgctcca gatgtcatcc 2700
tttatcagtc aacgcaggga gagaatgcat ct 2732

<210> SEQ ID NO 30
<211> LENGTH: 10665
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1522)..(1522)
<223> OTHER INFORMATION: a, c, g or t

<400> SEQUENCE: 30
gaattcgagc tcggtacccg gggatcctct agagtcgacc tgcaggcatg caagcttggc 60
actggccgtc gttttacaac gtcgtgactg ggaaaaccct ggcgttaccc aacttaatcg 120
ccttgcagca catccccctt tcgccagctg gcgtaatagc gaagaggccc gcaccgcgta 180
gaggatcgag atctcgatcc cgcgaaatta atacgactca ctatagggga attgtgagcg 240
gataacaatt cccctctagg ctcataactt cacgctcctg tatatatttt tatttattta 300
aaaatgagtc aaaatttagg aaatgattgc aatatgtata atatccaaat ttccattcaa 360
ataaccaaag taattttacc tctttttatg agctatttca atactttgtt agtaaattaa 420
catatatgag ctgtatatgg tttaatgaaa aaagttattt tgaagggata ttgtaaaaaa 480
cataatatat tatatggata aattttacat ttgacttatc atatgttaat atatgtaata 540
tgaatagcta atctaagcag gctactgcct agaaaaaagc ttataattat ccttaatttc 600
ctactacgtg cgcccagata gggtgttaag tcaagtagtt taaggtacta ctctgtaaga 660
taacacagaa aacagccaac ctaaccgaaa agcgaaagct gatacgggaa cagagcacgg 720
ttggaaagcg atgagttacc taaagacaat cgggtacgac tgagtcgcaa tgttaatcag 780
atataaggta taagttgtgt ttactgaacg caagtttcta atttcggttg aaatccgata 840
gaggaaagtg tctgaaacct ctagtacaaa gaaaggtaag ttacagtagt agacttatct 900
gttatcacca catttgtaca atctgtagga gaacctatgg gaacgaaacg aaagcgatgc 960
cgagaatctg aatttaccaa gacttaacac taactgggga taccctaaac aagaatgcct 1020
aatagaaagg aggaaaaagg ctatagcact agagcttgaa aatcttgcaa gggtacggag 1080
tactcgtagt agtctgagaa gggtaacgcc ctttacatgg caaaggggta cagttattgt 1140

-continued

```
gtactaaaat taaaaattga ttagggagga aaacctcaaa atgaaaccaa caatggcaat   1200
tttagaaaga atcagtaaaa attcacaaga aaatatagac gaagttttta caagacttta   1260
tcgttatctt ttacgtccag atatttatta cgtggcgacg cgttgggaaa tggcaatgat   1320
agcgaaacaa cgtaaaactc ttgttgtatg ctttcattgt catcgtcacg tgattcataa   1380
acacaagtga atgtcgacag tgaattttta cgaacgaaca ataacagagc cgtatactcc   1440
gagaggggta cgtacggttc ccgaagaggg tggtgcaaac cagtcacagt aatgtgaaca   1500
aggcggtacc tccctacttc ancatatcat tttctgcagc cccctagaaa taattttgtt   1560
taactttaag aaggagatat acatatatgg ctagatcgtc cattccgaca gcatcgccag   1620
tcactatggc gtgctgctag cgctatatgc gttgatgcaa tttctatgca ctcgtagtag   1680
tctgagaagg gtaacgccct ttacatggca aaggggtaca gttattgtgt actaaaatta   1740
aaaattgatt agggaggaaa acctcaaaat gaaaccaaca atggcaattt tagaaagaat   1800
cagtaaaaat tcacaagaaa atatagacga agtttttaca agactttatc gttatctttt   1860
acgtccagat atttattacg tggcgtatca aaatttatat tccaataaag gagcttccac   1920
aaaaggaata ttagatgata cagcggatgg ctttagtgaa gaaaaaataa aaaagattat   1980
tcaatcttta aaagacggaa cttactatcc tcaacctgta cgaagaatgt atattgcaaa   2040
aaagaattct aaaaagatga gacctttagg aattccaact ttcacagata aattgatcca   2100
agaagctgtg agaataattc ttgaatctat ctatgaaccg gtattcgaag atgtgtctca   2160
cggttttaga cctcaacgaa gctgtcacac agctttgaaa acaatcaaaa gagagtttgg   2220
cggcgcaaga tggtttgtgg agggagatat aaaaggctgc ttcgataata tagaccacgt   2280
tacactcatt ggactcatca atcttaaaat caaagatatg aaaatgagcc aattgattta   2340
taaatttcta aaagcaggtt atctggaaaa ctggcagtat cacaaaactt acagcggaac   2400
acctcaaggt ggaattctat ctcctctttt ggccaacatc tatcttcatg aattggataa   2460
gtttgtttta caactcaaaa tgaagtttga ccgagaaagt ccagaaagaa taacacctga   2520
atatcgggag ctccacaatg agataaaaag aatttctcac cgtctcaaga agttggaggg   2580
tgaagaaaaa gctaaagttc ttttagaata tcaagaaaaa cgtaaaagat tacccacact   2640
cccctgtacc tcacagacaa ataaagtatt gaaatacgtc cggtatgcgg acgacttcat   2700
tatctctgtt aaaggaagca aagaggactg tcaatggata aaagaacaat taaaactttt   2760
tattcataac aagctaaaaa tggaattgag tgaagaaaaa acactcatca cacatagcag   2820
tcaacccgct cgttttctgg gatatgatat acgagtaagg agatctggaa cgataaaacg   2880
atctggtaaa gtcaaaaaga gaacactcaa tgggagtgta gaactcctta ttcctcttca   2940
agacaaaatt cgtcaattta tttttgacaa gaaaatagct atccaaaaga aagatagctc   3000
atggtttcca gttcacagga aatatcttat tcgttcaaca gacttagaaa tcatcacaat   3060
ttataattct gaactccgcg ggatttgtaa ttactacggt ctagcaagta attttaacca   3120
gctcaattat tttgcttatc ttatggaata cagctgtcta aaaacgatag cctccaaaca   3180
taagggaaca ctttcaaaaa ccatttccat gtttaaagat ggaagtggtt cgtgggggat   3240
cccgtatgag ataaagcaag gtaagcagcg ccgttatttt gcaaatttta gtgaatgtaa   3300
atccccttat caatttacgg atgagataag tcaagctcct gtattgtatg gctatgcccg   3360
gaatactctt gaaaacaggt taaaagctaa atgttgtgaa ttatgtggga cgtctgatga   3420
aaatacttcc tatgaaattc accatgtcaa taaggtcaaa aatcttaaag gcaaagaaaa   3480
atgggaaatg gcaatgatag cgaaacaacg taaaactctt gttgtatgct ttcattgtca   3540
```

tcgtcacgtg attcataaac acaagtgaga tatctcgagc acccgttctc ggagcactgt 3600
ccgaccgctt tggccgccgc ccagtcctgc tcgcttcgct acttggagcc actatcgact 3660
acgcgatcat ggcgaccaca cccgtcctgt ggatcgccaa gctcgccgat ggtagtgtgg 3720
ggtctcccca tgcgagagta gggaactgcc aggcatcaaa taaaacgaaa ggctcagtcg 3780
aaagactggg cctttcgttt tatctgttgt ttgtcggtga acgctctcct gagtaggaca 3840
aatccgccgg gagcggattt gaacgttgcg aagcaacggc ccggagggtg gcgggcagga 3900
cgcccgccat aaactgccag gcatcaaatt aagcagaagg ccatcctgac ggatggcctt 3960
tttgcgtttc tacaaactct tcctgtcgtc atatctacaa gccatcccgc ccttcccaac 4020
agttgcgcag cctgaatggc gaatggcgcc tgatgcggta ttttctcctt acgcatctgt 4080
gcggtatttc acaccgcata tggtgcactc tcagtacaat ctgctctgat gccgcatagt 4140
taagccagcc ccgacacccg ccaacacccg ctgacgcgcc ctgacgggct tgtctgctcc 4200
cggcatccgc ttacagacaa gctgtgaccg tctccgggag ctgcatgtgt cagaggtttt 4260
caccgtcatc accgaaacgc gcgagacgaa agggcctcgt gatacgccta tttttatagg 4320
ttaatgtcat gataataatg gtttcttaga cgtcaggtgg cacttttcgg ggaaatgtgc 4380
gcggaacccc tatttgttta tttttctaaa tacattcaaa tatgtatccg ctcatgagac 4440
aataaccctg ataaatgctt caataatatt gaaaaaggaa gagtatgagt attcaacatt 4500
tccgtgtcgc ccttattccc ttttttgcgg cattttgcct tcctgttttt gctcacccag 4560
aaacgctggt gaaagtaaaa gatgctgaag atcagttggg tgcacgagtg ggttacatcg 4620
aactggatct caacagcggt aagatccttg agagttttcg ccccgaagaa cgttttccaa 4680
tgatgagcac ttttaaatta aaaatgaagt tttaaaactt catttttaat ttaaattaaa 4740
aatgaagttt tatcaaaaaa atttccaata atcccactct aagccacaaa cacgccctat 4800
aaaatcccgc tttaatccca ctttgagaca catgtaatat tactttacgc cctagtatag 4860
tgataatttt ttacattcaa tgccacgcaa aaaaataaag gggcactata ataaaagttc 4920
cttcggaact aactaaagta aaaaattatc tttacaacct ccccaaaaaa aagaacaggt 4980
acaaagtacc ctataataca agcgtaaaaa aatgagggta aaaataaaaa aataaaaaaa 5040
taaaaaaata aaaaaataaa aaaaataaaa aaataaaaaa ataaaaaaat aaaaaaataa 5100
aaaaataaaa aaataaaaaa ataaaaaaat ataaaaataa aaaaatataa aaataaaaaa 5160
atataaaaat aaaaaaatat aaaaataaaa aaataaaaaa atataaaaat aaaaaaataa 5220
aaaaatataa aaatattttt tatttaaagt ttgaaaaaaa tttttttata ttatataatc 5280
tttgaagaaa agaatataaa aaatgagcct ttataaaagc ccattttttt tcatatacgt 5340
aatatgacgt tctaatgttt ttattggtac ttctaacatt agagtaattt ctttattttt 5400
aaagcctttt tctttaaggg cttttatttt ttttcttaat acatttaatt cctctttttt 5460
tgttgctttt cctttagctt ttaattgctc ttgataattt tttttacctc taatattttc 5520
tcttctctta tattcctttt tagaaattat tattgtcata tatttttgtt cttcttctgt 5580
aatttctaat aactctataa gagtttcatt cttatactta tattgcttat ttttatctaa 5640
ataacatctt tcagcacttc tagttgctct tataacttct ctttcactta aatgttgtct 5700
aaacatacta ttaagttcta aaacatcatt taatgccttc tcaatgtctt ctgtaaagct 5760
acaaagataa tatctatata aaaataatat aagctctctg tgtcctttta aatcatattc 5820
tcttagttca caaagtttta ttatgtcttg tattcttcca taatataaac ttctttctct 5880
ataaatataa tttattttgc ttggtctacc ctttttcctt tcatatggtt ttaattcagg 5940

```
taaaaatcca ttttgtattt ctcttaagtc ataaatatat tcgtactcat ctaatatatt   6000
gactactgtt tttgatttag agtttatact tcctggaact cttaatattc tggttgcatc   6060
taaggcttgt ctatctgctc caaagtattt taattgatta tataaatatt cttgaaccgc   6120
tttccataat ggtaatgctt tactaggtac tgcatttatt atccatatta aatacattcc   6180
tcttccacta tctattacat agtttggtat aggaatactt tgattaaaat aattcttttc   6240
taagtccatt aatacctggt ctttagtttt gccagtttta taataatcca agtctataaa   6300
cagtgtattt aactctttta tattttctaa tcgcctacac ggcttataaa aggtatttag   6360
agttatatag atattttcat cactcatatc taaatctttt aattcagcgt atttatagtg   6420
ccattggcta tatccttttt tatctataac gctcctggtt atccaccctt tacttctact   6480
atgaatatta tctatatagt tctttttatt cagctttaat gcgtttctca cttattcacc   6540
tccccttctg taaaactaag aaaattatat catattttca ataattatta actattctta   6600
aactcttaat aaaaaataga gtaagtcccc aattgaaact taatctattt tttatgtttt   6660
aatttattat ttttattaaa atattttaaa ctaaattaaa tgattctttt taattttta    6720
ctatttcatt ccataatata ttactataat tatttacaaa taatatttct tcatttgtaa   6780
tatttagatg atttactaat tttagttttt atatattaaa taattaatgt ataatttata   6840
taaaaaatca aaggagctta taaattatga ttatttccaa agatactaaa gatttaattt   6900
tttcaatttt aacaatactt tttgtaatat tatgtttaaa tttaattgta tttttttcat   6960
ataataaagc cgttgaagta aaccaatcca ttttccttat gatgttatta ttaaatttaa   7020
gttttataat aatatcttta ttatatttat tgtttttaaa aaaactagtg aaatttccgg   7080
ctttattaaa cttattttta ggaattttat tttcattttc atctttacag gatttgatta   7140
tatctttaaa tatgttttat caaatattat ctttttctaa atttatatat atttttatta   7200
tatttattat tatatatatt ttatttttaa gtttctttct aacagctatt aaaaagaaac   7260
ttaaaaataa aaacacgtac tctaaaccaa taaataaaac tatttttatt attgctgcct   7320
tgattggaat agtttttagt aaaattaatt tcaatattcc acaatattat attataagct   7380
agctttgcat tgtacttttc aatcgcttca cgaatgcggt tatctccgaa agataaagtc   7440
ttttcatctt ccttgatgaa gataagattt tctccgtctc cgccggcaga attgaagcgg   7500
ggtactacgg tatcgtctgc gtcatcttcc gttgtctgat agatgatagt cataggctca   7560
ttttcttccg tttcggtaaa ggggataggt tcgccctttg agagcagggc ggcgatggaa   7620
agcattaact tgcttttccc atcgcccgga tctccctgca atagcgtaac tttgccaaac   7680
ggaatatacg gataccacag ccactttact tctttcggct cgatttcact tgccttgatg   7740
atttcaagag gtacgctgaa attcatttcg ttttcattta gtttcatttt ttcttgttct   7800
ccttttctct gaaaatataa aaaccacaga ttgatactaa aaccttggtt gtgttgcttt   7860
tcggggctta aatcaaggaa aaatccttgt tttaagcctt tcaaaaagaa acacaaggtc   7920
tttgtactaa cctgtggtta tgtataaaat tgtagatttt agggtaacaa aaaacaccgt   7980
atttctacga tgtttttgct taaatacttg tttttagtta cagacaaacc tgaagttgaa   8040
ttcatattta ttaaattaag cgtatatact attgaaaatg tttttgaaat attataaaat   8100
taactttggt ttaggaaaag taaccagttc ttttgtcgat aagcattaat ttgcttgact   8160
aattaataaa aaacttagga ggtaacacta atggtattcg agaaaattga caagaacagt   8220
tggaacagaa aagaatactt tgatcactat tttgctagtg taccttgcac atacagtatg   8280
actgtaaagg ttgatataac acagattaaa gagaagggaa tgaaattgta ccctgcaatg   8340
```

```
ctttattaca tagcaatgat agtaaacaga catagtgaat ttaggaccgc tatcaatcag   8400
gatggtgaac ttggaattta tgatgaaatg attccatcat atactatatt ccataatgac   8460
accgagacat tctcaagtct ttggactgaa tgcaagtcag attttaagtc atttcttgca   8520
gattatgaat ctgatactca aagatacggt aataatcacc gtatggaagg aaaacctaat   8580
gcacctgaga atattttcaa tgtttccatg ataccttggt caacatttga cggatttaat   8640
ctgaatctgc aaaaaggcta cgattactta atccctatct ttacaatggg caagtattat   8700
aaggaagaca ataaaatcat ccttcccctt gcaatccagg tacatcatgc agtatgtgat   8760
ggatttcata tttgtcgttt tgtaaatgaa ctgcaagaat taataaattc ctaactcgag   8820
ggcagtagcg cggtggtccc acctgacccc atgccgaact cagaagtgaa acgataaaac   8880
gaaaggctca gtcgaaagac tgggcctttc gttttatctg ttgtttgtcg gtgaacgctc   8940
tcctgagtag gacaaatccg ccgggagcgg atttgaacgt tgcgaagcaa cggcccggag   9000
ggtggcgggc aggacgcccg ccataaactg ccaggcatca aattaagcag aaggccatcc   9060
tgacggatgg cctttttat tgtaaattcc ggtaaccctt gtagcttagt gggaatttgt   9120
accccttatc gatacaaatt ccccgtaggc gctagggaca ctttttcact cgttaaaaag   9180
ttttgagaat attttatatt tttgttcatg taatcactcc ttcttaatta caaattttta   9240
gcatctaatt taacttcaat tcctattata caaaatttta agatactgca ctatcaacac   9300
actcttaagt ttgcttctaa gtcttatttc cataacttct tttacgtttc cgggtacaat   9360
tcgtaatcat gtcatagctg tttcctgtgt gaaattctta tccgctcaca attccacaca   9420
acatacgagc cggaagcata aagtgtaaag cctggggtgc ctaatgagtg agctaactca   9480
cattaattgc gttgcgctca ctgcccgctt tccagtcggg aaacctgtcg tgccagaaaa   9540
cttcattttt aatttaaaag gatctaggtg aagatccttt ttgataatct catgaccaaa   9600
atcccttaac gtgagttttc gttccactga gcgtcagacc ccgtagaaaa gatcaaagga   9660
tcttcttgag atcctttttt tctgcgcgta atctgctgct tgcaaacaaa aaaaccaccg   9720
ctaccagcgg tggtttgttt gccggatcaa gagctaccaa ctctttttcc gaaggtaact   9780
ggcttcagca gagcgcagat accaaatact gtccttctag tgtagccgta gttaggccac   9840
cacttcaaga actctgtagc accgcctaca tacctcgctc tgctaatcct gttaccagtg   9900
gctgctgcca gtggcgataa gtcgtgtctt accgggttgg actcaagacg atagttaccg   9960
gataaggcgc agcggtcggg ctgaacgggg ggttcgtgca cacagcccag cttggagcga  10020
acgacctaca ccgaactgag atacctacag cgtgagctat gagaaagcgc cacgcttccc  10080
gaagggagaa aggcggacag gtatccggta agcggcaggg tcggaacagg agagcgcacg  10140
agggagcttc caggggggaaa cgcctggtat ctttatagtc ctgtcgggtt tcgccacctc  10200
tgacttgagc gtcgattttt gtgatgctcg tcaggggggc ggagcctatg gaaaaacgcc  10260
agcaacgcgg cctttttacg gttcctggcc ttttgctggc cttttgctca catgttcttt  10320
cctgcgttat cccctgattc tgtggataac cgtattaccg cctttgagtg agctgatacc  10380
gctcgccgca gccgaacgac cgagcgcagc gagtcagtga gcgaggaagc ggaagagcgc  10440
ccaatacgca aaccgcctct ccccgcgcgt tggccgattc attaatgcag ctggcacgac  10500
aggtttcccg actggaaagc gggcagtgag cgcaacgcaa ttaatgtgag ttagctcact  10560
cattaggcac cccaggcttt acactttatg cttccggctc gtatgttgtg tggaattgtg  10620
agcggataac aatttcacac aggaaacagc tatgaccatg attac                  10665
```

<210> SEQ ID NO 31
<211> LENGTH: 10665
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1522)..(1522)
<223> OTHER INFORMATION: a, c, g or t

<400> SEQUENCE: 31
gaattcgagc tcggtacccg gggatcctct agagtcgacc tgcaggcatg caagcttggc 60
actggccgtc gttttacaac gtcgtgactg ggaaaaccct ggcgttaccc aacttaatcg 120
ccttgcagca catccccctt tcgccagctg gcgtaatagc gaagaggccc gcaccgcgta 180
gaggatcgag atctcgatcc cgcgaaatta atacgactca ctatagggga attgtgagcg 240
gataacaatt cccctctagg ctcataactt cacgctcctg tatatatttt tatttattta 300
aaaatgagtc aaaatttagg aaatgattgc aatatgtata atatccaaat ttccattcaa 360
ataaccaaag taattttacc tctttttatg agctatttca atactttgtt agtaaattaa 420
catatatgag ctgtatatgg tttaatgaaa aaagttattt tgaagggata ttgtaaaaaa 480
cataatatat tatatggata aattttacat ttgacttatc atatgttaat atatgtaata 540
tgaatagcta atctaagcag gctactgcct agaaaaaagc ttataattat ccttagctct 600
cttcaatgtg cgcccagata gggtgttaag tcaagtagtt taaggtacta ctctgtaaga 660
taacacagaa aacagccaac ctaaccgaaa agcgaaagct gatacgggaa cagagcacgg 720
ttggaaagcg atgagttacc taaagacaat cgggtacgac tgagtcgcaa tgttaatcag 780
atataaggta taagttgtgt ttactgaacg caagtttcta atttcgatta gagctcgata 840
gaggaaagtg tctgaaacct ctagtacaaa gaaaggtaag ttatcattga agacttatct 900
gttatcacca catttgtaca atctgtagga gaacctatgg gaacgaaacg aaagcgatgc 960
cgagaatctg aatttaccaa gacttaacac taactgggga taccctaaac aagaatgcct 1020
aatagaaagg aggaaaaagg ctatagcact agagcttgaa aatcttgcaa gggtacggag 1080
tactcgtagt agtctgagaa gggtaacgcc ctttacatgg caaaggggta cagttattgt 1140
gtactaaaat taaaaattga ttagggagga aaacctcaaa atgaaaccaa caatggcaat 1200
tttagaaaga atcagtaaaa attcacaaga aaatatagac gaagttttta caagacttta 1260
tcgttatctt ttacgtccag atatttatta cgtggcgacg cgttgggaaa tggcaatgat 1320
agcgaaacaa cgtaaaactc ttgttgtatg ctttcattgt catcgtcacg tgattcataa 1380
acacaagtga atgtcgacag tgaattttta cgaacgaaca ataacagagc cgtatactcc 1440
gagaggggta cgtacggttc ccgaagaggg tggtgcaaac cagtcacagt aatgtgaaca 1500
aggcggtacc tccctacttc ancatatcat tttctgcagc cccctagaaa taattttgtt 1560
taactttaag aaggagatat acatatatgg ctagatcgtc cattccgaca gcatcgccag 1620
tcactatggc gtgctgctag cgctatatgc gttgatgcaa tttctatgca ctcgtagtag 1680
tctgagaagg gtaacgccct ttacatggca aaggggtaca gttattgtgt actaaaatta 1740
aaaattgatt agggaggaaa acctcaaaat gaaaccaaca atggcaattt tagaaagaat 1800
cagtaaaaat tcacaagaaa atatagacga agtttttaca agactttatc gttatctttt 1860
acgtccagat atttattacg tggcgtatca aaatttatat tccaataaag gagcttccac 1920
aaaaggaata ttagatgata cagcggatgg ctttagtgaa gaaaaaataa aaaagattat 1980

-continued

```
tcaatcttta aaagacggaa cttactatcc tcaacctgta cgaagaatgt atattgcaaa   2040
aaagaattct aaaaagatga gacctttagg aattccaact ttcacagata aattgatcca   2100
agaagctgtg agaataattc ttgaatctat ctatgaaccg gtattcgaag atgtgtctca   2160
cggttttaga cctcaacgaa gctgtcacac agctttgaaa acaatcaaaa gagagtttgg   2220
cggcgcaaga tggtttgtgg agggagatat aaaaggctgc ttcgataata tagaccacgt   2280
tacactcatt ggactcatca atcttaaaat caaagatatg aaaatgagcc aattgattta   2340
taaatttcta aaagcaggtt atctggaaaa ctggcagtat cacaaaactt acagcggaac   2400
acctcaaggt ggaattctat ctcctctttt ggccaacatc tatcttcatg aattggataa   2460
gtttgtttta caactcaaaa tgaagtttga ccgagaaagt ccagaaagaa taacacctga   2520
atatcgggag ctccacaatg agataaaaag aatttctcac cgtctcaaga agttggaggg   2580
tgaagaaaaa gctaaagttc ttttagaata tcaagaaaaa cgtaaaagat tacccacact   2640
cccctgtacc tcacagacaa ataaagtatt gaaatacgtc cggtatgcgg acgacttcat   2700
tatctctgtt aaaggaagca aagaggactg tcaatggata aaagaacaat taaaactttt   2760
tattcataac aagctaaaaa tggaattgag tgaagaaaaa acactcatca cacatagcag   2820
tcaacccgct cgttttctgg gatatgatat acgagtaagg agatctggaa cgataaaacg   2880
atctggtaaa gtcaaaaaga gaacactcaa tgggagtgta gaactcctta ttcctcttca   2940
agacaaaatt cgtcaattta tttttgacaa gaaaatagct atccaaaaga aagatagctc   3000
atggtttcca gttcacagga aatatcttat tcgttcaaca gacttagaaa tcatcacaat   3060
ttataattct gaactccgcg ggatttgtaa ttactacggt ctagcaagta attttaacca   3120
gctcaattat tttgcttatc ttatggaata cagctgtcta aaaacgatag cctccaaaca   3180
taagggaaca ctttcaaaaa ccatttccat gtttaaagat ggaagtggtt cgtgggggat   3240
cccgtatgag ataaagcaag gtaagcagcg ccgttatttt gcaaatttta gtgaatgtaa   3300
atccccttat caatttacgg atgagataag tcaagctcct gtattgtatg gctatgcccg   3360
gaatactctt gaaaacaggt taaaagctaa atgttgtgaa ttatgtggga cgtctgatga   3420
aaatacttcc tatgaaattc accatgtcaa taaggtcaaa aatcttaaag gcaaagaaaa   3480
atgggaaatg gcaatgatag cgaaacaacg taaaactctt gttgtatgct ttcattgtca   3540
tcgtcacgtg attcataaac acaagtgaga tatctcgagc acccgttctc ggagcactgt   3600
ccgaccgctt tggccgccgc ccagtcctgc tcgcttcgct acttggagcc actatcgact   3660
acgcgatcat ggcgaccaca cccgtcctgt ggatcgccaa gctcgccgat ggtagtgtgg   3720
ggtctcccca tgcgagagta gggaactgcc aggcatcaaa taaaacgaaa ggctcagtcg   3780
aaagactggg cctttcgttt tatctgttgt ttgtcggtga acgctctcct gagtaggaca   3840
aatccgccgg gagcggattt gaacgttgcg aagcaacggc ccggagggtg gcgggcagga   3900
cgcccgccat aaactgccag gcatcaaatt aagcagaagg ccatcctgac ggatggcctt   3960
tttgcgtttc tacaaactct tcctgtcgtc atatctacaa gccatcccgc ccttcccaac   4020
agttgcgcag cctgaatggc gaatggcgcc tgatgcggta ttttctcctt acgcatctgt   4080
gcggtatttc acaccgcata tggtgcactc tcagtacaat ctgctctgat gccgcatagt   4140
taagccagcc ccgacacccg ccaacacccg ctgacgcgcc ctgacgggct tgtctgctcc   4200
cggcatccgc ttacagacaa gctgtgaccg tctccgggag ctgcatgtgt cagaggtttt   4260
caccgtcatc accgaaacgc gcgagacgaa agggcctcgt gatacgccta tttttatagg   4320
ttaatgtcat gataataatg gtttcttaga cgtcaggtgg cacttttcgg ggaaatgtgc   4380
```

```
gcggaacccc tatttgttta tttttctaaa tacattcaaa tatgtatccg ctcatgagac   4440
aataaccctg ataaatgctt caataatatt gaaaaaggaa gagtatgagt attcaacatt   4500
tccgtgtcgc ccttattccc ttttttgcgg cattttgcct tcctgttttt gctcacccag   4560
aaacgctggt gaaagtaaaa gatgctgaag atcagttggg tgcacgagtg ggttacatcg   4620
aactggatct caacagcggt aagatccttg agagttttcg ccccgaagaa cgttttccaa   4680
tgatgagcac ttttaaatta aaaatgaagt tttaaaactt catttttaat ttaaattaaa   4740
aatgaagttt tatcaaaaaa atttccaata atcccactct aagccacaaa cacgccctat   4800
aaaatcccgc tttaatccca ctttgagaca catgtaatat tactttacgc cctagtatag   4860
tgataatttt ttacattcaa tgccacgcaa aaaaataaag gggcactata ataaaagttc   4920
cttcggaact aactaaagta aaaaattatc tttacaacct ccccaaaaaa aagaacaggt   4980
acaaagtacc ctataataca agcgtaaaaa aatgagggta aaaataaaaa aataaaaaaa   5040
taaaaaaata aaaaaataaa aaaaataaaa aaataaaaaa ataaaaaaat aaaaaaataa   5100
aaaaataaaa aaataaaaaa ataaaaaaat ataaaaataa aaaaatataa aaataaaaaa   5160
atataaaaat aaaaaaatat aaaaataaaa aaataaaaaa atataaaaat aaaaaaataa   5220
aaaaatataa aaatattttt tatttaaagt ttgaaaaaaa tttttttata ttatataatc   5280
tttgaagaaa agaatataaa aaatgagcct ttataaaagc ccattttttt tcatatacgt   5340
aatatgacgt tctaatgttt ttattggtac ttctaacatt agagtaattt ctttattttt   5400
aaagcctttt tctttaaggg cttttatttt ttttcttaat acatttaatt cctctttttt   5460
tgttgctttt cctttagctt ttaattgctc ttgataattt tttttacctc taatattttc   5520
tcttctctta tattcctttt tagaaattat tattgtcata tatttttgtt cttcttctgt   5580
aatttctaat aactctataa gagtttcatt cttatactta tattgcttat ttttatctaa   5640
ataacatctt tcagcacttc tagttgctct tataacttct ctttcactta aatgttgtct   5700
aaacatacta ttaagttcta aaacatcatt taatgccttc tcaatgtctt ctgtaaagct   5760
acaaagataa tatctatata aaaataatat aagctctctg tgtcctttta aatcatattc   5820
tcttagttca caaagtttta ttatgtcttg tattcttcca taatataaac ttctttctct   5880
ataaatataa tttattttgc ttggtctacc ctttttcctt tcatatggtt ttaattcagg   5940
taaaaatcca ttttgtattt ctcttaagtc ataaatatat tcgtactcat ctaatatatt   6000
gactactgtt tttgatttag agtttatact tcctggaact cttaatattc tggttgcatc   6060
taaggcttgt ctatctgctc caaagtattt taattgatta tataaatatt cttgaaccgc   6120
tttccataat ggtaatgctt tactaggtac tgcatttatt atccatatta aatacattcc   6180
tcttccacta tctattacat agtttggtat aggaatactt tgattaaaat aattcttttc   6240
taagtccatt aatacctggt ctttagtttt gccagtttta taataatcca agtctataaa   6300
cagtgtattt aactctttta tattttctaa tcgcctacac ggcttataaa aggtatttag   6360
agttatatag atattttcat cactcatatc taaatctttt aattcagcgt atttatagtg   6420
ccattggcta tatccttttt tatctataac gctcctggtt atccaccctt tacttctact   6480
atgaatatta tctatatagt tctttttatt cagctttaat gcgtttctca cttattcacc   6540
tccccttctg taaaactaag aaaattatat catattttca ataattatta actattctta   6600
aactcttaat aaaaaataga gtaagtcccc aattgaaact taatctattt tttatgtttt   6660
aatttattat ttttattaaa atattttaaa ctaaattaaa tgattctttt taattttta    6720
ctatttcatt ccataatata ttactataat tatttacaaa taatatttct tcatttgtaa   6780
```

-continued

```
tatttagatg atttactaat tttagttttt atatattaaa taattaatgt ataatttata   6840
taaaaaatca aaggagctta taaattatga ttatttccaa agatactaaa gatttaattt   6900
tttcaatttt aacaatactt tttgtaatat tatgtttaaa tttaattgta ttttttttcat  6960
ataataaagc cgttgaagta aaccaatcca ttttccttat gatgttatta ttaaatttaa   7020
gttttataat aatatcttta ttatatttat tgtttttaaa aaaactagtg aaatttccgg   7080
ctttattaaa cttattttta ggaattttat tttcattttc atctttacag gatttgatta   7140
tatctttaaa tatgttttat caaatattat ctttttctaa atttatatat atttttatta   7200
tatttattat tatatatatt ttatttttaa gtttctttct aacagctatt aaaaagaaac   7260
ttaaaaataa aaacacgtac tctaaaccaa taaataaaac tatttttatt attgctgcct   7320
tgattggaat agtttttagt aaaattaatt tcaatattcc acaatattat attataagct   7380
agctttgcat tgtacttttc aatcgcttca cgaatgcggt tatctccgaa agataaagtc   7440
ttttcatctt ccttgatgaa gataagattt tctccgtctc cgccggcaga attgaagcgg   7500
ggtactacgg tatcgtctgc gtcatcttcc gttgtctgat agatgatagt cataggctca   7560
ttttcttccg tttcggtaaa ggggataggt tcgccctttg agagcagggc ggcgatggaa   7620
agcattaact tgcttttccc atcgcccgga tctccctgca atagcgtaac tttgccaaac   7680
ggaatatacg gataccacag ccactttact tctttcggct cgatttcact tgccttgatg   7740
atttcaagag gtacgctgaa attcatttcg ttttcattta gtttcatttt ttcttgttct   7800
ccttttctct gaaaatataa aaaccacaga ttgatactaa aaccttggtt gtgttgcttt   7860
tcggggctta aatcaaggaa aaatccttgt tttaagcctt tcaaaaagaa acacaaggtc   7920
tttgtactaa cctgtggtta tgtataaaat tgtagatttt agggtaacaa aaaacaccgt   7980
atttctacga tgtttttgct taaatacttg tttttagtta cagacaaacc tgaagttgaa   8040
ttcatattta ttaaattaag cgtatatact attgaaaatg tttttgaaat attataaaat   8100
taactttggt ttaggaaaag taaccagttc ttttgtcgat aagcattaat ttgcttgact   8160
aattaataaa aaacttagga ggtaacacta atggtattcg agaaaattga caagaacagt   8220
tggaacagaa aagaatactt tgatcactat tttgctagtg taccttgcac atacagtatg   8280
actgtaaagg ttgatataac acagattaaa gagaagggaa tgaaattgta ccctgcaatg   8340
ctttattaca tagcaatgat agtaaacaga catagtgaat ttaggaccgc tatcaatcag   8400
gatggtgaac ttggaattta tgatgaaatg attccatcat atactatatt ccataatgac   8460
accgagacat tctcaagtct ttggactgaa tgcaagtcag attttaagtc atttcttgca   8520
gattatgaat ctgatactca aagatacggt aataatcacc gtatggaagg aaaacctaat   8580
gcacctgaga atattttcaa tgtttccatg ataccttggt caacatttga cggatttaat   8640
ctgaatctgc aaaaaggcta cgattactta atccctatct ttacaatggg caagtattat   8700
aaggaagaca ataaaatcat ccttcccctt gcaatccagg tacatcatgc agtatgtgat   8760
ggatttcata tttgtcgttt tgtaaatgaa ctgcaagaat taataaattc ctaactcgag   8820
ggcagtagcg cggtggtccc acctgacccc atgccgaact cagaagtgaa acgataaaac   8880
gaaaggctca gtcgaaagac tgggcctttc gttttatctg ttgtttgtcg gtgaacgctc   8940
tcctgagtag gacaaatccg ccgggagcgg atttgaacgt tgcgaagcaa cggcccggag   9000
ggtggcgggc aggacgcccg ccataaactg ccaggcatca aattaagcag aaggccatcc   9060
tgacggatgg cctttttttat tgtaaattcc ggtaaccctt gtagcttagt gggaatttgt  9120
accccttatc gatacaaatt ccccgtaggc gctagggaca ctttttcact cgttaaaaag   9180
```

-continued

```
ttttgagaat attttatatt tttgttcatg taatcactcc ttcttaatta caaattttta   9240
gcatctaatt taacttcaat tcctattata caaaatttta agatactgca ctatcaacac   9300
actcttaagt ttgcttctaa gtcttatttc cataacttct tttacgtttc cgggtacaat   9360
tcgtaatcat gtcatagctg tttcctgtgt gaaattctta tccgctcaca attccacaca   9420
acatacgagc cggaagcata aagtgtaaag cctggggtgc ctaatgagtg agctaactca   9480
cattaattgc gttgcgctca ctgcccgctt tccagtcggg aaacctgtcg tgccagaaaa   9540
cttcattttt aatttaaaag gatctaggtg aagatccttt ttgataatct catgaccaaa   9600
atcccttaac gtgagttttc gttccactga gcgtcagacc ccgtagaaaa gatcaaagga   9660
tcttcttgag atcctttttt tctgcgcgta atctgctgct tgcaaacaaa aaaaccaccg   9720
ctaccagcgg tggtttgttt gccggatcaa gagctaccaa ctctttttcc gaaggtaact   9780
ggcttcagca gagcgcagat accaaatact gtccttctag tgtagccgta gttaggccac   9840
cacttcaaga actctgtagc accgcctaca tacctcgctc tgctaatcct gttaccagtg   9900
gctgctgcca gtggcgataa gtcgtgtctt accgggttgg actcaagacg atagttaccg   9960
gataaggcgc agcggtcggg ctgaacgggg ggttcgtgca cacagcccag cttggagcga  10020
acgacctaca ccgaactgag atacctacag cgtgagctat gagaaagcgc cacgcttccc  10080
gaagggagaa aggcggacag gtatccggta agcggcaggg tcggaacagg agagcgcacg  10140
agggagcttc cagggggaaa cgcctggtat ctttatagtc ctgtcgggtt tcgccacctc  10200
tgacttgagc gtcgattttt gtgatgctcg tcaggggggc ggagcctatg gaaaaacgcc  10260
agcaacgcgg cctttttacg gttcctggcc ttttgctggc cttttgctca catgttcttt  10320
cctgcgttat cccctgattc tgtggataac cgtattaccg cctttgagtg agctgatacc  10380
gctcgccgca gccgaacgac cgagcgcagc gagtcagtga gcgaggaagc ggaagagcgc  10440
ccaatacgca aaccgcctct ccccgcgcgt tggccgattc attaatgcag ctggcacgac  10500
aggtttcccg actggaaagc gggcagtgag cgcaacgcaa ttaatgtgag ttagctcact  10560
cattaggcac cccaggcttt acactttatg cttccggctc gtatgttgtg tggaattgtg  10620
agcggataac aatttcacac aggaaacagc tatgaccatg attac                  10665
```

<210> SEQ ID NO 32
<211> LENGTH: 1056
<212> TYPE: DNA
<213> ORGANISM: Thermoanaerobacterium saccharolyticum

<400> SEQUENCE: 32

```
gtgtatacaa tatatttctt cttagtaaga ggaatgtata aaaataaata ttttaaagga     60
agggacgatc ttatgagcat tattcaaaac atcattgaaa aagctaaaag cgataaaaag    120
aaaattgttc tgccagaagg tgcagaaccc aggacattaa aagctgctga aatagtttta    180
aaagaaggga ttgcagattt agtgcttctt ggaaatgaag atgagataag aaatgctgca    240
aaagacttgg acatatccaa agctgaaatc attgaccctg taaagtctga aatgtttgat    300
aggtatgcta atgatttcta tgagttaagg aagaacaaag gaatcacgtt ggaaaaagcc    360
agagaaacaa tcaaggataa tatctatttt ggatgtatga tggttaaaga aggttatgct    420
gatggattgg tatctggcgc tattcatgct actgcagatt tattaagacc tgcatttcag    480
ataattaaaa cggctccagg agcaaagata gtatcaagct tttttataat ggaagtgcct    540
aattgtgaat atggtgaaaa tggtgtattc ttgtttgctg attgtgcggt caacccatcg    600
cctaatgcag aagaacttgc ttctattgcc gtacaatctg ctaatactgc aaagaatttg    660
```

```
ttgggctttg aaccaaaagt tgccatgcta tcattttcta caaaaggtag tgcatcacat    720

gaattagtag ataaagtaag aaaagcgaca gagatagcaa aagaattgat gccagatgtt    780

gctatcgacg gtgaattgca attggatgct gctcttgtta aagaagttgc agagctaaaa    840

gcgccgggaa gcaaagttgc gggatgtgca aatgtgctta tattccctga tttacaagct    900

ggtaatatag gatataagct tgtacagagg ttagctaagg caaatgcaat tggacctata    960

acacaaggaa tgggtgcacc ggttaatgat ttatcaagag gatgcagcta tagagatatt   1020

gttgacgtaa tagcaacaac agctgtgcag gctcaa                             1056
```

<210> SEQ ID NO 33
<211> LENGTH: 1209
<212> TYPE: DNA
<213> ORGANISM: Thermoanaerobacterium saccharolyticum

<400> SEQUENCE: 33

```
atgaaaatta tgaaaatact ggttattaat tgcggaagtt cttcgctaaa atatcaactg     60

attgaatcaa ctgatggaaa tgtgttggca aaaggccttg ctgaaagaat cggcataaat    120

gattccatgt tgacacataa tgctaacgga gaaaaaatca agataaaaaa agacatgaaa    180

gatcacaaag acgcaataaa attggtttta gatgctttgg taaacagtga ctacggcgtt    240

ataaaagata tgtctgagat agatgctgta ggacatagag ttgttcacgg aggagaatct    300

tttacatcat cagttctcat aaatgatgaa gtgttaaaag cgataacaga ttgcatagaa    360

ttagctccac tgcacaatcc tgctaatata gaaggaatta aagcttgcca gcaaatcatg    420

ccaaacgttc caatggtggc ggtatttgat acagcctttc atcagacaat gcctgattat    480

gcatatcttt atccaatacc ttatgaatac tacacaaagt acaggattag aagatatgga    540

tttcatggca catcgcataa atatgtttca aatagggctg cagagatttt gaataaacct    600

attgaagatt tgaaaatcat aacttgtcat cttggaaatg gctccagcat tgctgctgtc    660

aaatatggta aatcaattga cacaagcatg ggatttacac cattagaagg tttggctatg    720

ggtacacgat ctggaagcat agacccatcc atcatttcgt atcttatgga aaaagaaaat    780

ataagcgctg aagaagtagt aaatatatta aataaaaaat ctggtgttta cggtatttca    840

ggaataagca gcgattttag agacttagaa gatgccgcct ttaaaaatgg agatgaaaga    900

gctcagttgg ctttaaatgt gtttgcatat cgagtaaaga agacgattgg cgcttatgca    960

gcagctatgg gaggcgtcga tgtcattgta tttacagcag gtgttggtga aaatggtcct   1020

gagatacgag aatttatact tgatggatta gagtttttag ggttcagctt ggataaagaa   1080

aaaaataaag tcagaggaaa agaaactatt atatctacgc cgaattcaaa agttagcgtg   1140

atggttgtgc ctactaatga agaatacatg attgctaaag atactgaaaa gattgtaaag   1200

agtataaaa                                                           1209
```

<210> SEQ ID NO 34
<211> LENGTH: 1358
<212> TYPE: DNA
<213> ORGANISM: Thermoanaerobacter pseudoethanolicus

<400> SEQUENCE: 34

```
gctaatgcta tcggaccaat ttctcaaggt cttgcaaaac ctatcaatga cttgtcaaga     60

ggttgtagtg tagaagatat tgttaatgtt atagcaataa cttgtgtaca agctcaaggg    120

gtgcaaaaat aactttgagg aggcagcgat tatgaaaatt ttagtcatga actgtggaag    180

ctcgtcatta aaagtatcaa ttgttagata tggataatgg gaaagtgcta gcgaaaggat    240
```

-continued

```
tggcggaaag gataggtatc aatgattctc ttttaactca tcaagtagag ggcaaagata    300

aaataaaaat acaaaaagat atgaaaaatc ataaagaagc tatacaaatt gttttagagg    360

ctttagtaga taaagaaatc ggaatattaa aagatatgaa agaaatagat gcagtaggac    420

atagagttgt gcacggggga gagtttttta ctgattccgt attgattgac gatgaggtaa    480

tcaaaaaatt agaagcatgt attgaccttg cacctttgca caatcctgct aatattgagg    540

gaataaaagc ttgtcggcag ataatgccag gggtgccaat ggtagcagtt tttgatacgg    600

ctttccatca aacaatgcca gattatgcgt atatttatcc cattccttat gaatactacg    660

aaaaatatag aataagaaga tatggattcc atgggacttc tcataaatat gtatctttaa    720

gagctgctga aatattaaag aggcctattg aagagttaaa aattattact tgccatttag    780

ggaatgggtc tagtattgct gcggttaaag gcggtaagtc gatagataca agtatgggat    840

ttactccatt agaagggctg gctatgggta caaggtccgg aaatgttgat ccttcaatta    900

taactttctt aatggaaaaa gaaggattga ctgcagaaca ggttatagat atacttaata    960

agaaatcagg tgtatacgga atttcaggaa taagtaatga ctttagagat atagaaaatg   1020

cagcttttaa agaagggcat aaaagggcta tgttggcatt aaaagttttc gcttataggg   1080

tgaaaaagac aataggttct tatacagctg ctatgggtgg ggttgatgta attgtgttta   1140

ctgctggagt tggagaaaat ggaccagaaa tgagagagtt tattttagag gatctagagt   1200

ttttaggctt taaactggac aaagagaaga ataaggtaag aggaaaagag gaaattatat   1260

ctacagaaga ttcaaaagtt aaagttatgg ttattcctac aaatgaagaa tatatgattg   1320

ctaaagatac tgaaaaattg gtaaaaggtt taaagtag                           1358
```

```
<210> SEQ ID NO 35
<211> LENGTH: 1196
<212> TYPE: DNA
<213> ORGANISM: Thermoanaerobacter pseudoethanolicus

<400> SEQUENCE: 35

atggcagtaa tggatagtat catacaaaag gctaaagcta ataaaaaaag gattgtgctt     60

cctgagggaa gtgaagctcg aactttaaaa gctgctgaaa aggttattaa agaaggtatt    120

gctgatgtag ttttattagg gaaggaagaa gaaataaaag aaaaagcaaa gggattggat    180

atctcgaaag cagaaattat agaccctgaa aagtcgcctc ttttacaaaa atatgctgaa    240

gaatattata atttgagaaa aaccaaagga gttacagaag aacaggcata tcaaattatg    300

aaagacccta tgtactatgg gtgcatgatg gtcaaattag acgatgttga tggtatggta    360

tctggggcga ttcacgctac tgctgatgtt ttcagaccgg cttttcaaat tgtaaaaact    420

gctgcaggtg tcaaagtagt atccagcgcc tttataatgg aagtacctaa ttgtacttat    480

ggaagcgatg gagtatttat ttttgctgat tgtgcaataa atcctaatcc taatgaagag    540

gaattagcag caattgccat tgcttctgcc catactgcaa aagtccttgc tggaattgag    600

cctagaattg ctatgctgtc attttctact aaaggaagtg caaaccatga attagtagat    660

aaggtgaaaa atgcgactaa aatcgcaaaa gaattggcgc ctgatttgct aattgatggt    720

gagcttcaat tagatgctgc gattgtcaaa gaagtaggag agttaaaggc tccaggaagt    780

cctgtagcgg ggaatgcaaa tgtgcttatt ttcccagatt tgcaagcggg aaacattgga    840

tataagctag tgcaaagact tgctaaagct aatgctatcg gaccaatttc tcaaggtctt    900

gcaaaaccta tcaatgactt gtcaagaggt tgtagtgtag aagatattgt taatgttata    960

gcaataactt gtgtacaagc tcaaggggtg caaaaataac tttgaggagg cagcgattat   1020
```

gaaaatttta gtcatgaact gtggaagctc gtcattaaaa gtatcaattg ttagatatgg 1080
ataatgggaa agtgctagcg aaaggattgg cggaaaggat aggtatcaat gattctcttt 1140
taactcatca agtagagggc aaagataaaa taaaaataca aaaagatatg aaaaat 1196

<210> SEQ ID NO 36
<211> LENGTH: 1053
<212> TYPE: DNA
<213> ORGANISM: Thermoanaerobacter sp.

<400> SEQUENCE: 36
gtgtatacaa tatatttctt ctttttagta agaggaatgt ataaaaataa atattttaaa 60
ggaagggacg atcttatgag cattattcaa aacatcattg aaaaagctaa aagtgataaa 120
aagaaaattg ttctgccgga aggtgcagaa cccagaacat taaaagctgc tgaaatagtt 180
ttaaaagaag gaattgcaga tttggtgctt cttggaaatg aagatgagat aagaaatgct 240
gcaaaagact tggacatatc taaagctgaa atcattgatc ctgtaaaatc tgaaatgttt 300
gataggtatg ctaatgattt ttatgagtta aggaagagca aaggaatcac gttggaaaaa 360
gccagagaaa caatcaagga taatatctat tttggatgta tgatggttaa agaaggttat 420
gctgatggat tggtatctgg cgctattcat gctactgcag atttattaag acctgcattt 480
cagataatta aaacggctcc aggagcaaag atagtatcaa gctttttat aatggaagtg 540 cctaattgtg aatatggtga aaatggtgta ttcttgtttg ctgattgcgc ggtcaaccca 600
tcgcctaatg cagaagaact tgcttctatt gctgtacaat ctgctaatac tgcaaagaat 660
ttgttgggct ttgaaccaaa agttgctatg ctatcatttt ccacaaaagg tagtgcatca 720
catgaattag tagataaagt aagaaaagcg acagaaatag caaaagaatt gatgccagat 780
gttgctatcg acggtgaatt gcaattggat gctgctcttg tcaaagaagt tgcagagcta 840
aaagcgccag gaagcaaagt tgcgggatgt gcaaatgtgc ttatattccc tgatttacaa 900
gctggtaata taggatataa gcttgtacag agattagcta gcaaatgcaa ttggacctat 960
aacacaggaa tgggtgcacc ggttaatgat ttatcaagag gatgcagcta tagagatatt 1020
gttgacgtaa tagcacacag ctgtacaggc tca 1053

<210> SEQ ID NO 37
<211> LENGTH: 1068
<212> TYPE: DNA
<213> ORGANISM: Thermoanaerobacter sp.

<400> SEQUENCE: 37
atgctaacgg agaaaaatca agataaaaaa agacatgaaa gatcacaaag acgcaataaa 60
attgttttag atgctttggt aagcagtgac tacggcgtta taaaggatat gtctgagata 120
gatgctgtag gacatagagt tgttcacgga ggagaatctt ttacatcatc agttctcata 180
aatgatgatg tgttaaaagc gataacagat tgcatagaat tagctccact gcacaatcct 240
gccaatatag aaggaattaa agcttgccag caaatcatgc caaacgttcc aatggtggcg 300
gtatttgata cagcctttca tcagacaatg cctgattatg catatcttta tccaatacct 360
tatgaatact acacaaagta caggatcaga agatatggat ttcatggcac atcgcataaa 420
tatgtttcaa atagggctgc agagatttta aataaaccta ttgaagattt gaaaatcata 480
acttgtcatc ttggaaatgg ctccagcatt gctgctgtca aatatggtaa atcaattgac 540
acaagcatgg gatttacacc attagaaggt ttggctatgg gtacacgatc tggaagcata 600
gacccatcca ttatttcgta tcttatggaa aaagaaaata taagcgctga agaagtagta 660

-continued aatatattaa ataaaaaatc tggtgtttac ggtatttcag gaataagcag cgattttaga 720
gacttagaag atgccgcctt taaaaatgga gatgaaagag ctcagttggc tttaaatgtg 780
tttgcatatc gagtaaagaa gatgattggc gcttatgcag cagctatggg aggcgtcgat 840
gccattgtat ttacagcagg tgttggtgaa aatggtcctg agatacgaga atttatactt 900
gatggattag agttcttagg gttcagcttg gataaagaaa aaaataaagt cagaggaaaa 960
gaaactatta tatctacgcc gaattcaaaa gttagcgtga tggttgtgcc cactaatgaa 1020
gaatacatga ttgctaaaga tactgaaaag attgtaaaga gtataaaa 1068

<210> SEQ ID NO 38
<211> LENGTH: 1059
<212> TYPE: DNA
<213> ORGANISM: Thermoanaerobacterium saccharolyticum

<400> SEQUENCE: 38
gtgtatacaa tatatttctt ctttttagta agaggaatgt ataaaaataa atattttaaa 60
ggaagggatg atcttatgag cattattcag aacatcattg aaaaagctaa aagcgataaa 120
aagaaaattg ttctgccaga aggtgcagaa cccaggacat taaaagctgc tgaaatagtt 180
ttaaaagaag gaattgcaga tttggtgctt cttggaaatg aagatgagat aagaaatgca 240
gcaaaagact tggacatatc caaagctgaa ataattgacc ctgtaaaatc tgaaatgttt 300
gataggtatg ctaatgattt ttacgaatta agaaagagca agggaatcac attggaaaaa 360
gccagagaaa caatcaagga taatatctat tttggatgta tgatggttaa agaaggttat 420
gctgatggat tagtatctgg cgctattcat gctactgcag atttattaag acctgcattt 480
cagataatta aaacagctcc aggagcaaag atagtatcaa gctttttat aatggaagtg 540 cctaattgtg aatatggtga aaatggcgta ttcttgtttg ctgattgtgc ggtcaatcca 600
tcacctaatg cagaagaact tgcttctatt gctgtacaat ctgctaatac tgcaaagaat 660
ttgttgggtt ttgaaccaaa agttgccatg ctatcatttt ccacaaaagg tagtgcatca 720
catgaattag tagacaaggt aagaaaagcg acagagatag caaaggattt gatgccagat 780
gttgctatcg atggtgaatt gcaactggat gctgctattg ttaaagaagt tgcagagcta 840
aaagcaccgg gaagcaaagt tgcgggatgt gcaaatgtgc ttatattccc tgacttacaa 900
gctggtaata taggatataa gcttgtacag agattagcta aggcaaatgc aattggaccg 960
ataacgcaag gaatgggtgc accagttaat gatttatcaa gaggatgcag ctataaagat 1020
attgttgacg taatagcgac aacagctgtg caggctcaa 1059

<210> SEQ ID NO 39
<211> LENGTH: 1209
<212> TYPE: DNA
<213> ORGANISM: Thermoanaerobacterium saccharolyticum

<400> SEQUENCE: 39
atgaaaacta tgaaaattct ggttattaat tgtggaagtt cttcactaaa atatcaattg 60
attgaatcaa ttgatggaaa tgtgctggca aaaggccttg ctgaaagaat cggcataaat 120
gattccctgt tgacgcataa tgctaacgga gaaaaaatca agataaaaaa agacatgaaa 180
gatcacaaag acgcaataaa attggtttta gatgctttgg taagtagcga ctacggcgtt 240
ataaaggata tgtctgagat agatgctgta ggacatagag ttgttcatgg aggagagtct 300
tttacatcat cagttcttat aaatgatgaa gtgttaaagg caataacaga ttgtatagaa 360
ttagctccac tgcataatcc tgctaatata gaaggaatta aagcttgcca gcaaatcatg 420

-continued

```
ccaaacgttc caatggtggc ggtatttgat acagcctttc atcaaacaat gcctgattat    480

gcatatcttt atccaatacc ttatgagtac tacacaaagt acaggatcag aagatatgga    540

tttcatggca cgtcgcataa atatgtttca agtagggctg cagagatttt gaataaacct    600

attgaagatt tgaaaatcat aacttgtcat cttggaaatg gctccagtat tgctgccgtc    660

aaatatggta aatcaattga cacaagcatg ggatttacac cattagaagg tttggctatg    720

ggtacacgat ctggaagtat agacccatcc atcatttctt atcttatgga aaaagaaaat    780

ataagtgctg aagaggtagt aaatatatta aataaaaaat ctggtgttta cggtatttcg    840

ggaataagca gcgattttag agatttagaa gatgctgcct ttaaaaatgg agatgaaaga    900

gctcagttgg ccttaaatgt gtttgcatat cgagtaaaga agacgattgg agcttatgca    960

gcagctatgg gaggcgttga tgtcattgta tttacggcag gtgttggtga aaatgggcct   1020

gagataagag aatttatact tgatggattg gagttcttag ggttcagctt ggataaagaa   1080

aaaaataaag tcagaggaaa ggaaactatt atatctacgc caaattcaaa aattagcgtg   1140

atggttgtgc cgactaatga agaatatatg attgctaaag atactgaaaa gattgtaaag   1200

agtataaaa                                                           1209
```

<210> SEQ ID NO 40
<211> LENGTH: 933
<212> TYPE: DNA
<213> ORGANISM: Thermoanaerobacterium saccharolyticum

<400> SEQUENCE: 40

```
atgagcaagg tagcaataat aggatctggt tttgtaggtg caacatcggc atttacgctg     60

gcattaagtg ggactgtgac agatatcgtg ctggtggatt taaacaagga caaggctata    120

ggcgatgcac tggacataag ccatggcata ccgctaatac agcctgtaaa tgtgtatgca    180

ggtgactaca aagatgtgaa aggcgcagat gtaatagttg tgacagcagg tgctgctcaa    240

aagccgggag agacacggct tgaccttgta aagaaaaata cagccatatt taagtccatg    300

atacctgagc ttttaaagta caatgacaag gccatatatt tgattgtgac aaatcccgta    360

gatatactga cgtacgttac atacaagatt tctggacttc catggggcag agtttttggt    420

tctggcaccg ttcttgacag ctcaaggttt agataccttt taagcaagca ctgcaatata    480

gatccgagaa atgtccacgg aaggataatc ggcgagcatg gtgacacaga gtttgcagca    540

tggagcataa caaacatatc gggtatatca tttaatgagt actgcagcat atgcggacgc    600

gtctgcaaca caaatttcag aaaggaagta gaagaagaag tcgtaaatgc tgcttacaag    660

ataatagaca aaaaaggtgc tacatactat gctgtggcag ttgcagtaag aaggattgtg    720

gagtgcatct taagagatga aaattccatc ctcacagtat catctccatt aaatggacag    780

tacggcgtga aagatgtttc attaagcttg ccatctatcg taggcaggaa tggcgttgcc    840

aggattttgg acttgccttt atctgacgaa gaagtggaga agtttaggca ttcagcaagt    900

gtcatggcag atgtcataaa acaattagat ata                                933
```

<210> SEQ ID NO 41
<211> LENGTH: 933
<212> TYPE: DNA
<213> ORGANISM: Thermoanaerobacter sp.

<400> SEQUENCE: 41

```
atgagtaaag tggccataat aggttcagga tttgtaggtg ctacatctgc atttacattg     60

gctctaagtg ggactgtgac agacattgtt ttagtagatt taaacaagga caaggcgata    120
```

```
ggcgatgcac tggatattag ccacggtata ccgcttatac agcctgtaaa tgtgtatgct    180

ggcgactaca aggatatcga gggcgcagat gtagtagttg taacagcagg tgcggctcaa    240

aagccaggag agtctaggct ggaccttgta aaaaagaata catctatatt caagtccatg    300

atacctgaac ttttaaaata caatgataaa gctatatacc tgattgtaac aaatcctgtt    360

gatatattaa cgtatgttac atacaaaata gcgaaacttc cgtgggggcg tgtattcggt    420

tcaggtactg tccttgacag ttcccgattt aggtatcttt taagtaaaca ttgcaatatt    480

gatcctagaa atgtacatgg aaggataatt ggagaacacg gcgatacaga atttgcggcg    540

tggagcataa caaatatttc aggaatatca tttaatgagt actgcaattt gtgcggacga    600

gtttgtaata caaatttcag aaaggaagtg gaagatgaag ttgtcaatgc ggcttacaaa    660

attattgata aaaagggtgc cacgtattac gctgtggctg tagcagtaag aagaatagtt    720

gagtgtatca taagggatga aaattcaatt cttacagttt catctccatt aaatggtcaa    780

tacggtgtaa gagatgtatc tttaagcttg ccatcaattg tgggcaaaaa tggtgttgca    840

agggttctgg atttgccttt ggctgatgac gaagttgaga agtttaaaca ttcggcaagc    900

gttatggctg atgttataaa acagttggac ata                                  933
```

<210> SEQ ID NO 42
<211> LENGTH: 936
<212> TYPE: DNA
<213> ORGANISM: Thermoanaerobacter pseudoethanolicus

<400> SEQUENCE: 42

```
atgaacaaaa tatctataat aggttctgga tttgtcggtg ctactactgc atacacactg     60

gctttgagtg ggattgccaa aactattgta ttaatagata ttaataaaga caaagcagaa    120

ggcgatgctc ttgatataag ccacggcgta ccgtttatta gtccagttga attgtacgcg    180

ggagattata gtgatgtttc aggttctgac ataataatca ttacagcggg agcagcacaa    240

aaaccgggag aaaccagact tgacttagtg aagagaaata cgatgatttt taaagacata    300

gtggcaaaac ttattaaagt aaatgacaca gcaatatacc ttatagttac aaatccagta    360

gatattctta catacgttac ctataaaata tctggcttgc catacggaag agtattgggg    420

tctggcacag ttctcgacag tgcgagattc agatatcttt taagcaaaca ttgtaacata    480

gatccgagga atatacacgg atatataatt ggggagcatg gcgattctga gcttgcagct    540

tggagcatta cgaacatagc aggcatacca attgataatt actgcaattt atgtggaaaa    600

gcatgtgaaa aagattttag agaggagatt tttaataatg ttgtaagagc tgcctatacg    660

ataatagaaa aaaagggtgc gacatattat gcggttgctc tcgcagtaag aagaatcgta    720

gaagctattt tcagagatga aaattccatt ttgactgtgt catctccgct aaccggccaa    780

tatggtgtta caaatgtggc tttgagcctt ccctccgttg ttggacgaaa tggaatcgta    840

aatatacttg aattaccact ttcacaggaa gaaattgctg cttttagaag atcagccgaa    900

gttatcaaaa gtgtaataca agagcttgat atataa                               936
```

<210> SEQ ID NO 43
<211> LENGTH: 631
<212> TYPE: DNA
<213> ORGANISM: Thermoanaerobacterium saccharolyticum

<400> SEQUENCE: 43

```
aggcgatgca ctggacataa gccatggcat accattaata cagcctgtaa atgtgtatgc     60

aggtgactac aaagatgttg aaggcgcgga cgtaatagtt gtgacagcag ggctgctca     120
```

-continued

```
aaagccaggt gagacgaggc ttgaccttgt gaagaaaaat acagctatat ttaagtccat    180

gatacctgag cttttaaagt acaatgacaa ggctatatat ttgattgtca caaatcctgt    240

agacatactg acgtacgtta catacaagat atctggactt ccatggggca gagttttcgg    300

ttctggcact gttcttgaca gttcaaggtt taggtacctt ttaagcaggc actgcaatat    360

agattccgag aaatgtccac ggaaggataa tcggcgagca tggtgacaca gagtttgcag    420

catggagcat aacaaacata tctggaatat catttaatga gtactgcagc atatgcgggc    480

gcatctgcaa cacaaatttc agaaaggaag tagaagaaga agtcgtaaat gctgcttata    540

agataataga caaaaaaggt gctacatact atgctgtcgc agttgcagta agaaggattg    600

tggagtgcat cttaagagat gaaaattcca t                                   631
```

<210> SEQ ID NO 44
<211> LENGTH: 2229
<212> TYPE: DNA
<213> ORGANISM: Thermoanaerobacterium saccharolyticum

<400> SEQUENCE: 44

```
atgatcaatg aatggcgcgg gtttcaggag ggcaaatggc aaaagactat tgacgttcaa     60

gattttatcc agaaaaatta cacattatac gaaggcgatg atagtttttt agaagggcct    120

acagaaaaga ctattaagct ttggaacaaa gttcttgagc taatgaagga agaactgaaa    180

aaaggtgtgt tagatattga tacaaaaact gtatcgtcta taacatccca tgatgcgggg    240

tatatagaca aagatcttga ggaaatagtt ggattgcaga cagacaaacc tcttaaaaga    300

gctataatgc cttacggtgg cataagaatg gtcaaaaaag cttgcgaagc ttatggatat    360

aaagtggacc caaaagtaga agagatattt acgaagtaca gaaagaccca caatgatggt    420

gtatttgatg catatactcc agaaataaga gcagcaagac atgccggcat aataacaggt    480

cttccagatg catatggcag aggaagaatc ataggtgatt acagaagagt tgctctttat    540

ggaattgata gactcatcga agaaaaggaa aaagaaaaac ttgagcttga ttacgatgaa    600

tttgatgaag caactattcg cttgagagaa gaattgacag aacagataaa agcattaaac    660

gaaatgaaag agatggcttt aaagtacggt tatgacatat caaagcctgc aaaaaatgca    720

aaagaagctg tgcagtggac ttactttgcc ttccttgctg ctataaagga acaaaatggt    780

gccgctatgt cgctgggcag agtatctact tttttagata tatacattga aagagatctt    840

aaagaaggaa cattgacaga gaaacaagca caagagttaa tggatcactt tgtcatgaag    900

cttagaatgg tgaggttctt aaggactcct gattacaatg aactatttag tggcgatcct    960

gtttgggtga ctgaatcaat tggcggtgta ggcgtagacg gaagacctct tgtcactaaa   1020

aattcattca ggatattaaa tactttatat aacttaggtc ctgcacctga gccaaacttg   1080

acggttttat ggtccaaaaa ccttcctgaa aactttaaaa gattctgtgc caaggtatca   1140

atagatacaa gttctattca atatgaaaat gacgacttaa tgaggccaat atacaatgac   1200

gactatagca tcgcctgctg tgtgtcagct atgaagacgg gagaacagat gcaatttttt   1260

ggagcaaggg caaatctcgc gaaggcgcta ctgtatgcta taaacggcgg tatcgatgaa   1320

aggtataaaa cgcaagtggc accaaaattt aatcctataa cgtctgagta tttagactac   1380

gatgaggtaa tggcagcata tgacaatatg ttagagtggc ttgcaaaagt gtatgttaaa   1440

gctatgaata taatacacta catgcacgat aaatacgctt atgaaagatc ccttatggct   1500

ttgcatgata gagacatcgt aaggacgatg gcttttggaa tcgcaggtct ttctgttgcg   1560

gcagattcgt taagcgccat aaagtatgct aaagtaaaag ccataagaga tgaaaatggc   1620
```

atagcaatag attatgaagt ggaaggagat ttccctaagt ttggcaatga tgatgacagg 1680
gttgactcaa tagcagttga cattgtagaa agattcatga ataagcttaa aaagcacaag 1740
acttacagaa actctatacc aacactgtct gttttgacaa taacgtcaaa tgtggtgtac 1800
ggcaaaaaga cgggtgctac acctgacgga agaaaagcgg gagaaccttt tgcgccaggc 1860
gcaaatccga tgcacggcag agatacaaaa ggtgccatag catcaatgaa ttcagtatca 1920
aaaatacctt atgacagttc attggatggt atatcataca catttacgat tgtaccaaat 1980
gcgcttggca aggatgacga agataaaatt aataatcttg taggactatt agatggatat 2040
gcatttaatg cggggcacca cataaacatc aatgttttaa acagagatat gttgcttgat 2100
gctatggagc atcctgaaaa atatccgcag cttactataa gggtttcagg gtatgctgtc 2160
aatttcaata aattaacgag agagcaacag ttggaggtta tatcccgcac ttttcacgaa 2220
tctatgtag 2229

<210> SEQ ID NO 45
<211> LENGTH: 2229
<212> TYPE: DNA
<213> ORGANISM: Clostridium thermocellum

<400> SEQUENCE: 45
atggatgcat ggcgcggatt taataaaggc aactggtgcc aggaaattga cgttcgtgat 60
tttataatta gaaattatac tccttatgaa ggcgatgaaa gctttcttgt aggacctacg 120
gatagaacgc ggaaactttg ggagaaggtt tccgaactgt taaagaaaga acgggagaac 180
ggcggggtat tggatgttga tacccataca atttcaacga ttacgtctca taaacctgga 240
tatatagata aagaacttga agttattgtc gggcttcaga cggatgagcc tttaaaaaga 300
gccataatgc cgtttggcgg tatacgtatg gtgattaagg gagccgaagc ttatggccac 360
agtgtggacc ctcaggttgt tgaaatattc acaaagtaca gaaagactca taaccaggga 420
gtttatgatg tatatactcc cgaaatgaga aaagccaaaa aagccgggat tattacagga 480
cttcccgacg catacggcag aggaagaata attggcgatt acagaagggt tgcactttat 540
ggcgttgaca ggctgattgc tgaaaaagag aaagaaatgg caagtcttga aagagattac 600
attgactatg agactgttcg agacagagaa gaaataagcg agcagattaa atctttaaaa 660
caacttaaag aaatggcttt aagttacggt tttgacatat cttgtcctgc aaaggatgcc 720
agagaagcct ttcaatggtt gtattttgca tatcttgcag cagtcaagga acagaacggc 780
gcggcaatga gtattggaag aatttcgact ttccttgaca tatacattga aagggatctc 840
aaagaaggaa aactcacgga ggagttggct caggaactgg ttgaccagct ggttataaag 900
ctgagaattg tgagattttt gagaactcct gagtatgaaa agctcttcag cggagacccc 960
acttgggtaa ccgaaagtat cggaggtatg gcgctggatg gaagaacgct ggttacaaaa 1020
tcttcgttca ggtttttgca cactcttttc aacctgggac atgcaccgga gcccaacctt 1080
acagtacttt ggtccgtcaa tcttcccgaa ggctttaaaa agtactgtgc aaaggtatca 1140
attcattcaa gctccatcca gtatgaaagc gacgacataa tgaggaaaca ctggggagac 1200
gattatggaa tagcatgctg tgtttctgct atgagaattg gaaaacagat gcagttcttc 1260
ggtgcaagat gcaatcttgc aaaagctctt ctttacgcta ttaacggcgg aaaggatgaa 1320
atgacgggag aacagattgc tccgatgttt gcaccggtgg aaaccgaata ccttgattac 1380
gaggacgtaa tgaagaggtt tgacatggtg cttgactggg tggcaaggct ttatatgaac 1440
accctcaata taattcacta catgcatgac aaatatgcct atgaggcgct gcagatggca 1500

```
ttgcatgaca aagacgtgtt caggacgatg gcatgcggaa tagccggttt gtctgtggtg   1560

gcagactccc ttagcgcgat aaaatatgca aaggttaaac cgatacgcaa tgaaaacaac   1620

ctcgttgttg actacgaagt tgagggtgat tatcctaaat tcggaaataa cgacgaacgt   1680

gttgatgaaa ttgcagtgca agtagtaaaa atgttcatga acaagcttag aaagcaaagg   1740

gcttacagaa gtgccactcc gaccctttcc atacttacca taacttcaaa cgtggtatat   1800

ggaaagaaaa ccggaaacac tcctgacggc agaaaagctg gagaaccttt ggcgccggga   1860

gcaaatccga tgcatggaag ggatataaac ggagcattgg ctgtactgaa cagtattgcg   1920

aagcttccct atgaatatgc ccaggacggc atttcatata ctttctccat aattccaaaa   1980

gctctgggaa gagacgagga aaccagaata aacaatctta aatcaatgct tgacggatat   2040

ttcaagcagg gcggccacca cataaatgta aatgtgtttg aaaaagagac actgttagat   2100

gccatggaac atccggaaaa atatccacaa cttaccataa gagtgtccgg gtatgcagtg   2160

aactttataa agcttacacg ggagcaacag ctggatgtta ttaacagaac gattcacgga   2220

aagatttaa                                                           2229
```

<210> SEQ ID NO 46
<211> LENGTH: 2061
<212> TYPE: DNA
<213> ORGANISM: Clostridium phytofermentans

<400> SEQUENCE: 46

```
atgatgactt cagttatgaa acaggaatgg gaaggtttta aacaaggtag atggatcact     60

tcagtaaatg ttcgagactt catacagaac aattacacaa tgtatgatgg tgatgaatcc    120

tttttagcag gtccaaccga agccaccaat aaactatggg cccaggttat ggagctttca    180

aagcaggaaa gtgagaaagg tggagtcctt gatatggaca ccaagatagt atctactatt    240

gtttctcacg gtcctggtta tttagataaa gatattgaaa caattgttgg ttttcagacc    300

gataagccat ttaagagatc actacaggtc tttggtggta ttcgtatggc acagagtgct    360

tgccatgaat atggatatga ggtagacgaa gaggtagcac gtatttttac agactaccgc    420

aagacacata atcaaggtgt atttgatgca tacactgacg aaatgaagct cgctagaaaa    480

tcagcaatca ttactggttt gcctgatgct tatggtagag gtagaattat tggcgattac    540

cgtcgagtgg cactttacgg tactgattta cttattgaag acaagaaaga acaacttaca    600

acttccttaa agagaatgac tagtgataat attcgcttaa gagaagaatt agcagaacaa    660

attcgtgcat taaaagaatt agcgaagctt ggtgaaatct atggttacga tattacgaag    720

ccagcaataa atgcaaagga agcaattcag tggctttact ttggatatct tgcagcggta    780

aaagagcaaa acggtgctgc aatgagctta ggccgtactt ctacattcct tgatatttat    840

atccagagag atttagataa tggtgttatc acagaaaaag aagcacaaga gtatatcgat    900

cattttatta tgaaacttcg tctagtgaag tttgcaagaa ctccagaata caatgcctta    960

ttctccggtg accctacttg ggtaacagaa agtatcgctg ggattggtac agatggacgc   1020

catatggtaa caaagacatc cttccgttac cttcatacgt tagacaacct tggaactgct   1080

ccagaaccaa acatgacagt tctatggtca actagattac caagattatt taaagagtac   1140

tgtgctaaga tgtcaattaa gtcatcctct attcaatacg aaaatgatga tatcatgcgt   1200

ccaactcatg gtgatgatta tgcaattgct tgttgtgtat cctctatgaa aattggtaaa   1260

gagatgcagt tctttggagc acgtgcaaat cttgctaagt gtcttcttta cgcaatcaat   1320

ggtggtgtag atgaagttct taaaattcag gttggtccaa agtaccgtcc agttgagggt   1380
```

-continued gaataccta attatgagga cgtaatgtcg aaatacaaag atatgatgga gtggctagca 1440
gaactttatg tgaatacttt aaatgtaatc cactacatgc atgataaata tagctatgaa 1500
agaattcaaa tggcacttca tgatcgtgaa gtaaaacgtt actttgcaac tggtattgcg 1560
ggtctttctg ttgtagcgga ctctttaagt gcaattaagt atgctaaggt aaaagtaatt 1620
cgtgatgaga atggcgttgt aaccgattac gaaattgaag gtgattatcc aaagtacggc 1680
aacaatgatg atcgtgtaga cgatatcgct gtacagttag tgcatgactt tatgaacatg 1740
attcgcaagc atcatactta tcgtgatgga tacccaacga tgtcaatctt aacgataact 1800
tctaatgtag tttatggaaa gaagacaggt aatactccag acggacgtaa gaagggtgaa 1860
ccattagcac caggtgctaa cccaatgcat cgtcgtgata ctcatggtgc agcagcgtcc 1920
ctagcatcgg tagcaaagct tccattccgt gatgcgcagg atggtatttc taatacgttc 1980
tctattgtac caggagcatt aggtaagaat gatgtgttat ttgctggaga cttagattta 2040
gacgatatgt ctgagaacta a 2061

<210> SEQ ID NO 47
<211> LENGTH: 5003
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47
agagctataa tgccttacgg tggcataaga atggtcaaaa aagcttgcga agcttatgga 60
tataaagtgg acccaaaagt agaagagata tttacgaagt acagaaagac ccacaatgat 120
ggtgtatttg atgcatatac tccagaaata agagcagcaa gacatgccgg cataataaca 180
ggtcttccag atgcatatgg cagaggaaga atcataggtg attacagaag agttgctctt 240
tatggaattg atagactcat cgaagaaaag gaaaaagaaa aacttgagct tgattacgat 300
gaatttgatg aagcaactat tcgcttgaga gaagaattga cagaacagat aaaagcatta 360
aacgaaatga aagagatggc tttaaagtac ggttatgaca tatcaaagcc tgcaaaaaat 420
gcaaaagaag ctgtgcagtg gacttacttt gccttccttg ctgctataaa ggaacaaaat 480
ggtgccgcta tgtcgctggg cagagtatct actttttag atatatacat tgaaagagat 540
cttaaagaag gaacattgac agagaaacaa gcacaagagt taatggatca ctttgtcatg 600
aagcttagaa tggtgaggtt cttaaggact cctgattaca atgaactatt tagtggcgat 660
cctgtttggg tgactgaatc aattggcggt gtaggcgtag acggaagacc tcttgtcact 720
aaaaattcat tcaggatatt aaatacttta tataacttag gtcctgcacc tgagccaaac 780
ttgacggttt tatggtccaa aaaccttcct gaaggtcaat ctatgaaatg cgattaagct 840
tggctgcagg tcgataaacc cagcgaacca tttgaggtga taggtaagat tataccgagg 900
tatgaaaacg agaattggac ctttacagaa ttactctatg aagcgccata tttaaaaagc 960
taccaagacg aagaggatga agaggatgag gaggcagatt gccttgaata tattgacaat 1020
actgataaga taatatatct tttatataga agatatcgcc gtatgtaagg atttcagggg 1080
gcaaggcata ggcagcgcgc ttatcaatat atctatagaa tgggcaaagc ataaaaactt 1140
gcatggacta atgcttgaaa cccaggacaa taaccttata gcttgtaaat tctatcataa 1200
ttgtggtttc aaaatcggct ccgtcgatac tatgttatac gccaactttc aaaacaactt 1260
tgaaaaagct gttttctggt atttaaggtt ttagaatgca aggaacagtg aattggagtt 1320
cgtcttgtta taattagctt cttggggtat ctttaaatac tgtagaaaag aggaaggaaa 1380

```
taataaatgg ctaaaatgag aatatcaccg gaattgaaaa aactgatcga aaaataccgc   1440
tgcgtaaaag atacggaagg aatgtctcct gctaaggtat ataagctggt gggagaaaat   1500
gaaaacctat atttaaaaat gacggacagc cggtataaag ggaccaccta tgatgtggaa   1560
cgggaaaagg acatgatgct atggctggaa ggaaagctgc ctgttccaaa ggtcctgcac   1620
tttgaacggc atgatggctg gagcaatctg ctcatgagtg aggccgatgg cgtcctttgc   1680
tcggaagagt atgaagatga acaaagccct gaaaagatta tcgagctgta tgcggagtgc   1740
atcaggctct ttcactccat cgacatatcg gattgtccct atacgaatag cttagacagc   1800
cgcttagccg aattggatta cttactgaat aacgatctgg ccgatgtgga ttgcgaaaac   1860
tgggaagaag acactccatt taaagatccg cgcgagctgt atgatttttt aaagacggaa   1920
aagcccgaag aggaacttgt cttttcccac ggcgacctgg gagacagcaa catctttgtg   1980
aaagatggca aagtaagtgg ctttattgat cttgggagaa gcggcagggc ggacaagtgg   2040
tatgacattg ccttctgcgt ccggtcgatc agggaggata tcggggaaga acagtatgtc   2100
gagctatttt ttgacttact ggggatcaag cctgattggg agaaaataaa atattatatt   2160
ttactggatg aattgtttta gtacctagat ttagatgtct aaaaagcttt ttagacatct   2220
aatcttttct gaagtacatc cgcaactgtc catactctga tgttttatat cttttctaaa   2280
agttcgctag ataggggtcc cgagcgccta cgaggaattt gtatcgactc tagaggatcc   2340
ccgggtaccg agctcgaatt cactggccgc aagcttggcg taatcatggt catagctgtt   2400
tcctgtgtga aattgttatc cgctcacaat tccacacaac atacgagccg gaagcataaa   2460
gtgtaaagcc tggggtgcct aatgagtgag ctaactcaca ttaattgcgt tgcgctcact   2520
gcccgctttc cagtcgggaa acctgtcgtg ccagctgcat taatgaatcg gccaacgcgc   2580
ggggagaggc ggtttgcgta ttgggcgctc ttccgcttcc tcgctcactg actcgctgcg   2640
ctcggtcgtt cggctgcggc gagcggtatc agctcactca aaggcggtaa tacggttatc   2700
cacagaatca ggggataacg caggaaagaa catgtgagca aaaggccagc aaaaggccag   2760
gaaccgtaaa aaggccgcgt tgctggcgtt tttccatagg ctccgccccc ctgacgagca   2820
tcacaaaaat cgacgctcaa gtcagaggtg gcgaaacccg acaggactat aaagatacca   2880
ggcgtttccc cctggaagct ccctcgtgcg ctctcctgtt ccgaccctgc cgcttaccgg   2940
atacctgtcc gcctttctcc cttcgggaag cgtggcgctt tctcatagct cacgctgtag   3000
gtatctcagt tcggtgtagg tcgttcgctc caagctgggc tgtgtgcacg aaccccccgt   3060
tcagcccgac cgctgcgcct tatccggtaa ctatcgtctt gagtccaacc cggtaagaca   3120
cgacttatcg ccactggcag cagccactgg taacaggatt agcagagcga ggtatgtagg   3180
cggtgctaca gagttcttga agtggtggcc taactacggc tacactagaa ggacagtatt   3240
tggtatctgc gctctgctga agccagttac cttcggaaaa agagttggta gctcttgatc   3300
cggcaaacaa accaccgctg gtagcggtgg tttttttgtt tgcaagcagc agattacgcg   3360
cagaaaaaaa ggatctcaag aagatccttt gatcttttct acggggtctg acgctcagtg   3420
gaacgaaaac tcacgttaag ggattttggt catgagatta tcaaaaagga tcttcaccta   3480
gatcctttta aattaaaaat gaagttttaa atcaatctaa agtatatatg agtaaacttg   3540
gtctgacagt taccaatgct taatcagtga ggcacctatc tcagcgatct gtctatttcg   3600
ttcatccata gttgcctgac tccccgtcgt gtagataact acgatacggg agggcttacc   3660
atctggcccc agtgctgcaa tgataccgcg agacccacgc tcaccggctc cagatttatc   3720
agcaataaac cagccagccg gaagggccga gcgcagaagt ggtcctgcaa ctttatccgc   3780
```

ctccatccag tctattaatt gttgccggga agctagagta agtagttcgc cagttaatag 3840
tttgcgcaac gttgttgcca ttgctacagg catcgtggtg tcacgctcgt cgtttggtat 3900
ggcttcattc agctccggtt cccaacgatc aaggcgagtt acatgatccc ccatgttgtg 3960
caaaaaagcg gttagctcct tcggtcctcc gatcgttgtc agaagtaagt tggccgcagt 4020
gttatcactc atggttatgg cagcactgca taattctctt actgtcatgc catccgtaag 4080
atgcttttct gtgactggtg agtactcaac caagtcattc tgagaatagt gtatgcggcg 4140
accgagttgc tcttgcccgg cgtcaatacg ggataatacc gcgccacata gcagaacttt 4200
aaaagtgctc atcattggaa aacgttcttc ggggcgaaaa ctctcaagga tcttaccgct 4260
gttgagatcc agttcgatgt aacccactcg tgcacccaac tgatcttcag catcttttac 4320
tttcaccagc gtttctgggt gagcaaaaac aggaaggcaa aatgccgcaa aaaagggaat 4380
aagggcgaca cggaaatgtt gaatactcat actcttcctt tttcaatatt attgaagcat 4440
ttatcagggt tattgtctca tgagcggata catatttgaa tgtatttaga aaaataaaca 4500
aataggggtt ccgcgcacat ttccccgaaa agtgccacct gacgtctaag aaaccattat 4560
tatcatgaca ttaacctata aaaataggcg tatcacgagg ccctttcgtc tcgcgcgttt 4620
cggtgatgac ggtgaaaacc tctgacacat gcagctcccg gagacggtca cagcttgtct 4680
gtaagcggat gccgggagca gacaagcccg tcagggcgcg tcagcgggtg ttggcgggtg 4740
tcggggctgg cttaactatg cggcatcaga gcagattgta ctgagagtgc accatatgcg 4800
gtgtgaaata ccgcacagat gcgtaaggag aaaataccgc atcaggcgcc attcgccatt 4860
caggctgcgc aactgttggg aagggcgatc ggtgcgggcc tcttcgctat tacgccagct 4920
ggcgaaaggg ggatgtgctg caaggcgatt aagttgggta acgccagggt tttcccagtc 4980
acgacgttgt aaaacgacgg cca 5003

<210> SEQ ID NO 48
<211> LENGTH: 6033
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48
cccattgtgc aatcgatcaa ttgaaatagc tattcaattg atttaagcaa ttttatttct 60
tcttcattta attctcgcca ttccccttct tttaaatttt catctaattt taattggcct 120
attgaaagcc tttttaagta gacgactttt gagcctatcg cttcaaacat tctttttatt 180
tgatgatatt taccttctct gattgagaca tatactttcg atgtactgcc tgaagatatt 240
atttccagtt ttgccggcat agtcttgtaa ccatcgtcta atagtatgcc atctgaaaac 300
aaagatacgt catcttcatc gataaaaccc aaaacttctg catagtattt tttgaaaacg 360
tgtttttttg gcgataagag cttatgagat agttcaccgt catttgtaat taaaagtaat 420
ccctctgtgt ctttatcaag ccttcctgct gggaaaacct ttcttgcctt tatatggtgt 480
ggcaaaagat ctacaacggt tttttctgat ggatcatatg ttgcacagat tacacctttc 540
ggtttattca tcattatata tatgtattct ttgtacgata ttttttcact tctaaacgtg 600
attatatctt tatcaggttg tactgcaaaa ccggggtcgt caatcgtcac attatttatt 660
gcaacaaggc cttcttttat aaaattttta atttcttttc ttgtgccata acccatattt 720
gataaaagct tatctattct catttttgac atcttaaatt cctcctaaac aatatgactg 780

```
tgcttcttag taaattatat cccaaaaata taaaatttgt agcaaaaatg tgatatatat    840
catatttttt gcgttttcct gatgatacaa ttaagatgat gtttcaagat aataaatttt    900
tctgaagtgt atacagtata ttgactacaa agaacaaaat actgcaggtc gataaaccca    960
gcgaaccatt tgaggtgata ggtaagatta taccgaggta tgaaaacgag aattggacct   1020
ttacagaatt actctatgaa gcgccatatt taaaaagcta ccaagacgaa gaggatgaag   1080
aggatgagga ggcagattgc cttgaatata ttgacaatac tgataagata atatatcttt   1140
tatatagaag atatcgccgt atgtaaggat ttcagggggc aaggcatagg cagcgcgctt   1200
atcaatatat ctatagaatg ggcaaagcat aaaaacttgc atggactaat gcttgaaacc   1260
caggacaata accttatagc ttgtaaattc tatcataatt gtggtttcaa aatcggctcc   1320
gtcgatacta tgttatacgc caactttcaa aacaactttg aaaaagctgt tttctggtat   1380
ttaaggtttt agaatgcaag gaacagtgaa ttggagttcg tcttgttata attagcttct   1440
tggggtatct ttaaatactg tagaaaagag gaaggaaata ataaatggct aaaatgagaa   1500
tatcaccgga attgaaaaaa ctgatcgaaa aataccgctg cgtaaaagat acggaaggaa   1560
tgtctcctgc taaggtatat aagctggtgg gagaaaatga aaacctatat ttaaaaatga   1620
cggacagccg gtataaaggg accacctatg atgtggaacg ggaaaaggac atgatgctat   1680
ggctggaagg aaagctgcct gttccaaagg tcctgcactt tgaacggcat gatggctgga   1740
gcaatctgct catgagtgag gccgatggcg tcctttgctc ggaagagtat gaagatgaac   1800
aaagccctga aaagattatc gagctgtatg cggagtgcat caggctcttt cactccatcg   1860
acatatcgga ttgtccctat acgaatagct tagacagccg cttagccgaa ttggattact   1920
tactgaataa cgatctggcc gatgtggatt gcgaaaactg ggaagaagac actccattta   1980
aagatccgcg cgagctgtat gatttttaa agacggaaaa gcccgaagag gaacttgtct   2040
tttcccacgg cgacctggga gacagcaaca tctttgtgaa agatggcaaa gtaagtggct   2100
ttattgatct tgggagaagc ggcagggcgg acaagtggta tgacattgcc ttctgcgtcc   2160
ggtcgatcag ggaggatatc ggggaagaac agtatgtcga gctatttttt gacttactgg   2220
ggatcaagcc tgattgggag aaaataaaat attatatttt actggatgaa ttgttttagt   2280
acctagattt agatgtctaa aaagcttttt agacatctaa tcttttctga agtacatccg   2340
caactgtcca tactctgatg ttttatatct tttctaaaag ttcgctagat aggggtcccg   2400
agcgcctacg aggaatttgt atcgactcta gaggatcccc gggtaccgaa aaggtgattg   2460
tcatggttat ggggaagata cattcaatag agacatgtgg tactgtagat gggcctggca   2520
taaggtacgt agtctttatg caaggttgtc ctttaaggtg cgcttattgc cataaccctg   2580
acacatggaa ttataacggt ggtaaagaag tatcaacaga tgagatattt aacgatgcaa   2640
aaagatatat accgtacatg aaatcatcag gcggcggcgt gacgctgaca ggtggagagc   2700
ctacattaca gcctgaattt tgcgaagatc tatttaaaaa gcttaaagcg tctggcatac   2760
acactgcatt agacacatcg ggatatgtga atatagataa agtaaaagaa cttgtaaaac   2820
acactgatct ttttttgctt gatataaagc acattgatga tgaaagccat aaaaagctta   2880
caggagtgtc gaatagaaag actttggagt ttgcaagata cctttccgat gaaggcaaga   2940
aaatgtggat aaggcatgtg atagtacctg gaataacgga tgatatggaa gagataagga   3000
aattggctga ttttgtctca tcattgaaaa atgtagatag agttgagata cttccgtatc   3060
ataaaatggg tgtgtataaa tatgaggcac ttgggatacc atatagattg aagggaataa   3120
atcctcctga cacatcaaaa attaaagaga taaaagaaga gtttaggaaa agagatataa   3180
```

```
aagtggtcta aaagcctcat gattcgtatc atggggcttt tcctttgaat taatttgata   3240
aagggtgtaa aattatcatg tgatgatgtg attttggagg taatcgcatg aatttaaata   3300
agataaatag aaacacgtac tacatagata atcctacgaa tattggcgtt tatgcctata   3360
aaaataaaaa ttgtctatta gtagatactg gtataaacgc aagcttggcg taatcatggt   3420
catagctgtt tcctgtgtga aattgttatc cgctcacaat tccacacaac atacgagccg   3480
gaagcataaa gtgtaaagcc tggggtgcct aatgagtgag ctaactcaca ttaattgcgt   3540
tgcgctcact gcccgctttc cagtcgggaa acctgtcgtg ccagctgcat taatgaatcg   3600
gccaacgcgc ggggagaggc ggtttgcgta ttgggcgctc ttccgcttcc tcgctcactg   3660
actcgctgcg ctcggtcgtt cggctgcggc gagcggtatc agctcactca aaggcggtaa   3720
tacggttatc cacagaatca ggggataacg caggaaagaa catgtgagca aaaggccagc   3780
aaaaggccag gaaccgtaaa aaggccgcgt tgctggcgtt tttccatagg ctccgccccc   3840
ctgacgagca tcacaaaaat cgacgctcaa gtcagaggtg gcgaaacccg acaggactat   3900
aaagatacca ggcgtttccc cctggaagct ccctcgtgcg ctctcctgtt ccgaccctgc   3960
cgcttaccgg atacctgtcc gcctttctcc cttcgggaag cgtggcgctt tctcatagct   4020
cacgctgtag gtatctcagt tcggtgtagg tcgttcgctc caagctgggc tgtgtgcacg   4080
aaccccccgt tcagcccgac cgctgcgcct tatccggtaa ctatcgtctt gagtccaacc   4140
cggtaagaca cgacttatcg ccactggcag cagccactgg taacaggatt agcagagcga   4200
ggtatgtagg cggtgctaca gagttcttga agtggtggcc taactacggc tacactagaa   4260
ggacagtatt tggtatctgc gctctgctga agccagttac cttcggaaaa agagttggta   4320
gctcttgatc cggcaaacaa accaccgctg gtagcggtgg tttttttgtt tgcaagcagc   4380
agattacgcg cagaaaaaaa ggatctcaag aagatccttt gatcttttct acggggtctg   4440
acgctcagtg gaacgaaaac tcacgttaag ggattttggt catgagatta tcaaaaagga   4500
tcttcaccta gatcctttta aattaaaaat gaagttttaa atcaatctaa agtatatatg   4560
agtaaacttg gtctgacagt taccaatgct taatcagtga ggcacctatc tcagcgatct   4620
gtctatttcg ttcatccata gttgcctgac tccccgtcgt gtagataact acgatacggg   4680
agggcttacc atctggcccc agtgctgcaa tgataccgcg agacccacgc tcaccggctc   4740
cagatttatc agcaataaac cagccagccg gaagggccga gcgcagaagt ggtcctgcaa   4800
ctttatccgc ctccatccag tctattaatt gttgccggga agctagagta agtagttcgc   4860
cagttaatag tttgcgcaac gttgttgcca ttgctacagg catcgtggtg tcacgctcgt   4920
cgtttggtat ggcttcattc agctccggtt cccaacgatc aaggcgagtt acatgatccc   4980
ccatgttgtg caaaaaagcg gttagctcct tcggtcctcc gatcgttgtc agaagtaagt   5040
tggccgcagt gttatcactc atggttatgg cagcactgca taattctctt actgtcatgc   5100
catccgtaag atgcttttct gtgactggtg agtactcaac caagtcattc tgagaatagt   5160
gtatgcggcg accgagttgc tcttgcccgg cgtcaatacg ggataatacc gcgccacata   5220
gcagaacttt aaaagtgctc atcattggaa aacgttcttc ggggcgaaaa ctctcaagga   5280
tcttaccgct gttgagatcc agttcgatgt aacccactcg tgcacccaac tgatcttcag   5340
catcttttac tttcaccagc gtttctgggt gagcaaaaac aggaaggcaa aatgccgcaa   5400
aaaagggaat aagggcgaca cggaaatgtt gaatactcat actcttcctt tttcaatatt   5460
attgaagcat ttatcagggt tattgtctca tgagcggata catatttgaa tgtatttaga   5520
aaaataaaca aataggggtt ccgcgcacat ttccccgaaa agtgccacct gacgtctaag   5580
```

-continued

```
aaaccattat tatcatgaca ttaacctata aaaataggcg tatcacgagg ccctttcgtc   5640

tcgcgcgttt cggtgatgac ggtgaaaacc tctgacacat gcagctcccg gagacggtca   5700

cagcttgtct gtaagcggat gccgggagca gacaagcccg tcagggcgcg tcagcgggtg   5760

ttggcgggtg tcggggctgg cttaactatg cggcatcaga gcagattgta ctgagagtgc   5820

accatatgcg gtgtgaaata ccgcacagat gcgtaaggag aaaataccgc atcaggcgcc   5880

attcgccatt caggctgcgc aactgttggg aagggcgatc ggtgcgggcc tcttcgctat   5940

tacgccagct ggcgaaaggg ggatgtgctg caaggcgatt aagttgggta acgccagggt   6000

tttcccagtc acgacgttgt aaaacgacgg cca                                6033
```

<210> SEQ ID NO 49
<211> LENGTH: 4542
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
gtttatgatg tatatactcc cgaaatgaga aaagccaaaa aagccgggat tattacagga     60

cttcccgacg catacggcag aggaagaata attggcgatt acagaagggt tgcactttat    120

ggcgttgaca ggctgattgc tgaaaaagag aaagaaatgg caagtcttga aagagattac    180

attgactatg agactgttcg agacagagaa gaaataagcg agcagattaa atctttaaaa    240

caacttaaag aaatggcttt aagttacggt tttgacatat cttgtcctgc aaaggatgcc    300

agagaagcct ttcaatggtt gtattttgca tatcttgcag cagtcaagga acagaacggc    360

gcggcaatga gtattggaag aatttcgact ttccttgaca tatacattga aagggatctc    420

aaagaaggaa aactcacgga ggagttggct caggaactgg ttgaccagct ggttataaag    480

ctgagaattg tgagattttt gagaactcct gagtatgaaa agctcttcag cggagacccc    540

acttgggtaa ccgaaagtat cggaggtatg gcgctggatg gaagaacgct ggttacaaaa    600

tcttcgttca ggtttttgca cactcttttc aacctgggac atgcaccgga gcccaacctt    660

acagtacttt ggtccgtcaa tcttcccgaa ggctttaaaa agtactgtgc aaaggtatca    720

attcattcaa gctccatcca gtatgaaagc gacgacataa tgaggaaaca ctggggagac    780

gattatggaa tagcagatgg attttctatt attgcaatgt ggaattggga acggaaaaat    840

tattttatta aagagtagtt caacaaacgg gattgacttt taaaaaagga ttgattctaa    900

tgaagaaagc agacaagtaa gcctcctaaa ttcactttag ataaaaattt aggaggcata    960

tcaaatgaac tttaataaaa ttgatttaga caattggaag agaaaagaga tatttaatca   1020

ttatttgaac caacaaacga cttttagtat aaccacagaa attgatatta gtgttttata   1080

ccgaaacata aaacaagaag gatataaatt ttaccctgca tttattttct tagtgacaag   1140

ggtgataaac tcaaatacag cttttagaac tggttacaat agcgacggag agttaggtta   1200

ttgggataag ttagagccac tttatacaat ttttgatggt gtatctaaaa cattctctgg   1260

tatttggact cctgtaaaga atgacttcaa agagttttat gatttatacc tttctgatgt   1320

agagaaatat aatggttcgg ggaaattgtt tcccaaaaca cctatacctg aaaatgcttt   1380

ttctctttct attattccat ggacttcatt tactgggttt aacttaaata tcaataataa   1440

tagtaattac cttctaccca ttattacagc aggaaaattc attaataaag gtaattcaat   1500

atatttaccg ctatctttac aggtacatca ttctgtttgt gatggttatc atgcaggatt   1560

gtttatgaac tctattcagg aattgtcaga taggcctaat gactggcttt tataatatga   1620
```

-continued

```
gataatgccg actgtacttt ttacagtcgg ttttctaatg tcactagggc tcgcctttgg   1680
gaagtttgaa gggctggcac gacaggtttc ccgactggaa agcgggcagt gagcgcaacg   1740
caattaatgt gagttagctc actcattagg caccccaggc tttacacttt atgcttccgg   1800
ctcgtatgtt gtgtggaatt gtgagcggat aacaatttca cacaggaaac agctatgacc   1860
atgattacgc caagcttgca tgcctgcagg tcgactctag aggatccgca agcttggcgt   1920
aatcatggtc atagctgttt cctgtgtgaa attgttatcc gctcacaatt ccacacaaca   1980
tacgagccgg aagcataaag tgtaaagcct ggggtgccta atgagtgagc taactcacat   2040
taattgcgtt gcgctcactg cccgctttcc agtcgggaaa cctgtcgtgc cagctgcatt   2100
aatgaatcgg ccaacgcgcg gggagaggcg gtttgcgtat tgggcgctct tccgcttcct   2160
cgctcactga ctcgctgcgc tcggtcgttc ggctgcggcg agcggtatca gctcactcaa   2220
aggcggtaat acggttatcc acagaatcag gggataacgc aggaaagaac atgtgagcaa   2280
aaggccagca aaaggccagg aaccgtaaaa aggccgcgtt gctggcgttt ttccataggc   2340
tccgcccccc tgacgagcat cacaaaaatc gacgctcaag tcagaggtgg cgaaacccga   2400
caggactata aagataccag gcgtttcccc ctggaagctc cctcgtgcgc tctcctgttc   2460
cgaccctgcc gcttaccgga tacctgtccg cctttctccc ttcgggaagc gtggcgcttt   2520
ctcatagctc acgctgtagg tatctcagtt cggtgtaggt cgttcgctcc aagctgggct   2580
gtgtgcacga accccccgtt cagcccgacc gctgcgcctt atccggtaac tatcgtcttg   2640
agtccaaccc ggtaagacac gacttatcgc cactggcagc agccactggt aacaggatta   2700
gcagagcgag gtatgtaggc ggtgctacag agttcttgaa gtggtggcct aactacggct   2760
acactagaag gacagtattt ggtatctgcg ctctgctgaa gccagttacc ttcggaaaaa   2820
gagttggtag ctcttgatcc ggcaaacaaa ccaccgctgg tagcggtggt ttttttgttt   2880
gcaagcagca gattacgcgc agaaaaaaag gatctcaaga agatcctttg atcttttcta   2940
cggggtctga cgctcagtgg aacgaaaact cacgttaagg gattttggtc atgagattat   3000
caaaaaggat cttcacctag atccttttaa attaaaaatg aagttttaaa tcaatctaaa   3060
gtatatatga gtaaacttgg tctgacagtt accaatgctt aatcagtgag gcacctatct   3120
cagcgatctg tctatttcgt tcatccatag ttgcctgact ccccgtcgtg tagataacta   3180
cgatacggga gggcttacca tctggcccca gtgctgcaat gataccgcga gacccacgct   3240
caccggctcc agatttatca gcaataaacc agccagccgg aagggccgag cgcagaagtg   3300
gtcctgcaac tttatccgcc tccatccagt ctattaattg ttgccgggaa gctagagtaa   3360
gtagttcgcc agttaatagt ttgcgcaacg ttgttgccat tgctacaggc atcgtggtgt   3420
cacgctcgtc gtttggtatg gcttcattca gctccggttc ccaacgatca aggcgagtta   3480
catgatcccc catgttgtgc aaaaaagcgg ttagctcctt cggtcctccg atcgttgtca   3540
gaagtaagtt ggccgcagtg ttatcactca tggttatggc agcactgcat aattctctta   3600
ctgtcatgcc atccgtaaga tgcttttctg tgactggtga gtactcaacc aagtcattct   3660
gagaatagtg tatgcggcga ccgagttgct cttgcccggc gtcaatacgg gataataccg   3720
cgccacatag cagaacttta aaagtgctca tcattggaaa acgttcttcg gggcgaaaac   3780
tctcaaggat cttaccgctg ttgagatcca gttcgatgta acccactcgt gcacccaact   3840
gatcttcagc atcttttact ttcaccagcg tttctgggtg agcaaaaaca ggaaggcaaa   3900
atgccgcaaa aaagggaata agggcgacac ggaaatgttg aatactcata ctcttccttt   3960
ttcaatatta ttgaagcatt tatcagggtt attgtctcat gagcggatac atatttgaat   4020
```

gtatttagaa aaataaacaa ataggggttc cgcgcacatt tccccgaaaa gtgccacctg 4080
acgtctaaga aaccattatt atcatgacat taacctataa aaataggcgt atcacgaggc 4140
cctttcgtct cgcgcgtttc ggtgatgacg gtgaaaacct ctgacacatg cagctcccgg 4200
agacggtcac agcttgtctg taagcggatg ccgggagcag acaagcccgt cagggcgcgt 4260
cagcgggtgt tggcgggtgt cggggctggc ttaactatgc ggcatcagag cagattgtac 4320
tgagagtgca ccatatgcgg tgtgaaatac cgcacagatg cgtaaggaga aaataccgca 4380
tcaggcgcca ttcgccattc aggctgcgca actgttggga agggcgatcg gtgcgggcct 4440
cttcgctatt acgccagctg gcgaaagggg gatgtgctgc aaggcgatta agttgggtaa 4500
cgccagggtt ttcccagtca cgacgttgta aaacgacggc ca 4542

<210> SEQ ID NO 50
<211> LENGTH: 5648
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
cccgcaataa tggaagtaaa gagcatgaaa gtgggaatgc tggcttacac cgatatggcg 60
gaaattgtgt acaagggcaa tccgaactac aagtttgcgg ccggagagga caagccgggg 120
gttgcaccaa gacctttgaa atttgacgat tccataaaaa aagacataga agagttacgg 180
agcaaggtgg atattttaat tgtttcactt cactggggag tggaggaaag ctttgaagtt 240
ctgcctgaac agagggaatt tgcccacagt cttatagata acggagtgga tgtaatattg 300
ggacaccatc cccaccagtt ccaaggtata gaaatctaca agggcaaacc tgttttctac 360
agtctgggta attttatttt tgatcagaac gatcccgaaa accaggagtc ctttattgtg 420
acacttgatt acaaaggcag cagactgaca ggaatagagg ctgtacccgt gagaacaatc 480 ggaaaaaatac aggtagttcc tcaaaaagga gatgaagcaa aacctatttt ggaaagagag 540
aaaaatttat gtaataggct tgatacaaac tgcattataa aagatgacaa attatatttt 600
gaaattggaa aataatgata atataattaa gttggacgta ttttgacaaa ataaaatcat 660
aaagtggttg catttgtcga gatttgtgat atcattggat agtaaattat attttaggtt 720
aaaaatggaa aaatagtttt ttatttaaac tttattttta aactttattt aaaatatcaa 780
aataattgcc tttgtatttt acttattgta caatatattt gtacaatata ttaaggaaaa 840
aaatactttt gtagcgactt aaaagtcaat tgaatggacc aataaaggac cttttcaaat 900
ttgtcaaggt attttaggac aatttttttt attttggata ttgttcttgt ttattgggta 960
aataagatgg attttctatt attgcaatgt ggaattggga acggaaaaat tattttatta 1020
aagagtagtt caacaaacgg gattgacttt taaaaaagga ttgattctaa tgaagaaagc 1080
agacaagtaa gcctcctaaa ttcactttag ataaaaattt aggaggcata tcaaatgaac 1140
tttaataaaa ttgatttaga caattggaag agaaaagaga tatttaatca ttatttgaac 1200
caacaaacga cttttagtat aaccacagaa attgatatta gtgttttata ccgaaacata 1260
aaacaagaag gatataaatt ttaccctgca tttattttct tagtgacaag ggtgataaac 1320
tcaaatacag cttttagaac tggttacaat agcgacggag agttaggtta ttgggataag 1380
ttagagccac tttatacaat ttttgatggt gtatctaaaa cattctctgg tatttggact 1440
cctgtaaaga atgacttcaa agagttttat gatttatacc tttctgatgt agagaaatat 1500

-continued

```
aatggttcgg ggaaattgtt tcccaaaaca cctatacctg aaaatgcttt ttctctttct   1560
attattccat ggacttcatt tactgggttt aacttaaata tcaataataa tagtaattac   1620
cttctaccca ttattacagc aggaaaattc attaataaag gtaattcaat atatttaccg   1680
ctatctttac aggtacatca ttctgtttgt gatggttatc atgcaggatt gtttatgaac   1740
tctattcagg aattgtcaga taggcctaat gactggcttt tataatatga gataatgccg   1800
actgtacttt ttacagtcgg ttttctaatg tcactagggc tcgcctttgg gaagtttgaa   1860
gggctggcac gacaggtttc ccgactggaa agcgggcagt gagcgcaacg caattaatgt   1920
gagttagctc actcattagg caccccaggc tttacacttt atgcttccgg ctcgtatgtt   1980
gtgtggaatt gtgagcggat aacaatttca cacaggaaac agctatgacc atgattacgc   2040
caagcttgca tgcctgcagg tcgactctag aggatcccat taaagggcag gatacactca   2100
tttgaatctt ttgggacact ggacggaccg ggtataagat ttgtggtttt catgcagggc   2160
tgtcccttgc gttgtatata ttgccacaac agggatacct gggatgttaa tgcggggagt   2220
gagtacactc cccggcaagt aattgatgaa atgatgaaat acatagacta tataaaggtc   2280
tccggaggcg gaataactgt taccggcggg gagcctgttc tccaggccga ttttgtggcc   2340
gaggtgttca gacttgcaaa agagcaggga gtgcatacgg cgctggatac caatggattt   2400
gctgacatag agaaggttga aaggcttata aaatacaccg atcttgtatt gctggatata   2460
aagcatgccc gggaggataa acataagata attaccggtg tgtccaacga aaaaatcaag   2520
cgttttgcgc tgtatctttc ggaccaggga gtgcctatct ggataagata tgtccttgtc   2580
cccggatata ccgacgatga agatgacctt aaaatggcgg ctgatttcat aaaaaagctt   2640
aaaacggtgg aaaaaatcga agttcttcct tatcacaaca tgggagcata caaatgggaa   2700
aaacttggtc agaaatacat gcttgaagga gtaaaggggc cgagtgcgca agaggtggaa   2760
aaagcaaaga ggattctgtc aggcaaataa taaaagcttt tttcttttat tatttgcttt   2820
tttctattac caatttgctt tgcttaagtt taggtttggt tttgatgagt tttttaatgt   2880
ttcttttata tttatctttt atatgaacag tgttgtaaac ttccaaatcc agtttgtcaa   2940
atattgattt aaaaatcttt gccgtatact gggcgtcagt taatgcccgg tgaagatttt   3000
cgtctatttc aacgcaagct tggcgtaatc atggtcatag ctgtttcctg tgtgaaattg   3060
ttatccgctc acaattccac acaacatacg agccggaagc ataaagtgta aagcctgggg   3120
tgcctaatga gtgagctaac tcacattaat tgcgttgcgc tcactgcccg ctttccagtc   3180
gggaaacctg tcgtgccagc tgcattaatg aatcggccaa cgcgcgggga gaggcggttt   3240
gcgtattggg cgctcttccg cttcctcgct cactgactcg ctgcgctcgg tcgttcggct   3300
gcggcgagcg gtatcagctc actcaaaggc ggtaatacgg ttatccacag aatcagggga   3360
taacgcagga aagaacatgt gagcaaaagg ccagcaaaag gccaggaacc gtaaaaaggc   3420
cgcgttgctg gcgtttttcc ataggctccg cccccctgac gagcatcaca aaaatcgacg   3480
ctcaagtcag aggtggcgaa acccgacagg actataaaga taccaggcgt ttccccctgg   3540
aagctccctc gtgcgctctc ctgttccgac cctgccgctt accggatacc tgtccgcctt   3600
tctcccttcg ggaagcgtgg cgctttctca tagctcacgc tgtaggtatc tcagttcggt   3660
gtaggtcgtt cgctccaagc tgggctgtgt gcacgaaccc cccgttcagc ccgaccgctg   3720
cgccttatcc ggtaactatc gtcttgagtc caacccggta agacacgact tatcgccact   3780
ggcagcagcc actggtaaca ggattagcag agcgaggtat gtaggcggtg ctacagagtt   3840
cttgaagtgg tggcctaact acggctacac tagaaggaca gtatttggta tctgcgctct   3900
```

gctgaagcca gttaccttcg gaaaaagagt tggtagctct tgatccggca aacaaaccac 3960
cgctggtagc ggtggttttt ttgtttgcaa gcagcagatt acgcgcagaa aaaaaggatc 4020
tcaagaagat cctttgatct tttctacggg gtctgacgct cagtggaacg aaaactcacg 4080
ttaagggatt ttggtcatga gattatcaaa aaggatcttc acctagatcc ttttaaatta 4140
aaaatgaagt tttaaatcaa tctaaagtat atatgagtaa acttggtctg acagttacca 4200
atgcttaatc agtgaggcac ctatctcagc gatctgtcta tttcgttcat ccatagttgc 4260
ctgactcccc gtcgtgtaga taactacgat acgggagggc ttaccatctg gccccagtgc 4320
tgcaatgata ccgcgagacc cacgctcacc ggctccagat ttatcagcaa taaaccagcc 4380
agccggaagg gccgagcgca gaagtggtcc tgcaacttta tccgcctcca tccagtctat 4440
taattgttgc cgggaagcta gagtaagtag ttcgccagtt aatagtttgc gcaacgttgt 4500
tgccattgct acaggcatcg tggtgtcacg ctcgtcgttt ggtatggctt cattcagctc 4560
cggttcccaa cgatcaaggc gagttacatg atcccccatg ttgtgcaaaa aagcggttag 4620
ctccttcggt cctccgatcg ttgtcagaag taagttggcc gcagtgttat cactcatggt 4680
tatggcagca ctgcataatt ctcttactgt catgccatcc gtaagatgct tttctgtgac 4740
tggtgagtac tcaaccaagt cattctgaga atagtgtatg cggcgaccga gttgctcttg 4800
cccggcgtca atacgggata ataccgcgcc acatagcaga actttaaaag tgctcatcat 4860
tggaaaacgt tcttcggggc gaaaactctc aaggatctta ccgctgttga gatccagttc 4920
gatgtaaccc actcgtgcac ccaactgatc ttcagcatct tttactttca ccagcgtttc 4980
tgggtgagca aaaacaggaa ggcaaaatgc cgcaaaaaag ggaataaggg cgacacggaa 5040
atgttgaata ctcatactct tcctttttca atattattga agcatttatc agggttattg 5100
tctcatgagc ggatacatat ttgaatgtat ttagaaaaat aaacaaatag gggttccgcg 5160
cacatttccc cgaaaagtgc cacctgacgt ctaagaaacc attattatca tgacattaac 5220
ctataaaaat aggcgtatca cgaggccctt tcgtctcgcg cgtttcggtg atgacggtga 5280
aaacctctga cacatgcagc tcccggagac ggtcacagct tgtctgtaag cggatgccgg 5340
gagcagacaa gcccgtcagg gcgcgtcagc gggtgttggc gggtgtcggg gctggcttaa 5400
ctatgcggca tcagagcaga ttgtactgag agtgcaccat atgcggtgtg aaataccgca 5460
cagatgcgta aggagaaaat accgcatcag gcgccattcg ccattcaggc tgcgcaactg 5520
ttgggaaggg cgatcggtgc gggcctcttc gctattacgc cagctggcga aaggggggatg 5580 tgctgcaagg cgattaagtt gggtaacgcc agggttttcc cagtcacgac gttgtaaaac 5640
gacggcca 5648

<210> SEQ ID NO 51
<211> LENGTH: 4648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51
tttggtggta ttcgtatggc acagagtgct tgccatgaat atggatatga ggtagacgaa 60
gaggtagcac gtatttttac agactaccgc aagacacata atcaaggtgt atttgatgca 120
tacactgacg aaatgaagct cgctagaaaa tcagcaatca ttactggttt gcctgatgct 180
tatggtagag gtagaattat tggcgattac cgtcgagtgg cactttacgg tactgattta 240
cttattgaag acaagaaaga acaacttaca acttccttaa agagaatgac tagtgataat 300

```
attcgcttaa gagaagaatt agcagaacaa attcgtgcat taaaagaatt agcgaagctt    360
ggtgaaatct atggttacga tattacgaag ccagcaataa atgcaaagga agcaattcag    420
tggctttact ttggatatct tgcagcggta aaagagcaaa acggtgctgc aatgagctta    480
ggccgtactt ctacattcct tgatatttat atccagagag atttagataa tggtgttatc    540
acagaaaaag aagcacaaga gtatatcgat cattttatta tgaaacttcg tctagtgaag    600
tttgcaagaa ctccagaata caatgcctta ttctccggtg accctacttg ggtaacagaa    660
agtatcgctg ggattggtac agatggacgc catatggtaa caaagacatc cttccgttac    720
cttcatacgt tagacaacct tggaactgct ccagaaccaa acatgacagt tctatggtca    780
actagattac caagattatt taaagagtac tgtgctaaga tgtcaattaa gtcatcctct    840
attcaatacg aaaatgatga tatcatgcgt ccaactcatg gtgatgatta tgcaattgct    900
agatggattt tctattattg caatgtggaa ttgggaacgg aaaaattatt ttattaaaga    960
gtagttcaac aaacgggatt gacttttaaa aaaggattga ttctaatgaa gaaagcagac   1020
aagtaagcct cctaaattca ctttagataa aaatttagga ggcatatcaa atgaacttta   1080
ataaaattga tttagacaat tggaagagaa aagagatatt taatcattat ttgaaccaac   1140
aaacgacttt tagtataacc acagaaattg atattagtgt tttataccga aacataaaac   1200
aagaaggata taaattttac cctgcattta ttttcttagt gacaagggtg ataaactcaa   1260
atacagcttt tagaactggt tacaatagcg acggagagtt aggttattgg gataagttag   1320
agccacttta tacaattttt gatggtgtat ctaaaacatt ctctggtatt tggactcctg   1380
taaagaatga cttcaaagag ttttatgatt tatacctttc tgatgtagag aaatataatg   1440
gttcggggaa attgtttccc aaaacaccta tacctgaaaa tgctttttct ctttctatta   1500
ttccatggac ttcatttact gggtttaact taaatatcaa taataatagt aattaccttc   1560
tacccattat tacagcagga aaattcatta ataaaggtaa ttcaatatat ttaccgctat   1620
ctttacaggt acatcattct gtttgtgatg gttatcatgc aggattgttt atgaactcta   1680
ttcaggaatt gtcagatagg cctaatgact ggcttttata atatgagata atgccgactg   1740
tactttttac agtcggtttt ctaatgtcac tagggctcgc ctttgggaag tttgaagggc   1800
tggcacgaca ggtttcccga ctggaaagcg ggcagtgagc gcaacgcaat taatgtgagt   1860
tagctcactc attaggcacc ccaggcttta cactttatgc ttccggctcg tatgttgtgt   1920
ggaattgtga gcggataaca atttcacaca ggaaacagct atgaccatga ttacgccaag   1980
cttgcatgcc tgcaggtcga ctctagagga tccgcaagct tggcgtaatc atggtcatag   2040
ctgtttcctg tgtgaaattg ttatccgctc acaattccac acaacatacg agccggaagc   2100
ataaagtgta aagcctgggg tgcctaatga gtgagctaac tcacattaat tgcgttgcgc   2160
tcactgcccg ctttccagtc gggaaacctg tcgtgccagc tgcattaatg aatcggccaa   2220
cgcgcgggga gaggcggttt gcgtattggg cgctcttccg cttcctcgct cactgactcg   2280
ctgcgctcgg tcgttcggct gcggcgagcg gtatcagctc actcaaaggc ggtaatacgg   2340
ttatccacag aatcagggga taacgcagga aagaacatgt gagcaaaagg ccagcaaaag   2400
gccaggaacc gtaaaaaggc cgcgttgctg gcgtttttcc ataggctccg cccccctgac   2460
gagcatcaca aaaatcgacg ctcaagtcag aggtggcgaa acccgacagg actataaaga   2520
taccaggcgt ttccccctgg aagctccctc gtgcgctctc ctgttccgac cctgccgctt   2580
accggatacc tgtccgcctt tctcccttcg ggaagcgtgg cgctttctca tagctcacgc   2640
tgtaggtatc tcagttcggt gtaggtcgtt cgctccaagc tgggctgtgt gcacgaaccc   2700
```

cccgttcagc ccgaccgctg cgccttatcc ggtaactatc gtcttgagtc caacccggta 2760
agacacgact tatcgccact ggcagcagcc actggtaaca ggattagcag agcgaggtat 2820
gtaggcggtg ctacagagtt cttgaagtgg tggcctaact acggctacac tagaaggaca 2880
gtatttggta tctgcgctct gctgaagcca gttaccttcg gaaaaagagt tggtagctct 2940
tgatccggca aacaaaccac cgctggtagc ggtggttttt ttgtttgcaa gcagcagatt 3000
acgcgcagaa aaaaaggatc tcaagaagat cctttgatct tttctacggg gtctgacgct 3060
cagtggaacg aaaactcacg ttaagggatt ttggtcatga gattatcaaa aaggatcttc 3120
acctagatcc ttttaaatta aaaatgaagt tttaaatcaa tctaaagtat atatgagtaa 3180
acttggtctg acagttacca atgcttaatc agtgaggcac ctatctcagc gatctgtcta 3240
tttcgttcat ccatagttgc ctgactcccc gtcgtgtaga taactacgat acgggagggc 3300
ttaccatctg gccccagtgc tgcaatgata ccgcgagacc cacgctcacc ggctccagat 3360
ttatcagcaa taaaccagcc agccggaagg gccgagcgca gaagtggtcc tgcaacttta 3420
tccgcctcca tccagtctat taattgttgc cgggaagcta gagtaagtag ttcgccagtt 3480
aatagtttgc gcaacgttgt tgccattgct acaggcatcg tggtgtcacg ctcgtcgttt 3540
ggtatggctt cattcagctc cggttcccaa cgatcaaggc gagttacatg atcccccatg 3600
ttgtgcaaaa aagcggttag ctccttcggt cctccgatcg ttgtcagaag taagttggcc 3660
gcagtgttat cactcatggt tatggcagca ctgcataatt ctcttactgt catgccatcc 3720
gtaagatgct tttctgtgac tggtgagtac tcaaccaagt cattctgaga atagtgtatg 3780
cggcgaccga gttgctcttg cccggcgtca atacgggata ataccgcgcc acatagcaga 3840
actttaaaag tgctcatcat tggaaaacgt tcttcggggc gaaaactctc aaggatctta 3900
ccgctgttga gatccagttc gatgtaaccc actcgtgcac ccaactgatc ttcagcatct 3960
tttactttca ccagcgtttc tgggtgagca aaaacaggaa ggcaaaatgc cgcaaaaaag 4020
ggaataaggg cgacacggaa atgttgaata ctcatactct tcctttttca atattattga 4080
agcatttatc agggttattg tctcatgagc ggatacatat ttgaatgtat ttagaaaaat 4140
aaacaaatag gggttccgcg cacatttccc cgaaaagtgc cacctgacgt ctaagaaacc 4200
attattatca tgacattaac ctataaaaat aggcgtatca cgaggccctt tcgtctcgcg 4260
cgtttcggtg atgacggtga aaacctctga cacatgcagc tcccggagac ggtcacagct 4320
tgtctgtaag cggatgccgg gagcagacaa gcccgtcagg gcgcgtcagc gggtgttggc 4380
gggtgtcggg gctggcttaa ctatgcggca tcagagcaga ttgtactgag agtgcaccat 4440
atgcggtgtg aaataccgca cagatgcgta aggagaaaat accgcatcag gcgccattcg 4500
ccattcaggc tgcgcaactg ttgggaaggg cgatcggtgc gggcctcttc gctattacgc 4560
cagctggcga aagggggatg tgctgcaagg cgattaagtt gggtaacgcc agggttttcc 4620
cagtcacgac gttgtaaaac gacggcca 4648

<210> SEQ ID NO 52
<211> LENGTH: 5706
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52
tcacccagca gcagccatga ttataaacac cggagttccg gagcttagta gcgaagcatc 60

-continued

```
taaaagcgga aagccttata tttacggcgg aacgggaaat ggaccagtct ttattgaacg    120
taccgctgat gtaagaaaag cggtagagga tatcattgca agccgcacct ttgattacgg    180
aatcgtgtct gcggcagaac aatatatggt agtagacagt cttattgcag ctgaagtaaa    240
agctgagatg ttaagaaacg gtgcctactt catgaacgag gaagaggaga aaaagctaat    300
agacctccta aaccttacga gtggaaaggc agatacagaa attatgggaa gaccagccga    360
agaacttgcc aaacgagcag gatttatggt acctaatacc acgactgtgc tggtttccga    420
acagaaatat atttccgaca ggaacccatt tgcaaaagag cttctttgtc ctgtattggc    480
ttactacatc gaaaatgact ggatgcatgc ttgtgagaag tgcatgagtc ttttagtaaa    540
cgaaagccat ggacataccc tggtgattca ttccagggat gaagaagtaa taggccagtt    600
cgccttaaag aaaccagtag gcagagtact tgtaaatacc cccgctaccc tgggtagtat    660
gggtgcaacc acaaacttgt ttccggctat gaccctagga agcattacag caggcgccgg    720
aatcacagcg gacaatgttt ctcctatgaa tttcatatac attcgtaaag taggatatgg    780
agttcgggga gtacaagaat ttcttggttc ggttgagaaa acctcaagcg gatacgcgaa    840
agctcctgaa acaatcagga acaatgccct tgaaacaaac aaggtcaatg cctttgaaac    900
aagcaaaggc atggaagatg ctagagatct tttgaaacag attttacaag ccttgtccaa    960
agaactagat ggattttcta ttattgcaat gtggaattgg gaacggaaaa attattttat   1020
taaagagtag ttcaacaaac gggattgact tttaaaaaag gattgattct aatgaagaaa   1080
gcagacaagt aagcctccta aattcacttt agataaaaat ttaggaggca tatcaaatga   1140
actttaataa aattgattta gacaattgga agagaaaaga gatatttaat cattatttga   1200
accaacaaac gacttttagt ataaccacag aaattgatat tagtgtttta taccgaaaca   1260
taaaacaaga aggatataaa ttttaccctg catttatttt cttagtgaca agggtgataa   1320
actcaaatac agcttttaga actggttaca atagcgacgg agagttaggt tattgggata   1380
agttagagcc actttataca atttttgatg gtgtatctaa aacattctct ggtatttgga   1440
ctcctgtaaa gaatgacttc aaagagtttt atgatttata cctttctgat gtagagaaat   1500
ataatggttc ggggaaattg tttcccaaaa cacctatacc tgaaaatgct tttctcttt    1560
ctattattcc atggacttca tttactgggt ttaacttaaa tatcaataat aatagtaatt   1620
accttctacc cattattaca gcaggaaaat tcattaataa aggtaattca atatatttac   1680
cgctatcttt acaggtacat cattctgttt gtgatggtta tcatgcagga ttgtttatga   1740
actctattca ggaattgtca gataggccta atgactggct tttataatat gagataatgc   1800
cgactgtact ttttacagtc ggttttctaa tgtcactagg gctcgccttt gggaagtttg   1860
aagggctggc acgacaggtt tcccgactgg aaagcgggca gtgagcgcaa cgcaattaat   1920
gtgagttagc tcactcatta ggcaccccag gctttacact ttatgcttcc ggctcgtatg   1980
ttgtgtggaa ttgtgagcgg ataacaattt cacacaggaa acagctatga ccatgattac   2040
gccaagcttg catgcctgca ggtcgactct agaggatcca acggagagta atcaaaatgg   2100
accatggaaa atcaggagag attgaacgta aggcgtttat atttaacgtg cagaagtaca   2160
acatgtatga cgggccggga atcagaacct tggtattctt taaaggctgt cctcttcggt   2220
gtaaatggtg ctccaatccg gaaggtctgg aacgaaaatt tcaggtaatg tataagcaaa   2280
gtttttgtac aaactgcggg gcgtgcgctg atgtgtgccc cgtaggaatc cacgtgatgt   2340
cgaacggaac acatgaaatt gttcgggaaa aggaatgcat cggctgcatg aagtgtaaaa   2400
acatctgccc aaagtcggcg cttaccattg caggagaggt aaagaccatt tcagaactgc   2460
```

-continued

```
ttaagattgt ggaagaggac gctgcttttt atgatatgtc cggaggtggc gtgacccttg   2520
ggggtggtga agtaaccgca caaccagaag cggccttaaa tcttttgatg gcttgtaaac   2580
aggagggaat caacacagca attgaaactt gcggttattc gaatacagag aacattttaa   2640
aaattgcgga atatgtggat cttttcctgt ttgatatcaa acatatggat ccagtacgtc   2700
acaacgagtt aacaggtgtg aacaatgaac agattcttac taaccttgag gaactgcttc   2760
accgccgcta taacgtaaaa gtccgtatgc caatgttaaa aggaattaat gacagcaggg   2820
aagaaattga tgcggttatc aagtttttaa tgccataccg tactgataag aactttaagg   2880
gaattgactt acttccatac cataagctcg gagttaataa atacaatcag cttgataagg   2940
tatatccgat tgacggcgat cctagcttaa gtgctgagga tttagaccga attgaaggtt   3000
ggatgaaaga atacgatttt ccggttaacg tggtaaaaca ctaagaaagg ggaaggacgc   3060
catggaagaa ggcaagcttg gcgtaatcat ggtcatagct gtttcctgtg tgaaattgtt   3120
atccgctcac aattccacac aacatacgag ccggaagcat aaagtgtaaa gcctggggtg   3180
cctaatgagt gagctaactc acattaattg cgttgcgctc actgcccgct ttccagtcgg   3240
gaaacctgtc gtgccagctg cattaatgaa tcggccaacg cgcggggaga ggcggtttgc   3300
gtattgggcg ctcttccgct tcctcgctca ctgactcgct gcgctcggtc gttcggctgc   3360
ggcgagcggt atcagctcac tcaaaggcgg taatacggtt atccacagaa tcaggggata   3420
acgcaggaaa gaacatgtga gcaaaaggcc agcaaaaggc caggaaccgt aaaaaggccg   3480
cgttgctggc gtttttccat aggctccgcc cccctgacga gcatcacaaa aatcgacgct   3540
caagtcagag gtggcgaaac ccgacaggac tataaagata ccaggcgttt ccccctggaa   3600
gctccctcgt gcgctctcct gttccgaccc tgccgcttac cggatacctg tccgcctttc   3660
tcccttcggg aagcgtggcg ctttctcata gctcacgctg taggtatctc agttcggtgt   3720
aggtcgttcg ctccaagctg ggctgtgtgc acgaaccccc cgttcagccc gaccgctgcg   3780
ccttatccgg taactatcgt cttgagtcca acccggtaag acacgactta tcgccactgg   3840
cagcagccac tggtaacagg attagcagag cgaggtatgt aggcggtgct acagagttct   3900
tgaagtggtg gcctaactac ggctacacta gaaggacagt atttggtatc tgcgctctgc   3960
tgaagccagt taccttcgga aaaagagttg gtagctcttg atccggcaaa caaaccaccg   4020
ctggtagcgg tggttttttt gtttgcaagc agcagattac gcgcagaaaa aaaggatctc   4080
aagaagatcc tttgatcttt tctacggggt ctgacgctca gtggaacgaa aactcacgtt   4140
aagggatttt ggtcatgaga ttatcaaaaa ggatcttcac ctagatcctt ttaaattaaa   4200
aatgaagttt taaatcaatc taaagtatat atgagtaaac ttggtctgac agttaccaat   4260
gcttaatcag tgaggcacct atctcagcga tctgtctatt tcgttcatcc atagttgcct   4320
gactccccgt cgtgtagata actacgatac gggagggctt accatctggc cccagtgctg   4380
caatgatacc gcgagaccca cgctcaccgg ctccagattt atcagcaata aaccagccag   4440
ccggaagggc cgagcgcaga agtggtcctg caactttatc cgcctccatc cagtctatta   4500
attgttgccg ggaagctaga gtaagtagtt cgccagttaa tagtttgcgc aacgttgttg   4560
ccattgctac aggcatcgtg gtgtcacgct cgtcgtttgg tatggcttca ttcagctccg   4620
gttcccaacg atcaaggcga gttacatgat cccccatgtt gtgcaaaaaa gcggttagct   4680
ccttcggtcc tccgatcgtt gtcagaagta agttggccgc agtgttatca ctcatggtta   4740
tggcagcact gcataattct cttactgtca tgccatccgt aagatgcttt tctgtgactg   4800
gtgagtactc aaccaagtca ttctgagaat agtgtatgcg gcgaccgagt tgctcttgcc   4860
```

-continued

```
cggcgtcaat acgggataat accgcgccac atagcagaac tttaaaagtg ctcatcattg   4920

gaaaacgttc ttcggggcga aaactctcaa ggatcttacc gctgttgaga tccagttcga   4980

tgtaacccac tcgtgcaccc aactgatctt cagcatcttt tactttcacc agcgtttctg   5040

ggtgagcaaa aacaggaagg caaaatgccg caaaaaaggg aataagggcg acacggaaat   5100

gttgaatact catactcttc ctttttcaat attattgaag catttatcag ggttattgtc   5160

tcatgagcgg atacatattt gaatgtattt agaaaaataa acaaataggg gttccgcgca   5220

catttccccg aaaagtgcca cctgacgtct aagaaaccat tattatcatg acattaacct   5280

ataaaaatag gcgtatcacg aggccctttc gtctcgcgcg tttcggtgat gacggtgaaa   5340

acctctgaca catgcagctc ccggagacgg tcacagcttg tctgtaagcg gatgccggga   5400

gcagacaagc ccgtcagggc gcgtcagcgg gtgttggcgg gtgtcggggc tggcttaact   5460

atgcggcatc agagcagatt gtactgagag tgcaccatat gcggtgtgaa ataccgcaca   5520

gatgcgtaag gagaaaatac cgcatcaggc gccattcgcc attcaggctg cgcaactgtt   5580

gggaagggcg atcggtgcgg gcctcttcgc tattacgcca gctggcgaaa gggggatgtg   5640

ctgcaaggcg attaagttgg gtaacgccag ggttttccca gtcacgacgt tgtaaaacga   5700

cggcca                                                              5706
```

<210> SEQ ID NO 53
<211> LENGTH: 5780
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
tctatcagct gtccctcctg ttcagctact gacggggtgg tgcgtaacgg caaaagcacc     60

gccggacatc agcgctagcg gagtgtatac tggcttacta tgttggcact gatgagggtg    120

tcagtgaagt gcttcatgtg gcaggagaaa aaaggctgca ccggtgcgtc agcagaatat    180

gtgatacagg atatattccg cttcctcgct cactgactcg ctacgctcgg tcgttcgact    240

gcggcgagcg gaaatggctt acgaacgggg cggagatttc ctggaagatg ccaggaagat    300

acttaacagg gaagtgagag ggccgcggca aagccgtttt tccataggct ccgcccccct    360

gacaagcatc acgaaatctg acgctcaaat cagtggtggc gaaacccgac aggactataa    420

agataccagg cgtttccccc tggcggctcc ctcgtgcgct ctcctgttcc tgcctttcgg    480

tttaccggtg tcattccgct gttatggccg cgtttgtctc attccacgcc tgacactcag    540

ttccgggtag gcagttcgct ccaagctgga ctgtatgcac gaaccccccg ttcagtccga    600

ccgctgcgcc ttatccggta actatcgtct tgagtccaac ccggaaagac atgcaaaagc    660

accactggca gcagccactg gtaattgatt tagaggagtt agtcttgaag tcatgcgccg    720

gttaaggcta aactgaaagg acaagttttg gtgactgcgc tcctccaagc cagttacctc    780

ggttcaaaga gttggtagct cagagaacct tcgaaaaacc gccctgcaag gcggtttttt    840

cgttttcaga gcaagagatt acgcgcagac caaaacgatc tcaagaagat catcttatta    900

atcagataaa atatttctag atttcagtgc aatttatctc ttcaaatgta gcacctgaag    960

tcagccccat acgatataag ttgtaattct catgtttgac agcttatcat cgataagctt   1020

taatgcggta gtttatcaca gttaaattgc taacgcagtc aggcacctat acatgcattt   1080

acttataata cagtttttta gttttgctgg ccgcatcttc tcaaatatgc ttcccagcct   1140

gcttttctgt aacgttcacc ctctacctta gcatcccttc cctttgcaaa tagtcctctt   1200
```

-continued

```
ccaacaataa taatgtcaga tcctgtagag accacatcat ccacggttct atactgttga   1260
cccaatgcgt ctcccttgtc atctaaaccc acaccgggtg tcataatcaa ccaatcgtaa   1320
ccttcatctc ttccacccat gtctctttga gcaataaagc cgataacaaa atctttgtcg   1380
ctcttcgcaa tgtcaacagt acccttagta tattctccag tagataggga gcccttgcat   1440
gacaattctg ctaacatcaa aaggcctcta ggttcctttg ttacttcttc tgccgcctgc   1500
ttcaaaccgc taacaatacc tgggcccacc acaccgtgtg cattcgtaat gtctgcccat   1560
tctgctattc tgtatacacc cgcagagtac tgcaatttga ctgtattacc aatgtcagca   1620
aattttctgt cttcgaagag taaaaaattg tacttggcgg ataatgcctt tagcggctta   1680
actgtgccct ccatggaaaa atcagtcaag atatccacat gtgtttttag taaacaaatt   1740
ttgggaccta atgcttcaac taactccagt aattccttgg tggtacgaac atccaatgaa   1800
gcacacaagt ttgtttgctt ttcgtgcatg atattaaata gcttggcagc aacaggacta   1860
ggatgagtag cagcacgttc cttatatgta gctttcgaca tgatttatct tcgtttcctg   1920
caggtttttg ttctgtgcag ttgggttaag aatactgggc aatttcatgt ttcttcaaca   1980
ctacatatgc gtatatatac caatctaagt ctgtgctcct tccttcgttc ttccttctgt   2040
tcggagatta ccgaatcaaa aaaatttcaa agaaaccgaa atcaaaaaaa agaataaaaa   2100
aaaaatgatg aattgaattg aaaagctagc ttatcgatgg gtccttttca tcacgtgcta   2160
taaaaataat tataatttaa attttttaat ataaatatat aaattaaaaa tagaaagtaa   2220
aaaaagaaat taaagaaaaa atagtttttg ttttccgaag atgtaaaaga ctctaggggg   2280
atcgccaaca aatactacct tttatcttgc tcttcctgct ctcaggtatt aatgccgaat   2340
tgtttcatct tgtctgtgta gaagaccaca cacgaaaatc ctgtgatttt acattttact   2400
tatcgttaat cgaatgtata tctatttaat ctgcttttct tgtctaataa atatatatgt   2460
aaagtacgct tttgttgaaa atttttaaa cctttgttta tttttttttc ttcattccgt   2520
aactcttcta ccttctttat ttactttcta aaatccaaat acaaaacata aaaataaata   2580
aacacagagt aaattcccaa attattccat cattaaaaga tacgaggcgc gtgtaagtta   2640
caggcaagcg atctctaaga aaccattatt atcatgacat taacctataa aaaaggcctc   2700
tcgagctaga gtcgatcttc gccagcaggg cgaggatcgt ggcatcaccg aaccgcgccg   2760
tgcgcgggtc gtcggtgagc cagagtttca gcaggccgcc caggcggccc aggtcgccat   2820
tgatgcgggc cagctcgcgg acgtgctcat agtccacgac gcccgtgatt ttgtagccct   2880
ggccgacggc cagcaggtag gccgacaggc tcatgccggc cgccgccgcc ttttcctcaa   2940
tcgctcttcg ttcgtctgga aggcagtaca ccttgatagg tgggctgccc ttcctggttg   3000
gcttggtttc atcagccatc cgcttgccct catctgttac gccggcggta gccggccagc   3060
ctcgcagagc aggattcccg ttgagcaccg ccaggtgcga ataagggaca gtgaagaagg   3120
aacacccgct cgcgggtggg cctacttcac ctatcctgcc cggctgacgc cgttggatac   3180
accaaggaaa gtctacacga accctttggc aaaatcctgt atatcgtgcg aaaaaggatg   3240
gatataccga aaaaatcgct ataatgaccc cgaagcaggg ttatgcagcg gaaaagcgct   3300
gcttccctgc tgttttgtgg aatatctacc gactggaaac aggcaaatgc aggaaattac   3360
tgaactgagg ggacaggcga gagacgatgc caaagagcta caccgacgag ctggccgagt   3420
gggttgaatc ccgcgcggcc aagaagcgcc ggcgtgatga ggctgcggtt gcgttcctgg   3480
cggtgagggc ggatgtcgat atgcgtaagg agaaaatacc gcatcaggcg catatttgaa   3540
tgtatttaga aaaataaaca aaaagagttt gtagaaacgc aaaaaggcca tccgtcagga   3600
```

```
tggccttctg cttaatttga tgcctggcag tttatggcgg gcgtcctgcc cgccaccctc   3660
cgggccgttg cttcgcaacg ttcaaatccg ctcccggcgg atttgtccta ctcaggagag   3720
cgttcaccga caaacaacag ataaaacgaa aggcccagtc tttcgactga gcctttcgtt   3780
ttatttgatg cctggaaacc cagcgaacca tttgaggtga taggtaagat tataccgagg   3840
tatgaaaacg agaattggac ctttacagaa ttactctatg aagcgccata tttaaaaagc   3900
taccaagacg aagaggatga agaggatgag gaggcagatt gccttgaata tattgacaat   3960
actgataaga taatatatct tttatataga agatatcgcc gtatgtaagg atttcagggg   4020
gcaaggcata ggcagcgcgc ttatcaatat atctatagaa tgggcaaagc ataaaaactt   4080
gcatggacta atgcttgaaa cccaggacaa taaccttata gcttgtaaat tctatcataa   4140
ttgtggtttc aaaatcggct ccgtcgatac tatgttatac gccaactttc aaaacaactt   4200
tgaaaaagct gttttctggt atttaaggtt ttagaatgca aggaacagtg aattggagtt   4260
cgtcttgtta taattagctt cttggggtat ctttaaatac tgtagaaaag aggaaggaaa   4320
taataaatgg ctaaaatgag aatatcaccg gaattgaaaa aactgatcga aaaataccgc   4380
tgcgtaaaag atacggaagg aatgtctcct gctaaggtat ataagctggt gggagaaaat   4440
gaaaacctat atttaaaaat gacggacagc cggtataaag ggaccaccta tgatgtggaa   4500
cgggaaaagg acatgatgct atggctggaa ggaaagctgc ctgttccaaa ggtcctgcac   4560
tttgaacggc atgatggctg gagcaatctg ctcatgagtg aggccgatgg cgtcctttgc   4620
tcggaagagt atgaagatga acaaagccct gaaaagatta tcgagctgta tgcggagtgc   4680
atcaggctct ttcactccat cgacatatcg gattgtccct atacgaatag cttagacagc   4740
cgcttagccg aattggatta cttactgaat aacgatctgg ccgatgtgga ttgcgaaaac   4800
tgggaagaag acactccatt taaagatccg cgcgagctgt atgatttttt aaagacggaa   4860
aagcccgaag aggaacttgt cttttcccac ggcgacctgg gagacagcaa catctttgtg   4920
aaagatggca aagtaagtgg ctttattgat cttgggagaa gcggcagggc ggacaagtgg   4980
tatgacattg ccttctgcgt ccggtcgatc agggaggata tcggggaaga acagtatgtc   5040
gagctatttt ttgacttact ggggatcaag cctgattggg agaaaataaa atattatatt   5100
ttactggatg aattgtttta gtacctagat ttagatgtct aaaaagcttt ttagacatct   5160
aatcttttct gaagtacatc cgcaactgtc catactctga tgttttatat cttttctaaa   5220
agttcgctag ataggggtcc cgagcgccta cgaggaattt gtatcgtaca aggatatcga   5280
gggcgcagat gtagtagttg taacagcagg tgcggctcaa aagccaggag agtctaggct   5340
ggaccttgta aaaaagaata catctatatt caagtccatg atacctgaac ttttaaaata   5400
caatgataaa gctatatacc tgattgtaac aaatcctgtt gatatattaa cgtatgttac   5460
atacaaaata gcgaaacttc cgtgggggcg tgtattcggt tcaggtactg tccttgacag   5520
ttcccgattt aggtatcttt taagtaaaca ttgcaatatt gatcctagaa atgtacatgg   5580
aaggataatt ggagaacacg gcgatacaga atttgcggcg tggagcataa caaatatttc   5640
aggaatatca tttaatgagt actgcaattt gtgcggacga gtttgtaata caaatttcag   5700
aaaggaagtg gaagatgaag ttgtcaatgc ggcttacaaa attattgata aaaagggtgc   5760
cacgtattac gctgtggctg                                                 5780
```

<210> SEQ ID NO 54
<211> LENGTH: 6539
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (92)..(92)
<223> OTHER INFORMATION: a, c, g or t
<220> FEATURE:
<221> NAME/KEY: modified_base
<222> LOCATION: (151)..(151)
<223> OTHER INFORMATION: a, c, g or t
<220> FEATURE:
<221> NAME/KEY: modified_base
<222> LOCATION: (153)..(153)
<223> OTHER INFORMATION: a, c, g or t

<400> SEQUENCE: 54
gcacatattg atagagaaca tggctggata attactataa ctccaagaaa acgaatagta 60
aaagaatgga ggcgaattaa tgagtaatgt cncaatacaa ttaatagaaa tttgtcggca 120
atatgtaaat aataacttaa acataaatga ntntatcgaa gatttccaag tgctttatga 180
acaaaagcaa gatttattaa cagatgaaga aatgagtttg tttgatgata tttatatggc 240
ttgtgaatat tatgaacagg atgaaaatat aagaaatgaa tatcacttgt atattggaga 300
aaatgaatta agacaaaaag tgcaaaaact tgtaaaaaag ttagcagcat aataaaccgc 360
taaggcatga tagctaaagc ggtatttta tgcaattaaa aggaaaaatg atatctgata 420
aaccgcggaa aagtatttta gaaaacaact ataaagataa tatttcaaag caagaaggat 480
aaaataagat taaactatta gacactttta ttagaaaatg ttataatatt attaagagaa 540
aatttatatt atttaggagg taattttatg agtaaagtgg ccataatagg ttcaggattt 600
gtaggtgcta catctgcatt tacattggct ctaagtggga ctgtgacaga cattgtttta 660
gtagatttaa acaaggacaa ggcgataggc gatgcactgg atattagcca aaacccagcg 720
aaccatttga ggtgataggt aagattatac cgaggtatga aaacgagaat tggaccttta 780
cagaattact ctatgaagcg ccatatttaa aaagctacca agacgaagag gatgaagagg 840
atgaggaggc agattgcctt gaatatattg acaatactga taagataata tatcttttat 900
atagaagata tcgccgtatg taaggatttc agggggcaag gcataggcag cgcgcttatc 960
aatatatcta tagaatgggc aaagcataaa aacttgcatg gactaatgct tgaaacccag 1020
gacaataacc ttatagcttg taaattctat cataattgtg gtttcaaaat cggctccgtc 1080
gatactatgt tatacgccaa ctttcaaaac aactttgaaa aagctgtttt ctggtattta 1140
aggttttaga atgcaaggaa cagtgaattg gagttcgtct tgttataatt agcttcttgg 1200
ggtatcttta aatactgtag aaaagaggaa ggaaataata aatggctaaa atgagaatat 1260
caccggaatt gaaaaaactg atcgaaaaat accgctgcgt aaaagatacg gaaggaatgt 1320
ctcctgctaa ggtatataag ctggtgggag aaaatgaaaa cctatattta aaaatgacgg 1380
acagccggta taaagggacc acctatgatg tggaacggga aaggacatg atgctatggc 1440 tggaaggaaa gctgcctgtt ccaaaggtcc tgcactttga acggcatgat ggctggagca 1500
atctgctcat gagtgaggcc gatggcgtcc tttgctcgga agagtatgaa gatgaacaaa 1560
gccctgaaaa gattatcgag ctgtatgcgg agtgcatcag gctctttcac tccatcgaca 1620
tatcggattg tccctatacg aatagcttag acagccgctt agccgaattg gattacttac 1680
tgaataacga tctggccgat gtggattgcg aaaactggga agaagacact ccatttaaag 1740
atccgcgcga gctgtatgat tttttaaaga cggaaaagcc cgaagaggaa cttgtctttt 1800
cccacggcga cctgggagac agcaacatct ttgtgaaaga tggcaaagta agtggcttta 1860

```
ttgatcttgg gagaagcggc agggcggaca agtggtatga cattgccttc tgcgtccggt   1920
cgatcaggga ggatatcggg gaagaacagt atgtcgagct atttttgac ttactgggga   1980
tcaagcctga ttgggagaaa ataaaatatt atattttact ggatgaattg ttttagtacc   2040
tagatttaga tgtctaaaaa gctttttaga catctaatct tttctgaagt acatccgcaa   2100
ctgtccatac tctgatgttt tatatctttt ctaaaagttc gctagatagg ggtcccgagc   2160
gcctacgagg aatttgtatc gacgtattac gctgtggctg tagcagtaag aagaatagtt   2220
gagtgtatca taagggatga aaattcaatt cttacagttt catctccatt aaatggtcaa   2280
tacggtgtaa gagatgtatc tttaagcttg ccatcaattg tgggcaaaaa tggtgttgca   2340
agggttctgg atttgccttt ggctgatgac gaagttgaga agtttaaaca ttcggcaagc   2400
gttatggctg atgttataaa acagttggac atataaaata aatcattgta taaggtttat   2460
aagacggctt ttatcatgta tggtaaaggc cgctttttta tgaatataaa aatacaaagt   2520
ggaaaatcta aataaaggtg atgcaatatg cagaatatga gtcctcaaga aattatatcg   2580
agtgccttta tgaaggcaaa aaaatctgag aatattatac atgctaaggc tatagattat   2640
gggaaaaata tatcagataa ccagatgcaa gcgatattga agcaaataga gataacggct   2700
ttaaaccatg tggacaaaat agtgacagct gagaagacga tgcatctatc agctgtccct   2760
cctgttcagc tactgacggg gtggtgcgta acggcaaaag caccgccgga catcagcgct   2820
agcggagtgt atactggctt actatgttgg cactgatgag ggtgtcagtg aagtgcttca   2880
tgtggcagga gaaaaaaggc tgcaccggtg cgtcagcaga atatgtgata caggatatat   2940
tccgcttcct cgctcactga ctcgctacgc tcggtcgttc gactgcggcg agcggaaatg   3000
gcttacgaac ggggcggaga tttcctggaa gatgccagga agatacttaa cagggaagtg   3060
agagggccgc ggcaaagccg tttttccata ggctccgccc ccctgacaag catcacgaaa   3120
tctgacgctc aaatcagtgg tggcgaaacc cgacaggact ataaagatac caggcgtttc   3180
cccctggcgg ctccctcgtg cgctctcctg ttcctgcctt tcggtttacc ggtgtcattc   3240
cgctgttatg gccgcgtttg tctcattcca cgcctgacac tcagttccgg gtaggcagtt   3300
cgctccaagc tggactgtat gcacgaaccc cccgttcagt ccgaccgctg cgccttatcc   3360
ggtaactatc gtcttgagtc caacccggaa agacatgcaa aagcaccact ggcagcagcc   3420
actggtaatt gatttagagg agttagtctt gaagtcatgc gccggttaag gctaaactga   3480
aaggacaagt tttggtgact gcgctcctcc aagccagtta cctcggttca aagagttggt   3540
agctcagaga accttcgaaa aaccgccctg caaggcggtt ttttcgtttt cagagcaaga   3600
gattacgcgc agaccaaaac gatctcaaga agatcatctt attaatcaga taaaatattt   3660
ctagatttca gtgcaattta tctcttcaaa tgtagcacct gaagtcagcc ccatacgata   3720
taagttgtaa ttctcatgtt tgacagctta tcatcgataa gctttaatgc ggtagtttat   3780
cacagttaaa ttgctaacgc agtcaggcac ctatacatgc atttacttat aatacagttt   3840
tttagttttg ctggccgcat cttctcaaat atgcttccca gcctgctttt ctgtaacgtt   3900
caccctctac cttagcatcc cttccctttg caaatagtcc tcttccaaca ataataatgt   3960
cagatcctgt agagaccaca tcatccacgg ttctatactg ttgacccaat gcgtctccct   4020
tgtcatctaa acccacaccg ggtgtcataa tcaaccaatc gtaaccttca tctcttccac   4080
ccatgtctct ttgagcaata aagccgataa caaaatcttt gtcgctcttc gcaatgtcaa   4140
cagtaccctt agtatattct ccagtagata gggagccctt gcatgacaat tctgctaaca   4200
tcaaaaggcc tctaggttcc tttgttactt cttctgccgc ctgcttcaaa ccgctaacaa   4260
```

```
tacctgggcc caccacaccg tgtgcattcg taatgtctgc ccattctgct attctgtata   4320

cacccgcaga gtactgcaat ttgactgtat taccaatgtc agcaaatttt ctgtcttcga   4380

agagtaaaaa attgtacttg gcggataatg cctttagcgg cttaactgtg ccctccatgg   4440

aaaaatcagt caagatatcc acatgtgttt ttagtaaaca aattttggga cctaatgctt   4500

caactaactc cagtaattcc ttggtggtac gaacatccaa tgaagcacac aagtttgttt   4560

gcttttcgtg catgatatta aatagcttgg cagcaacagg actaggatga gtagcagcac   4620

gttccttata tgtagctttc gacatgattt atcttcgttt cctgcaggtt tttgttctgt   4680

gcagttgggt taagaatact gggcaatttc atgtttcttc aacactacat atgcgtatat   4740

ataccaatct aagtctgtgc tccttccttc gttcttcctt ctgttcggag attaccgaat   4800

caaaaaaatt tcaaagaaac cgaaatcaaa aaaaagaata aaaaaaaaat gatgaattga   4860

attgaaaagc tagcttatcg atgggtcctt ttcatcacgt gctataaaaa taattataat   4920

ttaaattttt taatataaat atataaatta aaaatagaaa gtaaaaaaag aaattaaaga   4980

aaaaatagtt tttgttttcc gaagatgtaa aagactctag ggggatcgcc aacaaatact   5040

accttttatc ttgctcttcc tgctctcagg tattaatgcc gaattgtttc atcttgtctg   5100

tgtagaagac cacacacgaa aatcctgtga ttttacattt tacttatcgt taatcgaatg   5160

tatatctatt taatctgctt ttcttgtcta ataaatatat atgtaaagta cgctttttgt   5220

tgaaattttt taaacctttg tttatttttt tttcttcatt ccgtaactct tctaccttct   5280

ttatttactt tctaaaatcc aaatacaaaa cataaaaata aataaacaca gagtaaattc   5340

ccaaattatt ccatcattaa aagatacgag gcgcgtgtaa gttacaggca agcgatctct   5400

aagaaaccat tattatcatg acattaacct ataaaaaagg cctctcgagc tagagtcgat   5460

cttcgccagc agggcgagga tcgtggcatc accgaaccgc gccgtgcgcg ggtcgtcggt   5520

gagccagagt ttcagcaggc cgcccaggcg gcccaggtcg ccattgatgc gggccagctc   5580

gcggacgtgc tcatagtcca cgacgcccgt gattttgtag ccctggccga cggccagcag   5640

gtaggccgac aggctcatgc cggccgccgc cgccttttcc tcaatcgctc ttcgttcgtc   5700

tggaaggcag tacaccttga taggtgggct gcccttcctg gttggcttgg tttcatcagc   5760

catccgcttg ccctcatctg ttacgccggc ggtagccggc cagcctcgca gagcaggatt   5820

cccgttgagc accgccaggt gcgaataagg gacagtgaag aaggaacacc cgctcgcggg   5880

tgggcctact tcacctatcc tgcccggctg acgccgttgg atacaccaag gaaagtctac   5940

acgaaccctt tggcaaaatc ctgtatatcg tgcgaaaaag gatggatata ccgaaaaaat   6000

cgctataatg accccgaagc agggttatgc agcggaaaag cgctgcttcc ctgctgtttt   6060

gtggaatatc taccgactgg aaacaggcaa atgcaggaaa ttactgaact gaggggacag   6120

gcgagagacg atgccaaaga gctacaccga cgagctggcc gagtgggttg aatcccgcgc   6180

ggccaagaag cgccggcgtg atgaggctgc ggttgcgttc ctggcggtga gggcggatgt   6240

cgatatgcgt aaggagaaaa taccgcatca ggcgcatatt tgaatgtatt tagaaaaata   6300

aacaaaaaga gtttgtagaa acgcaaaaag gccatccgtc aggatggcct tctgcttaat   6360

ttgatgcctg gcagtttatg gcgggcgtcc tgcccgccac cctccgggcc gttgcttcgc   6420

aacgttcaaa tccgctcccg gcggatttgt cctactcagg agagcgttca ccgacaaaca   6480

acagataaaa cgaaaggccc agtctttcga ctgagccttt cgttttattt gatgcctgg    6539
```

<210> SEQ ID NO 55
<211> LENGTH: 6086
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 55
tctatcagct gtccctcctg ttcagctact gacggggtgg tgcgtaacgg caaaagcacc 60
gccggacatc agcgctagcg gagtgtatac tggcttacta tgttggcact gatgagggtg 120
tcagtgaagt gcttcatgtg gcaggagaaa aaaggctgca ccggtgcgtc agcagaatat 180
gtgatacagg atatattccg cttcctcgct cactgactcg ctacgctcgg tcgttcgact 240
gcggcgagcg gaaatggctt acgaacgggg cggagatttc ctggaagatg ccaggaagat 300
acttaacagg gaagtgagag ggccgcggca aagccgtttt tccataggct ccgcccccct 360
gacaagcatc acgaaatctg acgctcaaat cagtggtggc gaaacccgac aggactataa 420
agataccagg cgtttccccc tggcggctcc ctcgtgcgct ctcctgttcc tgcctttcgg 480
tttaccggtg tcattccgct gttatggccg cgtttgtctc attccacgcc tgacactcag 540
ttccgggtag gcagttcgct ccaagctgga ctgtatgcac gaaccccccg ttcagtccga 600
ccgctgcgcc ttatccggta actatcgtct tgagtccaac ccggaaagac atgcaaaagc 660
accactggca gcagccactg gtaattgatt tagaggagtt agtcttgaag tcatgcgccg 720
gttaaggcta aactgaaagg acaagttttg gtgactgcgc tcctccaagc cagttacctc 780
ggttcaaaga gttggtagct cagagaacct tcgaaaaacc gccctgcaag gcggtttttt 840
cgttttcaga gcaagagatt acgcgcagac caaaacgatc tcaagaagat catcttatta 900
atcagataaa atatttctag atttcagtgc aatttatctc ttcaaatgta gcacctgaag 960
tcagccccat acgatataag ttgtaattct catgtttgac agcttatcat cgataagctt 1020
taatgcggta gtttatcaca gttaaattgc taacgcagtc aggcacctat acatgcattt 1080
acttataata cagtttttta gttttgctgg ccgcatcttc tcaaatatgc ttcccagcct 1140
gcttttctgt aacgttcacc ctctacctta gcatcccttc cctttgcaaa tagtcctctt 1200
ccaacaataa taatgtcaga tcctgtagag accacatcat ccacggttct atactgttga 1260
cccaatgcgt ctcccttgtc atctaaaccc acaccgggtg tcataatcaa ccaatcgtaa 1320
ccttcatctc ttccacccat gtctctttga gcaataaagc cgataacaaa atctttgtcg 1380
ctcttcgcaa tgtcaacagt acccttagta tattctccag tagataggga gcccttgcat 1440
gacaattctg ctaacatcaa aaggcctcta ggttcctttg ttacttcttc tgccgcctgc 1500
ttcaaaccgc taacaatacc tgggcccacc acaccgtgtg cattcgtaat gtctgcccat 1560
tctgctattc tgtatacacc cgcagagtac tgcaatttga ctgtattacc aatgtcagca 1620
aattttctgt cttcgaagag taaaaaattg tacttggcgg ataatgcctt tagcggctta 1680
actgtgccct ccatggaaaa atcagtcaag atatccacat gtgtttttag taaacaaatt 1740
ttgggaccta atgcttcaac taactccagt aattccttgg tggtacgaac atccaatgaa 1800
gcacacaagt ttgtttgctt ttcgtgcatg atattaaata gcttggcagc aacaggacta 1860
ggatgagtag cagcacgttc cttatatgta gctttcgaca tgatttatct tcgtttcctg 1920
caggtttttg ttctgtgcag ttgggttaag aatactgggc aatttcatgt ttcttcaaca 1980
ctacatatgc gtatatatac caatctaagt ctgtgctcct tccttcgttc ttccttctgt 2040
tcggagatta ccgaatcaaa aaaatttcaa agaaaccgaa atcaaaaaaa agaataaaaa 2100
aaaaatgatg aattgaattg aaaagctagc ttatcgatgg gtccttttca tcacgtgcta 2160
taaaaataat tataatttaa attttttaat ataaatatat aaattaaaaa tagaaagtaa 2220

```
aaaaagaaat taaagaaaaa atagtttttg ttttccgaag atgtaaaaga ctctaggggg   2280
atcgccaaca aatactacct tttatcttgc tcttcctgct ctcaggtatt aatgccgaat   2340
tgtttcatct tgtctgtgta gaagaccaca cacgaaaatc ctgtgatttt acattttact   2400
tatcgttaat cgaatgtata tctatttaat ctgcttttct tgtctaataa atatatatgt   2460
aaagtacgct tttgttgaa atttttaaa cctttgttta ttttttttc ttcattccgt   2520
aactcttcta ccttctttat ttactttcta aaatccaaat acaaaacata aaaataaata   2580
aacacagagt aaattcccaa attattccat cattaaaaga tacgaggcgc gtgtaagtta   2640
caggcaagcg atctctaaga aaccattatt atcatgacat taacctataa aaaaggcctc   2700
tcgagctaga gtcgatcttc gccagcaggg cgaggatcgt ggcatcaccg aaccgcgccg   2760
tgcgcgggtc gtcggtgagc cagagtttca gcaggccgcc caggcggccc aggtcgccat   2820
tgatgcgggc cagctcgcgg acgtgctcat agtccacgac gcccgtgatt ttgtagccct   2880
ggccgacggc cagcaggtag gccgacaggc tcatgccggc cgccgccgcc ttttcctcaa   2940
tcgctcttcg ttcgtctgga aggcagtaca ccttgatagg tgggctgccc ttcctggttg   3000
gcttggtttc atcagccatc cgcttgccct catctgttac gccggcggta gccggccagc   3060
ctcgcagagc aggattcccg ttgagcaccg ccaggtgcga ataagggaca gtgaagaagg   3120
aacacccgct cgcgggtggg cctacttcac ctatcctgcc cggctgacgc cgttggatac   3180
accaaggaaa gtctacacga accctttggc aaaatcctgt atatcgtgcg aaaaaggatg   3240
gatataccga aaaaatcgct ataatgaccc cgaagcaggg ttatgcagcg gaaaagcgct   3300
gcttccctgc tgttttgtgg aatatctacc gactggaaac aggcaaatgc aggaaattac   3360
tgaactgagg ggacaggcga gagacgatgc caaagagcta caccgacgag ctggccgagt   3420
gggttgaatc ccgcgcggcc aagaagcgcc ggcgtgatga ggctgcggtt gcgttcctgg   3480
cggtgagggc ggatgtcgat atgcgtaagg agaaaatacc gcatcaggcg catatttgaa   3540
tgtatttaga aaaataaaca aaaagagttt gtagaaacgc aaaaaggcca tccgtcagga   3600
tggccttctg cttaatttga tgcctggcag tttatggcgg gcgtcctgcc cgccaccctc   3660
cgggccgttg cttcgcaacg ttcaaatccg ctcccggcgg atttgtccta ctcaggagag   3720
cgttcaccga caaacaacag ataaaacgaa aggcccagtc tttcgactga gcctttcgtt   3780
ttatttgatg cctggaaacc cagcgaacca tttgaggtga taggtaagat tataccgagg   3840
tatgaaaacg agaattggac ctttacagaa ttactctatg aagcgccata tttaaaaagc   3900
taccaagacg aagaggatga agaggatgag gaggcagatt gccttgaata tattgacaat   3960
actgataaga taatatatct tttatataga agatatcgcc gtatgtaagg atttcagggg   4020
gcaaggcata ggcagcgcgc ttatcaatat atctatagaa tgggcaaagc ataaaaactt   4080
gcatggacta atgcttgaaa cccaggacaa taaccttata gcttgtaaat tctatcataa   4140
ttgtggtttc aaaatcggct ccgtcgatac tatgttatac gccaactttc aaaacaactt   4200
tgaaaaagct gttttctggt atttaaggtt ttagaatgca aggaacagtg aattggagtt   4260
cgtcttgtta taattagctt cttggggtat ctttaaatac tgtagaaaag aggaaggaaa   4320
taataaatgg ctaaaatgag aatatcaccg gaattgaaaa aactgatcga aaaataccgc   4380
tgcgtaaaag atacggaagg aatgtctcct gctaaggtat ataagctggt gggagaaaat   4440
gaaaacctat atttaaaaat gacggacagc cggtataaag ggaccaccta tgatgtggaa   4500
cgggaaaagg acatgatgct atggctggaa ggaaagctgc ctgttccaaa ggtcctgcac   4560
tttgaacggc atgatggctg gagcaatctg ctcatgagtg aggccgatgg cgtcctttgc   4620
```

-continued

```
tcggaagagt atgaagatga acaaagccct gaaaagatta tcgagctgta tgcggagtgc   4680

atcaggctct ttcactccat cgacatatcg gattgtccct atacgaatag cttagacagc   4740

cgcttagccg aattggatta cttactgaat aacgatctgg ccgatgtgga ttgcgaaaac   4800

tgggaagaag acactccatt taaagatccg cgcgagctgt atgatttttt aaagacggaa   4860

aagcccgaag aggaacttgt cttttcccac ggcgacctgg gagacagcaa catctttgtg   4920

aaagatggca aagtaagtgg ctttattgat cttgggagaa gcggcagggc ggacaagtgg   4980

tatgacattg ccttctgcgt ccggtcgatc agggaggata tcggggaaga acagtatgtc   5040

gagctatttt ttgacttact ggggatcaag cctgattggg agaaaataaa atattatatt   5100

ttactggatg aattgtttta gtacctagat ttagatgtct aaaaagcttt ttagacatct   5160

aatcttttct gaagtacatc cgcaactgtc catactctga tgttttatat cttttctaaa   5220

agttcgctag ataggggtcc cgagcgccta cgaggaattt gtatcggctg tacaatctgc   5280

taatactgca aagaatttgt tgggctttga accaaaagtt gctatgctat cattttccac   5340

aaaaggtagt gcatcacatg aattagtaga taaagtaaga aaagcgacag aaatagcaaa   5400

agaattgatg ccagatgttg ctatcgacgg tgaattgcaa ttggatgctg ctcttgtcaa   5460

agaagttgca gagctaaaag cgccaggaag caaagttgcg ggatgtgcaa atgtgcttat   5520

attccctgat ttacaagctg gtaatatagg atataagctt gtacagagat tagctagcaa   5580

atgcaattgg acctataaca caggaatggg tgcaccggtt aatgatttat caagaggatg   5640

cagctataga gatattgttg acgtaatagc acacagctgt acaggctcat aaatgtaaag   5700

tatggaggat gaaattatga aaatactggt atatgcgaag tctcactaaa tatcactgat   5760

gatcatgatg aaatgtgctg gcaaaggcct tgctgagaga atcggcataa atgatccctg   5820

ttgacacata tgctaacgga gaaaaatcaa gataaaaaaa gacatgaaag atcacaaaga   5880

cgcaataaaa ttgttttaga tgctttggta agcagtgact acggcgttat aaaggatatg   5940

tctgagatag atgctgtagg acatagagtt gttcacggag gagaatcttt tacatcatca   6000

gttctcataa atgatgatgt gttaaaagcg ataacagatt gcatagaatt agctccactg   6060

cacaatcctg ccaatataga aggaat                                        6086
```

```
<210> SEQ ID NO 56
<211> LENGTH: 7284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

taacagggcc atgaccttct gcaaagcact tttttaaaat ttcaagagaa tattgtggca     60

tatatttttc taatgcagaa tagtttttat catttataac ctttctaaga tatgtagcac    120

ttgcaaaaga ttctactgtt tccagagaat tatatcctgg accaaatctt tttaatgtca    180

aaggcttaat attgctgttt aacttgatta agctttttat gtattcaatt ccaagtatgt    240

tatttggatt tccgataata ttgttaatgg tccttccgaa atattttgat aatgctgctt    300

cacgtgcctt tgcatatgtg atgccgcttt ttaaataggt tttcaaagag ctttataatc    360

ttctggttcg tctaaaagaa attttgatat ttggcataat tcgtcaatag agccatgttc    420

gcttccaaac gatatgtaat caatgacatt taatgaatcc agcagcttta ctgctccata    480

tgcgaaattt tctgcggtag aaactgcata tatagtgggc aattctatta ctaagtcaat    540
```

acctgatagc aatgcagctt ctgtccttga ccacttgtca ataatagacg gtattcctcg 600
ctgaacaaag ttaccactca taattgcaat gacaaaatct gcacctgttg tttcaattga 660
tttttttata tggtatatgt gtccgttatg gagagggtta tattctacaa ttactcccaa 720
tatactcatt attaaaaacc tttctaaaaa attattaatt gtacttatta ttttataaaa 780
aatatgttaa aatgtaaaat gtgtatacaa tatatttctt ctttttagta agaggaatgt 840
ataaaaataa atattttaaa ggaagggacg atcttatgag cattattcaa aacatcattg 900
aaaaagctaa aagtgataaa aagaaaattg ttctgccgga aggtgcagaa acccagcgaa 960
ccatttgagg tgataggtaa gattataccg aggtatgaaa acgagaattg gacctttaca 1020
gaattactct atgaagcgcc atatttaaaa agctaccaag acgaagagga tgaagaggat 1080
gaggaggcag attgccttga atatattgac aatactgata agataatata tcttttatat 1140
agaagatatc gccgtatgta aggatttcag gggcaaggc ataggcagcg cgcttatcaa 1200
tatatctata gaatgggcaa agcataaaaa cttgcatgga ctaatgcttg aaacccagga 1260
caataacctt atagcttgta aattctatca taattgtggt ttcaaaatcg gctccgtcga 1320
tactatgtta tacgccaact ttcaaaacaa ctttgaaaaa gctgttttct ggtatttaag 1380
gttttagaat gcaaggaaca gtgaattgga gttcgtcttg ttataattag cttcttgggg 1440
tatctttaaa tactgtagaa aagaggaagg aaataataaa tggctaaaat gagaatatca 1500
ccggaattga aaaaactgat cgaaaaatac cgctgcgtaa aagatacgga aggaatgtct 1560
cctgctaagg tatataagct ggtgggagaa aatgaaaacc tatatttaaa aatgacggac 1620
agccggtata aagggaccac ctatgatgtg gaacgggaaa aggacatgat gctatggctg 1680
gaaggaaagc tgcctgttcc aaaggtcctg cactttgaac ggcatgatgg ctggagcaat 1740
ctgctcatga gtgaggccga tggcgtcctt tgctcggaag agtatgaaga tgaacaaagc 1800
cctgaaaaga ttatcgagct gtatgcggag tgcatcaggc tctttcactc catcgacata 1860
tcggattgtc cctatacgaa tagcttagac agccgcttag ccgaattgga ttacttactg 1920
aataacgatc tggccgatgt ggattgcgaa aactgggaag aagacactcc atttaaagat 1980
ccgcgcgagc tgtatgattt tttaaagacg gaaaagcccg aagaggaact tgtcttttcc 2040
cacggcgacc tgggagacag caacatcttt gtgaaagatg gcaaagtaag tggctttatt 2100
gatcttggga gaagcggcag ggcggacaag tggtatgaca ttgccttctg cgtccggtcg 2160
atcagggagg atatcgggga agaacagtat gtcgagctat tttttgactt actggggatc 2220
aagcctgatt gggagaaaat aaaatattat attttactgg atgaattgtt ttagtaccta 2280
gatttagatg tctaaaaagc tttttagaca tctaatcttt tctgaagtac atccgcaact 2340
gtccatactc tgatgtttta tatcttttct aaaagttcgc tagataggggg tcccgagcgc 2400
ctacgaggaa tttgtatcga aagttagcgt gatggttgtg cccactaatg aagaatacat 2460
gattgctaaa gatactgaaa agattgtaaa gagtataaaa tagcattctt gacaaatgtt 2520
taccccatta gtataattaa ttttggcaat tatattgggg tgagaaaatg aaaattgatt 2580
tatcaaaatt aagggacata ggggccgcag catcgaagtc aactacgtag aaaatctgag 2640
tgttcttgag gcaaatagca atagatacgt agttataaag cctattagcg taactggaag 2700
cataacatac gatagtgaag gaatagtttt aaaacttttg gcacgcgggg ctattaaagt 2760
aacatgcgat aggtgccttg acgaatttga gtatgagttc gtaataccta ttgacgaaat 2820
agtaaacgag tctgatgatg aattttcagg tgaagtggaa gatgaaaagc ttgatttgac 2880
gaaaattgtg attgaaaatg tggaactttc tcttccgatg aagttcattt gctcgaatga 2940

-continued

```
ttgcaagggt ctatgttcta cttgcggtaa aaatcttaat catgaaaaat gcgattgcca   3000
aataaaagaa attgatccac gcctttcagt tttgaataaa ttactgcaga agatgtagga   3060
ggtgtataat atgccagttc caaagcgtag aacatctaag gcaagaagag ataaaagaag   3120
gcatagccat agtttagctg tacctgctta tgttttgtgc ccacaatgtc atgaaccaaa   3180
attgccccac agagtttgtt taagctgtgg ttattacgac ggtaaagagg tattgaaagt   3240
ggaagaaaag taatggagtt ttctctatta cttttctttt ttatttcttg acttttatgt   3300
atggcgtaat ttataattat gagtaagtca taaaaacaac ctatatttgg agctgataat   3360
gtggccacga agcttagtaa aagagataga ttaaaaaagt taaaaattga aatcgaaaaa   3420
tatccatttt acactgatga tgagttagct gatttgtttt cggttagcgt tcagacgata   3480
aggctggatt ctatcagctg tccctcctgt tcagctactg acggggtggt gcgtaacggc   3540
aaaagcaccg ccggacatca gcgctagcgg agtgtatact ggcttactat gttggcactg   3600
atgagggtgt cagtgaagtg cttcatgtgg caggagaaaa aaggctgcac cggtgcgtca   3660
gcagaatatg tgatacagga tatattccgc ttcctcgctc actgactcgc tacgctcggt   3720
cgttcgactg cggcgagcgg aaatggctta cgaacggggc ggagatttcc tggaagatgc   3780
caggaagata cttaacaggg aagtgagagg gccgcggcaa agccgttttt ccataggctc   3840
cgcccccctg acaagcatca cgaaatctga cgctcaaatc agtggtggcg aaacccgaca   3900
ggactataaa gataccaggc gtttccccct ggcggctccc tcgtgcgctc tcctgttcct   3960
gcctttcggt ttaccggtgt cattccgctg ttatggccgc gtttgtctca ttccacgcct   4020
gacactcagt tccgggtagg cagttcgctc caagctggac tgtatgcacg aaccccccgt   4080
tcagtccgac cgctgcgcct tatccggtaa ctatcgtctt gagtccaacc cggaaagaca   4140
tgcaaaagca ccactggcag cagccactgg taattgattt agaggagtta gtcttgaagt   4200
catgcgccgg ttaaggctaa actgaaagga caagttttgg tgactgcgct cctccaagcc   4260
agttacctcg gttcaaagag ttggtagctc agagaacctt cgaaaaaccg ccctgcaagg   4320
cggttttttc gttttcagag caagagatta cgcgcagacc aaaacgatct caagaagatc   4380
atcttattaa tcagataaaa tatttctaga tttcagtgca atttatctct tcaaatgtag   4440
cacctgaagt cagccccata cgatataagt tgtaattctc atgtttgaca gcttatcatc   4500
gataagcttt aatgcggtag tttatcacag ttaaattgct aacgcagtca ggcacctata   4560
catgcattta cttataatac agttttttag ttttgctggc cgcatcttct caaatatgct   4620
tcccagcctg cttttctgta acgttcaccc tctaccttag catcccttcc ctttgcaaat   4680
agtcctcttc caacaataat aatgtcagat cctgtagaga ccacatcatc cacggttcta   4740
tactgttgac ccaatgcgtc tcccttgtca tctaaaccca caccgggtgt cataatcaac   4800
caatcgtaac cttcatctct tccacccatg tctctttgag caataaagcc gataacaaaa   4860
tctttgtcgc tcttcgcaat gtcaacagta cccttagtat attctccagt agatagggag   4920
cccttgcatg acaattctgc taacatcaaa aggcctctag gttcctttgt tacttcttct   4980
gccgcctgct tcaaaccgct aacaatacct gggcccacca caccgtgtgc attcgtaatg   5040
tctgcccatt ctgctattct gtatacaccc gcagagtact gcaatttgac tgtattacca   5100
atgtcagcaa attttctgtc ttcgaagagt aaaaaattgt acttggcgga taatgccttt   5160
agcggcttaa ctgtgccctc catggaaaaa tcagtcaaga tatccacatg tgtttttagt   5220
aaacaaattt tgggacctaa tgcttcaact aactccagta attccttggt ggtacgaaca   5280
tccaatgaag cacacaagtt tgtttgcttt tcgtgcatga tattaaatag cttggcagca   5340
```

-continued

```
acaggactag gatgagtagc agcacgttcc ttatatgtag ctttcgacat gatttatctt   5400

cgtttcctgc aggtttttgt tctgtgcagt tgggttaaga atactgggca atttcatgtt   5460

tcttcaacac tacatatgcg tatatatacc aatctaagtc tgtgctcctt ccttcgttct   5520

tccttctgtt cggagattac cgaatcaaaa aaatttcaaa gaaaccgaaa tcaaaaaaaa   5580

gaataaaaaa aaaatgatga attgaattga aaagctagct tatcgatggg tccttttcat   5640

cacgtgctat aaaaataatt ataatttaaa tttttttaata taaatatata aattaaaaat   5700

agaaagtaaa aaaagaaatt aaagaaaaaa tagtttttgt tttccgaaga tgtaaaagac   5760

tctagggggga tcgccaacaa atactacctt ttatcttgct cttcctgctc tcaggtatta   5820

atgccgaatt gtttcatctt gtctgtgtag aagaccacac acgaaaatcc tgtgatttta   5880

cattttactt atcgttaatc gaatgtatat ctatttaatc tgcttttctt gtctaataaa   5940

tatatatgta aagtacgctt tttgttgaaa ttttttaaac ctttgtttat ttttttttct   6000

tcattccgta actcttctac cttctttatt tactttctaa aatccaaata caaaacataa   6060

aaataaataa acacagagta aattcccaaa ttattccatc attaaaagat acgaggcgcg   6120

tgtaagttac aggcaagcga tctctaagaa accattatta tcatgacatt aacctataaa   6180

aaaggcctct cgagctagag tcgatcttcg ccagcagggc gaggatcgtg gcatcaccga   6240

accgcgccgt gcgcgggtcg tcggtgagcc agagtttcag caggccgccc aggcggccca   6300

ggtcgccatt gatgcgggcc agctcgcgga cgtgctcata gtccacgacg cccgtgattt   6360

tgtagccctg gccgacggcc agcaggtagg ccgacaggct catgccggcc gccgccgcct   6420

tttcctcaat cgctcttcgt tcgtctggaa ggcagtacac cttgataggt gggctgccct   6480

tcctggttgg cttggtttca tcagccatcc gcttgccctc atctgttacg ccggcggtag   6540

ccggccagcc tcgcagagca ggattcccgt tgagcaccgc caggtgcgaa taagggacag   6600

tgaagaagga acacccgctc gcgggtgggc ctacttcacc tatcctgccc ggctgacgcc   6660

gttggataca ccaaggaaag tctacacgaa ccctttggca aaatcctgta tatcgtgcga   6720

aaaaggatgg atataccgaa aaaatcgcta taatgacccc gaagcagggt tatgcagcgg   6780

aaaagcgctg cttccctgct gttttgtgga atatctaccg actggaaaca ggcaaatgca   6840

ggaaattact gaactgaggg gacaggcgag agacgatgcc aaagagctac accgacgagc   6900

tggccgagtg ggttgaatcc cgcgcggcca agaagcgccg gcgtgatgag gctgcggttg   6960

cgttcctggc ggtgagggcg gatgtcgata tgcgtaagga gaaaataccg catcaggcgc   7020

atatttgaat gtatttagaa aaataaacaa aaagagtttg tagaaacgca aaaaggccat   7080

ccgtcaggat ggccttctgc ttaatttgat gcctggcagt ttatggcggg cgtcctgccc   7140

gccaccctcc gggccgttgc ttcgcaacgt tcaaatccgc tcccggcgga tttgtcctac   7200

tcaggagagc gttcaccgac aaacaacaga taaaacgaaa ggcccagtct ttcgactgag   7260

cctttcgttt tatttgatgc ctgg                                          7284
```

<210> SEQ ID NO 57
<211> LENGTH: 4621
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
cagcacaaaa accgggagaa accagacttg acttagtgaa gagaaatacg atgattttta     60

aagacatagt ggcaaaactt attaaagtaa atgacacagc aatatacctt atagttacaa    120
```

```
atccagtaga tattcttaca tacgttacct ataaaatatc tggcttgcca tacggaagag    180
tattggggtc tggcacagtt ctcgacagtg cgagattcag atatctttta agcaaacatt    240
gtaacataga tccgaggaat atacacggat atataattgg ggagcatggc gattctgagc    300
ttgcagcttg gagcattacg aacatagcag gcataccaat tgataattac tgcaatttat    360
gtggaaaagc atgtgaaaaa gattttagag aggagatttt taataatgtt gtaagagctg    420
cctatacgat aatagaaaaa aagggtgcga catattatgc ggttgctctc gcagtaagaa    480
gaatcgtaga agctattaaa cccagcgaac catttgaggt gataggtaag attataccga    540
ggtatgaaaa cgagaattgg acctttacag aattactcta tgaagcgcca tatttaaaaa    600
gctaccaaga cgaagaggat gaagaggatg aggaggcaga ttgccttgaa tatattgaca    660
atactgataa gataatatat cttttatata gaagatatcg ccgtatgtaa ggatttcagg    720
gggcaaggca taggcagcgc gcttatcaat atatctatag aatgggcaaa gcataaaaac    780
ttgcatggac taatgcttga aacccaggac aataacctta tagcttgtaa attctatcat    840
aattgtggtt tcaaaatcgg ctccgtcgat actatgttat acgccaactt tcaaaacaac    900
tttgaaaaag ctgttttctg gtatttaagg ttttagaatg caaggaacag tgaattggag    960
ttcgtcttgt tataattagc ttcttggggt atctttaaat actgtagaaa agaggaagga   1020
aataataaat ggctaaaatg agaatatcac cggaattgaa aaaactgatc gaaaaatacc   1080
gctgcgtaaa agatacggaa ggaatgtctc ctgctaaggt atataagctg gtgggagaaa   1140
atgaaaacct atatttaaaa atgacggaca gccggtataa agggaccacc tatgatgtgg   1200
aacgggaaaa ggacatgatg ctatggctgg aaggaaagct gcctgttcca aaggtcctgc   1260
actttgaacg gcatgatggc tggagcaatc tgctcatgag tgaggccgat ggcgtccttt   1320
gctcggaaga gtatgaagat gaacaaagcc ctgaaaagat tatcgagctg tatgcggagt   1380
gcatcaggct ctttcactcc atcgacatat cggattgtcc ctatacgaat agcttagaca   1440
gccgcttagc cgaattggat tacttactga ataacgatct ggccgatgtg gattgcgaaa   1500
actgggaaga agacactcca tttaaagatc cgcgcgagct gtatgatttt ttaaagacgg   1560
aaaagcccga agaggaactt gtcttttccc acggcgacct gggagacagc aacatctttg   1620
tgaaagatgg caaagtaagt ggctttattg atcttgggag aagcggcagg gcggacaagt   1680
ggtatgacat tgccttctgc gtccggtcga tcagggagga tatcggggaa gaacagtatg   1740
tcgagctatt ttttgactta ctggggatca agcctgattg ggagaaaata aaatattata   1800
ttttactgga tgaattgttt tagtacctag atttagatgt ctaaaaagct ttttagacat   1860
ctaatctttt ctgaagtaca tccgcaactg tccatactct gatgttttat atcttttcta   1920
aaagttcgct agataggggt cccgagcgcc tacgaggaat ttgtatcgct gcaggcatgc   1980
aagcttggcg taatcatggt catagctgtt tcctgtgtga aattgttatc cgctcacaat   2040
tccacacaac atacgagccg gaagcataaa gtgtaaagcc tggggtgcct aatgagtgag   2100
ctaactcaca ttaattgcgt tgcgctcact gcccgctttc cagtcgggaa acctgtcgtg   2160
ccagctgcat taatgaatcg gccaacgcgc ggggagaggc ggtttgcgta ttgggcgctc   2220
ttccgcttcc tcgctcactg actcgctgcg ctcggtcgtt cggctgcggc gagcggtatc   2280
agctcactca aaggcggtaa tacggttatc cacagaatca ggggataacg caggaaagaa   2340
catgtgagca aaaggccagc aaaaggccag gaaccgtaaa aaggccgcgt tgctggcgtt   2400
tttccatagg ctccgccccc ctgacgagca tcacaaaaat cgacgctcaa gtcagaggtg   2460
gcgaaacccg acaggactat aaagatacca ggcgtttccc cctggaagct ccctcgtgcg   2520
```

-continued ctctcctgtt ccgaccctgc cgcttaccgg atacctgtcc gcctttctcc cttcgggaag 2580
cgtggcgctt tctcatagct cacgctgtag gtatctcagt tcggtgtagg tcgttcgctc 2640
caagctgggc tgtgtgcacg aaccccccgt tcagcccgac cgctgcgcct tatccggtaa 2700
ctatcgtctt gagtccaacc cggtaagaca cgacttatcg ccactggcag cagccactgg 2760
taacaggatt agcagagcga ggtatgtagg cggtgctaca gagttcttga agtggtggcc 2820
taactacggc tacactagaa ggacagtatt tggtatctgc gctctgctga agccagttac 2880
cttcggaaaa agagttggta gctcttgatc cggcaaacaa accaccgctg gtagcggtgg 2940
tttttttgtt tgcaagcagc agattacgcg cagaaaaaaa ggatctcaag aagatccttt 3000
gatcttttct acggggtctg acgctcagtg gaacgaaaac tcacgttaag ggattttggt 3060
catgagatta tcaaaaagga tcttcaccta gatcctttta aattaaaaat gaagttttaa 3120
atcaatctaa agtatatatg agtaaacttg gtctgacagt taccaatgct taatcagtga 3180
ggcacctatc tcagcgatct gtctatttcg ttcatccata gttgcctgac tccccgtcgt 3240
gtagataact acgatacggg agggcttacc atctggcccc agtgctgcaa tgataccgcg 3300
agacccacgc tcaccggctc cagatttatc agcaataaac cagccagccg gaagggccga 3360
gcgcagaagt ggtcctgcaa ctttatccgc ctccatccag tctattaatt gttgccggga 3420
agctagagta agtagttcgc cagttaatag tttgcgcaac gttgttgcca ttgctacagg 3480
catcgtggtg tcacgctcgt cgtttggtat ggcttcattc agctccggtt cccaacgatc 3540
aaggcgagtt acatgatccc ccatgttgtg caaaaaagcg gttagctcct tcggtcctcc 3600
gatcgttgtc agaagtaagt tggccgcagt gttatcactc atggttatgg cagcactgca 3660
taattctctt actgtcatgc catccgtaag atgcttttct gtgactggtg agtactcaac 3720
caagtcattc tgagaatagt gtatgcggcg accgagttgc tcttgcccgg cgtcaatacg 3780
ggataatacc gcgccacata gcagaacttt aaaagtgctc atcattggaa aacgttcttc 3840
ggggcgaaaa ctctcaagga tcttaccgct gttgagatcc agttcgatgt aacccactcg 3900
tgcacccaac tgatcttcag catcttttac tttcaccagc gtttctgggt gagcaaaaac 3960
aggaaggcaa aatgccgcaa aaaagggaat aagggcgaca cggaaatgtt gaatactcat 4020
actcttcctt tttcaatatt attgaagcat ttatcagggt tattgtctca tgagcggata 4080
catatttgaa tgtatttaga aaaataaaca aataggggtt ccgcgcacat ttccccgaaa 4140
agtgccacct gacgtctaag aaaccattat tatcatgaca ttaacctata aaaataggcg 4200
tatcacgagg ccctttcgtc tcgcgcgttt cggtgatgac ggtgaaaacc tctgacacat 4260
gcagctcccg gagacggtca cagcttgtct gtaagcggat gccgggagca gacaagcccg 4320
tcagggcgcg tcagcgggtg ttggcgggtg tcggggctgg cttaactatg cggcatcaga 4380
gcagattgta ctgagagtgc accatatgcg gtgtgaaata ccgcacagat gcgtaaggag 4440
aaaataccgc atcaggcgcc attcgccatt caggctgcgc aactgttggg aagggcgatc 4500
ggtgcgggcc tcttcgctat tacgccagct ggcgaaaggg ggatgtgctg caaggcgatt 4560
aagttgggta acgccagggt tttcccagtc acgacgttgt aaaacgacgg ccagtgaatt 4620
c 4621

<210> SEQ ID NO 58
<211> LENGTH: 6130
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58
aggtttatcg ccgccttgta cagttttaaa ttgcatagaa atcatgagac ccattgcaat 60
aaatacaagt atcaaagata aagtttgcaa tgcctttcct ttcaatttct ccacatcctt 120
tctctatata aaaagacatc ttcgtcttgc ttttggtttc agcttatatg cacttttata 180
aataactatg atactctata aatactataa catggaaaat gttaaaattt attaagaaat 240
tattaagttt ttattacaaa aaagttacaa aacctctgac atttttcata tcagaggttg 300 tcattttttta ttttatttc tatagaattt tttagtgaca atatttcttc taattcttta 360
ttgtatttat ctattttcaa catggtactt ctatataggc gtatatcttc ttcgtttttt 420
tgtatacatt ttttaaggga gttttttaca gtttcaaaaa gcgtatcata agtaatgtaa 480
ttatgcattt caaggtcgga gattggaact gcgattaatt cctccccttc tattttatag 540
tgataaaaaa tgttgtcggg ttttaaaact atttttttcat ctatgctttt atcgtaaatt 600 attataccctt ctcctatttc aaaagttttt ccgctataac ttctaagttt tatattttcg 660
actcctatgt atttttttat tgccaaaagt atgtttttta tttctgaaat ggattttaca 720
agcacttctt gcattttttt atttgccatc tctttatctt tttcactttt tatgagttct 780
tccatcaaag actttatttc atgtatatct cccataaaat atcacctctt tcttaatatt 840
ccacagagga atcattttaa acgttgaata ttttaaatta ttagagaaaa aatagacttg 900
actatttttt gaaatttgat agactattat taatagaaaa ttaatattga aaaggagaag 960
atattatgaa caaaatatct ataataggtt ctggatttgt cggaaaccca gcgaaccatt 1020
tgaggtgata ggtaagatta taccgaggta tgaaaacgag aattggacct ttacagaatt 1080
actctatgaa gcgccatatt taaaaagcta ccaagacgaa gaggatgaag aggatgagga 1140
ggcagattgc cttgaatata ttgacaatac tgataagata atatatcttt tatatagaag 1200
atatcgccgt atgtaaggat ttcagggggc aaggcatagg cagcgcgctt atcaatatat 1260
ctatagaatg ggcaaagcat aaaaacttgc atggactaat gcttgaaacc caggacaata 1320
accttatagc ttgtaaattc tatcataatt gtggtttcaa aatcggctcc gtcgatacta 1380
tgttatacgc caactttcaa aacaactttg aaaaagctgt tttctggtat ttaaggtttt 1440
agaatgcaag gaacagtgaa ttggagttcg tcttgttata attagcttct tggggtatct 1500
ttaaatactg tagaaaagag gaaggaaata ataaatggct aaaatgagaa tatcaccgga 1560
attgaaaaaa ctgatcgaaa aataccgctg cgtaaaagat acggaaggaa tgtctcctgc 1620
taaggtatat aagctggtgg gagaaaatga aaacctatat ttaaaaatga cggacagccg 1680
gtataaaggg accacctatg atgtggaacg ggaaaaggac atgatgctat ggctggaagg 1740
aaagctgcct gttccaaagg tcctgcactt tgaacggcat gatggctgga gcaatctgct 1800
catgagtgag gccgatggcg tcctttgctc ggaagagtat gaagatgaac aaagccctga 1860
aaagattatc gagctgtatg cggagtgcat caggctcttt cactccatcg acatatcgga 1920
ttgtccctat acgaatagct tagacagccg cttagccgaa ttggattact tactgaataa 1980
cgatctggcc gatgtggatt gcgaaaactg ggaagaagac actccattta aagatccgcg 2040
cgagctgtat gattttttaa agacggaaaa gcccgaagag gaacttgtct tttcccacgg 2100
cgacctggga gacagcaaca tctttgtgaa agatggcaaa gtaagtggct ttattgatct 2160
tgggagaagc ggcagggcgg acaagtggta tgacattgcc ttctgcgtcc ggtcgatcag 2220
ggaggatatc ggggaagaac agtatgtcga gctatttttt gacttactgg ggatcaagcc 2280

-continued

```
tgattgggag aaaataaaat attatatttt actggatgaa ttgttttagt acctagattt   2340
agatgtctaa aaagcttttt agacatctaa tcttttctga agtacatccg caactgtcca   2400
tactctgatg ttttatatct tttctaaaag ttcgctagat aggggtcccg agcgcctacg   2460
aggaatttgt atcgaagatc agccgaagtt atcaaaagtg taatacaaga gcttgatata   2520
taagagggga aaccctcttt ttttgtatat aaaaagtcac agcgtgaaaa tataataatt   2580
aaaataatga tttttttaggg tgtgatagtc gtgcagaaaa taactcagca ggagattatt   2640
ttaagtgcct ttgttgaagc acaaaattta gaaaagatac tgttggataa agtaagagaa   2700
tatgggaaag aatcagtaga taatcaaata aaagcattgt taaagcaaat tgaaataatg   2760
ataaaaaatc ataaagaaga cataaaaaag gcacaaaaga ctatgcatat taattccctt   2820
gtcaaaaaaa atatgtctca agagccttta gacatgcttc aagatttatt aaaaaattta   2880
gttaatattc aagcctttta taatgaaact gttgtgaata ttactaatcc ttacgttaga   2940
cagttgttta ctcaaatgag ggatgatgtt atgagattta tttctattct tcaaatggag   3000
attgaaagtc tggaatcgaa accttctatt ccaaataaca cagttttaaa tacaccggag   3060
atgagttaat atgaaagtgg ctattattgg tgctggtgtt tcagggctgg ctgcggcaat   3120
tacttttcaa aggtatggca ttacaccaga tatttttgaa aaaaagtgca aaataggtga   3180
attatttaac catgttgcgg ggttattaaa agtgataaat aggcctataa aggatccgct   3240
tcatcatctt aaaaatgttt atggaataga agttaaacca attaacacca ttgacaaaat   3300
agtaatgaag gggccaactg taacagcttc tgttactggg agtaatcttg ggtatatgat   3360
tttaagagga caggacgcaa actctcttga aaatcaattg tataataagt tagaaatacc   3420
agttaatttc aatatagaag ctgattataa gaagttaaaa aataattacg attatgtctg   3480
caggcatgca agcttggcgt aatcatggtc atagctgttt cctgtgtgaa attgttatcc   3540
gctcacaatt ccacacaaca tacgagccgg aagcataaag tgtaaagcct ggggtgccta   3600
atgagtgagc taactcacat taattgcgtt gcgctcactg cccgctttcc agtcgggaaa   3660
cctgtcgtgc cagctgcatt aatgaatcgg ccaacgcgcg gggagaggcg gtttgcgtat   3720
tgggcgctct tccgcttcct cgctcactga ctcgctgcgc tcggtcgttc ggctgcggcg   3780
agcggtatca gctcactcaa aggcggtaat acggttatcc acagaatcag gggataacgc   3840
aggaaagaac atgtgagcaa aaggccagca aaaggccagg aaccgtaaaa aggccgcgtt   3900
gctggcgttt ttccataggc tccgcccccc tgacgagcat cacaaaaatc gacgctcaag   3960
tcagaggtgg cgaaacccga caggactata aagataccag gcgtttcccc ctggaagctc   4020
cctcgtgcgc tctcctgttc cgaccctgcc gcttaccgga tacctgtccg cctttctccc   4080
ttcgggaagc gtggcgcttt ctcatagctc acgctgtagg tatctcagtt cggtgtaggt   4140
cgttcgctcc aagctgggct gtgtgcacga accccccgtt cagcccgacc gctgcgcctt   4200
atccggtaac tatcgtcttg agtccaaccc ggtaagacac gacttatcgc cactggcagc   4260
agccactggt aacaggatta gcagagcgag gtatgtaggc ggtgctacag agttcttgaa   4320
gtggtggcct aactacggct acactagaag gacagtattt ggtatctgcg ctctgctgaa   4380
gccagttacc ttcggaaaaa gagttggtag ctcttgatcc ggcaaacaaa ccaccgctgg   4440
tagcggtggt ttttttgttt gcaagcagca gattacgcgc agaaaaaaag gatctcaaga   4500
agatcctttg atcttttcta cggggtctga cgctcagtgg aacgaaaact cacgttaagg   4560
gattttggtc atgagattat caaaaaggat cttcacctag atccttttaa attaaaaatg   4620
aagttttaaa tcaatctaaa gtatatatga gtaaacttgg tctgacagtt accaatgctt   4680
```

```
aatcagtgag gcacctatct cagcgatctg tctatttcgt tcatccatag ttgcctgact   4740
ccccgtcgtg tagataacta cgatacggga gggcttacca tctggcccca gtgctgcaat   4800
gataccgcga gacccacgct caccggctcc agatttatca gcaataaacc agccagccgg   4860
aagggccgag cgcagaagtg gtcctgcaac tttatccgcc tccatccagt ctattaattg   4920
ttgccgggaa gctagagtaa gtagttcgcc agttaatagt ttgcgcaacg ttgttgccat   4980
tgctacaggc atcgtggtgt cacgctcgtc gtttggtatg gcttcattca gctccggttc   5040
ccaacgatca aggcgagtta catgatcccc catgttgtgc aaaaaagcgg ttagctcctt   5100
cggtcctccg atcgttgtca gaagtaagtt ggccgcagtg ttatcactca tggttatggc   5160
agcactgcat aattctctta ctgtcatgcc atccgtaaga tgcttttctg tgactggtga   5220
gtactcaacc aagtcattct gagaatagtg tatgcggcga ccgagttgct cttgcccggc   5280
gtcaatacgg gataataccg cgccacatag cagaacttta aaagtgctca tcattggaaa   5340
acgttcttcg gggcgaaaac tctcaaggat cttaccgctg ttgagatcca gttcgatgta   5400
acccactcgt gcacccaact gatcttcagc atcttttact ttcaccagcg tttctgggtg   5460
agcaaaaaca ggaaggcaaa atgccgcaaa aaagggaata agggcgacac ggaaatgttg   5520
aatactcata ctcttccttt ttcaatatta ttgaagcatt tatcagggtt attgtctcat   5580
gagcggatac atatttgaat gtatttagaa aaataaacaa ataggggttc cgcgcacatt   5640
tccccgaaaa gtgccacctg acgtctaaga aaccattatt atcatgacat taacctataa   5700
aaataggcgt atcacgaggc cctttcgtct cgcgcgtttc ggtgatgacg gtgaaaacct   5760
ctgacacatg cagctcccgg agacggtcac agcttgtctg taagcggatg ccgggagcag   5820
acaagcccgt cagggcgcgt cagcgggtgt tggcgggtgt cggggctggc ttaactatgc   5880
ggcatcagag cagattgtac tgagagtgca ccatatgcgg tgtgaaatac cgcacagatg   5940
cgtaaggaga aaataccgca tcaggcgcca ttcgccattc aggctgcgca actgttggga   6000
agggcgatcg gtgcgggcct cttcgctatt acgccagctg gcgaaagggg gatgtgctgc   6060
aaggcgatta agttgggtaa cgccagggtt ttcccagtca cgacgttgta aaacgacggc   6120
cagtgaattc                                                          6130
```

<210> SEQ ID NO 59
<211> LENGTH: 4680
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59

```
tattgattga cgatgaggta atcaaaaaat tagaagcatg tattgacctt gcacctttgc     60
acaatcctgc taatattgag ggaataaaag cttgtcggca gataatgcca ggggtgccaa    120
tggtagcagt ttttgatacg gctttccatc aaacaatgcc agattatgcg tatatttatc    180
ccattcctta tgaatactac gaaaaatata gaataagaag atatggattc catgggactt    240
ctcataaata tgtatcttta agagctgctg aaatattaaa gaggcctatt gaagagttaa    300
aaattattac ttgccattta gggaatgggt ctagtattgc tgcggttaaa ggcggtaagt    360
cgatagatac aagtatggga tttactccat tagaagggct ggctatgggt acaaggtccg    420
gaaatgttga tccttcaatt ataactttct taatggaaaa agaaggattg actgcagaac    480
aggttataga tatacttaat aagaaatcag gtgtatacgg aatttcagga ataagtaatg    540
actttagaga tatagaaaac ccagcgaacc atttgaggtg ataggtaaga ttataccgag    600
```

-continued

```
gtatgaaaac gagaattgga cctttacaga attactctat gaagcgccat atttaaaaag    660
ctaccaagac gaagaggatg aagaggatga ggaggcagat tgccttgaat atattgacaa    720
tactgataag ataatatatc ttttatatag aagatatcgc cgtatgtaag gatttcaggg    780
ggcaaggcat aggcagcgcg cttatcaata tatctataga atgggcaaag cataaaaact    840
tgcatggact aatgcttgaa acccaggaca ataaccttat agcttgtaaa ttctatcata    900
attgtggttt caaaatcggc tccgtcgata ctatgttata cgccaacttt caaaacaact    960
ttgaaaaagc tgttttctgg tatttaaggt tttagaatgc aaggaacagt gaattggagt   1020
tcgtcttgtt ataattagct tcttggggta tctttaaata ctgtagaaaa gaggaaggaa   1080
ataataaatg gctaaaatga gaatatcacc ggaattgaaa aaactgatcg aaaaataccg   1140
ctgcgtaaaa gatacggaag gaatgtctcc tgctaaggta tataagctgg tgggagaaaa   1200
tgaaaaccta tatttaaaaa tgacggacag ccggtataaa gggaccacct atgatgtgga   1260
acgggaaaag gacatgatgc tatggctgga aggaaagctg cctgttccaa aggtcctgca   1320
ctttgaacgg catgatggct ggagcaatct gctcatgagt gaggccgatg gcgtcctttg   1380
ctcggaagag tatgaagatg aacaaagccc tgaaaagatt atcgagctgt atgcggagtg   1440
catcaggctc tttcactcca tcgacatatc ggattgtccc tatacgaata gcttagacag   1500
ccgcttagcc gaattggatt acttactgaa taacgatctg gccgatgtgg attgcgaaaa   1560
ctgggaagaa gacactccat ttaaagatcc gcgcgagctg tatgattttt taaagacgga   1620
aaagcccgaa gaggaacttg tcttttccca cggcgacctg ggagacagca acatctttgt   1680
gaaagatggc aaagtaagtg gctttattga tcttgggaga agcggcaggg cggacaagtg   1740
gtatgacatt gccttctgcg tccggtcgat cagggaggat atcggggaag aacagtatgt   1800
cgagctattt tttgacttac tggggatcaa gcctgattgg gagaaaataa aatattatat   1860
tttactggat gaattgtttt agtacctaga tttagatgtc taaaaagctt tttagacatc   1920
taatcttttc tgaagtacat ccgcaactgt ccatactctg atgttttata tcttttctaa   1980
aagttcgcta gataggggtc ccgagcgcct acgaggaatt tgtatcgctg caggcatgca   2040
agcttggcgt aatcatggtc atagctgttt cctgtgtgaa attgttatcc gctcacaatt   2100
ccacacaaca tacgagccgg aagcataaag tgtaaagcct ggggtgccta atgagtgagc   2160
taactcacat taattgcgtt gcgctcactg cccgctttcc agtcgggaaa cctgtcgtgc   2220
cagctgcatt aatgaatcgg ccaacgcgcg gggagaggcg gtttgcgtat tgggcgctct   2280
tccgcttcct cgctcactga ctcgctgcgc tcggtcgttc ggctgcggcg agcggtatca   2340
gctcactcaa aggcggtaat acggttatcc acagaatcag gggataacgc aggaaagaac   2400
atgtgagcaa aaggccagca aaaggccagg aaccgtaaaa aggccgcgtt gctggcgttt   2460
ttccataggc tccgcccccc tgacgagcat cacaaaaatc gacgctcaag tcagaggtgg   2520
cgaaacccga caggactata aagataccag gcgtttcccc ctggaagctc cctcgtgcgc   2580
tctcctgttc cgaccctgcc gcttaccgga tacctgtccg cctttctccc ttcgggaagc   2640
gtggcgcttt ctcatagctc acgctgtagg tatctcagtt cggtgtaggt cgttcgctcc   2700
aagctgggct gtgtgcacga accccccgtt cagcccgacc gctgcgcctt atccggtaac   2760
tatcgtcttg agtccaaccc ggtaagacac gacttatcgc cactggcagc agccactggt   2820
aacaggatta gcagagcgag gtatgtaggc ggtgctacag agttcttgaa gtggtggcct   2880
aactacggct acactagaag gacagtattt ggtatctgcg ctctgctgaa gccagttacc   2940
ttcggaaaaa gagttggtag ctcttgatcc ggcaaacaaa ccaccgctgg tagcggtggt   3000
```

```
tttttgttt gcaagcagca gattacgcgc agaaaaaaag gatctcaaga agatcctttg   3060

atcttttcta cggggtctga cgctcagtgg aacgaaaact cacgttaagg gattttggtc   3120

atgagattat caaaaaggat cttcacctag atccttttaa attaaaaatg aagttttaaa   3180

tcaatctaaa gtatatatga gtaaacttgg tctgacagtt accaatgctt aatcagtgag   3240

gcacctatct cagcgatctg tctatttcgt tcatccatag ttgcctgact ccccgtcgtg   3300

tagataacta cgatacggga gggcttacca tctggcccca gtgctgcaat gataccgcga   3360

gacccacgct caccggctcc agatttatca gcaataaacc agccagccgg aagggccgag   3420

cgcagaagtg gtcctgcaac tttatccgcc tccatccagt ctattaattg ttgccgggaa   3480

gctagagtaa gtagttcgcc agttaatagt ttgcgcaacg ttgttgccat tgctacaggc   3540

atcgtggtgt cacgctcgtc gtttggtatg gcttcattca gctccggttc ccaacgatca   3600

aggcgagtta catgatcccc catgttgtgc aaaaaagcgg ttagctcctt cggtcctccg   3660

atcgttgtca gaagtaagtt ggccgcagtg ttatcactca tggttatggc agcactgcat   3720

aattctctta ctgtcatgcc atccgtaaga tgcttttctg tgactggtga gtactcaacc   3780

aagtcattct gagaatagtg tatgcggcga ccgagttgct cttgcccggc gtcaatacgg   3840

gataataccg cgccacatag cagaacttta aaagtgctca tcattggaaa acgttcttcg   3900

gggcgaaaac tctcaaggat cttaccgctg ttgagatcca gttcgatgta acccactcgt   3960

gcacccaact gatcttcagc atcttttact ttcaccagcg tttctgggtg agcaaaaaca   4020

ggaaggcaaa atgccgcaaa aaagggaata agggcgacac ggaaatgttg aatactcata   4080

ctcttccttt ttcaatatta ttgaagcatt tatcagggtt attgtctcat gagcggatac   4140

atatttgaat gtatttagaa aaataaacaa ataggggttc cgcgcacatt tccccgaaaa   4200

gtgccacctg acgtctaaga aaccattatt atcatgacat taacctataa aaataggcgt   4260

atcacgaggc cctttcgtct cgcgcgtttc ggtgatgacg gtgaaaacct ctgacacatg   4320

cagctcccgg agacggtcac agcttgtctg taagcggatg ccgggagcag acaagcccgt   4380

cagggcgcgt cagcgggtgt tggcgggtgt cggggctggc ttaactatgc ggcatcagag   4440

cagattgtac tgagagtgca ccatatgcgg tgtgaaatac cgcacagatg cgtaaggaga   4500

aaataccgca tcaggcgcca ttcgccattc aggctgcgca actgttggga agggcgatcg   4560

gtgcgggcct cttcgctatt acgccagctg gcgaaagggg gatgtgctgc aaggcgatta   4620

agttgggtaa cgccagggtt ttcccagtca cgacgttgta aaacgacggc cagtgaattc   4680
```

```
<210> SEQ ID NO 60
<211> LENGTH: 5663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

gttttataag aagctttgta aattttattt tctaagcctt cagagacatc aaatatgtga     60

ttgagaggaa tgtgatttct caacagataa attaaaatat tagaaaattc ctctaaagat    120

acgggacctt gtttttttc aaaagaactt tgcaaaattt cttttgtaaa gtccgggata    180

tatttttcta agccttctag tccctttca aaaatatgct ttcttataga agaggcactg    240

gcaaattctc cttttagctc taaagaggtg tacaaagagc cttttctctt tatagtaaaa    300

ggtgtaatag aactacctat tttctttaaa gatttaaggt attctattgc caatatgtta    360
```

-continued

```
ttggatgttt gtaaaatctt ttctatttca ttattattta taacttttttg taatgctaat    420
tcccgtgctt ttgcaaaggt tatgccgctt tttaaatatt cttttaatgc ttttctataa    480
taaattggct cttctaaaag tatttcagca atttttgtga gttcgtttaa atcgcctttt    540
tcactcccaa aggaaaaaca atctactatt tttaaagagt ctaatagttt caccgctcca    600
taagcgaaat tttcagctgt agaggtagca taaactactg gtaactcgat taccaaatct    660
ataccggctt ttaatgccat ttgagttcgt ttccatttgt ctacaattgc tggttctcct    720
ctttgcacga agtttccact cattactgct atagtataat cgcatttggt taattctttt    780
gaagtttgca gatggtaaag gtggccattg tgaaaaggat tatattcgac aataattcct    840
aaaattccca tacaacttct taccctttca aaaaattttt taagatatac ttattatttt    900
acataaaata tgataaaatg taaaagggac atcgtgtata caatattata gtgataaaat    960
taaaaaagga agggagattt taaatggcag taatggatag taaaacccag cgaaccattt   1020
gaggtgatag gtaagattat accgaggtat gaaaacgaga attggacctt tacagaatta   1080
ctctatgaag cgccatattt aaaaagctac caagacgaag aggatgaaga ggatgaggag   1140
gcagattgcc ttgaatatat tgacaatact gataagataa tatatctttt atatagaaga   1200
tatcgccgta tgtaaggatt tcagggggca aggcataggc agcgcgctta tcaatatatc   1260
tatagaatgg gcaaagcata aaaacttgca tggactaatg cttgaaaccc aggacaataa   1320
ccttatagct tgtaaattct atcataattg tggtttcaaa atcggctccg tcgatactat   1380
gttatacgcc aactttcaaa acaactttga aaaagctgtt ttctggtatt taaggtttta   1440
gaatgcaagg aacagtgaat tggagttcgt cttgttataa ttagcttctt ggggtatctt   1500
taaatactgt agaaaagagg aaggaaataa taaatggcta aaatgagaat atcaccggaa   1560
ttgaaaaaac tgatcgaaaa ataccgctgc gtaaaagata cggaaggaat gtctcctgct   1620
aaggtatata agctggtggg agaaaatgaa aacctatatt taaaaatgac ggacagccgg   1680
tataaaggga ccacctatga tgtggaacgg gaaaaggaca tgatgctatg gctggaagga   1740
aagctgcctg ttccaaaggt cctgcacttt gaacggcatg atggctggag caatctgctc   1800
atgagtgagg ccgatggcgt cctttgctcg gaagagtatg aagatgaaca aagccctgaa   1860
aagattatcg agctgtatgc ggagtgcatc aggctctttc actccatcga catatcggat   1920
tgtccctata cgaatagctt agacagccgc ttagccgaat tggattactt actgaataac   1980
gatctggccg atgtggattg cgaaaactgg gaagaagaca ctccatttaa agatccgcgc   2040
gagctgtatg attttttaaa gacggaaaag cccgaagagg aacttgtctt ttcccacggc   2100
gacctgggag acagcaacat ctttgtgaaa gatggcaaag taagtggctt tattgatctt   2160
gggagaagcg gcagggcgga caagtggtat gacattgcct tctgcgtccg gtcgatcagg   2220
gaggatatcg gggaagaaca gtatgtcgag ctatttttg acttactggg gatcaagcct   2280
gattgggaga aaataaaata ttatatttta ctggatgaat tgttttagta cctagattta   2340
gatgtctaaa aagcttttta gacatctaat cttttctgaa gtacatccgc aactgtccat   2400
actctgatgt tttatatctt ttctaaaagt tcgctagata ggggtcccga gcgcctacga   2460
ggaatttgta tcgtgacttt agagatatag aaaatgcagc ttttaaagaa gggcataaaa   2520
gggctatgtt ggcattaaaa gttttcgctt atagggtgaa aaagacaata ggttcttata   2580
cagctgctat gggtggggtt gatgtaattg tgtttactgc tggagttgga gaaaatggac   2640
cagaaatgag agagtttatt ttagaggatc tagagttttt aggctttaaa ctggacaaag   2700
agaagaataa ggtaagagga aaagaggaaa ttatatctac agaagattca aaagttaaag   2760
```

-continued

```
ttatggttat tcctacaaat gaagaatata tgattgctaa agatactgaa aaattggtaa   2820

aaggtttaaa gtagataatc ttgacaacgg gttgtggggt tagtataata ggtgatgtca   2880

attattttaa ggtgtgagaa gaaaaatgaa aatcgatcta ttaaaaatca aaggacagct   2940

tggccgcagc ataaatatag actatgtaga ggacatagag aacattgaat ttaaagggga   3000

agaatacaaa ctgcaggcat gcaagcttgg cgtaatcatg gtcatagctg tttcctgtgt   3060

gaaattgtta tccgctcaca attccacaca acatacgagc cggaagcata aagtgtaaag   3120

cctggggtgc ctaatgagtg agctaactca cattaattgc gttgcgctca ctgcccgctt   3180

tccagtcggg aaacctgtcg tgccagctgc attaatgaat cggccaacgc gcggggagag   3240

gcggtttgcg tattgggcgc tcttccgctt cctcgctcac tgactcgctg cgctcggtcg   3300

ttcggctgcg gcgagcggta tcagctcact caaaggcggt aatacggtta tccacagaat   3360

caggggataa cgcaggaaag aacatgtgag caaaaggcca gcaaaaggcc aggaaccgta   3420

aaaaggccgc gttgctggcg tttttccata ggctccgccc ccctgacgag catcacaaaa   3480

atcgacgctc aagtcagagg tggcgaaacc cgacaggact ataaagatac caggcgtttc   3540

cccctggaag ctccctcgtg cgctctcctg ttccgaccct gccgcttacc ggatacctgt   3600

ccgcctttct cccttcggga agcgtggcgc tttctcatag ctcacgctgt aggtatctca   3660

gttcggtgta ggtcgttcgc tccaagctgg gctgtgtgca cgaacccccc gttcagcccg   3720

accgctgcgc cttatccggt aactatcgtc ttgagtccaa cccggtaaga cacgacttat   3780

cgccactggc agcagccact ggtaacagga ttagcagagc gaggtatgta ggcggtgcta   3840

cagagttctt gaagtggtgg cctaactacg gctacactag aaggacagta tttggtatct   3900

gcgctctgct gaagccagtt accttcggaa aaagagttgg tagctcttga tccggcaaac   3960

aaaccaccgc tggtagcggt ggtttttttg tttgcaagca gcagattacg cgcagaaaaa   4020

aaggatctca agaagatcct ttgatctttt ctacggggtc tgacgctcag tggaacgaaa   4080

actcacgtta agggattttg gtcatgagat tatcaaaaag gatcttcacc tagatccttt   4140

taaattaaaa atgaagtttt aaatcaatct aaagtatata tgagtaaact tggtctgaca   4200

gttaccaatg cttaatcagt gaggcaccta tctcagcgat ctgtctattt cgttcatcca   4260

tagttgcctg actccccgtc gtgtagataa ctacgatacg ggagggctta ccatctggcc   4320

ccagtgctgc aatgataccg cgagacccac gctcaccggc tccagattta tcagcaataa   4380

accagccagc cggaagggcc gagcgcagaa gtggtcctgc aactttatcc gcctccatcc   4440

agtctattaa ttgttgccgg gaagctagag taagtagttc gccagttaat agtttgcgca   4500

acgttgttgc cattgctaca ggcatcgtgg tgtcacgctc gtcgtttggt atggcttcat   4560

tcagctccgg ttcccaacga tcaaggcgag ttacatgatc ccccatgttg tgcaaaaaag   4620

cggttagctc cttcggtcct ccgatcgttg tcagaagtaa gttggccgca gtgttatcac   4680

tcatggttat ggcagcactg cataattctc ttactgtcat gccatccgta agatgctttt   4740

ctgtgactgg tgagtactca accaagtcat tctgagaata gtgtatgcgg cgaccgagtt   4800

gctcttgccc ggcgtcaata cgggataata ccgcgccaca tagcagaact ttaaaagtgc   4860

tcatcattgg aaaacgttct tcggggcgaa aactctcaag gatcttaccg ctgttgagat   4920

ccagttcgat gtaacccact cgtgcaccca actgatcttc agcatctttt actttcacca   4980

gcgtttctgg gtgagcaaaa acaggaaggc aaaatgccgc aaaaaaggga ataagggcga   5040

cacggaaatg ttgaatactc atactcttcc tttttcaata ttattgaagc atttatcagg   5100

gttattgtct catgagcgga tacatatttg aatgtattta gaaaaataaa caaatagggg   5160
```

```
ttccgcgcac atttccccga aaagtgccac ctgacgtcta agaaaccatt attatcatga   5220

cattaaccta taaaaatagg cgtatcacga ggccctttcg tctcgcgcgt ttcggtgatg   5280

acggtgaaaa cctctgacac atgcagctcc cggagacggt cacagcttgt ctgtaagcgg   5340

atgccgggag cagacaagcc cgtcagggcg cgtcagcggg tgttggcggg tgtcggggct   5400

ggcttaacta tgcggcatca gagcagattg tactgagagt gcaccatatg cggtgtgaaa   5460

taccgcacag atgcgtaagg agaaaatacc gcatcaggcg ccattcgcca ttcaggctgc   5520

gcaactgttg ggaagggcga tcggtgcggg cctcttcgct attacgccag ctggcgaaag   5580

ggggatgtgc tgcaaggcga ttaagttggg taacgccagg gttttcccag tcacgacgtt   5640

gtaaaacgac ggccagtgaa ttc                                           5663
```

<210> SEQ ID NO 61
<211> LENGTH: 5395
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61

```
aattcgagct cggtacccgg ggatcctcta gagtcgacct gcaggcatgc aagggaagat     60

atgcctgctt gacattattg tccgtcattt ttcggtttat cctggtaaaa aaagttttaa    120

tcctctcaag gctttcttcg tgtaaaacaa gctttttccc caaaacttcc gcaacagtct    180

cctttgtaag gtcatcctgc gtggggccga gtcctccggt cataataaca aggtcgcacc    240

tttccaaagc tgcaagaaga catttttca gccgaacgga attgtccccc accacactgt    300

gataatacac attcacacca atgtcattga gccttttgga tatatactgg gcattggtat    360

ttgctatctg ccccattaaa agctcggttc caaccgctaa tatctccgca ttcatattga    420

aagacccctt aaatttaaac tttttgtaac ttattatatc aattagtgtt ataaaataaa    480

agggaaaaag aattaaaatc aaaggtttca agagcagccg tatcacccgt aaaagtttca    540

gccgattcaa cctttttaca cataaaactt tcaaaaattg atgacttaca attatcaagt    600

aggatataat attactaatg ctaaacagtt attgataaag gaggaaggaa tatgaacaat    660

aacaaagtaa ttaaaaaagt aacccggact ttctgagaag ctgaatttct tcatcgttga    720

aaggcacgtt caatatttcc tcaataccgt ttacacccac gattgtcgga acacttaagc    780

atacatcgct aagtccgtac tgtccttcca aaaggcttga aacggtaagg atggagtttt    840

catttcttac aatggcttca acgattcttc ttacggcaag ggctacggca taataggttg    900

cacctttgtt cctgatgatt tcataagctg catttttaac actttcatat attttattcc    960

gggaaatctg ctcctcgcac tgatggcatt cgtcacagta gcgatccatg ggaattcccg   1020

caatatttgc aagactccag gccgcaactt cggtgtcacc gtgttcgcca ataatataag   1080

catgtacatt tcgtgcatcc acttttacat gttcgcttaa aagataacgg aacctggctg   1140

tgtccaaaac cgttccggaa cctattactt tgtttttcgg gaatccggat agtttgtaag   1200

ttacataggt taaaatatcc accggatttg tgactaccag aagaatacaa tcgttgttgt   1260

actttacaat ttcatttatg atatttttga atacttccgt gtttctttta acaagatcta   1320

ttctcgtttc gccttctttt tggttggcac cggcggtaat gattactatg tcggatccgg   1380

cacagtcttt gtagtcacca cgataaattt caacgggcct tacaaaaggc atgccgtgat   1440

ttaagtccat gacttctccg tcggcttttt ttgcatttat gtctatcagt acaatttcag   1500

atataagtcc gctgagcatc aatgtataag ctgtggtgga acctacaaag cctgcaccaa   1560
```

```
ctacgaaaca ctctaaaaga aataataaaa acactagata tatgaaagtt ctccttttct   1620
tttatgaaaa ggagaacttt cattattgat aaatatataa actagtatat aattttaata   1680
taaaacctat tttacataat ggaaattatc tatcgggga ggaaatatga acaattcagt    1740
ggaaatttta aataaaatcg tgtcaaatat tgaaaaagtc attgttggaa aaaagaaagc   1800
tatcgagttg atattaatat cacttatttg cgatggacat gttttgattg aagatgtccc   1860
cggtgtcgga aaaaccagta cttggcgtaa tcatggtcat agctgtttcc tgtgtgaaat   1920
tgttatccgc tcacaattcc acacaacata cgagccggaa gcataaagtg taaagcctgg   1980
ggtgcctaat gagtgagcta actcacatta attgcgttgc gctcactgcc cgctttccag   2040
tcgggaaacc tgtcgtgcca gcccttcaaa cttcccaaag gcgagcccta gtgacattag   2100
aaaaccgact gtaaaaagta cagtcggcat tatctcatat tataaaagcc agtcattagg   2160
cctatctgac aattcctgaa tagagttcat aaacaatcct gcatgataac catcacaaac   2220
agaatgatgt acctgtaaag atagcggtaa atatattgaa ttacctttat taatgaattt   2280
tcctgctgta ataatgggta gaaggtaatt actattatta ttgatattta agttaaaccc   2340
agtaaatgaa gtccatggaa taatagaaag agaaaaagca ttttcaggta taggtgtttt   2400
gggaaacaat ttccccgaac cattatattt ctctacatca gaaaggtata aatcataaaa   2460
ctctttgaag tcattcttta caggagtcca aataccagag aatgttttag atacaccatc   2520
aaaaattgta taaagtggct ctaacttatc ccaataacct aactctccgt cgctattgta   2580
accagttcta aaagctgtat ttgagtttat cacccttgtc actaagaaaa taaatgcagg   2640
gtaaaattta tatccttctt gttttatgtt tcggtataaa acactaatat caatttctgt   2700
ggttatacta aaagtcgttt gttggttcaa ataatgatta aatatctctt ttctcttcca   2760
attgtctaaa tcaattttat taaagttcat ttgatatgcc tcctaaattt ttatctaaag   2820
tgaatttagg aggcttactt gtctgctttc ttcattagaa tcaatccttt tttaaaagtc   2880
aatcccgttt gttgaactac tctttaataa aataattttt ccgttcccaa ttccacattg   2940
caataataga aaatccatct tcatcggctt tttcgtcatc atctgtatga atcaaatcgc   3000
cttcttctgt gtcatcaagg tttaattttt tatgtatttc ttttaacaaa ccaccatagg   3060
agattaacct tttacggtgt aaaccttcct ccaaatcaga caaacgtttc aaattctttt   3120
cttcatcatc ggtcataaaa tccgtatcct ttacaggata ttttgcagtt tcgtcaattg   3180
ccgattgtat atccgattta tatttatttt tcggtcgaat catttgaact tttacatttg   3240
gatcatagtc taatttcatt gccttttttcc aaaattgaat ccattgtttt tgattcacgt  3300
agttttctgt attcttaaaa taagttggtt ccacacatac caatacatgc atgtgctgat   3360
tataagaatt atctttatta tttattgtca cttccgttgc acgcataaaa ccaacaagat   3420
ttttattaat ttttttatat tgcatcattc ggcgaaatcc ttgagccata tctgacaaac   3480
tcttatttaa ttcttcgcca tcataaacat ttttaactgt taatgtgaga aacaaccaac   3540
gaactgttgg cttttgttta ataacttcag caacaacctt ttgtgactga atgccatgtt   3600
tcattgctct cctccagttg cacattggac aaagcctgga tttacaaaac cacactcgat   3660
acaactttct ttcgcctgtt tcacgatttt gtttatactc taatatttca gcacaatctt   3720
ttactctttc agccttttta aattcaagaa tatgcagaag ttcaaagtaa tcaacattag   3780
cgattttctt ttctctccat ggtctcactt ttccactttt tgtcttgtcc actaaaaccc   3840
ttgatttttc atctgaataa atgctactat taggacacat aatattaaaa gaaaccccca   3900
tctatttagt tatttgtttg gtcacttata actttaacag atggggtttt tctgtgcaac   3960
```

caattttaag ggttttcaat actttaaaac acatacatac caacacttca acgcaccttt 4020
cagcaactaa aataaaaatg acgttatttc tatatgtatc aagaatagaa agaactcgtt 4080
tttcgctacg ctcaaaacgc aaaaaaagca ctcattcgag tgctttttct tatcgctcca 4140
aatcatgcga tttttttcctc tttgcttttc tttgctcacg aagttctcga tcacgctgca 4200
aaacatcttg aagcgaaaaa gtattcttct tttcttccga tcgctcatgc tgacgcacga 4260
aaagccctct aggcgcatag gaacaactcc taaatgcatg tgaggggttt tctcgtccat 4320
gtgaacagtc gcatacgcaa tattttgttt cccatactgc attaatgaat cggccaacgc 4380
gcggggagag gcggtttgcg tattgggcgc tcttccgctt cctcgctcac tgactcgctg 4440
cgctcggtcg ttcggctgcg gcgagcggta tcagctcact caaaggcggt aatacggtta 4500
tccacagaat caggggataa cgcaggaaag aacatgtgag caaaaggcca gcaaaaggcc 4560
aggaaccgta aaaaggccgc gttgctggcg tttttccata ggctccgccc ccctgacgag 4620
catcacaaaa atcgacgctc aagtcagagg tggcgaaacc cgacaggact ataaagatac 4680
caggcgtttc cccctggaag ctccctcgtg cgctctcctg ttccgaccct gccgcttacc 4740
ggatacctgt ccgcctttct cccttcggga agcgtggcgc tttctcatag ctcacgctgt 4800
aggtatctca gttcggtgta ggtcgttcgc tccaagctgg gctgtgtgca cgaacccccc 4860
gttcagcccg accgctgcgc cttatccggt aactatcgtc ttgagtccaa cccggtaaga 4920
cacgacttat cgccactggc agcagccact ggtaacagga ttagcagagc gaggtatgta 4980
ggcggtgcta cagagttctt gaagtggtgg cctaactacg gctacactag aagaacagta 5040
tttggtatct gcgctctgct gaagccagtt accttcggaa aaagagttgg tagctcttga 5100
tccggcaaac aaaccaccgc tggtagcggt ggtttttttg tttgcaagca gcagattacg 5160
cgcagaaaaa aaggatctca agaagatcct ttgatctttt ctacggggtc tgacgctcag 5220
tggaacgaaa actcacgtta agggattttg gtcatgagat tatcaaaaag gatcttcacc 5280
tagatccttt taaattaaaa atgaagtttt aaatcaatct aaagtatata tgagtaaact 5340
tggtctgaca gttaccaatg cttaatcagt gaggcaccta tctcagcgat ctgtc 5395

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
atttacctgg ctgggaatac tgagacatat gtcattgagg ccgta 45

<210> SEQ ID NO 63
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
aaaaaagctt ataattatcc ttaatttcct actacgtgcg cccagatagg gtg 53

<210> SEQ ID NO 64
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
cagattgtac aaatgtggtg ataacagata agtctactac tgtaacttac ctttctttgt 60

<210> SEQ ID NO 65
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
tgaacgcaag tttctaattt cggttgaaat ccgatagagg aaagtgtct 49

<210> SEQ ID NO 66
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ttaaatgttg ataaggaagc tcttttcaat gaagttaagg tagca 45

<210> SEQ ID NO 67
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
aaaaaagctt ataattatcc ttagctctct tcaatgtgcg cccagatagg gtg 53

<210> SEQ ID NO 68
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
cagattgtac aaatgtggtg ataacagata agtcttcaat gataacttac ctttctttgt 60

<210> SEQ ID NO 69
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
tgaacgcaag tttctaattt cgattagagc tcgatagagg aaagtgtct 49

<210> SEQ ID NO 70
<211> LENGTH: 1509
<212> TYPE: DNA
<213> ORGANISM: Caldiscellulosiruptor kristjanssonii

<400> SEQUENCE: 70

```
atgtatttta ttggaattga cgttggaaca tctggaacaa agacaatcct gattgactca     60
aaaggtaaga ttctggcttc tgcaaccttt gaatatcctc tttatcagcc tcagattggc    120
tgggctgagc aaaatcccga agactggtgg gatgcaagcg taaaaggaat taaagctgtg    180
cttgaaaagt caaaagtaga ccccaaggaa gttaaggctg tgggacttac cgggcagatg    240
cacgggcttg tgctgcttga caaaaactac aacgttataa gaccatcaat catctggtgt    300
gaccagagaa cggcaaaaga atgtgatgaa ataacagaaa aggttggcaa ggaaaagctt    360
gtggagatta cagcaaaccc tgcactgaca ggttttacag cgtccaagat tctgtgggtg    420
agaaacaacg agccccaaaa ctatgagaag gtctacaaaa ttttgcttcc caaagactat    480
ataaggttta aacttacagg cgagtttgca acagatgtgt cggacgcctc gggtatgcag    540
cttttggaca ttaaaaacag gtgctggtct gatgaggtac ttgaaaagct tgagatagac    600
aaagggcttc ttggaaaagt ctatgagtcg ccagaggtaa cgggaaaagt tagcgggcaa    660
gcaagcgaac ttacaggtct ttgtgaaggt acgcttgttg ttgcaggtgg aggagaccag    720
gcagcaggtg cagttggaaa tggcatagta aagacgggtg tgatttcatc tacaattggt    780
tcgtctggcg ttgtttttgc ccatcttgac gagtttaaga ttgacccaca gggaagggtt    840
cacacatttt gtcatgcagt gccgggaaaa tggcatgtga tgggtgtaac acaaggtgcc    900
ggactttctc tcaagtggtt tagagacaac tttgcacaca tcgaaaaggc tgcgtttgag    960
tttattgaca aagacccata cattttgatg gaccaggagg cagaacttgc aaacccaggc   1020
gcagacggac ttgttttcct gccatatttg atgggggaaa gaacgcccat tttggaccca   1080
tacgccaaag gaatattctt tggaataaca gcaaagcata cacgaagaga gttcattaga   1140
gctgtcatgg aaggtgttgt attttcactt aaaaactgtc ttgatatttt gtatgagatg   1200
ggcatcgagg tgaaggaggt aagagtttca ggcggtggtg caaagagcaa gctctggaga   1260
cagatgcagg cagacatatt tgagatggat gtatggacac tgaattccaa agaaggacct   1320
gcgtttggtg cagctatcct ggcagcagtt ggtgcaggag aatatcagaa ggttgaagaa   1380
gcctgtgata ctatgattca aaaggtagat aactgcagcc caaatgaaaa actatttgaa   1440
atatatagaa aaacttataa actttacaac agtatatatc caagagttaa ggacttattc   1500
aacatgtaa                                                            1509
```

<210> SEQ ID NO 71
<211> LENGTH: 1317
<212> TYPE: DNA
<213> ORGANISM: Caldiscellulosiruptor kristjanssonii

<400> SEQUENCE: 71

```
atgaaatact tcaaagacat tccagaagta aaatatgaag gaccacagtc agacaatcca     60
tttgctttca agtattacaa tcctgacgag gttattgatg gcaagccttt aaaagaccac    120
cttcgttttg caattgctta ctggcacacg ttctgtgcaa ccggtagcga ccctttttgga    180
caacctacaa ttaatcgtcc atgggacagg ttctcaaacc caatggacaa tgcaaaagca    240
agagttgaag ctgcatttga attttttgaa aagctaaatg ttccattttt ctgcttccac    300
gacagagaca tcgcacctga aggagaaaat ttaagagaaa caaacaagaa tttggatgag    360
atagtctcta tgataaaaga atatttaaag acaagcaaaa caagagtttt gtggggaaca    420
gcaaacctat tttcacatcc gcgatatgtt catggtgctg caacatcctg caatgccgat    480
gtttttgcgt atgcagcagc gcaggtgaaa aaggcgttag aggttacaaa agagcttggc    540
ggcgaaaact atgtgttctg gggcggaaga gaaggttatg agacactttt gaacaccgac    600
```

```
atggagcttg agcttgacaa cttggcaaga tttttgcaca tggcagttga ctatgcaaaa    660
gagatagggt ttgacggtca gtttttgatt gaaccaaagc caaaagaacc aactaagcat    720
cagtacgatt ttgatgccgc tcatgtttat ggatttttga aaaaatatga ccttgacaag    780
tacttcaagc tcaacataga ggtaaaccat gcgactttgg caggacatga tttccaccat    840
gagttgagat ttgcacgaat aaacaacatg cttggctcaa ttgatgctaa catgggcgac    900
ttgcttttgg gctgggatac agaccagttc ccaacagatg taagacttac cacgcttgct    960
atgtatgagg ttattaaagc tggtggcttt gacaaaggcg ggctcaactt tgacgcaaag   1020
gtaagaagag gttcttttga gcttgaagac ttggtcattg gtcacattgc agggatggac   1080
gcttttgcaa aggatttaa gatagcatat aagcttgtca aagacggtgt atttgataag   1140
tttattgaag aaaggtatag aagctacaaa gaaggaattg gagctaagat tgtaagtggt   1200
caggcagatt ttaagacgtt agaagaatat gctttgaatc tttcaaagat agaaaacaaa   1260
tctggcaagc aagagcttct tgagatgatt ttgaacaaat atatgttcag tgaataa      1317
```

<210> SEQ ID NO 72
<211> LENGTH: 1536
<212> TYPE: DNA
<213> ORGANISM: Clostridium straminisolvens

<400> SEQUENCE: 72

```
ttgtcatatt tactgggagt agatataggt acatcaggca cgaaaactgt tttatatgat     60
gaactgggaa ataccgtagc aagcagcctt gaggaatatc cattgtacca gccccatatt    120
gggtgggcag agcaggaacc ggaagactgg tggagggcaa catgcctatc tatcaaacat    180
gttatttcca aaagaggaat tgatgcttcc tctattaagg gaatcggact ttcaggacag    240
atgcacgggg ctgttcttct ggacaaagac ggcaaagtgc taagaaaagc aattatatgg    300
tgtgaccaga gaagttttgc cgagtgcgag cagattactt caattatagg gaaggaaagg    360
ctcgttgaga taactgccaa ccctgcactg acgggattta cagcatcaaa ggttatgtgg    420
gttaaaaata atgaacctga aatttttgag aagatttata agatacttct ccctaaagac    480
tatataagat ataaattaac gggagaattt gctacagagg tatctgatgc cagtggaatg    540
cagtttatgg atataccggg gagaaaatgg agcgacgaag tcataagtaa actcggactt    600
gataaaagca tgctgggaga actctatgag tctcaggaag ttagcgggaa agtgaataag    660
tatgctgctt cattaaccgg acttaaggaa ggaactcctg tcgtgggtgg agcaggagac    720
caggcagcag gagctgtcgg taatggaatt gtgagacccg ggtggtttc atccactata     780
ggaacttcag gagtagtatt tgcattctct gaaaaggtta ctattgatcc aaagggtaga    840
gttcatactt tttgtcatgc ggtaccaaat acctggcaca ttatgggggt tacacaaggg    900
gccgggctgt ctcttaagtg gttccgtgac aatttctgta tagaagaaaa gagaactgca    960
gagctaatga aaatagaccc gtacataatt atggataaag aagctgaaaa agtggctccg   1020
ggctgtaacg gtttaatcta tttaccttat ctgatgggag aaagaacgcc acatcttgac   1080
cctaatgcca agggtgtctt tttcggatta acagcaaagc atgaaaaaca ggatatctta   1140
aggtcgatta tggaaggtgt tgtatatagc cttagagatt gccttgaaat tattgaggaa   1200
atgggtgtta acgtttctga agtaagagct tccggtggag gcggtaaaag tgaattgtgg   1260
agaaaaatgc aggcggatat attcggcact gatattacaa ccgtaaagtc aagtgaggga   1320
ccggcacttg ggtagcact tcttgccgga gtaggaacgg gtgtgtacaa caacattaat     1380
gaagcatgtg aagcagtaat aaaagaaaat acccggcagg cttcggaccc ggagctatat   1440
```

gtaaaataca cgaagtttta tgatatttat aaacgtctgt ataactcttt gaaaaaggaa 1500
tttgcagacc tttcggctat gctgcaaagt ttatag 1536

<210> SEQ ID NO 73
<211> LENGTH: 1320
<212> TYPE: DNA
<213> ORGANISM: Clostridium straminisolvens

<400> SEQUENCE: 73
atggcagagt attttaaaaa tgtaccgaaa atcaaatatg aaggaaagga ttcggacaat 60
cctttagcgt ttaagtacta taatcccgat gaggtcattg gcggtaaaac aatgaaagag 120
catctaaggt ttgctgttgc atattggcat acatatcagg gaacgggtgc agacccattt 180
gggccgggta ctgctgtaag accgtgggat gacatatcgg acccaatgga tcttgcaaag 240
gccaaagtgg ccgcaaattt cgagctgtgt gaaaaattgg gagtaccatt tttctgcttc 300
catgacagag atattgcgcc tgaagcttca actttaagag agaccaataa aagacttgat 360
gagattgttg cactgataaa ggactatatg aaaacaagta gtgtaaaact actctggggt 420
acaacaaatg cttttagcca cccaaggttt gtccatggtg catctacttc tccgaatgca 480
gatgtatttg catatgcagc agctcaggtt aaaaaggcta tggaaattac cctggaactt 540
ggcggtcaga actatgtgtt ctggggtgga agagaaggct atgaaacctt acttaatact 600
gatatgaaat tggagcttga caatatggca aggttccttg gaatggcagt tgactatgca 660
aaagagattg gttttaaagg gcagctcttg attgaaccta agccaaaaga accgacaaag 720
caccagtatg actttgatac agctacagtt atcggtttct taaggactta tggtcttgag 780
aattacttca aaatgaatat tgaagcaaat cacgctacac ttgcagctca tactttccag 840
catgaactta gggtttcaag aattaacggt gtgctaggaa gtatcgatgc aaaccagggt 900
gatcttcttt taggatggga cactgaccaa ttcccgacaa atatctacga tactaccctt 960
gctatgtatg aagtaattaa ggcaggcgga tttacaacgg gaggtctgaa ttttgattct 1020
aaagtcagaa gaggatcatt tgagcctgtg gacctgttct atgcacatat tgcaggtatg 1080
gacgcttttg caaaaggatt taaaatagca tataaaatgg tttccgacgg taagtttgac 1140
aaatttattg atgaaagata tgaaagctat aagagcggta ttggaaaaga tattgtagat 1200
ggaaaagtag ggtttaaaga gcttgaaaaa tatgctttag agcttgatgg tatcaagaat 1260
gtgtcgggaa gacaggaagt tctcgaagct atgttaaaca aatatattct tgaggactag 1320

<210> SEQ ID NO 74
<211> LENGTH: 8909
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 74
catgagacaa taaccctgat aaatgcttca ataatattga aaaaggaaga gtatccagta 60
ttctgacatg ggtgtatcaa taacccatgc gtttccgtat tgtatcggaa tggtttcgga 120
cagggcggtg ggaatagaca tggaaaagat ttttttgccc gaggatgcat tgataaagta 180
tttcttttcc gaaagagagg aaaagattct aaagagtttt ggaaatactg atgaatattg 240
tgtgcagagt acaattctat ggacaagaaa agaggctttg tcaaaacttt ttcgtctggg 300
aatgaggatg gattttaaaa agctggatac tttggaggac gaggtggttt ttcaggaaac 360

-continued

```
aaacagggcg cgtctgtttt cttttatatg caataattac tgtatctctc tggcattgcc    420
aggttttaat aaagattaaa attattgact agaaataaaa aaattgtcca taatattaat    480
ggacaaaaaa acaaagaatt acatcaaagg aagataaaaa tactttgtta aaaaattaat    540
tattttttat ctaaactatt gaaaatgaaa ataaaataat ataaaatgaa tcatagtgca    600
agagatactt gccagaggat gaatatttta ctgcattcat gctttatggc agctaataga    660
ggcattaaat taaattttaa tttacaatag gaggcgatat taatgaataa atattttgag    720
aacgtatcta aaataaaata tgaaggacca aaatcaaaca atccttattc ttttaaattt    780
tacaatccag aagaagtaat cgatggcaag acgatggagg agcatctacg cttttctata    840
gcttactggc acacttttac tgctgatgga acagatcaat ttggcaaagc taccatgcaa    900
agaccatgga accactacac agatcctatg gacatagcaa aggcaagggt agaagcagca    960
tttgagtttt ttgataagat aaatgcacct ttcttctgct tccatgacag ggatattgca   1020
cctgaaggag acactcttag agagacaaac aaaaacttag atacaatagt tgccatgata   1080
aaggattact tgaagaccag caagacgaaa gttttgtggg gcaccgcaaa tcttttctcc   1140
aatccgagat ttgtacatgg tgcatcaaca tcctgcaatg ctgatgtttt cgcatattct   1200
gcagctcaag ttaaaaaagc tcttgagatt actaaggagc ttggcggcga aaactacgta   1260
ttctggggtg gcagagaagg atatgaaaca cttctcaata cagacatgga gtttgagctt   1320
gacaactttg caagattttt gcacatggct gttgactacg cgaaggaaat cggctttgaa   1380
ggccagttct tgattgagcc gaagccaaag gagcctacga aacaccaata cgactttgac   1440
gtggcaaatg tattggcatt cttgagaaaa tacggccttg acaaatattt caaagtgaat   1500
atcgaggcaa accatgcgac attggcattc cacgacttcc aacatgagct aagatacgcc   1560
agaataaacg gtgtattagg atcaattgac gcaaatacag gcgatatgct tttaggatgg   1620
gatacagacc agttccctac agatatacgc atgacaacgc ttgctatgta tgaagtcata   1680
aagatgggtg gatttgacaa aggcggcctt aacttcgatg caaaagtaag acgtgcttca   1740
tttgaaccag aagatctttt cttaggtcat atagccggaa tggatgcctt tgcaaaaggc   1800
ttcaaagttg cttacaaact tgtgaaagat ggcgtatttg acaagttcat cgaggaaaga   1860
tacgcaagct acaaagacgg cattggcgct gacattgtaa gcgggaaagc tgacttcaag   1920
agccttgaaa agtacgcatt agagcacagc cagattgtca acaaatcagg caggcaagag   1980
ctgttagaat caatcctaaa tcagtatttg tttgcagaat aatgaaacat gagggcggct   2040
tcatgcttca ttaaagctgc cctcaacaaa aatcatggag gtaaatgtat gtatttttta   2100
gggatagatt tagggacatc atcagttaag ataatactga tgaatgaaag cggcaatgtg   2160
gtatcaagcg tttcaaaaga atatcctgtg tactatccag agccaggctg ggctgagcaa   2220
aatccagaag attggtggaa tggcacaagg gatggaataa gagagattat tgcgaaaagc   2280
ggcgtaaatg gcgatgaaat aaagggtgtt ggcttaagcg ggcagatgca tggactggtg   2340
cttttagaca aagacaataa cgttttaacg ccagccatac tttggtgtga ccagaggaca   2400
caggaagaat gcgactacat cacagagaaa ataggaaaag aaggcctttt gaagtacaca   2460
gggaataaag cattgacagg ttttactgca ccaaagatat tatgggtaaa gaagcacctt   2520
aaagacgtat atgaaagaat cgctcatatc cttttgccaa aagattatat aaggtttaaa   2580
ttgacaggtg agtacgctac agaagtttca gatgcatcag gtacacttct tttcgatgtg   2640
gaaaatagaa gatggtcaaa ggaaatgata gacatatttg aaataccgga aaaagccctt   2700
cctaagtgct acgaatcaac agatgtcaca gggtatgtca ccaaagaggc agcagatttg   2760
```

```
acagggcttc atgaagggac tattgtcgta ggcggtggtg gtgaccaagc cagcggcgct   2820
gtaggcactg gcacggtgaa aagcggcata gtgtccatcg cattaggaac ttcaggcgtc   2880
gtatttgcat cacaggacaa gtacgcagca gatgatgagc ttaggcttca ctcattctgc   2940
catgcaaacg gcaaatggca tgtgatgggt gtcatgcttt cggctgcatc atgtcttaaa   3000
tggtgggtag atgatgtaaa taattacaag accgatgtta tgacatttga tggactctta   3060
gaagaagcag agaaggtgaa gccaggcagt gatggattga tattcttgcc atacctgatg   3120
ggtgaaagga ccccttacag cgatccttat gcgagaggca gctttgtagg tttaacaatt   3180
acacacaata gaagccacat gacaagatct atattagaag gcgtcgcatt tggacttagg   3240
gattcgctgg agcttataaa ggctttaaat atacctgtaa atgaagccag ggtaagtggt   3300
ggtggtgcta aaagcaggct ttggaggcaa atacttgccg atgtattcaa tgtaaggata   3360
gacatgataa atgctacaga aggaccttca tttggtgcag caataatggc gtctgtggga   3420
tatggccttt acaaaaatgt agatgatgca tgcaatagtt taataaaagt tacagacagc   3480
gtatatccaa tcaaagaaaa cgtcgaaaag tacaacaaac tgtatccaat ctacgtgagc   3540
ttgtattcaa ggcttaaagg cgcctttgaa gaaattggga agttggattt gtaaaataaa   3600
ttcatttgga aataaattta tgacagtaca agggacattg attaacaaag cttcaggtta   3660
ataatagtaa agttaatatt tgctatgaaa tgaaagcata ataatctgtt ccttgtactt   3720
tgctttatca tgtttattta agatactaat taataaaagt caatttagcc aataataaaa   3780
tcctatatat agtaaatatt tacaataaaa tcactacaaa ataaaaaact ttatttaatc   3840
tcttaaaaat atctacataa gggggtgtta gatgaaaaag gccgtaatca tggtcatagc   3900
tgtttcctgt gtgaaattgt tatccgctca caattccaca caacatacga gccggaagca   3960
taaagtgtaa agcctggggt gcctaatgag tgagctaact cacattaatt gcgttgcgct   4020
cactgcccgc tttccagtcg ggaaacctgt cgtgccagcc cttcaaactt cccaaaggcg   4080
agccctagtg acattagaaa accgactgta aaaagtacag tcggcattat ctcatattat   4140
aaaagccagt cattaggcct atctgacaat tcctgaatag agttcataaa caatcctgca   4200
tgataaccat cacaaacaga atgatgtacc tgtaaagata gcggtaaata tattgaatta   4260
cctttattaa tgaattttcc tgctgtaata atgggtagaa ggtaattact attattattg   4320
atatttaagt taaacccagt aaatgaagtc catggaataa tagaaagaga aaaagcattt   4380
tcaggtatag gtgttttggg aaacaatttc cccgaaccat tatatttctc tacatcagaa   4440
aggtataaat cataaaactc tttgaagtca ttctttacag gagtccaaat accagagaat   4500
gttttagata caccatcaaa aattgtataa agtggctcta acttatccca ataacctaac   4560
tctccgtcgc tattgtaacc agttctaaaa gctgtatttg agtttatcac ccttgtcact   4620
aagaaaataa atgcagggta aaatttatat ccttcttgtt ttatgtttcg gtataaaaca   4680
ctaatatcaa tttctgtggt tatactaaaa gtcgtttgtt ggttcaaata atgattaaat   4740
atctcttttc tcttccaatt gtctaaatca attttattaa agttcatttg atatgcctcc   4800
taaattttta tctaaagtga atttaggagg cttacttgtc tgctttcttc attagaatca   4860
atcctttttt aaaagtcaat cccgtttgtt gaactactct ttaataaaat aatttttccg   4920
ttcccaattc cacattgcaa taatagaaaa tccatcttca tcggcttttt cgtcatcatc   4980
tgtatgaatc aaatcgcctt cttctgtgtc atcaaggttt aatttttat gtatttcttt    5040
taacaaacca ccataggaga ttaacctttt acggtgtaaa ccttcctcca aatcagacaa   5100
acgtttcaaa ttcttttctt catcatcggt cataaaatcc gtatccttta caggatattt   5160
```

-continued

```
tgcagtttcg tcaattgccg attgtatatc cgatttatat ttatttttcg gtcgaatcat   5220
ttgaactttt acatttggat catagtctaa tttcattgcc tttttccaaa attgaatcca   5280
ttgtttttga ttcacgtagt tttctgtatt cttaaaataa gttggttcca cacataccaa   5340
tacatgcatg tgctgattat aagaattatc tttattattt attgtcactt ccgttgcacg   5400
cataaaacca acaagatttt tattaatttt tttatattgc atcattcggc gaaatccttg   5460
agccatatct gacaaactct tatttaattc ttcgccatca taaacatttt taactgttaa   5520
tgtgagaaac aaccaacgaa ctgttggctt ttgtttaata acttcagcaa caacctttttg  5580
tgactgaatg ccatgtttca ttgctctcct ccagttgcac attggacaaa gcctggattt   5640
acaaaaccac actcgataca actttctttc gcctgtttca cgattttgtt tatactctaa   5700
tatttcagca caatctttta ctctttcagc ctttttaaat tcaagaatat gcagaagttc   5760
aaagtaatca acattagcga ttttcttttc tctccatggt ctcacttttc cactttttgt   5820
cttgtccact aaaacccttg atttttcatc tgaataaatg ctactattag gacacataat   5880
attaaaagaa acccccatct atttagttat ttgtttggtc acttataact ttaacagatg   5940
gggtttttct gtgcaaccaa ttttaagggt tttcaatact ttaaaacaca tacataccaa   6000
cacttcaacg cacctttcag caactaaaat aaaaatgacg ttatttctat atgtatcaag   6060
aatagaaaga actcgttttt cgctacgctc aaaacgcaaa aaaagcactc attcgagtgc   6120
tttttcttat cgctccaaat catgcgattt tttcctcttt gcttttcttt gctcacgaag   6180
ttctcgatca cgctgcaaaa catcttgaag cgaaaaagta ttcttctttt cttccgatcg   6240
ctcatgctga cgcacgaaaa gccctctagg cgcataggaa caactcctaa atgcatgtga   6300
ggggtttcct cgtccatgtg aacagtcgca tacgcaatat tttgtttccc atactgcatt   6360
aatgaatcgg ccaacgcgcg gggagaggcg gtttgcgtat tgggcgctct tccgcttcct   6420
cgctcactga ctcgctgcgc tcggtcgttc ggctgcggcg agcggtatca gctcactcaa   6480
aggcggtaat acggttatcc acagaatcag gggataacgc aggaaagaac atgtgagcaa   6540
aaggccagca aaaggccagg aaccgtaaaa aggccgcgtt gctggcgttt ttccataggc   6600
tccgcccccc tgacgagcat cacaaaaatc gacgctcaag tcagaggtgg cgaaacccga   6660
caggactata aagataccag gcgtttcccc ctggaagctc cctcgtgcgc tctcctgttc   6720
cgaccctgcc gcttaccgga tacctgtccg cctttctccc ttcgggaagc gtggcgcttt   6780
ctcatagctc acgctgtagg tatctcagtt cggtgtaggt cgttcgctcc aagctgggct   6840
gtgtgcacga accccccgtt cagcccgacc gctgcgcctt atccggtaac tatcgtcttg   6900
agtccaaccc ggtaagacac gacttatcgc cactggcagc agccactggt aacaggatta   6960
gcagagcgag gtatgtaggc ggtgctacag agttcttgaa gtggtggcct aactacggct   7020
acactagaag aacagtattt ggtatctgcg ctctgctgaa gccagttacc ttcggaaaaa   7080
gagttggtag ctcttgatcc ggcaaacaaa ccaccgctgg tagcggtggt ttttttgttt   7140
gcaagcagca gattacgcgc agaaaaaaag gatctcaaga agatcctttg atcttttcta   7200
cggggatcgc ttgcctgtaa cttacacgcg cctcgtatct tttaatgatg gaataatttg   7260
ggaatttact ctgtgtttat ttatttttat gttttgtatt tggattttag aaagtaaata   7320
aagaaggtag aagagttacg gaatgaagaa aaaaaaataa acaaaggttt aaaaaatttc   7380
aacaaaaagc gtactttaca tatatattta ttagacaaga aaagcagatt aaatagatat   7440
acattcgatt aacgataagt aaaatgtaaa atcacaggat tttcgtgtgt ggtcttctac   7500
acagacaaga tgaaacaatt cggcattaat acctgagagc aggaagagca agataaaagg   7560
```

```
tagtatttgt tggcgatccc cctagagtct tttacatctt cggaaaacaa aaactatttt   7620
ttctttaatt tcttttttta ctttctattt ttaatttata tatttatatt aaaaaattta   7680
aattataatt atttttatag cacgtgatga aaaggaccca tcgataagct agcttttcaa   7740
ttcaattcat catttttttt ttattctttt ttttgatttc ggtttctttg aaattttttt   7800
gattcggtaa tctccgaaca gaaggaagaa cgaaggaagg agcacagact tagattggta   7860
tatatacgca tatgtagtgt tgaagaaaca tgaaattgcc cagtattctt aacccaactg   7920
cacagaacaa aaacctgcag gaaacgaaga taaatcatgt cgaaagctac atataaggaa   7980
cgtgctgcta ctcatcctag tcctgttgct gccaagctat ttaatatcat gcacgaaaag   8040
caaacaaact tgtgtgcttc attggatgtt cgtaccacca aggaattact ggagttagtt   8100
gaagcattag gtcccaaaat ttgtttacta aaaacacatg tggatatctt gactgatttt   8160
tccatggagg gcacagttaa gccgctaaag gcattatccg ccaagtacaa tttttttactc   8220
ttcgaagaca gaaaatttgc tgacattggt aatacagtca aattgcagta ctctgcgggt   8280
gtatacagaa tagcagaatg ggcagacatt acgaatgcac acggtgtggt gggcccaggt   8340
attgttagcg gtttgaagca ggcggcagaa gaagtaacaa aggaacctag aggccttttg   8400
atgttagcag aattgtcatg caagggctcc ctatctactg gagaatatac taagggtact   8460
gttgacattg cgaagagcga caaagatttt gttatcggct ttattgctca aagagacatg   8520
ggtggaagag atgaaggtta cgattggttg attatgacac ccggtgtggg tttagatgac   8580
aagggagacg cattgggtca acagtataga accgtggatg atgtggtctc tacaggatct   8640
gacattatta ttgttggaag aggactattt gcaaagggaa gggatgctaa ggtagagggt   8700
gaacgttaca gaaaagcagg ctgggaagca tatttgagaa gatgcggcca gcaaaactaa   8760
aaaactgtat tataagtaaa tgcatgtata ctaaactcac aaattagagc ttcaatttaa   8820
ttatatcagt tattacccac ttttcgggga aatgtgcgcg gaacccctat ttgtttattt   8880
ttctaaatac attcaaatat gtatccgct                                     8909
```

<210> SEQ ID NO 75
<211> LENGTH: 6972
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
gacgctcagt ggaacgaaaa ctcacgttaa gggattttgg tcatgagatt atcaaaaagg     60
atcttcacct agatcctttt aaattaaaaa tgaagtttta aatcaatcta aagtatatat    120
gagtaaactt ggtctgacag ttaccaatgc ttaatcagtg aggcacctat ctcagcgatc    180
tgtcaattcg agctcggtac ccggggatcc ttaagaagac taataaaaag tttctaaaag    240
catgaaatat cctgtatttt ggagttactt gccgttattt atggctaaag ccgaaaaaaa    300
gataaggagg gtgttgtata caaaaaacat tttgtatata attagagttg cttggaaccc    360
agtaaaatag ctgtttatag tgagtaggta ttattacctg atgagttata ctgtcggtac    420
ctatttagcg gagcggcttg tccagattgg tctcaagcat cacttcgcag tcgcgggcga    480
ctacaacctc gtccttcttg acaacctgct tttgaacaaa aacatggagc aggtttattg    540
ctgtaacgaa ctgaactgcg gtttcagtgc agaaggttat gctcgtgcca aaggcgcagc    600
agcagccgtc gttacctaca gcgtcggtgc gctttccgca tttgatgcta tcggtggcgc    660
ctatgcagaa aaccttccgg ttatcctgat ctccggtgct ccgaacaaca atgatcacgc    720
```

-continued

```
tgctggtcac gtgttgcatc acgctcttgg caaaaccgac tatcactatc agttggaaat    780
ggccaagaac atcacggccg ccgctgaagc gatttacacc ccggaagaag ctccggctaa    840
aatcgatcac gtgattaaaa ctgctcttcg tgagaagaag ccggtttatc tcgaaatcgc    900
ttgcaacatt gcttccatgc cctgcgccgc tcctggaccg gcaagcgcat tgttcaatga    960
cgaagccagc gacgaagctt ctttgaatgc agcggttgaa gaaaccctga aattcatcgc   1020
caaccgcgac aaagttgccg tcctcgtcgg cagcaagctg cgcgcagctg gtgctgaaga   1080
agctgctgtc aaatttgctg atgctctcgg tggcgcagtt gctaccatgg ctgctgcaaa   1140
aagcttcttc ccagaagaaa acccgcatta catcggcacc tcatggggtg aagtcagcta   1200
tccgggcgtt gaaaagacga tgaaagaagc cgatgcggtt atcgctctgg ctcctgtctt   1260
caacgactac tccaccactg gttggacgga tattcctgat cctaagaaac tggttctcgc   1320
tgaaccgcgt tctgtcgtcg ttaacggcat tcgcttcccc agcgtccatc tgaaagacta   1380
tctgacccgt ttggctcaga aagtttccaa gaaaaccggt gcattggact tcttcaaatc   1440
cctcaatgca ggtgaactga agaaagccgc tccggctgat ccgagtgctc cgttggtcaa   1500
cgcagaaatc gcccgtcagg tcgaagctct tctgaccccg aacacgacgg ttattgctga   1560
aaccggtgac tcttggttca atgctcagcg catgaagctc ccgaacggtg ctcgcgttga   1620
atatgaaatg cagtggggtc acattggttg gtccgttcct gccgccttcg gttatgccgt   1680
cggtgctccg gaacgtcgca acatcctcat ggttggtgat ggttccttcc agctgacggc   1740
tcaggaagtc gctcagatgg ttcgcctgaa actgccggtt atcatcttct tgatcaataa   1800
ctatggttac accatcgaag ttatgatcca tgatggtccg tacaacaaca tcaagaactg   1860
ggattatgcc ggtctgatgg aagtgttcaa cggtaacggt ggttatgaca gcggtgctgg   1920
taaaggcctg aaggctaaaa ccggtggcga actggcagaa gctatcaagg ttgctctggc   1980
aaacaccgac ggcccaaccc tgatcgaatg cttcatcggt cgtgaagact gcactgaaga   2040
attggtcaaa tggggtaagc gcgttgctgc cgccaacagc cgtaagcctg ttaacaagct   2100
cctctagatt ctgttaaaac cggacattga agaaggtgtt gcgcagcgtt taataaaaac   2160
atctgtttat cgaagtttag gaataggaaa attaaaaaaa acaagacggg agtgagtttt   2220
tgaaatggct tcttcaactt tttatattcc tttcgtcaac gaaatgggcg aaggttcgct   2280
tgaaaaagca atcaaggatc ttaacggcag cggctttaaa aatgcgctga tcgtttctga   2340
tgctttcatg aacaaatccg gtgttgtgaa gcaggttgct gacctgttga aagcacaggg   2400
tattaattct gctgtttatg atggcgttat gccgaacccg actgttaccg cagttctgga   2460
aggccttaag atcctgaagg ataacaattc agacttcgtc atctccctcg gtggtggttc   2520
tccccatgac tgcgccaaag ccatcgctct ggtcgcaacc aatggtggtg aagtcaaaga   2580
ctacgaaggt atcgacaaat ctaagaaacc tgccctgcct ttgatgtcaa tcaacacgac   2640
ggctggtacg gcttctgaaa tgacgcgttt ctgcatcatc actgatgaag tccgtcacgt   2700
taagatggcc attgttgacc gtcacgttac cccgatggtt tccgtcaacg atcctctgtt   2760
gatggttggt atgccaaaag gcctgaccgc cgccaccggt atggatgctc tgacccacgc   2820
atttgaagct tattcttcaa cggcagctac tccgatcacc gatgcttgcg ctttgaaagc   2880
agcttccatg atcgctaaga atctgaagac cgcttgcgac aacggtaagg atatgccggc   2940
tcgtgaagct atggcttatg cccaattcct cgctggtatg gccttcaaca acgcttcgct   3000
tggttatgtc catgctatgg ctcaccagtt gggcggttac tacaacctgc cgcatggtgt   3060
ctgcaacgct gttctgcttc cgcatgttct ggcttataac gcctctgtcg ttgctggtcg   3120
```

```
tctgaaagac gttggtgttg ctatgggtct cgatatcgcc aatctcggtg ataaagaagg   3180
cgcagaagcc accattcagg ctgttcgcga tctggctgct tccattggta ttccagcaaa   3240
cctgaccgag ctgggtgcta agaaagaaga tgtgccgctt cttgctgacc acgctctgaa   3300
agatgcttgt gctctgacca acccgcgtca gggtgatcag aaagaagttg aagaactctt   3360
cctgagcgct ttctaaaaga tgcgttataa ttttacaagc ctgttttttt aggaaacggg   3420
cttataaaat ttttttattt ttttgccggg ttttttcttg tattaatatg tggaatatgt   3480
taataatatt aagaagaaat tccgaattta actaaacaaa attatttttg ttatttaagc   3540
caatctgtca tataattctt gacatgaggg ttattagtta gtataatagt ccttgtcggt   3600
tttaagaggg atcctctaga gtcgacctgc aggcatgcaa gcttggcgta atcatggtca   3660
tagctgtttc ctgtgtgaaa ttgttatccg ctcacaattc cacacaacat acgagccgga   3720
agcataaagt gtaaagcctg gggtgcctaa tgagtgagct aactcacatt aattgcgttg   3780
cgctcactgc ccgctttcca gtcgggaaac ctgtcgtgcc agcccttcaa acttcccaaa   3840
ggcgagccct agtgacatta gaaaaccgac tgtaaaaagt acagtcggca ttatctcata   3900
ttataaaagc cagtcattag gcctatctga caattcctga atagagttca taaacaatcc   3960
tgcatgataa ccatcacaaa cagaatgatg tacctgtaaa gatagcggta aatatattga   4020
attaccttta ttaatgaatt ttcctgctgt aataatgggt agaaggtaat tactattatt   4080
attgatattt aagttaaacc cagtaaatga agtccatgga ataatagaaa gagaaaaagc   4140
attttcaggt ataggtgttt tgggaaacaa tttccccgaa ccattatatt tctctacatc   4200
agaaaggtat aaatcataaa actctttgaa gtcattcttt acaggagtcc aaataccaga   4260
gaatgtttta gatacaccat caaaaattgt ataaagtggc tctaacttat cccaataacc   4320
taactctccg tcgctattgt aaccagttct aaaagctgta tttgagttta tcacccttgt   4380
cactaagaaa ataaatgcag ggtaaaattt atatccttct tgttttatgt ttcggtataa   4440
aacactaata tcaatttctg tggttatact aaaagtcgtt tgttggttca aataatgatt   4500
aaatatctct tttctcttcc aattgtctaa atcaatttta ttaaagttca tttgatatgc   4560
ctcctaaatt tttatctaaa gtgaatttag gaggcttact tgtctgcttt cttcattaga   4620
atcaatcctt ttttaaaagt caatcccgtt tgttgaacta ctctttaata aaataatttt   4680
tccgttccca attccacatt gcaataatag aaaatccatc ttcatcggct ttttcgtcat   4740
catctgtatg aatcaaatcg ccttcttctg tgtcatcaag gtttaatttt ttatgtattt   4800
cttttaacaa accaccatag gagattaacc ttttacggtg taaaccttcc tccaaatcag   4860
acaaacgttt caaattcttt tcttcatcat cggtcataaa atccgtatcc tttacaggat   4920
attttgcagt ttcgtcaatt gccgattgta tatccgattt atatttattt ttcggtcgaa   4980
tcatttgaac ttttacattt ggatcatagt ctaatttcat tgccttttc caaaattgaa   5040
tccattgttt ttgattcacg tagttttctg tattcttaaa ataagttggt tccacacata   5100
ccaatacatg catgtgctga ttataagaat tatctttatt atttattgtc acttccgttg   5160
cacgcataaa accaacaaga tttttattaa tttttttata ttgcatcatt cggcgaaatc   5220
cttgagccat atctgacaaa ctcttattta attcttcgcc atcataaaca tttttaactg   5280
ttaatgtgag aaacaaccaa cgaactgttg gcttttgttt aataacttca gcaacaacct   5340
tttgtgactg aatgccatgt ttcattgctc tcctccagtt gcacattgga caaagcctgg   5400
atttacaaaa ccacactcga tacaactttc tttcgcctgt ttcacgattt tgtttatact   5460
ctaatatttc agcacaatct tttactcttt cagccttttt aaattcaaga atatgcagaa   5520
```

```
gttcaaagta atcaacatta gcgattttct tttctctcca tggtctcact tttccacttt   5580

ttgtcttgtc cactaaaacc cttgattttt catctgaata aatgctacta ttaggacaca   5640

taatattaaa agaaaccccc atctatttag ttatttgttt ggtcacttat aactttaaca   5700

gatggggttt ttctgtgcaa ccaattttaa gggttttcaa tactttaaaa cacatacata   5760

ccaacacttc aacgcacctt tcagcaacta aaataaaaat gacgttattt ctatatgtat   5820

caagaataga aagaactcgt ttttcgctac gctcaaaacg caaaaaaagc actcattcga   5880

gtgctttttc ttatcgctcc aaatcatgcg attttttcct ctttgctttt ctttgctcac   5940

gaagttctcg atcacgctgc aaaacatctt gaagcgaaaa agtattcttc ttttcttccg   6000

atcgctcatg ctgacgcacg aaaagccctc taggcgcata ggaacaactc ctaaatgcat   6060

gtgaggggtt ttctcgtcca tgtgaacagt cgcatacgca atattttgtt tcccatactg   6120

cattaatgaa tcggccaacg cgcggggaga ggcggtttgc gtattgggcg ctcttccgct   6180

tcctcgctca ctgactcgct gcgctcggtc gttcggctgc ggcgagcggt atcagctcac   6240

tcaaaggcgg taatacggtt atccacagaa tcaggggata acgcaggaaa gaacatgtga   6300

gcaaaaggcc agcaaaaggc caggaaccgt aaaaaggccg cgttgctggc gtttttccat   6360

aggctccgcc cccctgacga gcatcacaaa aatcgacgct caagtcagag gtggcgaaac   6420

ccgacaggac tataaagata ccaggcgttt ccccctggaa gctccctcgt gcgctctcct   6480

gttccgaccc tgccgcttac cggatacctg tccgcctttc tcccttcggg aagcgtggcg   6540

ctttctcata gctcacgctg taggtatctc agttcggtgt aggtcgttcg ctccaagctg   6600

ggctgtgtgc acgaaccccc cgttcagccc gaccgctgcg ccttatccgg taactatcgt   6660

cttgagtcca acccggtaag acacgactta tcgccactgg cagcagccac tggtaacagg   6720

attagcagag cgaggtatgt aggcggtgct acagagttct tgaagtggtg gcctaactac   6780

ggctacacta gaagaacagt atttggtatc tgcgctctgc tgaagccagt taccttcgga   6840

aaaagagttg gtagctcttg atccggcaaa caaaccaccg ctggtagcgg tggttttttt   6900

gtttgcaagc agcagattac gcgcagaaaa aaaggatctc aagaagatcc tttgatcttt   6960

tctacggggt ct                                                       6972
```

<210> SEQ ID NO 76
<211> LENGTH: 6936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
gacgctcagt ggaacgaaaa ctcacgttaa gggattttgg tcatgagatt atcaaaaagg     60

atcttcacct agatcctttt aaattaaaaa tgaagtttta aatcaatcta aagtatatat    120

gagtaaactt ggtctgacag ttaccaatgc ttaatcagtg aggcacctat ctcagcgatc    180

tgtcaattcg agctcggtac ccggggatcc ttaagaagac taataaaaag tttctaaaag    240

catgaaatat cctgtatttt ggagttactt gccgttattt atggctaaag ccgaaaaaaa    300

gataaggagg gtgttgtata caaaaaacat tttgtatata attagagttg cttggaaccc    360

agtaaaatag ctgtttatag tgagtaggta ttattacctg atgtataccg ttggtatgta    420

cttggcagaa cgcctagccc agatcggcct gaaacaccac tttgccgtgg ccggtgacta    480

caacctggtg ttgcttgatc agctcctgct gaacaaagac atggagcagg tctactgctg    540
```

-continued

```
taacgaactt aactgcggct ttagcgccga aggttacgct cgtgcacgtg gtgccgccgc    600
tgccatcgtc acgttcagcg taggtgctat ctctgcaatg aacgccatcg gtggcgccta    660
tgcagaaaac ctgccggtca tcctgatctc tggctcaccg aacaccaatg actacggcac    720
aggccacatc ctgcaccaca ccattggtac tactgactat aactatcagc tggaaatggt    780
aaaacacgtt acctgcgcac gtgaaagcat cgtttctgcc gaagaagcac cggcaaaaat    840
cgaccacgtc atccgtacgg ctctacgtga acgcaaaccg gcttatctgg aaatcgcatg    900
caacgtcgct ggcgctgaat gtgttcgtcc gggcccgatc aatagcctgc tgcgtgaact    960
cgaagttgac cagaccagtg tcactgccgc tgtagatgcc gccgtagaat ggctgcagga   1020
ccgccagaac gtcgtcatgc tggtcggtag caaactgcgt gccgctgccg ctgaaaaaca   1080
ggctgttgcc ctagcggacc gcctgggctg cgctgtcacg atcatggctg ccgaaaaagg   1140
cttcttcccg gaagatcatc cgaacttccg cggcctgtac tggggtgaag tcagctccga   1200
aggtgcacag gaactggttg aaaacgccga tgccatcctg tgtctggcac cggtattcaa   1260
cgactatgct accgttggct ggaactcctg gccgaaaggc gacaatgtca tggtcatgga   1320
caccgaccgc gtcactttcg caggacagtc cttcgaaggt ctgtcattga gcaccttcgc   1380
cgcagcactg gctgagaaag caccttctcg cccggcaacg actcaaggca ctcaagcacc   1440
ggtactgggt attgaggccg cagagcccaa tgcaccgctg accaatgacg aaatgacgcg   1500
tcagatccag tcgctgatca cttccgacac tactctgaca gcagaaacag gtgactcttg   1560
gttcaacgct tctcgcatgc cgattcctgg cggtgctcgt gtcgaactgg aaatgcaatg   1620
gggtcatatc ggttggtccg taccttctgc attcggtaac gccgttggtt ctccggagcg   1680
tcgccacatc atgatggtcg gtgatggctc tttccagctg actgctcaag aagttgctca   1740
gatgatccgc tatgaaatcc cggtcatcat cttcctgatc aacaaccgcg gttacgtcat   1800
cgaaatcgct atccatgacg gcccttacaa ctacatcaaa aactggaact acgctggcct   1860
gatcgacgtc ttcaatgacg aagatggtca tggcctgggt ctgaaagctt ctactggtgc   1920
agaactagaa ggcgctatca agaaagcact cgacaatcgt cgcggtccga cgctgatcga   1980
atgtaacatc gctcaggacg actgcactga aaccctgatt gcttggggta aacgtgtagc   2040
agctaccaac tctcgcaaac cacaagcgta aattctgtta aaaccggaca ttgaagaagg   2100
tgttgcgcag cgtttaataa aaacatctgt ttatcgaagt ttaggaatag gaaaattaaa   2160
aaaaacaaga cgggagtgag tttttgaaat ggcttcttca actttttata ttcctttcgt   2220
caacgaaatg ggcgaaggtt cgcttgaaaa agcaatcaag gatcttaacg gcagcggctt   2280
taaaaatgcg ctgatcgttt ctgatgcttt catgaacaaa tccggtgttg tgaagcaggt   2340
tgctgacctg ttgaaagcac agggtattaa ttctgctgtt tatgatggcg ttatgccgaa   2400
cccgactgtt accgcagttc tggaaggcct taagatcctg aaggataaca attcagactt   2460
cgtcatctcc ctcggtggtg gttctcccca tgactgcgcc aaagccatcg ctctggtcgc   2520
aaccaatggt ggtgaagtca aagactacga aggtatcgac aaatctaaga aacctgccct   2580
gcctttgatg tcaatcaaca cgacggctgg tacggcttct gaaatgacgc gtttctgcat   2640
catcactgat gaagtccgtc acgttaagat ggccattgtt gaccgtcacg ttaccccgat   2700
ggtttccgtc aacgatcctc tgttgatggt tggtatgcca aaaggcctga ccgccgccac   2760
cggtatggat gctctgaccc acgcatttga agcttattct tcaacggcag ctactccgat   2820
caccgatgct tgcgctttga aagcagcttc catgatcgct aagaatctga agaccgcttg   2880
cgacaacggt aaggatatgc cggctcgtga agctatggct tatgcccaat tcctcgctgg   2940
```

-continued

```
tatggccttc aacaacgctt cgcttggtta tgtccatgct atggctcacc agttgggcgg   3000
ttactacaac ctgccgcatg gtgtctgcaa cgctgttctg cttccgcatg ttctggctta   3060
taacgcctct gtcgttgctg gtcgtctgaa agacgttggt gttgctatgg gtctcgatat   3120
cgccaatctc ggtgataaag aaggcgcaga agccaccatt caggctgttc gcgatctggc   3180
tgcttccatt ggtattccag caaacctgac cgagctgggt gctaagaaag aagatgtgcc   3240
gcttcttgct gaccacgctc tgaaagatgc ttgtgctctg accaacccgc gtcagggtga   3300
tcagaaagaa gttgaagaac tcttcctgag cgctttctaa aagatgcgtt ataattttac   3360
aagcctgttt ttttaggaaa cgggcttata aaattttttt attttttgc cgggtttttt    3420
cttgtattaa tatgtggaat atgttaataa tattaagaag aaattccgaa tttaactaaa   3480
caaaattatt tttgttattt aagccaatct gtcatataat tcttgacatg agggttatta   3540
gttagtataa tagtccttgt cggttttaag agggatcctc tagagtcgac ctgcaggcat   3600
gcaagcttgg cgtaatcatg gtcatagctg tttcctgtgt gaaattgtta tccgctcaca   3660
attccacaca acatacgagc cggaagcata aagtgtaaag cctggggtgc ctaatgagtg   3720
agctaactca cattaattgc gttgcgctca ctgcccgctt tccagtcggg aaacctgtcg   3780
tgccagccct tcaaacttcc caaaggcgag ccctagtgac attagaaaac cgactgtaaa   3840
aagtacagtc ggcattatct catattataa aagccagtca ttaggcctat ctgacaattc   3900
ctgaatagag ttcataaaca atcctgcatg ataaccatca caaacagaat gatgtacctg   3960
taaagatagc ggtaaatata ttgaattacc tttattaatg aattttcctg ctgtaataat   4020
gggtagaagg taattactat tattattgat atttaagtta aacccagtaa atgaagtcca   4080
tggaataata gaaagagaaa aagcattttc aggtataggt gttttgggaa acaatttccc   4140
cgaaccatta tatttctcta catcagaaag gtataaatca taaaactctt tgaagtcatt   4200
ctttacagga gtccaaatac cagagaatgt tttagataca ccatcaaaaa ttgtataaag   4260
tggctctaac ttatcccaat aacctaactc tccgtcgcta ttgtaaccag ttctaaaagc   4320
tgtatttgag tttatcaccc ttgtcactaa gaaaataaat gcagggtaaa atttatatcc   4380
ttcttgtttt atgtttcggt ataaaacact aatatcaatt tctgtggtta tactaaaagt   4440
cgtttgttgg ttcaaataat gattaaatat ctcttttctc ttccaattgt ctaaatcaat   4500
tttattaaag ttcatttgat atgcctccta aatttttatc taaagtgaat ttaggaggct   4560
tacttgtctg ctttcttcat tagaatcaat ccttttttaa aagtcaatcc cgtttgttga   4620
actactcttt aataaaataa tttttccgtt cccaattcca cattgcaata atagaaaatc   4680
catcttcatc ggctttttcg tcatcatctg tatgaatcaa atcgccttct tctgtgtcat   4740
caaggtttaa tttttatgt atttctttta acaaaccacc ataggagatt aacctttac     4800
ggtgtaaacc ttcctccaaa tcagacaaac gtttcaaatt cttttcttca tcatcggtca   4860
taaaatccgt atcctttaca ggatattttg cagtttcgtc aattgccgat tgtatatccg   4920
atttatattt atttttcggt cgaatcattt gaacttttac atttggatca tagtctaatt   4980
tcattgcctt tttccaaaat tgaatccatt gtttttgatt cacgtagttt tctgtattct   5040
taaaataagt tggttccaca cataccaata catgcatgtg ctgattataa gaattatctt   5100
tattatttat tgtcacttcc gttgcacgca taaaaccaac aagattttta ttaattttt    5160
tatattgcat cattcggcga aatccttgag ccatatctga caaactctta tttaattctt   5220
cgccatcata aacattttta actgttaatg tgagaaacaa ccaacgaact gttggctttt   5280
gtttaataac ttcagcaaca acctttttgtg actgaatgcc atgtttcatt gctctcctcc   5340
```

-continued

```
agttgcacat tggacaaagc ctggatttac aaaaccacac tcgatacaac tttctttcgc   5400
ctgtttcacg attttgttta tactctaata tttcagcaca atcttttact ctttcagcct   5460
ttttaaattc aagaatatgc agaagttcaa agtaatcaac attagcgatt ttcttttctc   5520
tccatggtct cacttttcca ctttttgtct tgtccactaa aacccttgat tttcatctg    5580
aataaatgct actattagga cacataatat taaaagaaac ccccatctat ttagttattt   5640
gtttggtcac ttataacttt aacagatggg gtttttctgt gcaaccaatt ttaagggttt   5700
tcaatacttt aaaacacata cataccaaca cttcaacgca cctttcagca actaaaataa   5760
aaatgacgtt atttctatat gtatcaagaa tagaaagaac tcgtttttcg ctacgctcaa   5820
aacgcaaaaa aagcactcat tcgagtgctt tttcttatcg ctccaaatca tgcgattttt   5880
tcctctttgc ttttctttgc tcacgaagtt ctcgatcacg ctgcaaaaca tcttgaagcg   5940
aaaaagtatt cttcttttct tccgatcgct catgctgacg cacgaaaagc cctctaggcg   6000
cataggaaca actcctaaat gcatgtgagg ggtttttctcg tccatgtgaa cagtcgcata  6060
cgcaatattt tgtttcccat actgcattaa tgaatcggcc aacgcgcggg gagaggcggt   6120
ttgcgtattg ggcgctcttc cgcttcctcg ctcactgact cgctgcgctc ggtcgttcgg   6180
ctgcggcgag cggtatcagc tcactcaaag gcggtaatac ggttatccac agaatcaggg   6240
gataacgcag gaaagaacat gtgagcaaaa ggccagcaaa aggccaggaa ccgtaaaaag   6300
gccgcgttgc tggcgttttt ccataggctc cgcccccctg acgagcatca caaaaatcga   6360
cgctcaagtc agaggtggcg aaacccgaca ggactataaa gataccaggc gtttccccct   6420
ggaagctccc tcgtgcgctc tcctgttccg accctgccgc ttaccggata cctgtccgcc   6480
tttctccctt cgggaagcgt ggcgctttct catagctcac gctgtaggta tctcagttcg   6540
gtgtaggtcg ttcgctccaa gctgggctgt gtgcacgaac cccccgttca gcccgaccgc   6600
tgcgccttat ccggtaacta tcgtcttgag tccaacccgg taagacacga cttatcgcca   6660
ctggcagcag ccactggtaa caggattagc agagcgaggt atgtaggcgg tgctacagag   6720
ttcttgaagt ggtggcctaa ctacggctac actagaagaa cagtatttgg tatctgcgct   6780
ctgctgaagc cagttacctt cggaaaaaga gttggtagct cttgatccgg caaacaaacc   6840
accgctggta gcggtggttt ttttgtttgc aagcagcaga ttacgcgcag aaaaaaagga   6900
tctcaagaag atcctttgat cttttctacg gggtct                             6936
```

<210> SEQ ID NO 77
<211> LENGTH: 1509
<212> TYPE: DNA
<213> ORGANISM: Clostridium thermocellum

<400> SEQUENCE: 77

```
tttgatcctg gctcaggacg aacgctggcg gcgtgcctaa cacatgcaag tcgagcgggg     60
atatacggaa ggtttaccgg aagtatatcc tagcggcgga cgggtgagta acgcgtgggt    120
aacctacctc atacaggggg ataacacagg gaaacctgtg ctaataccgc ataacggggc    180
ggcatcgtcc tgttatcaaa ggagaaatcc ggtatgagat gggcccgcgt ccgattagct    240
agttggtgag gtaacggctc accaaggcga cgatcggtag ccgaactgag aggttggtcg    300
gccacattgg gactgagaca cggcccagac tcctacggga ggcagcagtg gggaatattg    360
cgcaatgggg gaaaccctga cgcagcaacg ccgcgtgaag gaagaaggcc ttcgggttgt    420
aaacttcttt gattggggac gaaggaagtg acggtaccca aagaacaagc cacggctaac    480
tacgtgccag cagccgcggt aatacgtagg tggcgagcgt tgtccggaat tactgggtgt    540
```

-continued

```
aaagggcgcg taggcgggat gcaagtcaga tgtgaaattc cggggcttaa ccccggggct    600

gcatctgaaa ctgtatctct tgagtgctgg agaggaaagc ggaattccta gtgtagcggt    660

gaaatgcgta gatattagga ggaacaccag tggcgaaggc ggctttctgg acagtaactg    720

acgctgaggc gcgaaagcgt ggggagcaaa caggattaga taccctggta gtccacgccg    780

taaacgatgg atactaggtg taggaggtat cgaccccttc tgtgccggag ttaacacaat    840

aagtatccca cctggggagt acggccgcaa ggttgaaact caaaggaatt gacgggggcc    900

cgcacaagca gtggagtatg tggtttaatt cgaagcaacg cgaagaacct taccagggct    960

tgacatccct ctgacagctc tagagatagg gcttccttcg ggcagagga gacaggtggt    1020

gcatggttgt cgtcagctcg tgtcgtgaga tgttgggtta agtcccgcaa cgagcgcaac   1080

ccttgtcgtt agttgccagc acgttaaggt gggcactcta gcgagactgc cggcgacaag   1140

tcggaggaag gtggggacga cgtcaaatca tcatgcccct tatgtcctgg gctacacacg   1200

tactacaatg gctgctacaa agggaagcga taccgcgagg tggagcaaat ccccaaaagc   1260

agtcccagtt cggattgcag gctgaaactc gcctgcatga agtcggaatt gctagtaatg   1320

gcaggtcagc atactgccgt gaatacgttc ccgggccttg tacacaccgc ccgtcacacc   1380

atgagagtct gcaacacccg aagtcatagt ctaaccgcaa ggagggcgct gccgaaggtg   1440

gggcagatga ttggggtgaa gtcgtaacaa ggtagccgta tcggaaggtg cggctggatc   1500

acctccttt                                                           1509
```

<210> SEQ ID NO 78
<211> LENGTH: 1642
<212> TYPE: DNA
<213> ORGANISM: Clostridium cellulolyticum
<220> FEATURE:
<221> NAME/KEY: modified_base
<222> LOCATION: (9)..(9)
<223> OTHER INFORMATION: a, c, g or t
<220> FEATURE:
<221> NAME/KEY: modified_base
<222> LOCATION: (16)..(16)
<223> OTHER INFORMATION: a, c, g or t
<220> FEATURE:
<221> NAME/KEY: modified_base
<222> LOCATION: (26)..(26)
<223> OTHER INFORMATION: a, c, g or t
<220> FEATURE:
<221> NAME/KEY: modified_base
<222> LOCATION: (70)..(70)
<223> OTHER INFORMATION: a, c, g or t
<220> FEATURE:
<221> NAME/KEY: modified_base
<222> LOCATION: (86)..(86)
<223> OTHER INFORMATION: a, c, g or t
<220> FEATURE:
<221> NAME/KEY: modified_base
<222> LOCATION: (96)..(96)
<223> OTHER INFORMATION: a, c, g or t
<220> FEATURE:
<221> NAME/KEY: modified_base
<222> LOCATION: (113)..(115)
<223> OTHER INFORMATION: a, c, g or t
<220> FEATURE:
<221> NAME/KEY: modified_base
<222> LOCATION: (320)..(320)
<223> OTHER INFORMATION: a, c, g or t
<220> FEATURE:
<221> NAME/KEY: modified_base
<222> LOCATION: (443)..(443)
<223> OTHER INFORMATION: a, c, g or t
<220> FEATURE:
<221> NAME/KEY: modified_base
<222> LOCATION: (1109)..(1109)
<223> OTHER INFORMATION: a, c, g or t

<400> SEQUENCE: 78

```
tgatcctgng acaggncgag cgctgncggc gtgcctaaca catgcgagtc gagcggagtt     60
acctttagcn ctgagtattc ttgganatga tgctgncccg acagcgtcat ccnnnaacaa    120
ccttaatgaa atatttagtt ggagttttgc atcacgcgtt ttatcaaagt gtcaacacat    180
aatagtagaa gagaatgttc agtgctgaag gtaacttagc ggcggacggg tgagtaacgc    240
gtgggcaacc tgcctgttac agggggataa cacagggaaa cttgtgctaa taccgcataa    300
cacaacgaag aagcatttcn ttgttgtcaa aggagcaatc cggtgacaga tgggcccgcg    360
tccaattagc tagttggtga tgtaacggat caccaaggcg acgattggta gccgaactga    420
gaggttgatc ggccacattg ggnctgagac acggcccaga ctcctacggg aggcagcagt    480
ggggaatatt gcacaatggg ggaaaccctg atgcagcaac gccgcgtgaa ggatgaaggt    540
tttcggattg taaacttctt tagtcaggga cgaagaaaat gacggtacct gaagaataag    600
ccacggctaa ctacgtgcca gcagccgcgg taatacgtag gtggcaagcg ttgtccggaa    660
ttactgggtg taaagggcgt gtaggcggga atgtaagtca gatgtgaaat cccagggctt    720
aaccctggag ctgcatctga aactatgttt cttgagtgcc ggagaggaaa gcggaattcc    780
tagtgtagcg gtgaaatgcg tagatattag gaggaacacc agtggcgaag gcggctttct    840
ggacggtaac tgacgctgag gcgcgaaagc gtggggagca aacaggatta gataccctgg    900
tagtccacgc tgtaaacgat ggatactagg tgtaggaggt atcgacccct tctgtgccgg    960
agttaacaca ataagtatcc cacctgggga gtacggccgc aaggttgaaa ctcaaaggaa   1020
ttgacggggg cccgcacaag cagtggagta tgtggtttaa ttcgaagcaa cgcgaagaac   1080
cttaccaagg cttgacatat agcggaatnc ggcagagatg tcgtagtcct tcgggactgc   1140
tatacacagg tggtgcatgg ttgtcgtcag ctcgtgtcgt gagatgttgg gttaagtccc   1200
gcaacgagcg caacccctgt tgctagttga taacattaag atgatcactc tagcgagact   1260
gccggtgaca aatcggagga aggtggggac gacgtcaaat catcatgccc cttatgtctt   1320
gggctacaca cgtactacaa tggctataac agagggaagc taagctgcaa agtggagcaa   1380
atccccaaaa atagtcccag ttcagatggt gggctgcaac ccgcccacat gaagtcggaa   1440
ttgctagtaa tggtaggtca gtatactgtc gtgaatacgt tcccgggcct tgtacacacc   1500
gcccgtcaca ccatgagagt ctgcaacacc cgaagtcgat agtctaaccg caaggaggac   1560
gtcgccgaag gtggggccga tgattggtgt gaagtcgtaa caaggtagcc gtatcggaag   1620
gtgcggctgg atcacctcct tt                                            1642
```

<210> SEQ ID NO 79
<211> LENGTH: 1552
<212> TYPE: DNA
<213> ORGANISM: Thermoanaerobacterium saccharolyticum
<220> FEATURE:
<221> NAME/KEY: modified_base
<222> LOCATION: (64)..(64)
<223> OTHER INFORMATION: a, c, g or t
<220> FEATURE:
<221> NAME/KEY: modified_base
<222> LOCATION: (100)..(100)
<223> OTHER INFORMATION: a, c, g or t
<220> FEATURE:
<221> NAME/KEY: modified_base
<222> LOCATION: (343)..(343)
<223> OTHER INFORMATION: a, c, g or t

<400> SEQUENCE: 79

```
tttgatcctg gctcaggacg aacgctggcg gcgtgcctaa cacatgcaag tcgagcgatc     60
```

```
cggnactcaa ttaagcgctt acagaaaaag agagagaaan tgagtaaacg caaagttgag    120

tgccggatag cggcggacgg gtgagtaacg cgtggacaat ctaccctgta gtttgggata    180

acacctcgaa aggggtgcta ataccggata atgtcaagaa gtggcatcac tttttgaaga    240

aaggagaaat ccgctatagg atgagtccgc gtcccattag ctagttggcg gggtaaaagc    300

ccaccaaggc gacgatgggt agccggcctg agagggtgaa cgnccacact ggaactgaga    360

cacggtccag actcctacgg gaggcagcag tggggaatat tgttcaatgg gggaaaccct    420

gacacagcga cgccgcgtga gcgaagaagg ccttcgggtc gtaaagctca atagtatggg    480

aagatagtga cggtaccata cgaaagcccc ggctaactac gtgccagcag ccgcggtaat    540

acgtaggggg cgagcgttgt ccggaattac tgggcgtaaa gagcacgtag gcggctgtaa    600

aagtcagatg tgaaaaacct gggctcaacc gagggtgtgc atctgaaact aaacagcttg    660

agtcaaggag aggagagcgg aattcctggt gtagcggtga aatgcgtaga gatcaggaag    720

aataccagtg gcgaaagcgg ctctctggac ttgaactgac gctgaggtgc gaaagcgtgg    780

ggagcaaaca ggattagata ccctggtagt ccacgccgta aacgatggat actaggtgtg    840

ggtgaagcat catccgtgcc ggagttaacg caataagtat cccgcctggg gagtacggcc    900

gcaaggttga aactcaaagg aattgacggg ggcccgcaca agcagcggag catgtggttt    960

aattcgaagc aacgcgaaga accttaccag ggcttgacat ccacagaatc aggtagaaat   1020

accagagtgc ctcgaaagag gagctgtgag acaggtggtg catggttgtc gtcagctcgt   1080

gtcgtgagat gttgggttaa gtcccgcaac gagcgcaacc cctgttggta gttaccagcg   1140

taaagacggg gactctaccg agactgccgt ggagaacacg gaggaaggcg gggatgacgt   1200

caaatcatca tgccctttat gccctgggct acacacgtgc tacaatggcc tgaacagagg   1260

gcagcgaagg agcgatccgg agcgaatccc agaaaacagg tcccagttca gattgcaggc   1320

tgcaacccgc ctgcatgaag acggagttgc tagtaatcgc ggatcagcat gccgcggtga   1380

atacgttccc gggccttgta cacaccgccc gtcacaccac gagagtttac aacacccgaa   1440

gtcagtgacc taaccgcaag ggaggagctg ccgaaggtgg ggtaaatgat tggggtgaag   1500

tcgtaacaag gtagccgtat cggaaggtgc ggctggatca cctcctttcc ct           1552
```

<210> SEQ ID NO 80
<211> LENGTH: 1519
<212> TYPE: DNA
<213> ORGANISM: Clostridium stercorarium

<400> SEQUENCE: 80

```
tttgatcctg gctcaggacg aacgctggcg gcgtgcctaa cacatgcaag tcgaacggga     60

tccgtgttac ggaggtcttt ggaccgaagt ggcatggtga gagtggcgga cgggcgagta    120

acgcgtgagc aacctgccct atgctggggg ataacaccgg gaaaccggtg ctaataccgc    180

ataagaccac agtgacgcat gtacagtggt aaagctgagg cggcatagga tgggctcgcg    240

gtccattagc tagttggtag ggtaacggcc taccaaggcg acgatcggta gccggactga    300

gaggttggcc ggccgcattg ggactgagac acggcccaga ctcctacggg aggcagcagt    360

ggggaatatt gcgcaatggg ggaaaccctg acgcagcgac gccgcgtgga ggaagaaggc    420

ctttgggttg taaactcctt tgatcgggga cgaagatgac ggtacccgaa gaacaagcca    480

cggctaacta cgtgccagca gccgcggtaa tacgtaggtg gcgagcgttg tccggaatta    540

ctgggtgtaa agggcgtgta ggcggggtgc caagtcaggt gtgaaatacc ggggcttaac    600

ctcgggggtg catctgaaac tggtgctctt gagtgccgga gaggaaagcg gaattcccag    660
```

-continued

```
tgtagcggtg aaatgcgtag atattgggag gaacaccagt ggcgaaggcg gctttctgga    720
cggtaactga cgctgaggcg cgaaagcgtg gggagcaaac aggattagat accctggtag    780
tccacgctgt aaacgatgga tactaggtgt aggaggtatc gaccccttct gtgccgtagt    840
taacacaata agtatcccac ctggggagta cggccgcaag gctgaaactc aaaggaattg    900
acgggggccc gcacaagcag tggagcatgt ggtttaattc gaagcaacgc gaagaacctt    960
accagggctt gacatccccc tgacggatgt agagatacat cttctccgca aggagcaggg   1020
gagacaggtg gtgcatggtg cagctcagct cgtgtcgtga gatgttgggt taagtcccgc   1080
aacgagcgca acccttgtcg ttagttgcca gcagtaagat gggcactcta acgagactgc   1140
cggcgagaag tcggaggaag gtggggatga cgtcaaatca tcatgcccct tatgtcctgg   1200
gctacacacg tgctacaatg gcgactacag agggaagcaa atccggcagg aggagcaaat   1260
cccgaaaggt cgtcccagtt cggattgcag gctcgaactc gcctgcatga agccggaatt   1320
gctagtaatg gcaggtcagc atactgccgt gaatacgttc ccgggccttg tacacaccgc   1380
ccgtcacacc atgagagctg gcaacacccg aagccgtagc ctaaccgaga ggggggcgcc   1440
gtcgaaggtg ggcaggtgga ttggggtgaa gtcgtaacaa ggtagccgta tcggaaggtg   1500
cggctggatc acctcctttt                                               1519
```

<210> SEQ ID NO 81
<211> LENGTH: 1500
<212> TYPE: DNA
<213> ORGANISM: Clostridium stercorarium II

<400> SEQUENCE: 81

```
cctggctcag gacgaacgct ggcggcgtgc ctaacacatg caagtcgaac gggatccgtg     60
ttacggaggt cttcggaccg aagtggcatg gtgagagtgg cggacgggcg agtaacgcgt    120
gagcaacctg ccctatgctg ggggataaca ccgggaaacc ggtgctaata ccgcataaga    180
ccacagtgac gcatgtcaca gtggtaaaag ctgaggcggc ataggatggg ctcgcgtccg    240
attagctagt tggtagggta acggcctacc aaggcgacga tcggtagccg gactgagagg    300
ttggccggcc gcattgggac tgagacacgg cccagactcc tacgggaggc agcagtgggg    360
aatattgcgc aatgggggaa accctgacgc agcgacgccg cgtggaggaa gaaggccttt    420
gggttgtaaa ctcctttgat cggggacgaa gatgacggta cccgaagaac aagccacggc    480
taactacgtg ccagcagccg cggtaatacg taggtggcga gcgttgtccg gaattactgg    540
gtgtaaaggg cgtgtaggcg ggtgccaag tcaggtgtga aataccgggg cttaacctcg     600
ggggtgcatc tgaaactggt gctcttgagt gccggagagg aaagcggaat tcccagtgta    660
gcggtgaaat gcgtagatat tgggaggaac accagtggcg aaggcggctt tctggacggt    720
aactgacgct gaggcgcgaa agcgtgggga gcaaacagga ttagataccc tggtagtcca    780
cgctgtaaac gatggatact aggtgtagac cccttctgtg ccgtagttaa cacaataagt    840
atcccacctg gggagtacga ggtatcgggc cgcaaggctg aaactcaaag gaattgacgg    900
gggcccgcac aagcagtgga gcatgtggtt taattcgaag caacgcgaag aaccttacca    960
gggcttgaca tccccctgac ggatgtagag atacatcttc tccgcaagga gcaggggaga   1020
caggtggtgc atggttgtcg tcagctcgtg tcgtgagatg ttgggttaag tcccgcaacg   1080
agcgcaaccc ttgtcgttag ttgccagcag taagatgggc actctaacga gactgccggc   1140
gagaagtcgg aggaaggtgg ggatgacgtc aaatcatcat gccccttatg tcctgggcta   1200
cacacgtgct acaatggcga ctacagaggg aagcaaatcc gcgaggagga gcaaatcccg   1260
```

-continued aaaggtcgtc ccagttcgga ttgcaggctg caactcgcct gcatgaagcc ggaattgcta 1320
gtaatggcag gtcagcatac tgccgtgaat acgttcccgg gccttgtaca caccgcccgt 1380
cacaccatga gagctggcaa cacccgaagc cggtagccta accgagaggg ggcgccgtc 1440 gaaggtgggg cacccgaagc cggtagccta accgagaggg gggcgccgtc gaaggtgggg 1500

<210> SEQ ID NO 82
<211> LENGTH: 1508
<212> TYPE: DNA
<213> ORGANISM: Caldiscellulosiruptor kristjanssonii
<220> FEATURE:
<221> NAME/KEY: modified_base
<222> LOCATION: (213)..(213)
<223> OTHER INFORMATION: a, c, g or t
<220> FEATURE:
<221> NAME/KEY: modified_base
<222> LOCATION: (223)..(223)
<223> OTHER INFORMATION: a, c, g or t
<220> FEATURE:
<221> NAME/KEY: modified_base
<222> LOCATION: (405)..(405)
<223> OTHER INFORMATION: a, c, g or t

<400> SEQUENCE: 82
ggctcaggac gaacgctggc ggcgtgccta acgcatgcaa gtcgagcgga gatggtagct 60
gaaggtgatg agctggaagc tatcatctta gcggcggacg ggtgagtaac acgtgagcaa 120
cctaccctca gcacggggat aacagctcga aagggctgct aatacccgat gggaccacgg 180
catcgcatgg tgctgtggtg aaagggtagc cgnagaggct atnccggctg gggatgggct 240
cgcggcccat cagctagttg gtggggtaac ggcctaccaa ggcgacgacg ggtagccggc 300
ctgagagggt gtacggccac agtgggactg agacacggcc cacactccta cgggaggcag 360
cagcggggaa tcttgcgcaa tgggcgaaag cctgacgcag cgacnccgcg tgagggaaga 420
agcccttcgg ggtgtaaacc tctttggacg gggagaagtg gaagatagta cccgtttaaa 480
aagccacggc taactacgtg ccagcagccg cggtaatacg taggtggcga gcgttgtccg 540
gaattactgg gcgtaaaggg tgcgtaggcg gcctggtaag ttgagcgtga aatttttggg 600
ctcaacccaa aaggagcgct caagactgcc gggcttgagt gcgggagagg acggcggaat 660
tcccggtgta gcggtgaaat gcgtagatat cgggaggaac accagtggcg aaggcggccg 720
tctggaccgt aactgacgct gaggcacgaa agcgtgggga gcaaacagga ttagataccc 780
tggtagtcca cgctgtaaac gatggatgct aggtgtgggg gagaagaact cttccgtgcc 840
gtagttaaca caataagcat cccgcctggg gagtacggtc gcaaggttga aactcaaagg 900
aattgacggg ggcccgcaca agcggtggag catgtggttt aattcgaagc aacgcgaaga 960
accttaccag ggcttgacat gccgggaacc ctgccgaaag gcgggggtgc ctgcttgtta 1020
agagcaggag cccggacaca ggtggtgcat ggttgtcgtc agctcgtgtc gtgagatgtt 1080
gggttaagtc ccgcaacgag cgcaacccct gcccttagtt gccagcggtt ttagccgggc 1140
actctaaggg gactgccgcc gatgaggcgg aggaaggtgg ggatgacgtc aaatcatcat 1200
gccccttatg ccctgggcta cacacgtgct acaatgggtg ctacagaggg cggcgaaggc 1260
gcgagccgga gcgaatccca aaaaagcacc cccagttcgg attgcaggct gcaactcgcc 1320
tgcatgaagt cggaatcgct agtaatcgcg gatcagcatg ccgcggtgaa tacgttcccg 1380
ggccttgtac acaccgcccg tcacaccatg agagtcagca acacctgaag acacaggata 1440
tctgtgttga aggtggggct gatgattggg gtgaagtcgt aacaaggtag ccgtacggga 1500
acgtgcgg 1508

<210> SEQ ID NO 83
<211> LENGTH: 1370
<212> TYPE: DNA
<213> ORGANISM: Clostridium phytofermentans
<220> FEATURE:
<221> NAME/KEY: modified_base
<222> LOCATION: (240)..(243)
<223> OTHER INFORMATION: a, c, g or t
<220> FEATURE:
<221> NAME/KEY: modified_base
<222> LOCATION: (247)..(247)
<223> OTHER INFORMATION: a, c, g or t
<220> FEATURE:
<221> NAME/KEY: modified_base
<222> LOCATION: (250)..(250)
<223> OTHER INFORMATION: a, c, g or t
<220> FEATURE:
<221> NAME/KEY: modified_base
<222> LOCATION: (293)..(293)
<223> OTHER INFORMATION: a, c, g or t
<220> FEATURE:
<221> NAME/KEY: modified_base
<222> LOCATION: (413)..(413)
<223> OTHER INFORMATION: a, c, g or t
<220> FEATURE:
<221> NAME/KEY: modified_base
<222> LOCATION: (421)..(427)
<223> OTHER INFORMATION: a, c, g or t
<220> FEATURE:
<221> NAME/KEY: modified_base
<222> LOCATION: (492)..(492)
<223> OTHER INFORMATION: a, c, g or t
<220> FEATURE:
<221> NAME/KEY: modified_base
<222> LOCATION: (510)..(511)
<223> OTHER INFORMATION: a, c, g or t
<220> FEATURE:
<221> NAME/KEY: modified_base
<222> LOCATION: (530)..(530)
<223> OTHER INFORMATION: a, c, g or t
<220> FEATURE:
<221> NAME/KEY: modified_base
<222> LOCATION: (587)..(587)
<223> OTHER INFORMATION: a, c, g or t
<220> FEATURE:
<221> NAME/KEY: modified_base
<222> LOCATION: (616)..(617)
<223> OTHER INFORMATION: a, c, g or t
<220> FEATURE:
<221> NAME/KEY: modified_base
<222> LOCATION: (646)..(648)
<223> OTHER INFORMATION: a, c, g or t
<220> FEATURE:
<221> NAME/KEY: modified_base
<222> LOCATION: (674)..(674)
<223> OTHER INFORMATION: a, c, g or t
<220> FEATURE:
<221> NAME/KEY: modified_base
<222> LOCATION: (687)..(687)
<223> OTHER INFORMATION: a, c, g or t
<220> FEATURE:
<221> NAME/KEY: modified_base
<222> LOCATION: (722)..(723)
<223> OTHER INFORMATION: a, c, g or t
<220> FEATURE:
<221> NAME/KEY: modified_base
<222> LOCATION: (771)..(771)
<223> OTHER INFORMATION: a, c, g or t
<220> FEATURE:
<221> NAME/KEY: modified_base
<222> LOCATION: (812)..(813)
<223> OTHER INFORMATION: a, c, g or t
<220> FEATURE:
<221> NAME/KEY: modified_base
<222> LOCATION: (848)..(849)
<223> OTHER INFORMATION: a, c, g or t
<220> FEATURE:
<221> NAME/KEY: modified_base
<222> LOCATION: (905)..(906)

<223> OTHER INFORMATION: a, c, g or t
<220> FEATURE:
<221> NAME/KEY: modified_base
<222> LOCATION: (916)..(916)
<223> OTHER INFORMATION: a, c, g or t
<220> FEATURE:
<221> NAME/KEY: modified_base
<222> LOCATION: (923)..(923)
<223> OTHER INFORMATION: a, c, g or t
<220> FEATURE:
<221> NAME/KEY: modified_base
<222> LOCATION: (1024)..(1025)
<223> OTHER INFORMATION: a, c, g or t
<220> FEATURE:
<221> NAME/KEY: modified_base
<222> LOCATION: (1076)..(1077)
<223> OTHER INFORMATION: a, c, g or t
<220> FEATURE:
<221> NAME/KEY: modified_base
<222> LOCATION: (1092)..(1093)
<223> OTHER INFORMATION: a, c, g or t
<220> FEATURE:
<221> NAME/KEY: modified_base
<222> LOCATION: (1149)..(1150)
<223> OTHER INFORMATION: a, c, g or t

<400> SEQUENCE: 83
cttagtggcg gacgggtgag taacgcgtgg gtaacctgcc tcatacaggg ggataacagt 60
cggaaacgat tgctaaaacc gcataatata gcgaaaccgc atgattttgc tatcaaatat 120
ttataggtat gagatgggcc cgcgtctgat tagctagttg gtggggtaat ggcctaccaa 180
ggcgacgatc agtagccggc ttgagagagt gaccggccac attgggactg agacacggcn 240
nnnactnctn cgggaggcag cagtggggaa tattggacaa tgggggaaac ccngatccag 300
cgacgccgcg tgagtgaaga agtatttcgg tatgtaaagc tctatcagca gggaagataa 360
tgacagtacc tgactaagaa gccccggcta actacgtgcc agcagccgcg gtnatacgta 420
nnnnnnnagc gttatccgga tttactgggt gtaaagggag cgtaggtggt aggtcaagtc 480
agatgtgaaa gnccagggct caaccctggn nctgcatttg aaactggctn actgagtgca 540
ggagaggtaa gtggaattcc tagtgtagcg gtgaaatgcg tagatantag gaggaacacc 600
agtggcgaag gcggcnnact ggactgtaac tgacactgag gctcgnnngc gtggggagca 660
aacaggatta gatnccctgg tagtccncgc cgtaaacgat gaatactagc tgttcggggt 720
cnnacagggc ttcggtggcg cacgtaacgc aataagtatt ccacctgggg ngtacgttcg 780
caagaatgaa actcaaagga attgacgggg anncgcacaa gcggtggagc atgtggttta 840
attcgaanna acgcgaagaa ccttaccaag tcttgacatc cctctgacaa ccgagtaacg 900
tcggnnttct tcgggncaga ggngacaggt ggtgcatggt tgtcgtcagc tcgtgtcgtg 960
agatgttggg ttaagtcccg caacgagcgc aacccctatc tttagtagcc agcagttcgg 1020
ctgnncactc tagagagact gccagggata acctggagga aggcggggat gacgtnnaat 1080
catcatgccc cnnatgattt gggctacaca cgtgctacaa tggtgactac aaagagaagc 1140
aagcctgcnn gggggagcaa atctcaaaaa ggtcatccca gttcggattg tactctgcaa 1200
ctcgagtaca tgaagctgga atcgctagta atcgcgaatc agaatgtcgc ggtgaatacg 1260
ttcccgggtc ttgtacacac cgyycgtcac tccatgggag taggtaacgc ccgaagtcag 1320
tgaccyaacc gtaaggaggg agctgccgaa ggcgggatct ataactgggg 1370

<210> SEQ ID NO 84
<211> LENGTH: 57
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 84
gaattcgagc tcggtacccg gggatcctct agagtcgacc tgcaggcatg caagctt 57

<210> SEQ ID NO 85
<211> LENGTH: 1515
<212> TYPE: DNA
<213> ORGANISM: Thermoanaerobacter pseudoethanolicus
<220> FEATURE:
<221> NAME/KEY: modified_base
<222> LOCATION: (69)..(69)
<223> OTHER INFORMATION: a, c, g or t
<220> FEATURE:
<221> NAME/KEY: modified_base
<222> LOCATION: (71)..(71)
<223> OTHER INFORMATION: a, c, g or t
<220> FEATURE:
<221> NAME/KEY: modified_base
<222> LOCATION: (1427)..(1427)
<223> OTHER INFORMATION: a, c, g or t

<400> SEQUENCE: 85
cctggctcag gacgaacgct ggcggcgtgc ctaacacatg caagtcgagc ggtccggcag 60
ccaacttang ncgggagccg gatagcggcg gacgggtgag taacgcgtgg gcaacctacc 120
cttaagaccg ggataacacc tcgaaagggg tgctaatact ggataagctc cttgtagggc 180
atggtatgag gaggaaggta gcgggactac cgcttaagga tgggcccgcg tcccatcagc 240
tagttggtag ggtaacggcc taccaaggcg acgacgggta gccggcctga gagggtggtc 300
ggccacactg ggactgagac acggcccaga ctcctacggg aggcagcagt ggggaatctt 360
gcgcaatggg cgaaagcctg acgcagcgac gccgcgtgag cgaggaaggc cttcgggtcg 420
taaagctcga tagtgtggga agaagggatg acggtaccac acgaaagccc cggctaacta 480
cgtgccagca gcctcggtaa gacgtagggg gcgagcgttg tccggaatta ctgggcgtaa 540
agggcgcgta ggcggccgtt caagtcaggt gtaaaatacc cgggctcaac ccggggatag 600
cacttgaaac tgggcggcta gagggcagga gaggggagtg gaattcccgg tgtagcggtg 660
aaatgcgtag atatcgggag gaataccagt ggcgaaggcg actctctgga ctgaccctga 720
cgctgaggcg cgaaagcgtg gggagcaaac aggattagat accctggtag tccacgccgt 780
aaacgatggg tactaggtgt gggatgcgga agcattccgt gccgtagtta acgcaataag 840
taccccgcct ggggagtacg gccgcaaggt tgaaactcaa aggaattgac gggggcccgc 900
acaagcggtg gagcatgtgg tttaattcga agcaacgcga agaaccttac cagggcttga 960
catgcaggta gtagcgagcc gaaaggtgag cgaccttacc ttaaaggtga ggagcctgca 1020
caggtggtgc atggttgtcg tcagctcgtg tcgtgagatg ttgggttaag tcccgcaacg 1080
agcgcaaccc ctgcctctag ttgccagcgg gtgaagccgg gcacgctaga gggactgccg 1140
tggacaacac ggaggaaggt ggggatgacg tcaaatcatc atgccctata tgccctgggc 1200
cacacacgtg ctacaatggc cggtacagag ggaagcgaag ccgcgaggtg gagcgaaacc 1260
caaaaagccg gtccaagttc ggattgcagg ctgcaactcg cctgcatgaa gtcggaatcg 1320
ctagtaatcg cggatcagca tgccgcggtg aatacgttcc cgggccttgt acacaccgcc 1380
cgtcacacca cgagagtctg caacacccga agccgtgacc caaccgnaag gagggagccg 1440
tcgaaggtgg ggcagatgat tggggtgaag tcgtaacaag gtagccgtat cggaaggtgc 1500
ggctggatca cctcc 1515

<210> SEQ ID NO 86
<211> LENGTH: 1395
<212> TYPE: DNA
<213> ORGANISM: Thermoanaerobacter sp.

<400> SEQUENCE: 86

```
ctacacatgc agtcgagcga agggagtact acggtacgaa cttagcggcg gacgggtgag     60

taacgcgtgg acaatctacc ctgtagaccg ggataacacc tcgaaagggg tgctaatacc    120

ggataatgtc gagaagcggc atcgcttttt gaagaaagga gagaatccgc tataggagga    180

gtccgcgtcc cattagctag ttggcgaggg taaaagccca ccaaggcgac gatgggtagc    240

cggcctgaga gggtgaacgg ccacactgga actgagacac ggtccagact cctacgggag    300

gcagcagtgg ggaatattgt gcaatggggg aaaccctgac acagcgacgc cgcgtgagtg    360

aagaaggcct tcgggtcgta aagctcaata gtatgggaag aaagaaatga cggtaccata    420

cgaaagcccc ggctaactac gtgccagcag ccgcggtaat acgtaggggg cgagcgttgt    480

ccggaattac tgggcgtaaa gagcacgtag gcggctataa aagtcagatg tgaaaaacct    540

gggctcaacc gagggtatgc atctgaaact aaatagcttg agtcaaggag aggagagcgg    600

aattcctggt gtagcggtga aatgcgtaga gatcaggaag aataccagtg gcgaaagcgg    660

ctctctggac ttgaactgac gctgaggtgc gaaagcgtgg ggagcaaaca ggattagata    720

ccctggtagt ccacgccgta aacgatggat actaggtgtg ggttagatat aatccgtgcc    780

ggagttaacg caataagtat cccgcctggg gagtacggcc gcaaggttga aactcaaagg    840

aattgacggg ggcccgcaca agcagcggag catgtggttt aattcgaagc aacgcgaaga    900

accttaccag ggcttgacat ccacagaatc gagtagaaat acttgagtgc ctcgtaagag    960

gagctgtgag acaggtggtg catggttgtc gtcagctcgt gtcgtgagat gttgggttaa   1020

gtcccgcaac gagcgcaacc cctgttggta gttaccagcg taaagacggg gactctaccg   1080

agactgccgt ggataacacg gaggaaggcg gggatgacgt caaatcatca tgccctttat   1140

gccctgggct acacacgtgc tacaatggcc tgaacagagg gcagcgaagg agcgatccgg   1200

agcgaatccc agaaaacagg tcccagttca gattgcaggc tgcaacccgc ctgcatgaag   1260

acggagttgc tagtaatcgc ggatcagcat gccgcggtga atacgttccc gggccttgta   1320

cacaccgccc gtcacaccac gagagtttac aacacccgaa gtcagtgacc taaccgcaag   1380

ggaggagctg ccgaa                                                    1395
```

<210> SEQ ID NO 87
<211> LENGTH: 1552
<212> TYPE: DNA
<213> ORGANISM: Thermoanaerobacterium saccharolyticum
<220> FEATURE:
<221> NAME/KEY: modified_base
<222> LOCATION: (64)..(64)
<223> OTHER INFORMATION: a, c, g or t
<220> FEATURE:
<221> NAME/KEY: modified_base
<222> LOCATION: (100)..(100)
<223> OTHER INFORMATION: a, c, g or t
<220> FEATURE:
<221> NAME/KEY: modified_base
<222> LOCATION: (343)..(343)
<223> OTHER INFORMATION: a, c, g or t

<400> SEQUENCE: 87

```
tttgatcctg gctcaggacg aacgctggcg gcgtgcctaa cacatgcaag tcgagcgatc     60

cggnactcaa ttaagcgctt acagaaaaag agagagaaan tgagtaaacg caaagttgag    120

tgccggatag cggcggacgg gtgagtaacg cgtggacaat ctaccctgta gtttgggata    180
```

-continued

```
acacctcgaa aggggtgcta ataccggata atgtcaagaa gtggcatcac tttttgaaga    240

aaggagaaat ccgctatagg atgagtccgc gtcccattag ctagttggcg ggtaaaagc    300

ccaccaaggc gacgatgggt agccggcctg agagggtgaa cgnccacact ggaactgaga    360

cacggtccag actcctacgg gaggcagcag tggggaatat tgttcaatgg gggaaaccct    420

gacacagcga cgccgcgtga gcgaagaagg ccttcgggtc gtaaagctca atagtatggg    480

aagatagtga cggtaccata cgaaagcccc ggctaactac gtgccagcag ccgcggtaat    540

acgtaggggg cgagcgttgt ccggaattac tgggcgtaaa gagcacgtag gcggctgtaa    600

aagtcagatg tgaaaaacct gggctcaacc gagggtgtgc atctgaaact aaacagcttg    660

agtcaaggag aggagagcgg aattcctggt gtagcggtga aatgcgtaga gatcaggaag    720

aataccagtg gcgaaagcgg ctctctggac ttgaactgac gctgaggtgc gaaagcgtgg    780

ggagcaaaca ggattagata ccctggtagt ccacgccgta aacgatggat actaggtgtg    840

ggtgaagcat catccgtgcc ggagttaacg caataagtat cccgcctggg gagtacggcc    900

gcaaggttga aactcaaagg aattgacggg ggcccgcaca agcagcggag catgtggttt    960

aattcgaagc aacgcgaaga accttaccag ggcttgacat ccacagaatc aggtagaaat   1020

accagagtgc ctcgaaagag gagctgtgag acaggtggtg catggttgtc gtcagctcgt   1080

gtcgtgagat gttgggttaa gtcccgcaac gagcgcaacc cctgttggta gttaccagcg   1140

taaagacggg gactctaccg agactgccgt ggagaacacg gaggaaggcg gggatgacgt   1200

caaatcatca tgccctttat gccctgggct acacacgtgc tacaatggcc tgaacagagg   1260

gcagcgaagg agcgatccgg agcgaatccc agaaaacagg tcccagttca gattgcaggc   1320

tgcaacccgc ctgcatgaag acggagttgc tagtaatcgc ggatcagcat gccgcggtga   1380

atacgttccc gggccttgta cacaccgccc gtcacaccac gagagtttac aacacccgaa   1440

gtcagtgacc taaccgcaag ggaggagctg ccgaaggtgg ggtaaatgat tggggtgaag   1500

tcgtaacaag gtagccgtat cggaaggtgc ggctggatca cctcctttcc ct           1552
```

```
<210> SEQ ID NO 88
<211> LENGTH: 1553
<212> TYPE: DNA
<213> ORGANISM: Thermoanaerobacterium saccharolyticum

<400> SEQUENCE: 88

tttgatcctg gctcaggacg aacgctggcg gcgtgcctaa cacatgcaag tcgagcgatc     60

cggcactcaa ctaagcgctt acagaaaaag agagagaaaa tgagtaaacg caaagttgag    120

tgccggatag cggcggacgg gtgagtaacg cgtggacaat ctaccctgta gtttgggata    180

acacctcgaa aggggtgcta ataccggata atgtcaagaa gtggcatcac tttttgaaga    240

aaggagaaat ccgctatagg atgagtccgc gtcccattag ctagttggcg ggtaaaagc    300

ccaccaaggc gacgatgggt agccggcctg agagggtgaa cggccacact ggaactgaga    360

cacggtccag actcctacgg gaggcagcag tggggaatat tgtgcaatgg gggaaaccct    420

gacacagcga cgccgcgtga gcgaagaagg ccttcgggtc gtaaagctca atagtatggg    480

aagatagtga cggtaccata cgaaagcccc gggctactac gtgccagcag ccgcggtaat    540

acgtaggggg cgagcgttgt ccggaattac tgggcgtaaa gagcacgtag gcggctgtaa    600

aagtcagatg tgaaaaacct gggctcaacc gagggtgtgc atctgaaact aaacagcttg    660

agtcaaggag aggagagcgg aattcctggt gtagcggtga aatgcgtaga gatcaggaag    720

aataccagtg gcgaaagcgg ctctctggac ttgaactgac gctgaggtgc gaaagcgtgg    780
```

```
ggagcaaaca ggattagata ccctggtagt ccacgccgta aacgatggat actaggtgtg    840

ggtgaagcat catccgtgcc ggagttaacg caataagtat cccgcctggg gagtacggcc    900

gcaaggttga aactcaaagg aattgacggg ggcccgcaca agcagcggag catgtggttt    960

aattcgaagc aacgcgaaga accttaccag ggcttgacat ccacagaatc tggtagaaat   1020

accggagtgc ctcgaaagag gagctgtgag acaggtggtg catggttgtc gtcagctcgt   1080

gtcgtgagat gttgggttaa gtcccgcaac gagcgcaacc cctgttggta gttaccagcg   1140

taaagacggg gactctaccg agactgccgt ggagaacacg gaggaaggcg gggatgacgt   1200

caaatcatca tgccctttat gccctgggct acacacgtgc tacaatggcc tgaacagagg   1260

gcagcgaagg agcgatccgg agcgaatccc agaaaacagg tcccagttca gattgcaggc   1320

tgcaacccgc ctgcatgaag acggagttgc tagtaatcgc ggatcagcat gccgcggtga   1380

atacgtttcc cgggccttgt acacaccgcc cgtcacacca cgagagttta caacacccga   1440

agtcagtgac ctaaccgaaa ggaaggagct gccgaaggtg gggtaaatga ttggggtgaa   1500

gtcgtaacaa ggtagccgta tcggaaggtg cggctggatc acctcctttc taa          1553
```

<210> SEQ ID NO 89
<211> LENGTH: 1569
<212> TYPE: DNA
<213> ORGANISM: Unknown
<220> FEATURE:
<223> OTHER INFORMATION: Description of Unknown Organism: Consensus
      Sequence
<220> FEATURE:
<221> NAME/KEY: modified_base
<222> LOCATION: (71)..(71)
<223> OTHER INFORMATION: a, c, g or t
<220> FEATURE:
<221> NAME/KEY: modified_base
<222> LOCATION: (92)..(92)
<223> OTHER INFORMATION: a, c, g or t
<220> FEATURE:
<221> NAME/KEY: modified_base
<222> LOCATION: (101)..(101)
<223> OTHER INFORMATION: a, c, g or t
<220> FEATURE:
<221> NAME/KEY: modified_base
<222> LOCATION: (250)..(251)
<223> OTHER INFORMATION: a, c, g or t
<220> FEATURE:
<221> NAME/KEY: modified_base
<222> LOCATION: (255)..(255)
<223> OTHER INFORMATION: a, c, g or t
<220> FEATURE:
<221> NAME/KEY: modified_base
<222> LOCATION: (296)..(296)
<223> OTHER INFORMATION: a, c, g or t
<220> FEATURE:
<221> NAME/KEY: modified_base
<222> LOCATION: (494)..(494)
<223> OTHER INFORMATION: a, c, g or t
<220> FEATURE:
<221> NAME/KEY: modified_base
<222> LOCATION: (496)..(496)
<223> OTHER INFORMATION: a, c, g or t
<220> FEATURE:
<221> NAME/KEY: modified_base
<222> LOCATION: (852)..(852)
<223> OTHER INFORMATION: a, c, g or t
<220> FEATURE:
<221> NAME/KEY: modified_base
<222> LOCATION: (864)..(864)
<223> OTHER INFORMATION: a, c, g or t
<220> FEATURE:
<221> NAME/KEY: modified_base
<222> LOCATION: (1016)..(1017)
<223> OTHER INFORMATION: a, c, g or t
<220> FEATURE:

<221> NAME/KEY: modified_base
<222> LOCATION: (1048)..(1050)
<223> OTHER INFORMATION: a, c, g or t
<220> FEATURE:
<221> NAME/KEY: modified_base
<222> LOCATION: (1067)..(1067)
<223> OTHER INFORMATION: a, c, g or t
<220> FEATURE:
<221> NAME/KEY: modified_base
<222> LOCATION: (1158)..(1159)
<223> OTHER INFORMATION: a, c, g or t
<220> FEATURE:
<221> NAME/KEY: modified_base
<222> LOCATION: (1407)..(1407)
<223> OTHER INFORMATION: a, c, g or t

<400> SEQUENCE: 89
tttgatcctg gctcaggacg aacgctggcg gcgtgcctaa cacatgcaag tcgagcgatc 60
cggcactcaa ntaagcgctt acagaaaaag angagcgaaa ntgagtaaac gctaagttga 120
gtgccggata gcggcggacg ggtgagtaac gcgtggacaa tctaccctgt agtttgggat 180
aacacctcga aaggggtgct aataccggat aatgtcaaga agtggcatcg ctttttgaag 240
aaaggagagn naatnccgct ataggatgag tccgcgtccc attagctagt tggcgngggt 300
aaaagcccac caaggcgacg atgggtagcc ggcctgagag ggtgaacggc cacactggaa 360
ctgagacacg gtccagactc ctacgggagg cagcagtggg gaatattgtg caatggggga 420
aaccctgaca cagcgacgcc gcgtgagcga agaaggcctt cgggtcgtaa agctcaatag 480
tatgggaaga tagnantgac ggtaccatac gaaagccccg gctaactacg tgccagcagc 540
cgcggtaata cgtagggggc gagcgttgtc cggaattact gggcgtaaag agcacgtagg 600
cggctgtaaa agtcagatgt gaaaaacctg ggctcaaccg agggtgtgca tctgaaacta 660
aacagcttga gtcaaggaga ggagagcgga attcctggtg tagcggtgaa atgcgtagag 720
atcaggaaga ataccagtgg cgaaagcggc tctctggact tgaactgacg ctgaggtgcg 780
aaagcgtggg gagcaaacag gattagatac cctggtagtc cacgccgtaa acgatggata 840
ctaggtgtgg gntgaggcat catnccgtgc cggagttaac gcaataagta tcccgcctgg 900
ggagtacggc cgcaaggttg aaactcaaag gaattgacgg gggcccgcac aagcagcgga 960
gcatgtggtt taattcgaag caacgcgaag aaccttacca gggcttgaca tccacnnaga 1020
atcgggtaga aataccagag tgcctcgnnn aaagaggagc tgtgagnaca ggtggtgcat 1080
ggttgtcgtc agctcgtgtc gtgagatgtt gggttaagtc ccgcaacgag cgcaacccct 1140
gttggtagtt accagcgnnt aaagacgggg actctaccga gactgccgtg gagaacacgg 1200
aggaaggcgg ggatgacgtc aaatcatcat gccctttatg ccctgggcta cacacgtgct 1260
acaatggcct gaacagaggg cagcgaagga gcgatccgga gcgaatccca gaaaacaggt 1320
cccagttcag attgcaggct gcaacccgcc tgcatgaaga cggagttgct agtaatcgcg 1380
gatcagcatg ccgcggtgaa tacgttnccc gggccttgta cacaccgccc gtcacaccac 1440
gagagtttac aacacccgaa gtcagtgacc taaccgcaag ggaggagctg ccgaaggtgg 1500
ggtaaatgat tggggtgaag tcgtaacaag gtagccgtat cggaaggtgc ggctggatca 1560
cctcctttc 1569

<210> SEQ ID NO 90
<211> LENGTH: 1061
<212> TYPE: DNA
<213> ORGANISM: Unknown
<220> FEATURE:
<223> OTHER INFORMATION: Description of Unknown Organism: Consensus
Sequence <220> FEATURE:
<221> NAME/KEY: modified_base
<222> LOCATION: (657)..(657)
<223> OTHER INFORMATION: a, c, g or t
<220> FEATURE:
<221> NAME/KEY: modified_base
<222> LOCATION: (789)..(789)
<223> OTHER INFORMATION: a, c, g or t

<400> SEQUENCE: 90
gtgtatacaa tatatttctt ctttttagta agaggaatgt ataaaaataa atattttaaa 60
ggaagggacg atcttatgag cattattcaa aacatcattg aaaaagctaa aagtgataaa 120
aagaaaattg ttctgccaga aggtgcagaa cccaggacat taaaagctgc tgaaatagtt 180
ttaaaagaag gaattgcaga tttggtgctt cttggaaatg aagatgagat aagaaatgct 240
gcaaaagact tggacatatc caaagctgaa atcattgacc ctgtaaagtc tgaaatgttt 300
gataggtatg ctaatgattt ttatgagtta aggaagagca aaggaatcac gttggaaaaa 360
gccagagaaa caatcaagga taatatctat tttggatgta tgatggttaa agaaggttat 420
gctgatggat tggtatctgg cgctattcat gctactgcag atttattaag acctgcattt 480
cagataatta aaacggctcc aggagcaaag atagtatcaa gctttttat aatggaagtg 540 cctaattgtg aatatggtga aaatggtgta ttcttgtttg ctgattgtgc ggtcaatcca 600
tcgcctaatg cagaagaact tgcttctatt gctgtacaat ctgctaatac tgcaaangaa 660
tttgttgggc tttgaaccaa aagttgctat gctatcattt tctacaaaag gtagtgcatc 720
acatgaatta gtagataagg taagaaaagc gacagagata gcaaaagaat tgatgccaga 780
tgttgctant cgatggtgaa ttgcaattgg atgctgctct tgttaaagaa gttgcagagc 840
taaaagcgcc gggaagcaaa gttgcgggat gtgcaaatgt gcttatattc cctgatttac 900
aagctggtaa tataggatat aagcttgtac agagattagc taaggcaaat gcaattggac 960
ctataacaca aggaatgggt gcaccggtta atgatttatc aagaggatgc agctatagag 1020
atattgttga cgtaatagca acaacagctg tgcaggctca a 1061

<210> SEQ ID NO 91
<211> LENGTH: 1213
<212> TYPE: DNA
<213> ORGANISM: Unknown
<220> FEATURE:
<223> OTHER INFORMATION: Description of Unknown Organism: Consensus
      Sequence
<220> FEATURE:
<221> NAME/KEY: modified_base
<222> LOCATION: (52)..(52)
<223> OTHER INFORMATION: a, c, g or t
<220> FEATURE:
<221> NAME/KEY: modified_base
<222> LOCATION: (72)..(72)
<223> OTHER INFORMATION: a, c, g or t
<220> FEATURE:
<221> NAME/KEY: modified_base
<222> LOCATION: (136)..(136)
<223> OTHER INFORMATION: a, c, g or t
<220> FEATURE:
<221> NAME/KEY: modified_base
<222> LOCATION: (151)..(153)
<223> OTHER INFORMATION: a, c, g or t

<400> SEQUENCE: 91
atgaaaatta tgaaaattct ggttattaat tgtggaagtt cttcactaaa antatcaatt 60
gattgaatca antgatggaa atgtgctggc aaaaggcctt gctgaaagaa tcggcataaa 120
tgattccctg ttgacncata atgctaacgg nnnagaaaaa atcaagataa aaaaagacat 180

-continued

```
gaaagatcac aaagacgcaa taaaattggt tttagatgct ttggtaagta gtgactacgg    240

cgttataaag gatatgtctg agatagatgc tgtaggacat agagttgttc acggaggaga    300

gtcttttaca tcatcagttc tcataaatga tgaagtgtta aaagcgataa cagattgtat    360

agaattagct ccactgcaca atcctgctaa tatagaagga attaaagctt gccagcaaat    420

catgccaaac gttccaatgg tggcggtatt tgatacagcc tttcatcaga caatgcctga    480

ttatgcatat ctttatccaa taccttatga atactacaca aagtacagga tcagaagata    540

tggatttcat ggcacatcgc ataaatatgt ttcaaatagg gctgcagaga ttttgaataa    600

acctattgaa gatttgaaaa tcataacttg tcatcttgga aatggctcca gtattgctgc    660

tgtcaaatat ggtaaatcaa ttgacacaag catgggattt acaccattag aaggtttggc    720

tatgggtaca cgatctggaa gtatagaccc atccattatt tcttatctta tggaaaaaga    780

aaatataagt gctgaagagg tagtaaatat attaaataaa aaatctggtg tttacggtat    840

ttcaggaata agcagcgatt ttagagattt agaagatgcc gcctttaaaa atggagatga    900

aagagctcag ttggctttaa atgtgtttgc atatcgagta aagaagacga ttggcgctta    960

tgcagcagct atgggaggcg ttgatgtcat tgtatttaca gcaggtgttg gtgaaaatgg   1020

tcctgagata cgagaattta tacttgatgg attagagttt ttagggttca gcttggataa   1080

agaaaaaaat aaagtcagag gaaaagaaac tattatatct acgccgaatt caaaagttag   1140

cgtgatggtt gtgcctacta atgaagaata tatgattgct aaagatactg aaaagattgt   1200

aaagagtata aaa                                                       1213
```

```
<210> SEQ ID NO 92
<211> LENGTH: 935
<212> TYPE: DNA
<213> ORGANISM: Unknown
<220> FEATURE:
<223> OTHER INFORMATION: Description of Unknown Organism: Consensus
      Sequence
<220> FEATURE:
<221> NAME/KEY: modified_base
<222> LOCATION: (15)..(15)
<223> OTHER INFORMATION: a, c, g or t
<220> FEATURE:
<221> NAME/KEY: modified_base
<222> LOCATION: (90)..(90)
<223> OTHER INFORMATION: a, c, g or t
<220> FEATURE:
<221> NAME/KEY: modified_base
<222> LOCATION: (117)..(117)
<223> OTHER INFORMATION: a, c, g or t
<220> FEATURE:
<221> NAME/KEY: modified_base
<222> LOCATION: (255)..(255)
<223> OTHER INFORMATION: a, c, g or t
<220> FEATURE:
<221> NAME/KEY: modified_base
<222> LOCATION: (313)..(313)
<223> OTHER INFORMATION: a, c, g or t
<220> FEATURE:
<221> NAME/KEY: modified_base
<222> LOCATION: (349)..(349)
<223> OTHER INFORMATION: a, c, g or t
<220> FEATURE:
<221> NAME/KEY: modified_base
<222> LOCATION: (485)..(485)
<223> OTHER INFORMATION: a, c, g or t
<220> FEATURE:
<221> NAME/KEY: modified_base
<222> LOCATION: (755)..(755)
<223> OTHER INFORMATION: a, c, g or t
<220> FEATURE:
<221> NAME/KEY: modified_base
<222> LOCATION: (761)..(761)
<223> OTHER INFORMATION: a, c, g or t
```

<220> FEATURE:
<221> NAME/KEY: modified_base
<222> LOCATION: (779)..(779)
<223> OTHER INFORMATION: a, c, g or t
<220> FEATURE:
<221> NAME/KEY: modified_base
<222> LOCATION: (791)..(791)
<223> OTHER INFORMATION: a, c, g or t
<220> FEATURE:
<221> NAME/KEY: modified_base
<222> LOCATION: (793)..(793)
<223> OTHER INFORMATION: a, c, g or t
<220> FEATURE:
<221> NAME/KEY: modified_base
<222> LOCATION: (800)..(800)
<223> OTHER INFORMATION: a, c, g or t
<220> FEATURE:
<221> NAME/KEY: modified_base
<222> LOCATION: (818)..(818)
<223> OTHER INFORMATION: a, c, g or t
<220> FEATURE:
<221> NAME/KEY: modified_base
<222> LOCATION: (824)..(824)
<223> OTHER INFORMATION: a, c, g or t
<220> FEATURE:
<221> NAME/KEY: modified_base
<222> LOCATION: (836)..(836)
<223> OTHER INFORMATION: a, c, g or t
<220> FEATURE:
<221> NAME/KEY: modified_base
<222> LOCATION: (854)..(854)
<223> OTHER INFORMATION: a, c, g or t
<220> FEATURE:
<221> NAME/KEY: modified_base
<222> LOCATION: (863)..(863)
<223> OTHER INFORMATION: a, c, g or t
<220> FEATURE:
<221> NAME/KEY: modified_base
<222> LOCATION: (869)..(869)
<223> OTHER INFORMATION: a, c, g or t
<220> FEATURE:
<221> NAME/KEY: modified_base
<222> LOCATION: (902)..(902)
<223> OTHER INFORMATION: a, c, g or t
<220> FEATURE:
<221> NAME/KEY: modified_base
<222> LOCATION: (917)..(917)
<223> OTHER INFORMATION: a, c, g or t
<220> FEATURE:
<221> NAME/KEY: modified_base
<222> LOCATION: (929)..(929)
<223> OTHER INFORMATION: a, c, g or t

<400> SEQUENCE: 92
atgagcaaag tagcnataat aggttctgga tttgtaggtg ctacatctgc atttacactg 60
gctttaagtg ggactgtgac agatattgtn ttagtagatt taaacaagga caaggcnata 120
ggcgatgcac tggatataag ccatggcata ccgtttatac agcctgtaaa tgtgtatgca 180
ggtgactaca aagatgttga aggcgcagat gtaatagttg tgacagcagg tgctgctcaa 240
aagccgggag agacnaggct tgaccttgtg aagaaaaata cagctatatt taagtccatg 300
atacctgagc ttnttaaagt acaatgacaa ggctatatat ttgattgtna caaatcctgt 360
agatatactg acgtacgtta catacaagat atctggactt ccatggggca gagttttcgg 420
ttctggcact gttcttgaca gttcaaggtt taggtatctt ttaagcaagc attgcaatat 480
agatnccgag aaatgtccac ggaaggataa ttggcgagca tggtgataca gagtttgcag 540
catggagcat aacaaacata tcaggaatat catttaatga gtactgcagt ttatgcggac 600
gcgtctgtaa cacaaatttc agaaaggaag tagaagatga agttgtaaat gctgcttata 660
agataataga caaaaagggt gctacatatt atgctgtggc tgttgcagta agaaggattg 720
tggagtgtat cttaagagat gaaaattcca ttctnacagt ntcatctcca ttaaatggnc 780

-continued

```
aatacggtgt nanagatgtn tctttaagct tgccatcnat tgtnggcaga aatggngttg    840

caaggattct gganttgcct ttntctgang aagaagttga gaagtttaga cattcagcaa    900

gngttatggc agatgtnata aaacagttng atata                               935
```

GENE KNOCKOUT MESOPHILIC AND THERMOPHILIC ORGANISMS, AND METHODS OF USE THEREOF

RELATED APPLICATIONS

This application is the National Stage of Patent Cooperation Treaty Application serial number PCT/US2008/063237, filed May 9, 2008; which claims the benefit of U.S. Provisional Patent Application Ser. No. 60/916,978, filed May 9, 2007; the entire contents of which are incorporated herein by reference.

BACKGROUND OF THE INVENTION

Energy conversion, utilization and access underlie many of the great challenges of our time, including those associated with sustainability, environmental quality, security, and poverty. New applications of emerging technologies are required to respond to these challenges. Biotechnology, one of the most powerful of the emerging technologies, can give rise to important new energy conversion processes. Plant biomass and derivatives thereof are a resource for the biological conversion of energy to forms useful to humanity.

Among forms of plant biomass, lignocellulosic biomass ('biomass') is particularly well-suited for energy applications because of its large-scale availability, low cost, and environmentally benign production. In particular, many energy production and utilization cycles based on cellulosic biomass have near-zero greenhouse gas emissions on a life-cycle basis. The primary obstacle impeding the more widespread production of energy from biomass feedstocks is the general absence of low-cost technology for overcoming the recalcitrance of these materials to conversion into useful fuels. Lignocellulosic biomass contains carbohydrate fractions (e.g., cellulose and hemicellulose) that can be converted into ethanol. In order to convert these fractions, the cellulose and hemicellulose must ultimately be converted or hydrolyzed into monosaccharides; it is the hydrolysis that has historically proven to be problematic.

Biologically mediated processes are promising for energy conversion, in particular for the conversion of lignocellulosic biomass into fuels. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

Many bacteria have the ability to ferment simple hexose sugars into a mixture of acidic and pH-neutral products via the process of glycolysis. The glycolytic pathway is abundant and comprises a series of enzymatic steps whereby a six carbon glucose molecule is broken down, via multiple intermediates, into two molecules of the three carbon compound pyruvate. This process results in the net generation of ATP (biological energy supply) and the reduced cofactor NADH.

Pyruvate is an important intermediary compound of metabolism. For example, under aerobic conditions pyruvate may be oxidized to acetyl coenzyme A (acetyl CoA), which then enters the tricarboxylic acid cycle (TCA), which in turn generates synthetic precursors, $CO_2$ and reduced cofactors. The cofactors are then oxidized by donating hydrogen equivalents, via a series of enzymatic steps, to oxygen resulting in the formation of water and ATP. This process of energy formation is known as oxidative phosphorylation.

Under anaerobic conditions (no available oxygen), fermentation occurs in which the degradation products of organic compounds serve as hydrogen donors and acceptors. Excess NADH from glycolysis is oxidized in reactions involving the reduction of organic substrates to products, such as lactate and ethanol. In addition, ATP is regenerated from the production of organic acids, such as acetate, in a process known as substrate level phosphorylation. Therefore, the fermentation products of glycolysis and pyruvate metabolism include a variety of organic acids, alcohols and $CO_2$.

The majority of facultative anaerobic bacteria do not produce high yields of ethanol under either aerobic or anaerobic conditions. Most facultative anaerobes metabolize pyruvate aerobically via pyruvate dehydrogenase (PDH) and the tricarboxylic acid cycle (TCA). Under anaerobic conditions, the main energy pathway for the metabolism of pyruvate is via pyruvate-formate-lyase (PFL) pathway to give formate and acetyl-CoA. Acetyl-CoA is then converted to acetate, via phosphotransacetylase (PTA) and acetate kinase (ACK) with the co-production of ATP, or reduced to ethanol via acetalaldehyde dehydrogenase (AcDH) and alcohol dehydrogenase (ADH). In order to maintain a balance of reducing equivalents, excess NADH produced from glycolysis is re-oxidized to $NAD^+$ by lactate dehydrogenase (LDH) during the reduction of pyruvate to lactate. NADH can also be re-oxidized by AcDH and ADH during the reduction of acetyl-CoA to ethanol, but this is a minor reaction in cells with a functional LDH. Theoretical yields of ethanol are therefore not achieved since most acetyl CoA is converted to acetate to regenerate ATP and excess NADH produced during glycolysis is oxidized by LDH.

Metabolic engineering of microorganisms could also result in the creation of a targeted knockout of the genes encoding for the production of enzymes, such as lactate dehydrogenase. In this case, "knock out" of the genes means partial, substantial, or complete deletion, silencing, inactivation, or down-regulation. If the conversion of pyruvate to lactate (the salt form of lactic acid) by the action of LDH was not available in the early stages of the glycolytic pathway, then the pyruvate could be more efficiently converted to acetyl CoA by the action of pyruvate dehydrogenase or pyruvate-ferredoxin oxidoreductase. If the further conversion of acetyl CoA to acetate (the salt form of acetic acid) by phosphotransacetylase and acetate kinase was also not available, i.e., if the genes encoding for the production of PTA and ACK were knocked out, then the acetyl CoA could be more efficiently converted to ethanol by AcDH and ADH. Accordingly, a genetically modified strain of microorganism with such targeted gene knockouts, which eliminates the production of organic acids, would have an increased ability to produce ethanol as a fermentation product.

Ethanologenic organisms, such as *Zymomonas mobilis, Zymobacter palmae, Acetobacter pasteurianus*, or *Sarcina ventriculi*, and some yeasts (e.g., *Saccharomyces cerevisiae*), are capable of a second type of anaerobic fermentation, commonly referred to as alcoholic fermentation, in which pyruvate is metabolized to acetaldehyde and $CO_2$ by pyruvate decarboxylase (PDC). Acetaldehyde is then reduced to ethanol by ADH regenerating $NAD^+$. Alcoholic fermentation results in the metabolism of one molecule of glucose to two molecules of ethanol and two molecules of $CO_2$. If the conversion of pyruvate to undesired organic acids could be avoided, as detailed above, then such a genetically modified microorganism would have an increased ability to produce ethanol as a fermentation product.

SUMMARY OF THE INVENTION

One aspect of the invention relates to an isolated nucleic acid molecule comprising the nucleotide sequence of any one of SEQ ID NOS:1-5, 30-31, and 47-61, or a complement thereof. Another aspect of the invention relates to an isolated nucleic acid molecule comprising a nucleotide sequence which shares at least 80% identity to a nucleotide sequence of any one of SEQ ID NOS:1-5, 30-31, and 47-61, or a complement thereof. In certain embodiments, the invention relates to the aforementioned nucleic acid molecule which shares at least about 95% sequence identity to the nucleotide sequence of any one of SEQ ID NOS:1-5, 30-31, and 47-61, or a complement thereof.

Another aspect of the present invention relates to a genetic construct comprising any one of SEQ ID NOS:1-5, 30-31, and 47-61 operably linked to a promoter expressible in a thermophilic or mesophilic bacterium. The present invention also relates to a recombinant thermophilic or mesophilic bacterium comprising the aforementioned genetic construct.

The present invention also encompasses a vector comprising any one of the aforementioned nucleic acid molecules. The present invention also encompasses a host cell comprising any one of the aforementioned nucleic acid molecules. In certain embodiments, the invention relates to the aforementioned host cell, wherein said host cell is a thermophilic or mesophilic bacterial cell.

Another aspect of the invention relates to a genetically modified thermophilic or mesophilic microorganism, wherein a first native gene is partially, substantially, or completely deleted, silenced, inactivated, or down-regulated, which first native gene encodes a first native enzyme involved in the metabolic production of an organic acid or a salt thereof, thereby increasing the native ability of said thermophilic or mesophilic microorganism to produce ethanol as a fermentation product. In certain embodiments, the present invention relates to the aforementioned genetically modified microorganism, wherein said microorganism is a Gram-negative bacterium or a Gram-positive bacterium. In certain embodiments, the present invention relates to the aforementioned genetically modified microorganism, wherein said microorganism is a species of the genera *Thermoanaerobacterium, Thermoanaerobacter, Clostridium, Geobacillus, Saccharococcus, Paenibacillus, Bacillus, Caldicellulosiruptor, Anaerocellum*, or *Anoxybacillus*. In certain embodiments, the present invention relates to the aforementioned genetically modified microorganism, wherein said microorganism is a bacterium selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus, and Anaerocellum thermophilum*. In certain embodiments, the present invention relates to the aforementioned genetically modified microorganism, wherein said microorganism is *Thermoanaerobacterium saccharolyticum*. In certain embodiments, the present invention relates to the aforementioned genetically modified microorganism, wherein said microorganism is selected from the group consisting of: (a) a thermophilic or mesophilic microorganism with a native ability to metabolize a hexose sugar; (b) a thermophilic or mesophilic microorganism with a native ability to metabolize a pentose sugar; and (c) a thermophilic or mesophilic microorganism with a native ability to metabolize a hexose sugar and a pentose sugar. In certain embodiments, the present invention relates to the aforementioned genetically modified microorganism, wherein said microorganism has a native ability to metabolize a hexose sugar. In certain embodiments, the present invention relates to the aforementioned genetically modified microorganism, wherein said microorganism is *Clostridium straminisolvens* or *Clostridium thermocellum*. In certain embodiments, the present invention relates to the aforementioned genetically modified microorganism, wherein said microorganism has a native ability to metabolize a hexose sugar and a pentose sugar. In certain embodiments, the present invention relates to the aforementioned genetically modified microorganism, wherein said microorganism is *Clostridium cellulolyticum, Clostridium kristjanssonii*, or *Clostridium stercorarium* subsp. *leptosaprartum*. In certain embodiments, the present invention relates to the aforementioned genetically modified microorganism, wherein a first non-native gene is inserted, which first non-native gene encodes a first non-native enzyme that confers the ability to metabolize a pentose sugar, thereby allowing said thermophilic or mesophilic microorganism to produce ethanol as a fermentation product from a pentose sugar. In certain embodiments, the present invention relates to the aforementioned genetically modified microorganism, wherein said microorganism has a native ability to metabolize a pentose sugar. In certain embodiments, the present invention relates to the aforementioned genetically modified microorganism, wherein said microorganism is selected from the group consisting of *Thermoanaerobacterium saccharolyticum, Thermoanaerobacterium xylanolyticum, Thermoanaerobacterium polysaccharolyticum*, and *Thermoanaerobacterium thermosaccharolyticum*. In certain embodiments, the present invention relates to the aforementioned genetically modified microorganism, wherein a first non-native gene is inserted, which first non-native gene encodes a first non-native enzyme that confers the ability to metabolize a hexose sugar, thereby allowing said thermophilic or mesophilic microorganism to produce ethanol as a fermentation product from a hexose sugar. In certain embodiments, the present invention relates to the aforementioned genetically modified microorganism, wherein said organic acid is selected from the group consisting of lactic acid and acetic acid. In certain embodiments, the present invention relates to the aforementioned genetically modified microorganism, wherein said organic acid is lactic acid. In certain embodiments, the present invention relates to the aforementioned genetically modified microorganism, wherein said organic acid is acetic acid. In certain embodiments, the present invention relates to the aforementioned genetically modified microorganism, wherein said first native enzyme is selected from the group consisting of lactate dehydrogenase, acetate kinase, and phosphotransacetylase. In certain embodiments, the present invention relates to the aforementioned genetically modified microorganism, wherein said first native enzyme is lactate dehydrogenase. In certain embodiments, the present invention relates to the aforementioned genetically modified microorganism, wherein said first native enzyme is acetate kinase. In certain embodiments, the present invention relates to the aforementioned genetically modified microorganism, wherein said first native enzyme is phosphotransacetylase. In certain embodiments, the present invention relates to the aforementioned genetically modified microorganism, wherein a second native gene is partially, substantially, or completely deleted, silenced, inactivated, or down-regulated, which second native gene encodes a second native enzyme involved in the metabolic production of an organic acid or a salt thereof. In certain embodiments, the present invention relates to the aforementioned genetically modified microorganism, wherein said second native enzyme is acetate kinase or phosphotransacetylase. In certain embodiments, the present invention relates to the aforementioned genetically modified microorganism, wherein said second native enzyme is lactate dehydrogenase.

Yet another aspect of the invention relates to a genetically modified thermophilic or mesophilic microorganism, wherein (a) a first native gene is partially, substantially, or completely deleted, silenced, inactivated, or down-regulated, which first native gene encodes a first native enzyme involved in the metabolic production of an organic acid or a salt thereof, and (b) a first non-native gene is inserted, which first non-native gene encodes a first non-native enzyme involved in the metabolic production of ethanol, thereby allowing said thermophilic or mesophilic microorganism to produce ethanol as a fermentation product. In certain embodiments, the present invention relates to the aforementioned genetically modified microorganism, wherein said first non-native gene encodes a first non-native enzyme that confers the ability to metabolize a hexose sugar, thereby allowing said thermophilic or mesophilic microorganism to metabolize a hexose sugar. In certain embodiments, the present invention relates to the aforementioned genetically modified microorganism, wherein said first non-native gene encodes a first non-native enzyme that confers the ability to metabolize a pentose sugar, thereby allowing said thermophilic or mesophilic microorganism to metabolize a pentose sugar. In certain embodiments, the present invention relates to the aforementioned genetically modified microorganism, wherein said first non-native gene encodes a first non-native enzyme that confers the ability to metabolize a hexose sugar; and a second non-native gene is inserted, which second non-native gene encodes a second non-native enzyme that confers the ability to metabolize a pentose sugar, thereby allowing said thermophilic or mesophilic microorganism to metabolize a hexose sugar and a pentose sugar. In certain embodiments, the present invention relates to the aforementioned genetically modified microorganism, wherein said organic acid is lactic acid. In certain embodiments, the present invention relates to the aforementioned genetically modified microorganism, wherein said organic acid is acetic acid. In certain embodiments, the present invention relates to the aforementioned genetically modified microorganism, wherein said first non-native enzyme is pyruvate decarboxylase (PDC) or alcohol dehydrogenase (ADH). In certain embodiments, the present invention relates to the aforementioned genetically modified microorganism, wherein said second non-native enzyme is xylose isomerase. In certain embodiments, the present invention relates to the aforementioned genetically modified microorganism, wherein said first non-native gene corresponds to SEQ ID NOS:6, 10, or 14. In certain embodiments, the present invention relates to the aforementioned genetically modified microorganism, wherein said non-native enzyme is xylulokinase. In certain embodiments, the present invention relates to the aforementioned genetically modified microorganism, wherein said non-native gene corresponds to SEQ ID NOS:7, 11, or 15. In certain embodiments, the present invention relates to the aforementioned genetically modified microorganism, wherein said non-native enzyme is L-arabinose isomerase. In certain embodiments, the present invention relates to the aforementioned genetically modified microorganism, wherein said non-native gene corresponds to SEQ ID NOS:8 or 12. In certain embodiments, the present invention relates to the aforementioned genetically modified microorganism, wherein said non-native enzyme is L-ribulose-5-phosphate 4-epimerase. In certain embodiments, the present invention relates to the aforementioned genetically modified microorganism, wherein said non-native gene corresponds to SEQ ID NO:9 or 13. In certain embodiments, the present invention relates to the aforementioned genetically modified microorganism, wherein said microorganism is able to convert at least 60% of carbon from metabolized biomass into ethanol. In certain embodiments, the present invention relates to the aforementioned genetically modified microorganism, wherein said microorganism is selected from the group consisting of: (a) a thermophilic or mesophilic microorganism with a native ability to hydrolyze cellulose; (b) a thermophilic or mesophilic microorganism with a native ability to hydrolyze xylan; and (c) a thermophilic or mesophilic microorganism with a native ability to hydrolyze cellulose and xylan. In certain embodiments, the present invention relates to the aforementioned genetically modified microorganism, wherein said microorganism has a native ability to hydrolyze cellulose. In certain embodiments, the present invention relates to the aforementioned genetically modified microorganism, wherein said microorganism has a native ability to hydrolyze cellulose and xylan. In certain embodiments, the present invention relates to the aforementioned genetically modified microorganism, wherein a first non-native gene is inserted, which first non-native gene encodes a first non-native enzyme that confers the ability to hydrolyze xylan. In certain embodiments, the present invention relates to the aforementioned genetically modified microorganism, wherein said microorganism has a native ability to hydrolyze xylan. In certain embodiments, the present invention relates to the aforementioned genetically modified microorganism, wherein a first non-native gene is inserted, which first non-native gene encodes a first non-native enzyme that confers the ability to hydrolyze cellulose. In certain embodiments, the present invention relates to the aforementioned genetically modified microorganism, wherein said organic acid is selected from the group consisting of lactic acid and acetic acid. In certain embodiments, the present invention relates to the aforementioned genetically modified microorganism, wherein said organic acid is lactic acid. In certain embodiments, the present invention relates to the aforementioned genetically modified microorganism, wherein said organic acid is acetic acid. In certain embodiments, the present invention relates to the aforementioned genetically modified microorganism, wherein said first native enzyme is selected from the group consisting of lactate dehydrogenase, acetate kinase, and phosphotransacetylase. In certain embodiments, the present invention relates to the aforementioned genetically modified microorganism, wherein said first native enzyme is lactate dehydrogenase. In certain embodiments, the present invention relates to the aforementioned genetically modified microorganism, wherein said first native enzyme is acetate kinase. In certain embodiments, the present invention relates to the aforementioned genetically modified microorganism, wherein said first native enzyme is phosphotransacetylase. In certain embodiments, the present invention relates to the aforementioned genetically modified microorganism, wherein a second native gene is partially, substantially, or completely deleted, silenced, inactivated, or down-regulated, which second native gene encodes a second native enzyme involved in the metabolic production of an organic acid or a salt thereof. In certain embodiments, the present invention relates to the aforementioned genetically modified microorganism, wherein said second native enzyme is acetate kinase or phosphotransacetylase. In certain embodiments, the present invention relates to the aforementioned genetically modified microorganism, wherein said second native enzyme is lactate dehydrogenase. In certain embodiments, the present invention relates to the aforementioned genetically modified microorganism, wherein (a) a first native gene is partially, substantially, or completely deleted, silenced, inactivated, or down-regulated, which first native gene encodes a first native enzyme involved in the metabolic production of an organic acid or a salt thereof, and (b) a first non-native gene is inserted, which first non-native gene encodes a first non-native enzyme involved in the hydrolysis of a polysaccharide, thereby allowing said thermophilic or mesophilic microorganism to produce ethanol as a fermentation product. In certain embodiments, the present invention relates to the aforementioned genetically modified microorganism, wherein said first non-native gene encodes a first non-native enzyme that confers the ability to hydrolyze cellulose, thereby allowing said thermophilic or mesophilic microorganism to hydrolyze cellulose. In certain embodiments, the present invention relates to the aforementioned genetically modified microorganism, wherein said first non-native gene encodes a first non-native enzyme that confers the ability to hydrolyze xylan, thereby allowing said thermophilic or mesophilic microorganism to hydrolyze xylan. In certain embodiments, the present invention relates to the aforementioned genetically modified microorganism, wherein said first non-native gene encodes a first non-native enzyme that confers the ability to hydrolyze cellulose; and a second non-native gene is inserted, which second non-native gene encodes a second non-native enzyme that confers the ability to hydrolyze xylan, thereby allowing said thermophilic or mesophilic microorganism to hydrolyze cellulose and xylan. In certain embodiments, the present invention relates to the aforementioned genetically modified microorganism, wherein said organic acid is lactic acid. In certain embodiments, the present invention relates to the aforementioned genetically modified microorganism, wherein said organic acid is acetic acid. In certain embodiments, the present invention relates to the aforementioned genetically modified microorganism, wherein said first non-native enzyme is pyruvate decarboxylase (PDC) or alcohol dehydrogenase (ADH). In certain embodiments, the present invention relates to the aforementioned genetically modified microorganism, wherein said microorganism is able to convert at least 60% of carbon from metabolized biomass into ethanol.

In certain embodiments, the present invention relates to any of the aforementioned genetically modified microorganisms, wherein said microorganism is mesophilic. In certain embodiments, the present invention relates to any of the aforementioned genetically modified microorganisms, wherein said microorganism is thermophilic.

Another aspect of the invention relates to a process for converting lignocellulosic biomass to ethanol, comprising contacting lignocellulosic biomass with any one of the aforementioned genetically modified thermophilic or mesophilic microorganisms. In certain embodiments, the present invention relates to the aforementioned process, wherein said lignocellulosic biomass is selected from the group consisting of grass, switch grass, cord grass, rye grass, reed canary grass, mixed prairie grass, miscanthus, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, and combinations thereof. In certain embodiments, the present invention relates to the aforementioned process, wherein said lignocellulosic biomass is selected from the group consisting of corn stover, sugarcane bagasse, switchgrass, and poplar wood. In certain embodiments, the present invention relates to the aforementioned process, wherein said lignocellulosic biomass is corn stover. In certain embodiments, the present invention relates to the aforementioned process, wherein said lignocellulosic biomass is sugarcane bagasse. In certain embodiments, the present invention relates to the aforementioned process, wherein said lignocellulosic biomass is switchgrass. In certain embodiments, the present invention relates to the aforementioned process, wherein said lignocellulosic biomass is poplar wood. In certain embodiments, the present invention relates to the aforementioned process, wherein said lignocellulosic biomass is willow. In certain embodiments, the present invention relates to the aforementioned process, wherein said lignocellulosic biomass is paper sludge.

BRIEF DESCRIPTION OF THE DRAWINGS

FIG. 6 shows an alignment of *Clostridium thermocellum* (SEQ ID NO: 77), *Clostridium cellulolyticum* (SEQ ID NO: 78), *Thermoanaerobacterium saccharolyticum* (SEQ ID NO: 79), *C. stercorarium* (SEQ ID NO: 80), *C. stercorarium* II (SEQ ID NO: 81), *Caldiscellulosiruptor kristjanssonii* (SEQ ID NO: 82), *C. phytofermentans* (SEQ ID NO: 83), indicating about 73-89% homology at the level of the 16S rDNA gene.

FIGS. 13A and 13B show product formation and $OD_{600}$ for *C. thermocellum* grown on cellobiose and Avicel®, respectively.

FIGS. 14A and 14B show product formation and $OD_{600}$ for *C. cellulolyticum* grown on cellobiose and Avicel®, respectively.

FIGS. 15A and 15B show product formation and $OD_{600}$ for *C. stercorarium* subs. *leptospartum* grown on cellobiose and Avicel®, respectively.

FIGS. 16A and 16B show product formation and $OD_{600}$ for *Caldicellulosiruptor kristjanssonii* grown on cellobiose and Avicel®, respectively.

FIGS. 17A and 17B show product formation and $OD_{600}$ for *Clostridium phytofermentans* grown on cellobiose and Avicel®, respectively.

FIG. 30 shows an alignment of *T. pseudoethanolicus* 39E (SEQ ID NO: 85), T. sp strain 59 (SEQ ID NO: 86), *T. saccharolyticum* B6A-RI (SEQ ID NO: 87), *T. saccharolyticum* YS485 (SEQ ID NO: 88) and consensus (SEQ ID NO: 89) at the level of the 16S rDNA gene.

FIG. 31 shows an alignment of T. sp. strain 59 (SEQ ID NO: 36), *T. pseudoethanolicus* (SEQ ID NO: 35), *T. saccharolyticum* B6A-RI (SEQ ID NO: 38), *T. saccharolyticum* YS485 (SEQ ID NO: 32) and consensus (SEQ ID NO: 90) at the level of the pta gene.

FIG. 32 shows an alignment of T. sp. strain 59 (SEQ ID NO: 37), *T. pseudoethanolicus* (SEQ ID NO: 34), *T. saccharolyticum* B6A-RI (SEQ ID NO: 39), *T. saccharolyticum* YS485 (SEQ ID NO: 33) and consensus (SEQ ID NO: 91) at the level of the ack gene.

FIG. 33 shows an alignment of T. sp. strain 59 (SEQ ID NO: 41), *T. pseudoethanolicus* 39E (SEQ ID NO: 42), *T. saccharolyticum* B6A-RI (SEQ ID NO: 43), *T. saccharolyticum* YS485 (SEQ ID NO: 40) and consensus (SEQ ID NO: 92) at the level of the ldh gene.

BRIEF DESCRIPTION OF THE TABLES

Figure 1:
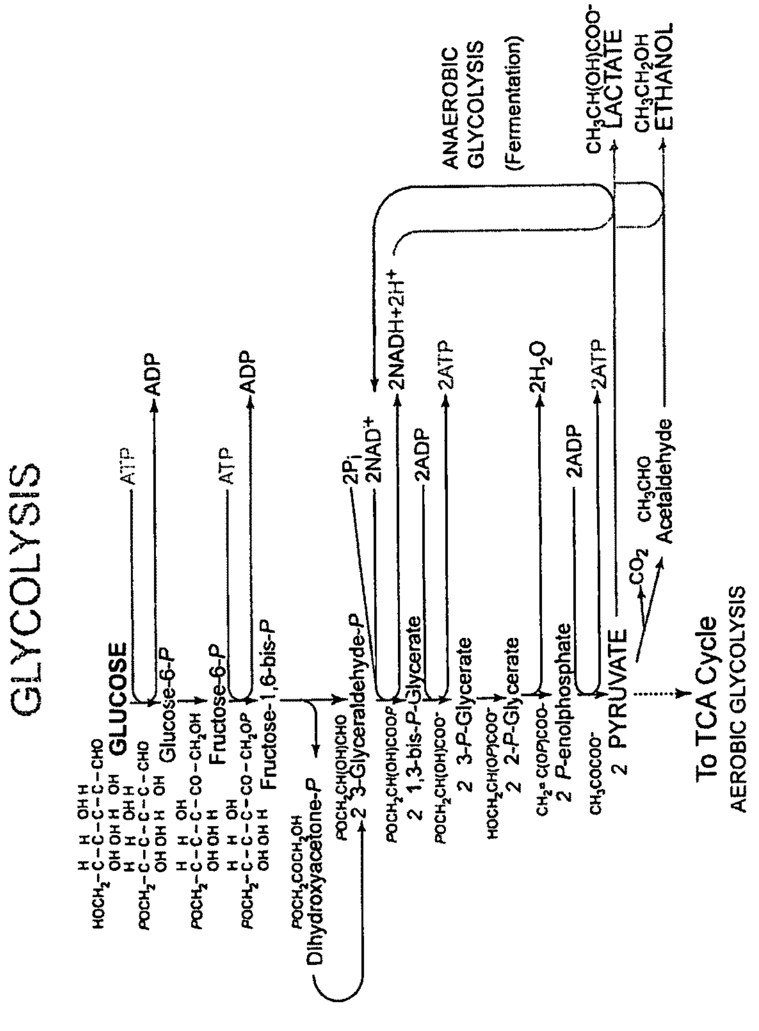
FIG. 1 depicts the glycolysis pathway.

Table 1 summarizes representative highly cellulolytic organisms.

Table 2 summarizes representative native cellulolytic and xylanolytic organisms.

Table 3 shows a categorization of bacterial strains based on their substrate utilization.

Table 4 shows insertion location and primers to retarget Intron to *C. cellulolyticum* acetate kinase.

Table 5 shows insertion location and primers to retarget Intron to *C. cellulolyticum* lactate dehydrogenase.

Table 6 shows fermentation performance of engineered *Thermoanaerobacter* and *Thermoanaerobacterium* strains.

DETAILED DESCRIPTION OF THE INVENTION

Aspects of the present invention relate to the engineering of thermophilic or mesophilic microorganisms for use in the production of ethanol from lignocellulosic biomass. The use of thermophilic bacteria for ethanol production offers many advantages over traditional processes based upon mesophilic ethanol producers. For example, the use of thermophilic organisms provides significant economic savings over traditional process methods due to lower ethanol separation costs, reduced requirements for external enzyme addition, and reduced processing times.

Aspects of the present invention relate to a process by which the cost of ethanol production from cellulosic biomass-containing materials can be reduced by using a novel processing configuration. In particular, the present invention provides numerous methods for increasing ethanol production in a genetically modified microorganism.

In certain other embodiments, the present invention relates to genetically modified thermophilic or mesophilic microorganisms, wherein a gene or a particular polynucleotide sequence is partially, substantially, or completely deleted, silenced, inactivated, or down-regulated, which gene or polynucleotide sequence encodes for an enzyme that confers upon the microorganism the ability to produce organic acids as fermentation products, thereby increasing the ability of the microorganism to produce ethanol as the major fermentation product. Further, by virtue of a novel integration of processing steps, commonly known as consolidated bioprocessing, aspects of the present invention provide for more efficient production of ethanol from cellulosic-biomass-containing raw materials. The incorporation of genetically modified thermophilic or mesophilic microorganisms in the processing of said materials allows for fermentation steps to be conducted at higher temperatures, improving process economics. For example, reaction kinetics are typically proportional to temperature, so higher temperatures are generally associated with increases in the overall rate of production. Additionally, higher temperature facilitates the removal of volatile products from the broth and reduces the need for cooling after pretreatment.

In certain embodiments, the present invention relates to genetically modified or recombinant thermophilic or mesophilic microorganisms with increased ability to produce enzymes that confer the ability to produce ethanol as a fermentation product, the presence of which enzyme(s) modify the process of metabolizing lignocellulosic biomass materials to produce ethanol as the major fermentation product. In one aspect of the invention, one or more non-native genes are inserted into a genetically modified thermophilic or mesophilic microorganism, wherein said non-native gene encodes an enzyme involved in the metabolic production of ethanol, for example, such enzyme may confer the ability to metabolize a pentose sugar and/or a hexose sugar. For example, in one embodiment, the enzyme may be involved in the D-xylose or L-arabinose pathway, thereby allowing the microorganism to metabolize a pentose sugar, i.e., D-xylose or L-arabinose. By inserting (e.g., introducing or adding) a non-native gene that encodes an enzyme involved in the metabolism or utilization of D-xylose or L-arabinose, the microorganism has an increased ability to produce ethanol relative to the native organism.

The present invention also provides novel compositions that may be integrated into the microorganisms of the invention. In one embodiment, an isolated nucleic acid molecule of the invention comprises a nucleic acid molecule which is a complement of a nucleotide sequence shown in any one of SEQ ID NOS:1-76. In another embodiment, an isolated nucleic acid molecule of the invention comprises a nucleic acid molecule which is a complement of a nucleotide sequence shown in any one of SEQ ID NOS:1-76, or a portion of any of these nucleotide sequences. A nucleic acid molecule which is complementary to a nucleotide sequence shown in any one of SEQ ID NOS:1-76, or the coding region thereof, is one which is sufficiently complementary to a nucleotide sequence shown in any one of SEQ ID NOS:1-76, or the coding region thereof, such that it can hybridize to a nucleotide sequence shown in any one of SEQ ID NOS:1-76, or the coding region thereof, thereby forming a stable duplex.

In still another preferred embodiment, an isolated nucleic acid molecule of the present invention comprises a nucleotide sequence which is at least about 50%, 54%, 55%, 60%, 62%, 65%, 70%, 75%, 78%, 80%, 85%, 86%, 87%, 88%, 89%, 90%, 91%, 92%, 93%, 94%, 95%, 96%, 97%, 98%, 99%, or more homologous to the nucleotide sequences (e.g., to the entire length of the nucleotide sequence) shown in any one of SEQ ID NOS:1-76, or a portion of any of these nucleotide sequences.

Moreover, the nucleic acid molecules of the invention may comprise only a portion of the nucleic acid sequence of any one of SEQ ID NOS:1-76, or the coding region thereof; for example, the nucleic acid molecule may be a fragment which can be used as a probe or primer or a fragment encoding a biologically active portion of a protein. In another embodiment, the nucleic acid molecules may comprise at least about 12 or 15, preferably about 20 or 25, more preferably about 30, 35, 40, 45, 50, 55, 60, 65, or 75 consecutive nucleotides of any one of SEQ ID NOS:1-76.

Definitions

The term "heterologous polynucleotide segment" is intended to include a polynucleotide segment that encodes one or more polypeptides or portions or fragments of polypeptides. A heterologous polynucleotide segment may be derived from any source, e.g., eukaryotes, prokaryotes, viruses, or synthetic polynucleotide fragments.

The terms "promoter" or "surrogate promoter" is intended to include a polynucleotide segment that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

The terms "gene(s)" or "polynucleotide segment" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. In certain embodiments, the gene of polynucleotide segment is involved in at least one step in the bioconversion of a carbohydrate to ethanol. Accordingly, the term is intended to include any gene encoding a polypeptide, such as the enzymes acetate kinase (ACK), phosphotransacetylase (PTA), and/or lactate dehydrogenase (LDH), enzymes in the D-xylose pathway, such as xylose isomerase and xylulokinase, enzymes in the L-arabinose pathway, such as L-arabinose isomerase and L-ribulose-5-phosphate 4-epimerase. The term gene is also intended to cover all copies of a particular gene, e.g., all of the DNA sequences in a cell encoding a particular gene product.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more gene is engineered to result in the optimal expression of such genes, e.g., in a desired ratio. The term also includes inducible transcriptional control as recognized in the art.

The term "expression" is intended to include the expression of a gene at least at the level of mRNA production.

The term "expression product" is intended to include the resultant product, e.g., a polypeptide, of an expressed gene.

The term "increased expression" is intended to include an alteration in gene expression at least at the level of increased mRNA production and, preferably, at the level of polypeptide expression. The term "increased production" is intended to include an increase in the amount of a polypeptide expressed, in the level of the enzymatic activity of the polypeptide, or a combination thereof.

The terms "activity," "activities," "enzymatic activity," and "enzymatic activities" are used interchangeably and are intended to include any functional activity normally attributed to a selected polypeptide when produced under favorable conditions. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof. Techniques for determining total activity as compared to secreted activity are described herein and are known in the art.

The term "xylanolytic activity" is intended to include the ability to hydrolyze glycosidic linkages in oligopentoses and polypentoses.

The term "cellulolytic activity" is intended to include the ability to hydrolyze glycosidic linkages in oligohexoses and polyhexoses. Cellulolytic activity may also include the ability to depolymerize or debranch cellulose and hemicellulose.

As used herein, the term "lactate dehydrogenase" or "LDH" is intended to include the enzyme capable of converting pyruvate into lactate. It is understood that LDH can also catalyze the oxidation of hydroxybutyrate.

As used herein the term "alcohol dehydrogenase" or "ADH" is intended to include the enzyme capable of converting acetaldehyde into an alcohol, advantageously, ethanol.

The term "pyruvate decarboxylase activity" is intended to include the ability of a polypeptide to enzymatically convert pyruvate into acetaldehyde (e.g., "pyruvate decarboxylase" or "PDC"). Typically, the activity of a selected polypeptide encompasses the total enzymatic activity associated with the produced polypeptide, comprising, e.g., the superior substrate affinity of the enzyme, thermostability, stability at different pHs, or a combination of these attributes.

The term "ethanologenic" is intended to include the ability of a microorganism to produce ethanol from a carbohydrate as a fermentation product. The term is intended to include, but is not limited to, naturally occurring ethanologenic organisms, ethanologenic organisms with naturally occurring or induced mutations, and ethanologenic organisms which have been genetically modified.

The terms "fermenting" and "fermentation" are intended to include the enzymatic process (e.g., cellular or acellular, e.g., a lysate or purified polypeptide mixture) by which ethanol is produced from a carbohydrate, in particular, as a product of fermentation.

The term "secreted" is intended to include the movement of polypeptides to the periplasmic space or extracellular milieu. The term "increased secretion" is intended to include situations in which a given polypeptide is secreted at an increased level (i.e., in excess of the naturally-occurring amount of secretion). In certain embodiments, the term "increased secreted" refers to an increase in secretion of a given polypeptide that is at least about 10% or at least about 100%, 200%, 300%, 400%, 500%, 600%, 700%, 800%, 900%, 1000%, or more, as compared to the naturally-occurring level of secretion.

The term "secretory polypeptide" is intended to include any polypeptide(s), alone or in combination with other polypeptides, that facilitate the transport of another polypeptide from the intracellular space of a cell to the extracellular milieu. In certain embodiments, the secretory polypeptide(s) encompass all the necessary secretory polypeptides sufficient to impart secretory activity to a Gram-negative or Gram-positive host cell. Typically, secretory proteins are encoded in a single region or locus that may be isolated from one host cell and transferred to another host cell using genetic engineering. In certain embodiments, the secretory polypeptide(s) are derived from any bacterial cell having secretory activity. In certain embodiments, the secretory polypeptide(s) are derived from a host cell having Type II secretory activity. In certain embodiments, the host cell is a thermophilic bacterial cell.

The term "derived from" is intended to include the isolation (in whole or in part) of a polynucleotide segment from an indicated source or the purification of a polypeptide from an indicated source. The term is intended to include, for example, direct cloning, PCR amplification, or artificial synthesis from or based on a sequence associated with the indicated polynucleotide source.

By "thermophilic" is meant an organism that thrives at a temperature of about 45° C. or higher.

By "mesophilic" is meant an organism that thrives at a temperature of about 20-45° C.

The term "organic acid" is art-recognized. The term "lactic acid" refers to the organic acid 2-hydroxypropionic acid in either the free acid or salt form. The salt form of lactic acid is referred to as "lactate" regardless of the neutralizing agent, i.e., calcium carbonate or ammonium hydroxide. The term "acetic acid" refers to the organic acid methanecarboxylic acid, also known as ethanoic acid, in either free acid or salt form. The salt form of acetic acid is referred to as "acetate."

Certain embodiments of the present invention provide for the "insertion," (e.g., the addition, integration, incorporation, or introduction) of certain genes or particular polynucleotide sequences within thermophilic or mesophilic microorganisms, which insertion of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

Certain embodiments of the present invention provide for the "inactivation" or "deletion" of certain genes or particular polynucleotide sequences within thermophilic or mesophilic microorganisms, which "inactivation" or "deletion" of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

The term "CBP organism" is intended to include microorganisms of the invention, e.g., microorganisms that have properties suitable for CBP.

In one aspect of the invention, the genes or particular polynucleotide sequences are inserted to activate the activity for which they encode, such as the expression of an enzyme. In certain embodiments, genes encoding enzymes in the metabolic production of ethanol, e.g., enzymes that metabolize pentose and/or hexose sugars, may be added to a mesophilic or thermophilic organism. In certain embodiments of the invention, the enzyme may confer the ability to metabolize a pentose sugar and be involved, for example, in the D-xylose pathway and/or L-arabinose pathway.

In one aspect of the invention, the genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" are used interchangeably with the term "deletion." In certain embodiments, strains of thermophilic or mesophilic microorganisms of interest may be engineered by site directed homologous recombination to knockout the production of organic acids. In still other embodiments, RNAi or antisense DNA (asDNA) may be used to partially, substantially, or completely silence, inactivate, or down-regulate a particular gene of interest.

In certain embodiments, the genes targeted for deletion or inactivation as described herein may be endogenous to the native strain of the microorganism, and may thus be understood to be referred to as "native gene(s)" or "endogenous gene(s)." An organism is in "a native state" if it has not been genetically engineered or otherwise manipulated by the hand of man in a manner that intentionally alters the genetic and/or phenotypic constitution of the organism. For example, wild-type organisms may be considered to be in a native state. In other embodiments, the gene(s) targeted for deletion or inactivation may be non-native to the organism.

Biomass

The terms "lignocellulosic material," "lignocellulosic substrate," and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, waste-water-treatment sludge, municipal solid waste, corn fiber from wet and dry mill corn ethanol plants, and sugar-processing residues.

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; and forestry wastes, such as but not limited to recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Particularly advantageous lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Paper sludge is also a viable feedstock for ethanol production. Paper sludge is solid residue arising from pulping and paper-making, and is typically removed from process wastewater in a primary clarifier. At a disposal cost of $30/wet ton, the cost of sludge disposal equates to $5/ton of paper that is produced for sale. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

Pyruvate Formate Lyase (PFL)

Pyruvate formate lyase (PFL) is an important enzyme (found in *Escherichia coli* and other organisms) that helps regulate anaerobic glucose metabolism. Using radical chemistry, it catalyzes the reversible conversion of pyruvate and coenzyme-A into formate and acetyl-CoA, a precursor of ethanol. Pyruvate formate lyase is a homodimer made of 85 kDa, 759-residue subunits. It has a 10-stranded beta/alpha barrel motif into which is inserted a beta finger that contains major catalytic residues. The active site of the enzyme, elucidated by x-ray crystallography, holds three essential amino acids that perform catalysis (Gly734, Cys418, and Cys419), three major residues that hold the substrate pyruvate close by (Arg435, Arg176, and Ala272), and two flanking hydrophobic residues (Trp333 and Phe432).

Studies have found structural similarities between the active site of pyruvate formate lyase and that of Class I and Class III ribonucleotide reductase (RNR) enzymes. The roles of the 3 catalytic residues are as follows: Gly734 (glycyl radical)—transfers the radical on and off Cys418, via Cys419; Cys418 (thiyl radical)—performs acylation chemistry on the carbon atom of the pyruvate carbonyl; Cys419 (thiyl radical)—performs hydrogen-atom transfers.

The proposed mechanism for pyruvate formate lyase begins with radical transfer from Gly734 to Cys418, via Cys419. The Cys418 thiyl radical adds covalently to C2 (second carbon atom) of pyruvate, generating an acetyl-enzyme intermediate (which now contains the radical). The acetyl-enzyme intermediate releases a formyl radical that undergoes hydrogen-atom transfer with Cys419. This generates formate and a Cys419 radical. Coenzyme-A undergoes hydrogen-atom transfer with the Cys419 radical to generate a coenzyme-A radical. The coenzyme-A radical then picks up the acetyl group from Cys418 to generate acetyl-CoA, leaving behind a Cys418 radical. Pyruvate formate lyase can then undergo radical transfer to put the radical back onto Gly734. Each of the above mentioned steps are also reversible.

Two additional enzymes regulate the "on" and "off" states of pyruvate formate lyase to regulate anaerobic glucose metabolism: PFL activase (AE) and PFL deactivase (DA). Activated pyruvate formate lyase allows formation of acetyl-CoA, a small molecule important in the production of energy, when pyruvate is available. Deactivated pyruvate formate lyase, even with substrates present, does not catalyze the reaction. PFL activase is part of the radical SAM (S-adenosylmethionine) superfamily.

The enzyme turns pyruvate formate lyase "on" by converting Gly734 (G-H) into a Gly734 radical (G*) via a 5'-deoxyadenosyl radical (radical SAM). PFL deactivase (DA) turns pyruvate formate lyase "off" by quenching the Gly734 radical. Furthermore, pyruvate formate lyase is sensitive to molecular oxygen ($O_2$), the presence of which shuts the enzyme off.

Xylose Metabolism

Xylose is a five-carbon monosaccharide that can be metabolized into useful products by a variety of organisms. There are two main pathways of xylose metabolism, each unique in the characteristic enzymes they utilize. One pathway is called the "Xylose Reductase-Xylitol Dehydrogenase" or XR-XDH pathway. Xylose reductase (XR) and xylitol dehydrogenase (XDH) are the two main enzymes used in this method of xylose degradation. XR, encoded by the XYL1 gene, is responsible for the reduction of xylose to xylitol and is aided by cofactors NADH or NADPH. Xylitol is then oxidized to xylulose by XDH, which is expressed through the XYL2 gene, and accomplished exclusively with the cofactor NAD+. Because of the varying cofactors needed in this pathway and the degree to which they are available for usage, an imbalance can result in an overproduction of xylitol byproduct and an inefficient production of desirable ethanol. Varying expression of the XR and XDH enzyme levels have been tested in the laboratory in the attempt to optimize the efficiency of the xylose metabolism pathway.

The other pathway for xylose metabolism is called the "Xylose Isomerase" (XI) pathway. Enzyme XI is responsible for direct conversion of xylose into xylulose, and does not proceed via a xylitol intermediate. Both pathways create xylulose, although the enzymes utilized are different. After production of xylulose both the XR-XDH and XI pathways proceed through enzyme xylulokinase (XK), encoded on gene XKS1, to further modify xylulose into xylulose-5-P where it then enters the pentose phosphate pathway for further catabolism.

Studies on flux through the pentose phosphate pathway during xylose metabolism have revealed that limiting the speed of this step may be beneficial to the efficiency of fermentation to ethanol. Modifications to this flux that may improve ethanol production include a) lowering phosphoglucose isomerase activity, b) deleting the GND1 gene, and c) deleting the ZWF1 gene (Jeppsson et al., 2002). Since the pentose phosphate pathway produces additional NADPH during metabolism, limiting this step will help to correct the already evident imbalance between NAD(P)H and NAD+ cofactors and reduce xylitol byproduct. Another experiment comparing the two xylose metabolizing pathways revealed that the XI pathway was best able to metabolize xylose to produce the greatest ethanol yield, while the XR-XDH pathway reached a much faster rate of ethanol production (Karhumaa et al., 2007).

Microorganisms

The present invention includes multiple strategies for the development of microorganisms with the combination of substrate-utilization and product-formation properties required for CBP. The "native cellulolytic strategy" involves engineering naturally occurring cellulolytic microorganisms to improve product-related properties, such as yield and titer. The "recombinant cellulolytic strategy" involves engineering natively non-cellulolytic organisms that exhibit high product yields and titers to express a heterologous cellulase system that enables cellulose utilization or hemicellulose utilization or both.

Cellulolytic Microorganisms

Several microorganisms reported in the literature to be cellulolytic or have cellulolytic activity have been characterized by a variety of means, including their ability to grow on microcrystalline cellulose as well as a variety of other sugars. Additionally, the organisms may be characterized by other means, including but not limited to, their ability to depolymerize and debranch cellulose and hemicellulose. *Clostridium thermocellum* (strain DSMZ 1237) was used to benchmark the organisms of interest. As used herein, *C. thermocellum* may include various strains, including, but not limited to, DSMZ 1237, DSMZ 1313, DSMZ 2360, DSMZ 4150, DSMZ 7072, and ATCC 31924. In certain embodiments of the invention, the strain of *C. thermocellum* may include, but is not limited to, DSMZ 1313 or DSMZ 1237. In another embodiment, particularly suitable organisms of interest for use in the present invention include cellulolytic microorganisms with a greater than 70% 16S rDNA homology to *C. thermocellum*. Alignment of *Clostridium thermocellum, Clostridium cellulolyticum, Thermoanaerobacterium saccharolyticum, C. stercorarium, C. stercorarium* II, *Caldiscellulosiruptor kristjanssonii, C. phytofermentans* indicate a 73-85% homology at the level of the 16S rDNA gene (FIG. 6).

*Clostridium straminisolvens* has been determined to grow nearly as well as *C. thermocellum* on Avicel®. Table 1 summarizes certain highly cellulolytic organisms.

TABLE 1

| Strain | DSMZ No. | T optimum; or range | pH optimum; or range | Gram Stain | Aero-tolerant | Utilizes | Products |
|---|---|---|---|---|---|---|---|
| *Clostridium thermocellum* | 1313 | 55-60 | 7 | positive | No | cellobiose, cellulose | acetic acid, lactic acid, ethanol, $H_2$, $CO_2$ |
| *Clostridium straminisolvens* | 16021 | 50-55; 45-60 | 6.5-6.8; 6.0-8.5 | positive | Yes | cellobiose, cellulose | acetic acid, lactic acid, ethanol, $H_2$, $CO_2$ |

Figure 12A:
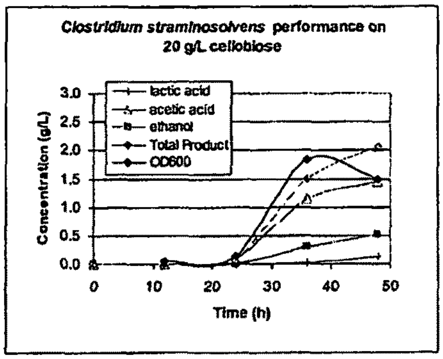
FIGS. 12A and 12B show product formation and $OD_{600}$ for *C. straminisolvens* grown on cellobiose and Avicel®, respectively.
Figure 12B:
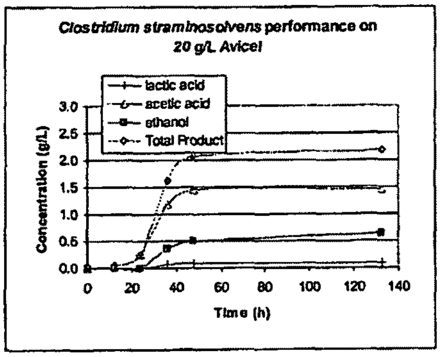

Organisms were grown on 20 g/L cellobiose or 20 g/L Avicel®. *C. thermocellum* was grown at 60° C. and *C. straminisolvens* was grown at 55° C. Both were pre-cultured from −80° C. freezer stock (origin DSMZ) on M122 with 50 mM MOPS. During mid to late log growth phase pre-cultures were used to inoculate the batch cultures in 100 mL serum bottles to a working volume of 50 mL. Liquid samples were removed periodically for HPLC analysis of metabolic byproducts and sugar consumption. $OD_{600}$ was taken at each of these time points. FIGS. 12A and 12B show product formation and $OD_{600}$ for *C. straminisolvens* on cellobiose and Avicel®, respectively. Substantial cellobiose (37%) was consumed with 48 hours before OD dropped and product formation leveled off. FIGS. 13A and 13B show product formation and $OD_{600}$ for *C. thermocellum* on cellobiose and Avicel®, respectively. *C. thermocellum* consumed ~60% of cellobiose within 48 hours, at which point product formation leveled out. Inhibition due to formation of organic acids caused incomplete utilization of substrates.

Certain microorganisms, including, for example, *C. thermocellum* and *C. straminisolvens*, cannot metabolize pentose sugars, such as D-xylose or L-arabinose, but are able to metabolize hexose sugars. Both D-xylose and L-arabinose are abundant sugars in biomass with D-xylose accounting for approximately 16-20% in soft and hard woods and L-arabinose accounting for approximately 25% in corn fiber. Accordingly, one object of the invention is to provide genetically-modified cellulolytic microorganisms, with the ability to metabolize pentose sugars, such as D-xylose and L-arabinose, thereby to enhance their use as biocatalysts for fermentation in the biomass-to-ethanol industry.

Cellulolytic And Xylanolytic Microorganisms

Several microorganisms determined from literature to be both cellulolytic and xylanolytic have been characterized by their ability to grow on microcrystalline cellulose and birchwood xylan as well as a variety of other sugars. *Clostridium thermocellum* was used to benchmark the organisms of interest. Of the strains selected for characterization *Clostridium cellulolyticum, Clostridium stercorarium* subs. *leptospartum, Caldicellulosiruptor kristjanssonii* and *Clostridium phytofermentans* grew weakly on Avicel® and well on birchwood xylan. Table 2 summarizes some of the native cellulolytic and xylanolytic organisms.

TABLE 2

| Strain | Source/ No. | T optimum; or range | pH optimum; or range | Gram Stain | Aero-tolerant | Utilizes | Products |
|---|---|---|---|---|---|---|---|
| *Clostridium cellulolyticum* | DSM 5812 | 34 | 7.2 | negative | no | Cellulose, xylan, arabinose, mannose, galactose, xylose, glucose, cellobiose | acetic acid, lactic acid, ethanol, $H_2$, $CO_2$ |
| *Clostridium stercorarium* subs. *leptospartum* | DSM 9219 | 60-65 | 7.0-7.5 | negative | no | Cellulose, cellobiose, lactose, xylose, melibiose, raffinose, ribose, fructose, sucrose | acetic acid, lactic acid, ethanol, $H_2$, $CO_2$ |
| *Caldicellulosiruptor kristjanssonii* | DSM 12137 | 78; 45-82 | 7; 5.8-8.0 | negative | No | cellobiose, glucose, xylose, galactose, mannose, cellulose | acetic acid, $H_2$, $CO_2$, lactic acid, ethanol formate |
| *Clostridium phytofermentans* | ATCC 700394 | 37; 5-45 | 8.5; 6-9 | Negative (gram type positive) | no | Cellulose, xylan, cellobiose, fructose, galactose, glucose, lactose, maltose, mannose, ribose, xylose | acetic acid, $H_2$, $CO_2$, lactic acid, ethanol formate |

Organisms were grown on 20 g/L cellobiose, 20 g/L Avicel® or 5 g/L birchwood xylan. *C. cellulolyticum* was grown at 37° C., *C. stercorarium* subs. *leptospartum* was grown at 60° C., *Caldicellulosiruptor kristjanssonii* was grown at 75° C. and *Clostridium phytofermentans* was grown at 37° C. All were pre-cultured from −80° C. freezer stock in M122c supplemented with 50 mM MOPS. During mid to late log growth phase pre-cultures were used to inoculate the batch cultures in 100 mL serum bottles to a working volume of 50 mL. Liquid samples were removed periodically for HPLC analysis of metabolic byproducts and sugar consumption. $OD_{600}$ was taken at each of these time points. FIGS. 14A-17B show product formation and $OD_{600}$ for growth on cellobiose and Avicel®.

Figure 18:
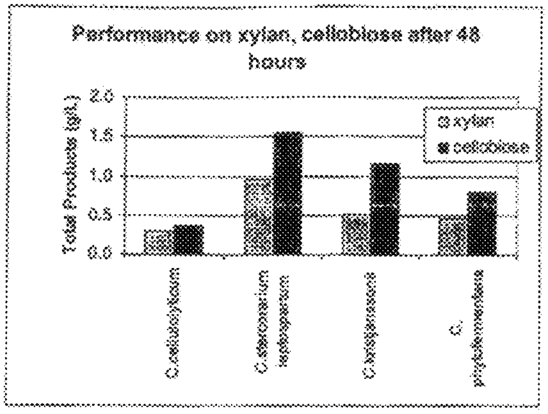
FIG. 18 shows total metabolic byproducts after 48 hours of fermentation of 2.5 g/L xylan and 2.5 g/L cellobiose.

In a separate experiment organisms were grown on 2.5 g/L single sugars including cellobiose, glucose, xylose, galactose, arabinose, mannose and lactose as well as 5 g/L Avicel® and birchwood xylan. In FIG. 18 product formation is compared on cellobiose and birchwood xylan after two days. Table 3 summarizes how bacterial strains may be categorized based on their substrate utilization.

TABLE 3

|  | cellobiose | glucose | xylose | galactose | arabinose | mannose | lactose |
|---|---|---|---|---|---|---|---|
| *C. cellulolyticum* | x | x | x | x | x |  |  |
| *C. stercorarium* subs. *leptospartum* | x | x | x | x | x | x | x |
| *C. kristjanssonii* | x | x | x | x |  | x | x |
| *C. phytofermentans* | x | x | x | x |  | x |  |

Transgenic Conversion of Microorganisms

The present invention provides compositions and methods for the transgenic conversion of certain microorganisms. When genes encoding enzymes involved in the metabolic pathway of ethanol, including, for example, D-xylose and/or L-arabinose, are introduced into a bacterial strain that lacks one or more of these genes, for example, *C. thermocellum* or *C. straminisolvens*, one may select transformed strains for growth on D-xylose or growth on L-arabinose. It is expected that genes from other Clostridial species should be expressed in *C. thermocellum* and *C. straminisolvens*. Target gene donors may include microorganisms that confer the ability to metabolize hexose and pentose sugars, e.g., *C. cellulolyticum, Caldicellulosiruptor kristjanssonii, C. phytofermentans, C. stercorarium*, and *Thermoanaerobacterium saccharolyticum*.

The genomes of *T. saccharolyticum, C. cellulolyticum*, and *C. phytofermentans* are available. Accordingly, the present invention provides sequences which correspond to xylose isomerase and xylulokinase in each of the three hosts set forth above. In particular, the sequences corresponding to xylose isomerase (SEQ ID NO:6), xylulokinase (SEQ ID NO:7), L-arabinose isomerase (SEQ ID NO:8), and L-ribulose-5-phosphate 4-epimerase (SEQ ID NO:9) from *T. saccharolyticum* are set forth herein. Similarly, the sequences corresponding to xylose isomerase (SEQ ID NO:10), xylulokinase (SEQ ID NO:11), L-arabinose isomerase (SEQ ID NO:12), and L-ribulose-5-phosphate 4-epimerase (SEQ ID NO:13) from *C. cellulolyticum* are provided herein. *C. phytofermentans* utilizes the D-xylose pathway and does not utilize L-arabinose. Accordingly, the sequences corresponding to xylose isomerase (SEQ ID NO:14) and xylulokinase (SEQ ID NO:15) from *C. phytofermentans* are set forth herein.

*C. kristjanssonii* does metabolize xylose. To this end, the xylose isomerase (SEQ ID NO:71) and xylulokinase (SEQ ID NO:70) genes of *C. kristjanssonii* have been sequenced and are provided herein. *C. straminisolvens* has not been shown to grow on xylose, however it does contain xylose isomerase (SEQ ID NO:73) and xylulokinase (SEQ ID NO:72) genes, which may be functional after adaptation on xylose as a carbon source.

Figure 2:
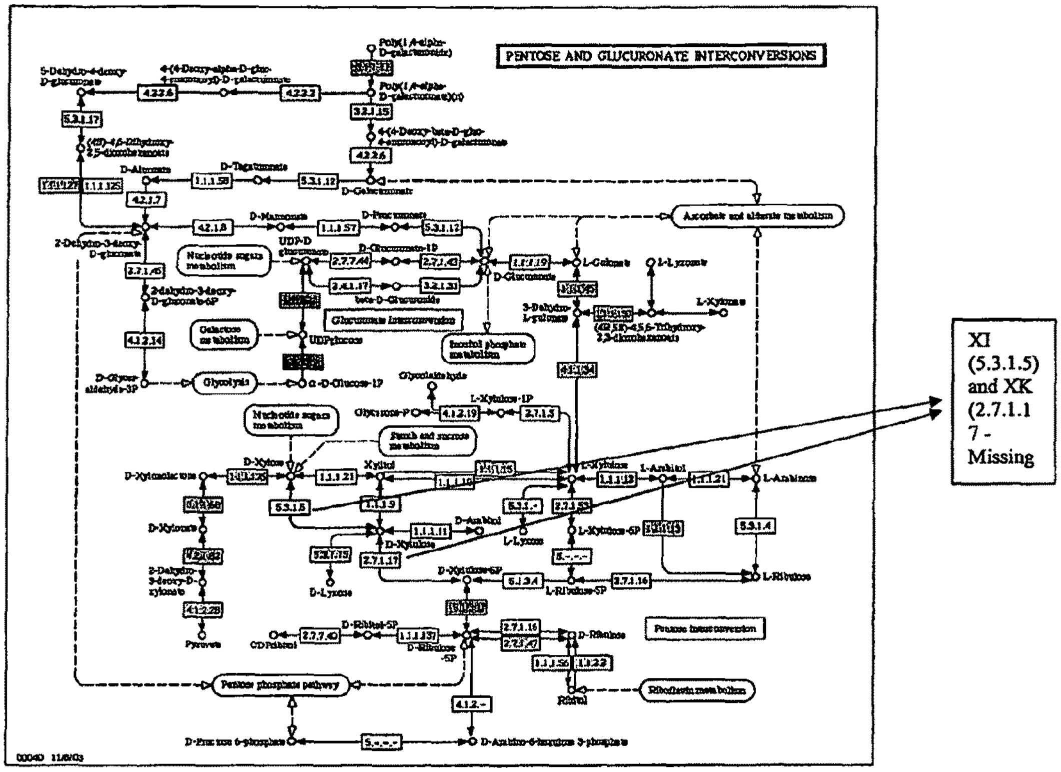
FIG. 2 depicts pentose and glucuronate interconversions and highlights the enzymes, xylose isomerase (XI or 5.3.1.5) and xylulokinase (XK or 2.7.1.17), in the D-xylose to ethanol pathway.
Figure 3:
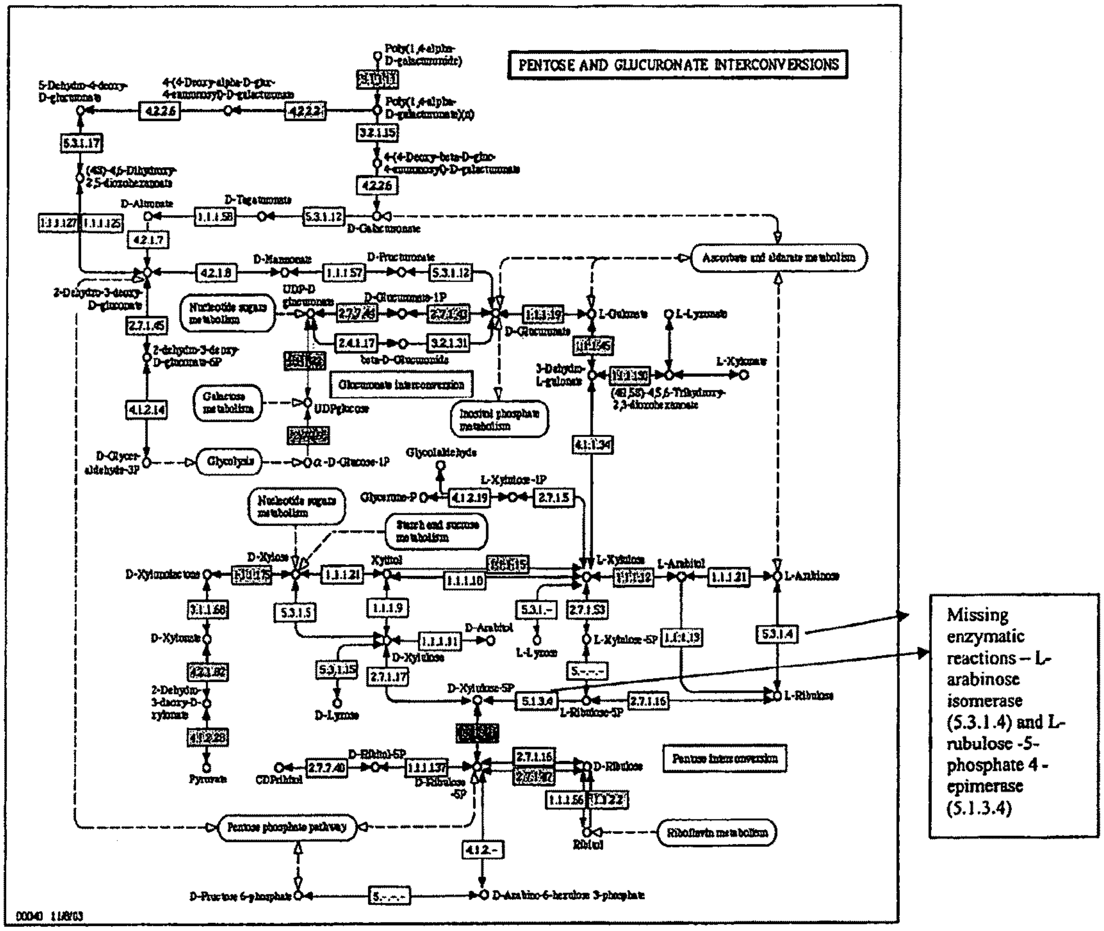
FIG. 3 depicts pentose and glucuronate interconversions and highlights the enzymes, L-arabinose isomerase (5.3.1.4) and L-ribulose-5-phosphate 4-epimerase (5.1.3.4), in the L-arabinose utilization pathway.

*C. thermocellum* and *C. straminisolvens* may lack one or more known genes or enzymes in the D-xylose to ethanol pathway and/or the L-arabinose utilization pathway. FIGS. 2 and 3 depict two key enzymes that are missing in each of these pathways in *C. thermocellum*. *C. straminisolvens* has xylose isomerase and xylulokinase, but the functionality of these enzymes is not known. Genomic sequencing has not revealed a copy of either L-arabinose isomerase or L-ribulose-5-phosphate 4-epimerase in *C. straminosolvens*.

*C. thermocellum* and *C. straminisolvens* are unable to metabolize xylulose which could reflect the absence (*C. thermocellum*) or lack of activity and/or expression (*C. straminsolvens*) of genes for xylose isomerase (referred to in FIG. 2 as "XI" or 5.3.1.5), which converts D-xylose to D-xylulose, and xylulokinase (also referred to in FIG. 2 as "XK" or 2.7.1.1), which converts D-xylulose to D-xylulose-5-phosphate. Furthermore, transport of xylose may be a limitation for *C. straminsolvens*. This potential limitation could be overcome by expression sugar transport genes from xylose utilizing organisms such as *T. saccharolyticum* and *C. kristjanssonii*.

*C. thermocellum* and *C. straminisolvens* are also unable to metabolize L-arabinose which could reflect the absence of genes for L-arabinose isomerase (also referred to in FIG. 3 as 5.3.1.4) and L-ribulose-5-phosphate 4-epimerase (also referred to in FIG. 3 as 5.1.3.4).

Figure 4:
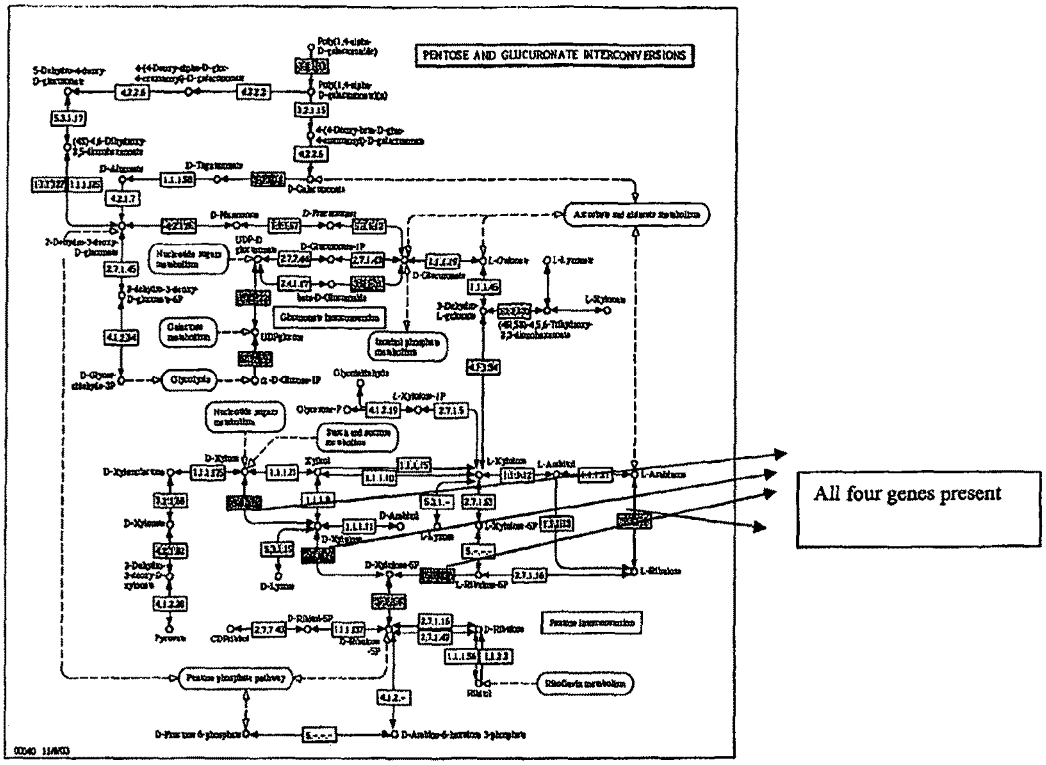
FIG. 4 depicts pentose and glucuronate interconversions and shows that the genes for xylose isomerase, xylulokinase, L-arabinose isomerase, and L-ribulose-5-phosphate 4-epimerase are present in *C. cellulolyticum.*

The four genes described above, e.g., xylose isomerase, xylulokinase, L-arabinose isomerase and L-ribulose-5-phosphate 4-epimerase, are present in several Clostridial species and *Thermoanaerobacterium saccharolyticum* species, including, but not limited to, *Clostridium cellulolyticum* (see FIG. 4), *Thermoanaerobacterium saccharolyticum, C. stercorarium, Caldiscellulosiruptor kristjanssonii,* and *C. phytofermentans*; these strains are good utilizers of these sugars. It will be appreciated that the foregoing bacterial strains may be used as donors of the genes described herein.

Figure 5:
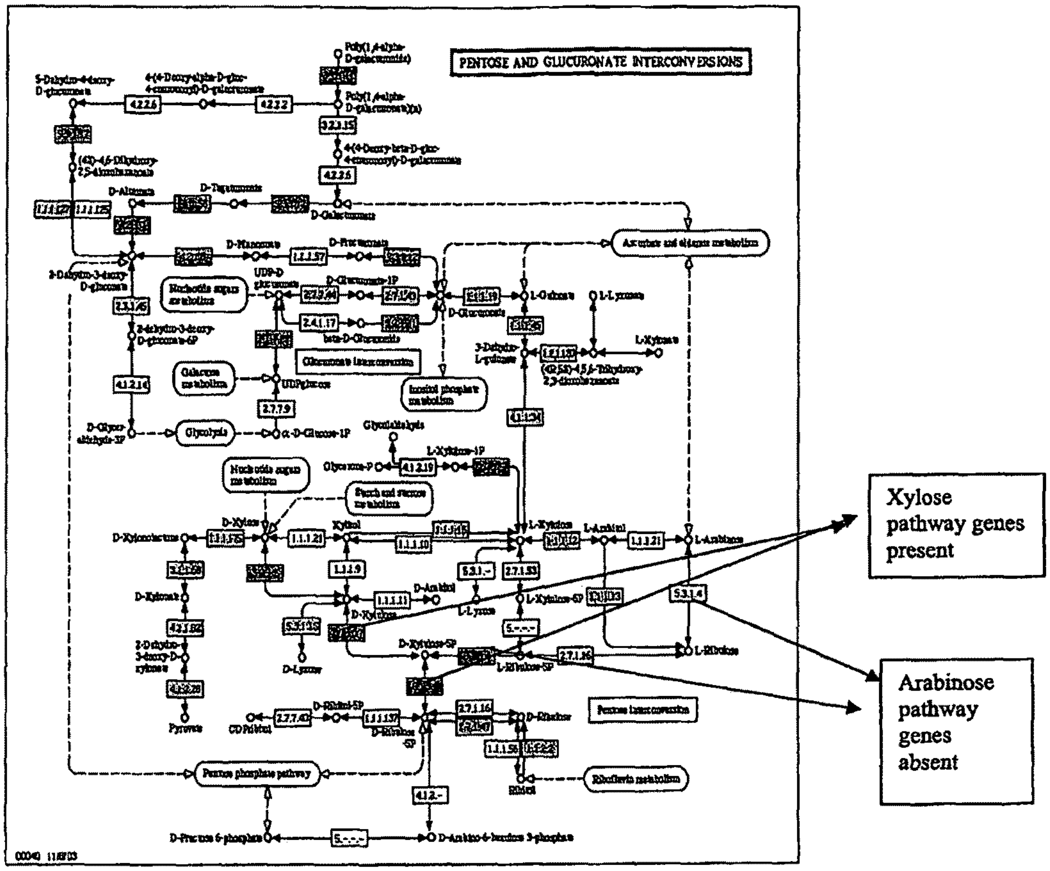
FIG. 5 depicts pentose and glucuronate interconversions and shows that xylose isomerase and xylulokinase are present, while L-arabinose isomerase and L-ribulose-5-phosphate 4-epimerase are absent in *C. phytofermentans.*

*C. phytofermentans* express the two xylose pathway genes described above (xylose isomerase and xylulokinase), but lack or do not express the arabinose pathway genes described above (L-arabinose isomerase and L-ribulose-5-phosphate 4-epimerase) (see FIG. 5).

Accordingly, it is an object of the invention to modify some of the above-described bacterial strains so as to optimize sugar utilization capability by, for example, introducing genes for one or more enzymes required for the production of ethanol from biomass-derived pentoses, e.g., D-xylose or L-arabinose metabolism. Promoters, including the native promoters of *C. thermocellum* or *C. straminisolvens*, such as triose phosphate isomerase (TPI), GAPDH, and LDH, may be used to express these genes. The sequences that correspond to native promoters of *C. thermocellum* include (TPI) (SEQ ID NO:16), GAPDH (SEQ ID NO:17), and LDH (SEQ ID NO:18). Once the gene has been cloned, codon optimization may be performed before expression. Cassettes containing, for example, the native promoter, a xylanolytic gene or arabinolytic gene, and a selectable marker may then be used to transform *C. thermocellum* or *C. straminisolvens* and select for D-xylose and L-arabinose growth on medium containing D-xylose or L-arabinose as the sole carbohydrate source.

Transposons

To select for foreign DNA that has entered a host it is preferable that the DNA be stably maintained in the organism of interest. With regard to plasmids, there are two processes by which this can occur. One is through the use of replicative plasmids. These plasmids have origins of replication that are recognized by the host and allow the plasmids to replicate as stable, autonomous, extrachromosomal elements that are partitioned during cell division into daughter cells. The second process occurs through the integration of a plasmid onto the chromosome. This predominately happens by homologous recombination and results in the insertion of the entire plasmid, or parts of the plasmid, into the host chromosome. Thus, the plasmid and selectable marker(s) are replicated as an integral piece of the chromosome and segregated into daughter cells. Therefore, to ascertain if plasmid DNA is entering a cell during a transformation event through the use of selectable markers requires the use of a replicative plasmid or the ability to recombine the plasmid onto the chromosome. These qualifiers cannot always be met, especially when handling organisms that do not have a suite of genetic tools.

One way to avoid issues regarding plasmid-associated markers is through the use of transposons. A transposon is a mobile DNA element, defined by mosaic DNA sequences that are recognized by enzymatic machinery referred to as a transposase. The function of the transposase is to randomly insert the transposon DNA into host or target DNA. A selectable marker can be cloned onto a transposon by standard genetic engineering. The resulting DNA fragment can be coupled to the transposase machinery in an in vitro reaction and the complex can be introduced into target cells by electroporation. Stable insertion of the marker onto the chromosome requires only the function of the transposase machinery and alleviates the need for homologous recombination or replicative plasmids.

The random nature associated with the integration of transposons has the added advantage of acting as a form of mutagenesis. Libraries can be created that comprise amalgamations of transposon mutants. These libraries can be used in screens or selections to produce mutants with desired phenotypes. For instance, a transposon library of a CBP organism could be screened for the ability to produce more ethanol, or less lactic acid and/or less acetate.

Native Cellulolytic Strategy

Naturally occurring cellulolytic microorganisms are starting points for CBP organism development via the native strategy. Anaerobes and facultative anaerobes are of particular interest. The primary objective is to engineer product yields and ethanol titers to satisfy the requirements of an industrial process. Metabolic engineering of mixed-acid fermentations in relation to these objectives has been successful in the case of mesophilic, non-cellulolytic, enteric bacteria. Recent developments in suitable gene-transfer techniques allow for this type of work to be undertaken with cellulolytic bacteria.

Recombinant Cellulolytic Strategy

Non-cellulolytic microorganisms with desired product-formation properties (e.g., high ethanol yield and titer) are starting points for CBP organism development by the recombinant cellulolytic strategy. The primary objective of such developments is to engineer a heterologous cellulase system that enables growth and fermentation on pretreated lignocellulose. The heterologous production of cellulases has been pursued primarily with bacterial hosts producing ethanol at high yield (engineered strains of *E. coli*, *Klebsiella oxytoca*, and *Zymomonas mobilis*) and the yeast *Saccharomyces cerevisiae*. Cellulase expression in strains of *K. oxytoca* resulted in increased hydrolysis yields—but not growth without added cellulase—for microcrystalline cellulose, and anaerobic growth on amorphous cellulose. Although dozens of saccharolytic enzymes have been functionally expressed in *S. cerevisiae*, anaerobic growth on cellulose as the result of such expression has not been definitively demonstrated.

Aspects of the present invention relate to the use of thermophilic or mesophilic microorganisms as hosts for modification via the native cellulolytic strategy. Their potential in process applications in biotechnology stems from their ability to grow at relatively high temperatures with attendant high metabolic rates, production of physically and chemically stable enzymes, and elevated yields of end products. Major groups of thermophilic bacteria include eubacteria and archaebacteria. Thermophilic eubacteria include: phototropic bacteria, such as cyanobacteria, purple bacteria, and green bacteria; Gram-positive bacteria, such as *Bacillus*, *Clostridium*, Lactic acid bacteria, and Actinomyces; and other eubacteria, such as *Thiobacillus*, Spirochete, *Desulfotomaculum*, Gram-negative aerobes, Gram-negative anaerobes, and *Thermotoga*. Within archaebacteria are considered Methanogens, extreme thermophiles (an art-recognized term), and *Thermoplasma*. In certain embodiments, the present invention relates to Gram-negative organotrophic thermophiles of the genera *Thermus*, Gram-positive eubacteria, such as genera *Clostridium*, and also which comprise both rods and cocci, genera in group of eubacteria, such as *Thermosipho* and *Thermotoga*, genera of Archaebacteria, such as *Thermococcus*, *Thermoproteus* (rod-shaped), *Thermofilum* (rod-shaped), *Pyrodictium*, *Acidianus*, *Sulfolobus*, *Pyrobaculum*, *Pyrococcus*, *Thermodiscus*, *Staphylothermus*, *Desulfurococcus*, *Archaeoglobus*, and *Methanopyrus*. Some examples of thermophilic or mesophilic (including bacteria, procaryotic microorganism, and fungi), which may be suitable for the present invention include, but are not limited to: *Clostridium thermosulfurogenes*, *Clostridium cellulolyticum*, *Clostridium thermocellum*, *Clostridium thermohydrosulfuricum*, *Clostridium thermoaceticum*, *Clostridium thermosaccharolyticum*, *Clostridium tartarivorum*, *Clostridium thermocellulaseum*, *Clostridium phytofermentans*, *Clostridium straminosolvens*, *Thermoanaerobacterium thermosaccarolyticum*, *Thermoanaerobacterium saccharolyticum*, *Thermobacteroides acetoethylicus*, *Thermoanaerobium brockii*, *Methanobacterium thermoautotrophicum*, *Anaerocellum thermophilium*, *Pyrodictium occultum*, *Thermoproteus neutrophilus*, *Thermofilum librum*, *Thermothrix thioparus*, *Desulfovibrio thermophilus*, *Thermoplasma acidophilum*, *Hydrogenomonas thermophilus*, *Thermomicrobium roseum*, *Thermus flavas*, *Thermus ruber*, *Pyrococcus furiosus*, *Thermus aquaticus*, *Thermus thermophilus*, *Chlo-*

*roflexus aurantiacus, Thermococcus litoralis, Pyrodictium abyssi, Bacillus stearothermophilus, Cyanidium caldarium, Mastigocladus laminosus, Chlamydothrix calidissima, Chlamydothrix penicillata, Thiothrix carnea, Phormidium tenuissimum, Phormidium geysericola, Phormidium subterraneum, Phormidium bijahensi, Oscillatoria filiformis, Synechococcus lividus, Chloroflexus aurantiacus, Pyrodictium brockii, Thiobacillus thiooxidans, Sulfolobus acidocaldarius, Thiobacillus thermophilica, Bacillus stearothermophilus, Cercosulcifer hamathensis, Vahlkampfia reichi, Cyclidium citrullus, Dactylaria gallopava, Synechococcus lividus, Synechococcus elongatus, Synechococcus minervae, Synechocystis aquatilus, Aphanocapsa thermalis, Oscillatoria terebriformis, Oscillatoria amphibia, Oscillatoria germinate, Oscillatoria okenii, Phormidium laminosum, Phormidium parparasiens, Symploca thermalis, Bacillus acidocaldarias, Bacillus coagulans, Bacillus thermocatenalatus, Bacillus licheniformis, Bacillus pamilas, Bacillus macerans, Bacillus circulans, Bacillus laterosporus, Bacillus brevis, Bacillus subtilis, Bacillus sphaericus, Desulfotomaculum nigrificans, Streptococcus thermophilus, Lactobacillus thermophilus, Lactobacillus bulgaricus, Bifidobacterium thermophilum, Streptomyces fragmentosporus, Streptomyces thermonitrificans, Streptomyces thermovulgaris, Pseudonocardia thermophile, Thermoactinomyces vulgaris, Thermoactinomyces sacchari, Thermoactinomyces candidas, Thermomonospora curvata, Thermomonospora viridis, Thermomonospora citrina, Microbispora thermodiastatica, Microbispora aerata, Microbispora bispora, Actinobifida dichotomica, Actinobifida chromogens, Micropolyspora caesia, Micropolyspora faeni, Micropolyspora cectivugida, Micropolyspora cabrobrunea, Micropolyspora thermovirida, Micropolyspora viridinigra, Methanobacterium thermoautothropicum, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus*, variants thereof, and/or progeny thereof.

In certain embodiments, the present invention relates to thermophilic bacteria selected from the group consisting of *Fervidobacterium gondwanense, Clostridium thermolacticum, Moorella* sp., and *Rhodothermus marinus.*

In certain embodiments, the present invention relates to thermophilic bacteria of the genera *Thermoanaerobacterium* or *Thermoanaerobacter*, including, but not limited to, species selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brockii*, variants thereof, and progeny thereof.

In certain embodiments, the present invention relates to microorganisms of the genera *Geobacillus, Saccharococcus, Paenibacillus, Bacillus*, and *Anoxybacillus*, including, but not limited to, species selected from the group consisting of: *Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis*, variants thereof, and progeny thereof.

In certain embodiments, the present invention relates to mesophilic bacteria selected from the group consisting of *Saccharophagus degradans; Flavobacterium johnsoniae; Fibrobacter succinogenes; Clostridium hungatei; Clostridium phytofermentans; Clostridium cellulolyticum; Clostridium aldrichii; Clostridium termitididis; Acetivibrio cellulolyticus; Acetivibrio ethanolgignens; Acetivibrio multivorans; Bacteroides cellulosolvens*; and *Alkalibacter saccharofomentans*, variants thereof and progeny thereof.

Methods of the Invention

During glycolysis, cells convert simple sugars, such as glucose, into pyruvic acid, with a net production of ATP and NADH. In the absence of a functioning electron transport system for oxidative phosphorylation, at least 95% of the pyruvic acid is consumed in short pathways which regenerate $NAD^+$, an obligate requirement for continued glycolysis and ATP production. The waste products of these $NAD^+$ regeneration systems are commonly referred to as fermentation products.

Microorganisms produce a diverse array of fermentation products, including organic acids, such as lactate (the salt form of lactic acid), acetate (the salt form of acetic acid), succinate, and butyrate, and neutral products, such as ethanol, butanol, acetone, and butanediol. End products of fermentation share to varying degrees several fundamental features, including: they are relatively nontoxic under the conditions in which they are initially produced, but become more toxic upon accumulation; and they are more reduced than pyruvate because their immediate precursors have served as terminal electron acceptors during glycolysis. Aspects of the present invention relate to the use of gene knockout technology to provide novel microorganisms useful in the production of ethanol from lignocellulosic biomass substrates. The transformed organisms are prepared by deleting or inactivating one or more genes that encode competing pathways, such as the non-limiting pathways to organic acids described herein, optionally followed by a growth-based selection for mutants with improved performance for producing ethanol as a fermentation product.

In certain embodiments, a thermophilic or mesophilic microorganism, which in a native state contains at least one gene that confers upon the microorganism an ability to produce lactic acid as a fermentation product, is transformed to decrease or eliminate expression of said at least one gene. The gene that confers upon said microorganism an ability to produce lactic acid as a fermentation product may code for expression of lactate dehydrogenase. The deletion or suppression of the gene(s) or particular polynucleotide sequence(s) that encode for expression of LDH diminishes or eliminates the reaction scheme in the overall glycolytic pathway whereby pyruvate is converted to lactic acid; the resulting relative abundance of pyruvate from these first stages of glycolysis should allow for the increased production of ethanol.

In certain embodiments, a thermophilic or mesophilic microorganism, which in a native state contains at least one gene that confers upon the microorganism an ability to produce acetic acid as a fermentation product, is transformed to eliminate expression of said at least one gene. The gene that confers upon the microorganism an ability to produce acetic acid as a fermentation product may code for expression of acetate kinase and/or phosphotransacetylase. The deletion or suppression of the gene(s) or particular polynucleotide sequence(s) that encode for expression of ACK and/or PTA diminishes or eliminates the reaction scheme in the overall glycolytic pathway whereby acetyl CoA is converted to acetic acid (FIG. 1); the resulting relative abundance of acetyl CoA from these later stages of glycolysis should allow for the increased production of ethanol.

In certain embodiments, the above-detailed gene knockout schemes can be applied individually or in concert. Eliminating the mechanism for the production of lactate (i.e., knocking out the genes or particular polynucleotide sequences that encode for expression of LDH) generates more acetyl CoA; it follows that if the mechanism for the production of acetate is also eliminated (i.e., knocking out the genes or particular polynucleotide sequences that encode for expression of ACK and/or PTA), the abundance of acetyl CoA will be further enhanced, which should result in increased production of ethanol.

In certain embodiments, it is not required that the thermophilic or mesophilic microorganisms have native or endogenous PDC or ADH. In certain embodiments, the genes encoding for PDC and/or ADH can be expressed recombinantly in the genetically modified microorganisms of the present invention. In certain embodiments, the gene knockout technology of the present invention can be applied to recombinant microorganisms, which may comprise a heterologous gene that codes for PDC and/or ADH, wherein said heterologous gene is expressed at sufficient levels to increase the ability of said recombinant microorganism (which may be thermophilic) to produce ethanol as a fermentation product or to confer upon said recombinant microorganism (which may be thermophilic) the ability to produce ethanol as a fermentation product.

In certain embodiments, aspects of the present invention relate to fermentation of lignocellulosic substrates to produce ethanol in a concentration that is at least 70% of a theoretical yield based on cellulose content or hemicellulose content or both.

In certain embodiments, aspects of the present invention relate to fermentation of lignocellulosic substrates to produce ethanol in a concentration that is at least 80% of a theoretical yield based on cellulose content or hemicellulose content or both.

In certain embodiments, aspects of the present invention relate to fermentation of lignocellulosic substrates to produce ethanol in a concentration that is at least 90% of a theoretical yield based on cellulose content or hemicellulose content or both.

In certain embodiments, substantial or complete elimination of organic acid production from microorganisms in a native state may be achieved using one or more site-directed DNA homologous recombination events.

Operating either a simultaneous saccharification and co-fermentation (SSCF) or CBP process at thermophilic temperatures offers several important benefits over conventional mesophilic fermentation temperatures of 30-37° C. In particular, costs for a process step dedicated to cellulase production are substantially reduced (e.g., 2-fold or more) for thermophilic SSCF and are eliminated for CBP. Costs associated with fermentor cooling and also heat exchange before and after fermentation are also expected to be reduced for both thermophilic SSCF and CBP. Finally, processes featuring thermophilic biocatalysts may be less susceptible to microbial contamination as compared to processes featuring conventional mesophilic biocatalysts.

The ability to redirect electron flow by virtue of modifications to carbon flow has broad implications. For example, this approach could be used to produce high ethanol yields in strains other than *T. saccharolyticum* and/or to produce solvents other than ethanol, for example, higher alcohols (i.e., butanol).

Metabolic Engineering Through Antisense Oligonucleotide (asRNA) Strategies

Fermentative microorganisms such as yeast and anaerobic bacteria ferment sugars to ethanol and other reduced organic end products. Theoretically, carbon flow can be directed to ethanol production if the formation of competing end-products, such as lactate and acetate, can be suppressed. The present invention provides several genetic engineering approaches designed to remove such competing pathways in the CBP organisms of the invention. The bulk of these approaches utilize knock-out constructs (for single crossover recombination) or allele-exchange constructs (for double crossover recombination) and target the genetic loci for ack and ldh. Although these tools employ "tried and true" strain development techniques, there are several potential issues that could stall progress: (i) they are dependent on the host recombination efficiency which in all cases is unknown for the CBP organisms; (ii) they can be used to knock out only one pathway at a time, so successive genetic alterations are incumbent upon having several selectable markers or a recyclable marker; (iii) deletion of target genes may be toxic or have polar effects on downstream gene expression.

The present invention provides additional approaches towards genetic engineering that do not rely on host recombination efficiency. One of these alternative tools is called antisense RNA (asRNA). Although antisense oligonucleotides have been used for over twenty-five years to inhibit gene expression levels both in vitro and in vivo, recent advances in mRNA structure prediction has facilitated smarter design of asRNA molecules. These advances have prompted a number of groups to demonstrate the usefulness of asRNA in metabolic engineering of bacteria.

The benefits of using asRNA over knock-out and allele-exchange technology are numerous: (i) alleviates the need for multiple selectable markers because multiple pathways can be targeted by a single asRNA construct; (ii) attenuation level of target mRNA can be adjusted by increasing or decreasing the association rate between asRNA; (iii) pathway inactivation can be conditional if asRNA transcripts are driven by conditional promoters. Recently, this technology has been used to increase solventogenesis in the Gram positive mesophile, *Clostridium acetobutylicum* (Tummala et al. (2003)). Although the exact molecular mechanism of how asRNA attenuates gene expression is unclear, the likely mechanism is triggered upon hybridization of the asRNA to the target mRNA. Mechanisms may include one or more of the following: (i) inhibition of translation of mRNA into protein by blocking the ribosome binding site from properly interacting with the ribosome, (ii) decreasing the half-life of mRNA through dsRNA-dependent RNases, such as RNase H, that rapidly degrade duplex RNA, and (iii) inhibition of transcription due to early transcription termination of mRNA.

Design of Antisense Sequences asRNAs are typically 18-25 nucleotides in length. There are several computation tools available for rational design of RNA-targeting nucleic acids (Sfold, Integrated DNA Technologies, STZ Nucleic Acid Design) which may be used to select asRNA sequences. For instance, the gene sequence for *Clostridium thermocellum* ack (acetate kinase) can be submitted to a rational design server and several asRNA sequences can be culled. In brief, the design parameters select for mRNA target sequences that do not contain predicted secondary structure.

Design of Delivery Vector

A replicative plasmid will be used to deliver the asRNA coding sequence to the target organism. Vectors such as, but not limited to, pNW33N, pJIR418, pJIR751, and pCTC1, will form the backbone of the asRNA constructs for delivery of the asRNA coding sequences to inside the host cell. In addition to extra-chromosomal (plasmid based) expression, asRNAs may be stably inserted at a heterologous locus into the genome of the microorganism to get stable expression of asRNAs. In certain embodiments, strains of thermophilic or mesophilic microorganisms of interest may be engineered by site directed homologous recombination to knockout the production of organic acids and other genes of interest may be partially, substantially, or completely deleted, silenced, inactivated, or down-regulated by asRNA.

Promoter Choice

To ensure expression of asRNA transcripts, compatible promoters for the given host will be fused to the asRNA coding sequence. The promoter-asRNA cassettes are constructed in a single PCR step. Sense and antisense primers designed to amplify a promoter region will be modified such that the asRNA sequence (culled from the rational design approach) is attached to the 5' end of the antisense primer. Additionally, restriction sites, such as EcoRI or BamHI, will be added to the terminal ends of each primer so that the final PCR amplicon can be digested directly with restriction enzymes and inserted into the vector backbone through traditional cloning techniques.

With respect to microorganisms that do not have the ability to metabolize pentose sugars, but are able to metabolize hexose sugars as described herein, it will be appreciated that the ack and ldh genes of *Clostridium thermocellum* and *Clostridium straminisolvens*, for example, may be targeted for inactivation using antisense RNA according to the methods described herein.

With respect to microorganisms that confer the ability to metabolize pentose and hexose sugars as described herein, it will be appreciated that the ack and ldh genes of *Clostridium cellulolyticum, Clostridium phytofermentans* and *Caldicellulosiruptor kristjanssonii*, for example, may be targeted for inactivation using antisense according to the methods described herein.

In addition to antibiotic selection for strains expressing the asRNA delivery vectors, such strains may be selected on conditional media that contains any of the several toxic metabolite analogues such as sodium fluoroacetate (SFA), bromoacetic acid (BAA), chloroacetic acid (CAA), 5-fluoroorotic acid (5-FOA) and chlorolactic acid. Use of chemical mutagens including, but not exclusively, ethane methyl sulfonate (EMS) may be used in combination with the expression of antisense oligonucleotide (asRNA) to generate strains that have one or more genes partially, substantially, or completely deleted, silenced, inactivated, or down-regulated.

EXEMPLIFICATION

The invention now being generally described, it will be more readily understood by reference to the following examples, which are included merely for purposes of illustration of certain aspects and embodiments of the present invention, and are not intended to limit the invention.

Example 1

Generation of Custom Transposons For Mesophilic And Thermophilic Cellulolytic, Xylanolytic Organisms The present invention provides methods for generating custom transposons for cellulolytic and/or xylanolytic and/or thermophilic organisms. To do this, a native promoter from the host organism will be fused to a selectable marker which has been determined to work in this organism. This fragment will be cloned into the EZ-Tn5™ transposon that is carried on the vector pMOD™-2<MCS> (Epicenter® Biotechnologies). For example, the *C. thermocellum* the gapDH promoter will be fused to the mLs drug marker, as well as the cat gene and then subcloned into vector pMOD™-2<MCS>.

Commercial transposons are lacking in thermostable drug markers and native promoters of cellulolytic and/or xylanolytic and/or thermophilic organisms. The mLs and cat markers have functioned in thermophilic bacteria and the gapDH promoter regulates a key glycolytic enzyme and should be constantly expressed. The combination of the above drug markers and the gapDH promoter will greatly enhance the probability of generating a functional transposon. This approach may be applied to other cellulolytic and/or xylanolytic and/or thermophilic organisms.

Experimental Design

Figure 26:
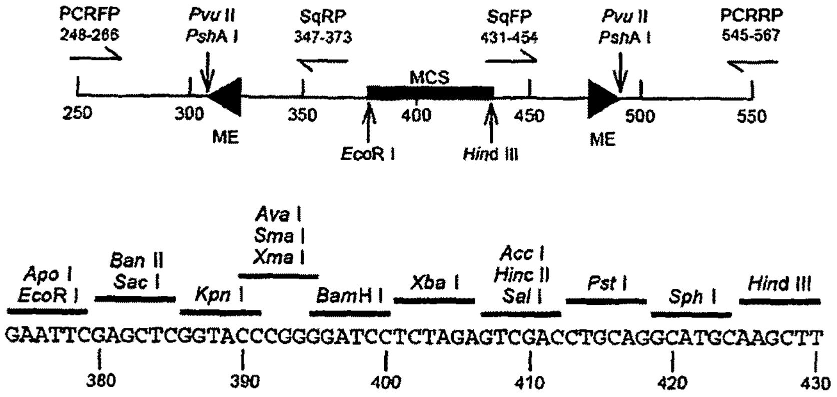
FIG. 26 is a diagram representing by 250-550 of pMOD™-2<MCS> (SEQ ID NO: 84).

FIG. 26 is a diagram taken from the Epicenter®Biotechnologies user manual, which is incorporated herein by reference, representing by 250-550 of pMOD™-2<MCS>. In the top portion, the black arrowheads labeled ME denote 19 bp mosaic ends that define the transposon. The EcoRI and HindIII sites define the multi-cloning site, which is represented by the black box labeled MCS. In the bottom portion, the DNA sequence and the restriction enzymes associated with the MCS are shown.

The following primers will be used to amplify promoter fusion fragments from pMQ87-gapDH-cat and pMQ87-gapDH-mls: GGCGgaattc CTT GGT CTG ACA ATC GAT GC (SEQ ID NO:19); GGCGgaattc TATCAGTTATTACCCACTTTTCG (SEQ ID NO:20). The lower case letters denote engineered EcoRI restriction sites. The size of the amplicon generated will be ~1.9 kb. Standard molecular procedures will allow the amplicon to be digested with EcoRI and cloned into the unique EcoRI site of pMOD™-2<MCS>. The transposon and subsequent transpososome will be generated and introduced into host organisms as described by the manufacturer.

Example 2

Constructs For Engineering Cellulolytic And Xylanolytic Strains

The present invention provides compositions and methods for genetically engineering an organism of interest to CBP by mutating genes encoding key enzymes of metabolic pathways which divert carbon flow away from ethanol. Single crossover knockout constructs are designed so as to insert large fragments of foreign DNA into the gene of interest to partially, substantially, or completely delete, silence, inactivate, or down-regulate it. Double crossover knockout constructs are designed so as to partially, substantially, or completely delete, silence, inactivate, or down-regulate the gene of interest from the chromosome or replace the gene of interest on the chromosome with a mutated copy of the gene, such as a form of the gene interrupted by an antibiotic resistance cassette.

The design of single crossover knockout vectors requires the cloning of an internal fragment of the gene of interest into a plasmid based system. Ideally, this vector will carry a selectable marker that is expressed in the host strain but will not replicate in the host strain. Thus, upon introduction into the host strain the plasmid will not replicate. If the cells are placed in a conditional medium that selects for the marker carried on the plasmid, only those cells that have found a way to maintain the plasmid will grow. Because the plasmid is unable to replicate as an autonomous DNA element, the most likely way that the plasmid will be maintained is through recombination onto the host chromosome. The most likely place for the recombination to occur is at a region of homology between the plasmid and the host chromosome.

Alternatively, replicating plasmids can be used to create single crossover interruptions. Cells that have taken up the knockout vector can be selected on a conditional medium, then passaged in the absence of selection. Without the positive selection provided by the conditional medium, many organisms will lose the plasmid. In the event that the plasmid is inserted onto the host chromosome, it will not be lost in the absence of selection. The cells can then be returned to a conditional medium and only those that have retained the marker, through chromosomal integration, will grow. A PCR based method will be devised to screen for organisms that contain the marker located on the chromosome.

The design of double crossover knockout vectors requires at least cloning the DNA flanking (~1 kb) the gene of interest into a plasmid and in some cases may include cloning the gene of interest. A selectable marker may be placed between the flanking DNA or if the gene of interest is cloned the marker is placed internally with respect to the gene. Ideally the plasmid used is not capable of replicating in the host strain. Upon the introduction of the plasmid into the host and selection on a medium conditional to the marker, only cells that have recombined the homologous DNA onto the chromosome will grow. Two recombination events are needed to replace the gene of interest with the selectable marker.

Alternatively, replicating plasmids can be used to create double crossover gene replacements. Cells that have taken up the knockout vector can be selected on a conditional medium, then passaged in the absence of selection. Without the positive selection provided by the conditional medium, many organisms will lose the plasmid. In the event that the drug marker is inserted onto the host chromosome, it will not be lost in the absence of selection. The cells can then be returned to a conditional medium and only those that have retained the marker, through chromosomal integration, will grow. A PCR based method may be devised to screen for organisms that contain the marker located on the chromosome.

In addition to antibiotic selection schemes, several toxic metabolite analogues such as sodium fluoroacetate (SFA), bromoacetic acid (BAA), chloroacetic acid (CAA), 5-fluoroorotic acid (5-FOA) and chlorolactic acid may be used to select mutants arising from either homologous recombinations, or transposon-based strategies. Use of chemical mutagens including, but not exclusively, ethane methyl sulfonate (EMS) may be used in combination with the directed mutagenesis schemes that employ homologous recombinations, or transposon-based strategies.

*C. Cellulolyticum Knockout Constructs*

Acetate Kinase (Gene 131 From *C. cellulolyticum* Published Genome)

Single Crossover

Figure 19:
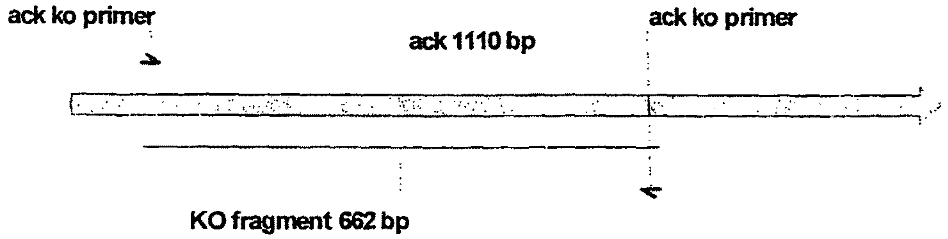
FIG. 19 shows a map of the ack gene and the region amplified by PCR for gene disruption.

The acetate kinase gene of *C. cellulolyticum* is 1,110 bp in length. A 662 bp internal fragment (SEQ ID NO:21) spanning nucleotides 91-752 was amplified by PCR and cloned into suicide vectors and replicating vectors that have different selectable markers. Selectable markers may include those that provide erythromycin and chloramphenicol resistance. These plasmids will be used to disrupt the ack gene. A map of the ack gene and the region amplified by PCR for gene disruption are shown in FIG. 19. The underlined portions of SEQ ID NO:21 set forth below correspond to the sites that are EcoRI sites that flank the knockout fragment.

```
gaattctgcgacagaatagggattgacaattcctttataaagcaatcaag
gggttcagaagaggctgttattttgaataaagagctaaagaatcacaaag
atgcaatagaggctgttatttctgcactgactgacgataatatgggcgtt
ataaaaaacatgtccgaaatatcagcagtgggacacagaatagtacacgg
cggtgaaaaattcaacagttctgtagttatagatgaaaacgttatgaatg
cagtaagagagtgtatagacgttgcaccgcttcataatccgccgaatatt
ataggtatagaggcttgccagcagattatgcccaatatacctatggtagc
tgtatttgataccactttccacagctccatgcctgattatgcataccttt
acgcattgccatatgaactttatgaaaagtacggtataagaaaatatggt
ttccacggaacatcacacaaatatgttgcagaaagagcttctgcaatgct
tgataagtctttgaacgaattaaagataattacatgccatcttgggaacg
gttcaagtatttgtgctgttaacaagggtaaatcaattgatacttccatg
ggctttacacctttgcagggacttgcaatgggtacaagaagcggtacaat
agaccctgaagttgttacgaattc
```

These sites were engineered during the design of the "ack KO primers" and will allow subsequent cloning of the fragment into numerous vectors.

Double Crossover

To construct a double crossover vector for the ack gene of *C. cellulolyticum* ~1 kb of DNA flanking each side of the ack gene will be cloned. A selectable marker will be inserted between the flanking DNA. Selectable markers may include those that provide erythromycin and chloramphenicol resistance. The 3' flanking region of the ack gene is not available in the available draft genome. To acquire this DNA, a kit such as GenomeWalker from Clontech will be used.

Lactate Dehydrogenase (Genes 2262 and 2744 of *C. cellulolyticum* Published Genome)

Single Crossover

Figure 20:
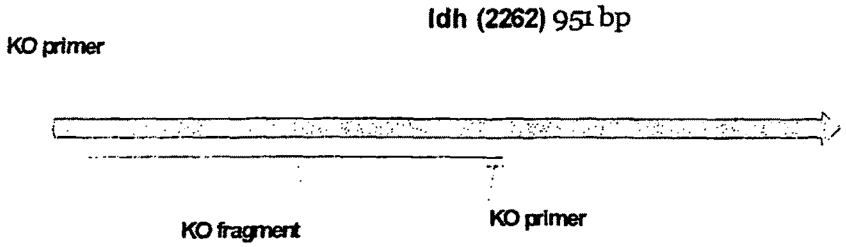
FIG. 20 shows a map of the ldh 2262 gene and the region amplified by PCR for gene disruption.

The ldh genes of *C. cellulolyticum* are 951 bp (for gene 2262) (SEQ ID NO:22) and 932 bp (for gene 2744) (SEQ ID NO:23) in length. A ~500 bp internal fragment near the 5' end of each gene will be amplified by PCR and cloned into suicide vectors and replicating vectors that have different selectable markers. Selectable markers may include those that provide drug resistance, such as erythromycin and chloramphenicol. These plasmids will be used to disrupt the ldh 2262 and ldh 2744 genes. As an example, a map of the ldh 2262 gene and the region amplified by PCR for gene disruption are shown in FIG. 20.

Double Crossover

Figure 21:
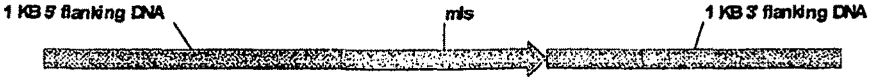
FIG. 21 shows an example of *C. cellulolyticum* (*C. cell.*) ldh (2262) double crossover knockout fragment.

To construct a double crossover knockout vector for the ldh gene(s) of *C. cellulolyticum* ~1 kb of DNA flanking each side of the ldh gene(s) will be cloned. A selectable marker will be inserted between the flanking DNA. Selectable markers may include those that provide drug resistance, such as erythromycin and chloramphenicol. FIG. 21 provides an example of *C. cellulolyticum* ldh (2262) double crossover knock out fragment.

In the sequence set forth below (SEQ ID NO:24) the mLs gene (selectable marker) is underlined and the flanking DNA is the remaining sequence. During primer design, restriction sites will be engineered and the 5' and 3' ends of the above fragment so that it can be cloned into a number of replicative and non-replicative vectors. The same strategy will be used to create a vector to delete ldh 2744.

```
gacgcatacaggttgtaacacccatttcccttagcttttcgggagatgaa
taaaacaaactttccgggtcctttaccacaccgcccacataaagagctat
gccgcatgaaagaaacgatatgttatcatttttttcgtaaactgttattt
ccgaacccggataaagctttaccatattattaactgctgccgtccctgca
tgtgtacaccctataaccactattttcatatacatcctcctttgtttgct
tgtaaatatatcccatatataccacctaaatatattttataaacaaattc
ggtatatcattcttttggtaaataaaaagtacatccgatattagaatgta
cctaaaaaaaattattattttattgtatatgctttatctgttttcattat
atggtttgctatccattctacggtaaaatcaagtaattccattaagtact
gatcctgatccttgtctatcctgctataatccgtattactgattttctca
ataaaatcatggtgttcaactttgtgggagagaagcttgcgatatcctat
gctatgcatgtattcttcttcataggtaaaatgaaagacagtgtaatctt
ttagttccgtaattagccgtacaatttcatcatatttgtctgtaataagc
tgatttttcgtggcctcataaatttccgaagcaatctggaatagtttctt
atgctgttcgtcgattttctcaattccaagaataaattcgtctctccatt
ctatcatatggaccctcctaaattgtaatgtataccaagattatacatac
ttcctagaatataaacaatacaaggataaaatttaatatcgtatacctta
cataaatgactaacttaaagctctctaaaacttctttttttattatttcta
tactactaaaatcaaaaatattctctaaagtatttctacaaatgttgttt
ttgcaacaaagtagtatacttttgcacccagaatgttttgttataactta
caaattaggggtatatttatagtaaatactaaatggaagagtaggatatt
gattatgaacgagaaaaatataaaacacagtcaaaactttattacttcaa
aacataatatagataaaataatgacaaatataagattaaatgaacatgat
aatatctttgaaatcggctcaggaaaagggcattttacccttgaattagt
acagaggtgtaatttcgtaactgccattgaaatagaccataaattatgca
aaactacagaaaataaacttgttgatcacgataatttccaagttttaaac
aaggatatattgcagtttaaatttcctaaaaaccaatcctataaaatatt
tggtaatataccttataacataagtacggatataatacgcaaaattgttt
ttgatagtatagctgatgagatttatttaatcgtggaatacgggtttgct
aaaagattattaaatacaaaacgctcattggcattatttttaatggcaga
agttgatatttctatattaagtatggttccaagagaatattttcatccta
aacctaaagtgaatagctcacttatcagattaaatagaaaaaaatcaaga
atatcacacaaagataaacagaagtataattatttcgttatgaaatgggt
taacaaagaatacaagaaaatatttacaaaaaatcaatttaacaattcct
```

-continued

```
taaaacatgcaggaattgacgatttaaacaatattagctttgaacaattc
ttatctcttttcaatagctataaattatttaataagatcccctttacttc
ggatgcatgccgcaggcaggcatccgaagtagtttctccattatacaagt
attctcttgagtacgtcgtcgcttctcagcagctgctttgctttttccct
gttttccggcacatggagataagtgtatctgttaggcttaatagtgtgtg
ccatgtcaattgccttttcgaagtcatctgccttcatttttaaggtttcc
acaaaattgataaaacccgtatcagtcagaaattttactacccgctgata
tctgtgttcttgaaccctgctcataagataggttgcaatcccaacctgaa
ttccatgaagctgaggtgtctccagcagcttatctaaagcatgagatatt
agatgctcactaccgctggctggagcactgctgtctgctatctgcatggc
aattccgctcattgtcagagagtctaccatttcctttaaaaagaagtttt
ctgtaacctgtgtgtagggcatccttacaatactgtttactgactttta
gcaatcattgcagcaaaatcgtcaacctttgccgcattgttcctttcttc
aaaataccagtcatacacagccgtaattttggatattatgtctccgagac
ctgaataaataaatttcataggtgcatttttttaatacatctaaatccact
aatattccaaatggcatcgaggcatgtacggaagtacgcctgccatttat
aatcaaagagcagcctgagctggaaaaaccatcgtttgaggttgatgtag
gtatactgataaaaggaagcttgtttaaaaaagctatatatttggctgca
tcaagcacctttcctcctcctactccgaccactgcatcggttttggaggg
aatagtaaaagccttgagcataagattttcaagctttatgtcatcatagt
cgtaagtttcaagtactgcaagagattttcttgactttatggaatccaga
atcttttcaccaaataagtcacgtattccctctccaaaaagtactacaac
attactaattcctgccctttcaatatgtgc
```

*C. phytofermentans* Knockout Constructs

For Acetate Kinase (Gene 327 From *C. Phytofermentans* Published Genome)

Single Crossover

Figure 22:
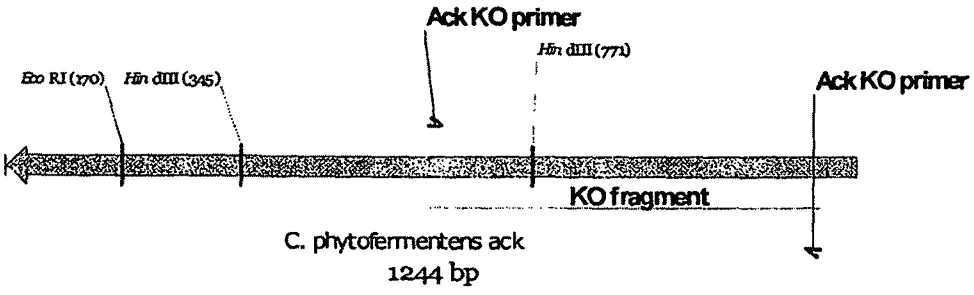
FIG. 22 shows a map of the ack gene of *Clostridium phytofermentans* and the region amplified by PCR for gene disruption.

The acetate kinase gene of *C. phytofermentans* is 1,244 bp in length. A 572 bp internal fragment spanning nucleotides 55-626 will be amplified by PCR and cloned into suicide vectors and replicating vectors that have different selectable markers. Selectable markers to use will include those that provide drug resistance to *C. phytofermentans*. These plasmids will be used to disrupt the ack gene. A map of the ack gene and the region amplified by PCR for gene disruption are shown in FIG. 22. Restriction sites will be engineered during the design of the "ack KO primers" and will allow subsequent cloning of the fragment into numerous vectors. The sequence of the knockout fragment described above is set forth as SEQ ID NO:25.

Double Crossover

Figure 23:
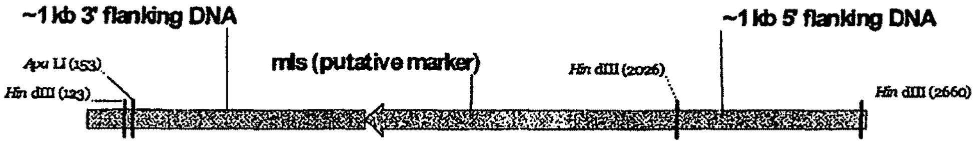
FIG. 23 shows an example of a putative double crossover knockout construct with the mLs gene as a selectable marker in *Clostridium phytofermentans.*

To construct a double crossover knockout vector for the ack gene of *C. phytofermentans* ~1 kb of DNA flanking each side of the ack gene will be cloned. A selectable marker will be inserted between the flanking DNA. Selectable markers to use will include those that provide drug resistance to this strain. An example of a putative double crossover knockout construct with the mLs gene as a putative selectable marker is shown in FIG. 23.

The sequence that corresponds to the fragment depicted in FIG. 23 (SEQ ID NO:26) is set forth below. The mLs gene (putative selectable marker) is underlined and the remainder of the sequence corresponds to the flanking DNA. During primer design, restriction sites will be engineered and the 5' and 3' ends of the above fragment so that it can be cloned into a number of replicative and non-replicative vectors.

```
ctgagtgcaatgtaaaaaaggatgcctcaagtattcttgaaacatcctta
tattatactacaaaatcataaagtaaattactcagctgtagcaatgatct
ctttttttgttgtaagatccacaagctttacaaactctatgaggcatcata
agtgcaccacacttgctgcatttcactaagtttggagcagtcatcttcca
gtttgcacgacgactatctcttctagctttggaatgtttattctttggac
aaatagctcccattgattacacctccttaaacttgttaaaaatatctcgg
atagcagacattcttgggtctagttctgtacggtcacacccgcactctcc
ttcatttaggttagcaccgcagaccttgcagattcctttacagtcttctt
tgcacagaaccttcattgggaaaccaatcaagacttcttcatagataagt
ttatctacgtctaaatcatatccggaaacaaaatttgtttcatctaaatc
ctcggtacgctgttcctctgttttcgatacatcaatctctgtagccacgt
cgatgtcttgttggatggtttcttccttcaaacaacgatcgcaaggaacg
gctaacgctaatttcgtttttgcttccaccagaatttttcggccacctag
attagttaatctaagtttaaccggttctttataggtaatagaataaccga
caccatttaattcgaatatatcaaattcaatcggtgcagtgtattctttg
agaccattaggaacattcatgacttcagacatttgtatcagcataagtaa
ctcctgtctaaaaaaacgcataatgtaagcgcccaaaaattcacactgtt
agtattataaacgcttaaaataggtttgtcaactcctaactgttaaaaat
gtcagaattgtgtaaccatatttctcttcattatcgttcttcccttatt
aaataatttatagctattgaaaagagataagaattgttcaaagctaatat
tgtttaaatcgtcaattcctgcatgttttaaggaattgttaaattgattt
tttgtaaatattttcttgtattctttgttaacccatttcataacgaaata
attatacttctgtttatctttgtgtgatattcttgatttttttctattta
atctgataagtgagctattcactttaggtttaggatgaaaatattctctt
ggaaccatacttaatatagaaatatcaacttctgccattaaaaataatgc
caatgagcgttttgtatttaataatcttttagcaaacccgtattccacga
ttaaataaatctcatcagctatactatcaaaaacaattttgcgtattata
tccgtacttatgttataaggtatattaccaaatattttataggattggtt
tttaggaaatttaaactgcaatatatccttgtttaaaacttggaaattat
cgtgatcaacaagtttattttctgtagttttgcataatttatggtctatt
tcaatggcagttacgaaattacacctctgtactaattcaagggtaaaatg
cccttttcctgagccgatttcaaagatattatcatgttcatttaatctta
tatttgtcattattttatctatattatgttttgaagtaataaagttttga
ctgtgttttatatttttctcgttcattgtatttctccttataatgttctt
aaattcatttatcacggggcaacttaatatatccgaaatatagttcttct
atatcgttcccccagtataatgattattatactatttaatcttcaactta
```

-continued

```
acaattggagtttccagttaagaaataataatttaatgccaaagcggata
ttcgcaatccgcttacgctacttgctcataacctcaacaggcaatgaagc
taagttaattatttactctgtgcctgaacagcagtgattgcaacaacacc
aacgatatcatcagaagaacaacctcttgataaatcatttactggagctg
caataccctgagttaatggtccataagcttctgcctttgcaagacgctgt
gttaacttatatccaatgttaccagcatcaaggtctgggaagattaatac
gttagcttttccagcaatatcactaccaggagcttttgaagcacctacac
taggaacgattgctgcatctaactggaactcgccgtcgatcttatattct
gggtataattcatttgcaatcttagttgcttctacaaccttatcaacatc
tgcatgctttgcgcttccctttgttgaatgagaaagcatagctacgatag
gttcagagccaactaattgttcaaaactcttcgctgtggaaccagcgatt
gctgctaactcttcagcatttggattctgatttaaaccagcatcagagaa
aaggaaagttccatttgcgcccatatcacaattaggtactaccattacga
agaaagcagaaactaacttagtatttggagcagtttttaaaatctgaaga
catggtcttaaggtatctgctgtagagtgacaagcaccagatactaaacc
atctgcatcgcccatcttaaccatcattacaccgtatgtaatgtagtctg
ttgttaaaagctcttttgctttttcaggggtcatgccttttgcctgtcta
agttctacaagcttgttaatgtaagc
```

For Lactate Dehydrogenase (Genes 1389 And 2971 of *C. phytofermentans* Published Genome)

Single Crossover

Figure 24:
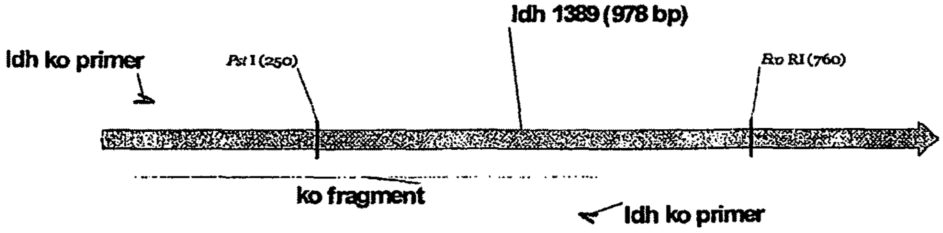
FIG. 24 shows a map of the ldh 1389 gene and the region amplified by PCR for gene disruption.

The ldh genes of *C. phytofermentans* are 978 bp (for gene 1389) (SEQ ID NO:27) and 960 bp (for gene 2971) (SEQ ID NO:28) in length. A ~500 bp internal fragment near the 5' end of each gene will be amplified by PCR and cloned into suicide vectors and replicating vectors that have different selectable markers. Selectable markers to use will include those that provide drug resistance. These plasmids will be used to disrupt the ldh 1389 and ldh 2971 genes. As an example, a map of the ldh 1389 gene and the region amplified by PCR for gene disruption are shown in FIG. 24.

Double Crossover

To construct a double crossover knockout vector for the ldh gene(s) of *C. phytofermentans* ~1 kb of DNA flanking each side of the ldh gene(s) will be cloned. A selectable marker will be inserted between the flanking DNA. Selectable markers to use will include those that provide drug resistance to this strain. An example of a putative double crossover knockout construct with the mLs gene as a putative selectable marker is shown in FIG. 25.

Figure 25:
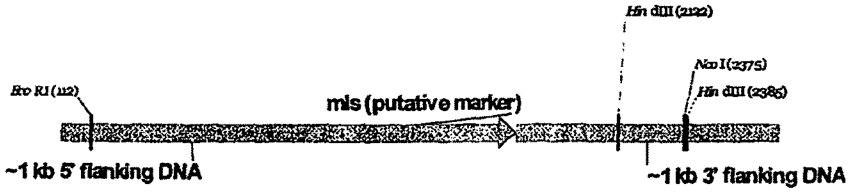
FIG. 25 shows an example of a putative double crossover knockout construct with the mLs gene as a selectable marker.

The sequence that corresponds to the fragment depicted in FIG. 25 is set forth below as SEQ ID NO:29. The mLs gene (selectable marker) is underlined and the remaining portion of the sequence corresponds to the flanking DNA. During primer design, restriction sites will be engineered and the 5' and 3' ends of the above fragment so that it can be cloned into a number of replicative and non-replicative vectors. The same strategy will be used to create a vector to delete ldh 2971.

```
tggaatctcactatgcaccaatgtggtactaaattatatctttatctatg
gaaaattaggttttccgcgaatggagatagagggagctgccattgctact
ttaatttgtagaattcttgagagtattttagttgttatttatatgtataa
gggtgagaaggtacttaagatgagactttcttatatttttaagagatcta
aacagtattttcgctctttggctcgttatagtgcgccagtgcttatgagt
gaggttaactggggggcttgggattgctgttcagtctgcaatcattgggcg
tatgggtgttagttttcttacagccgccagcttcattaatgtagtacaac
agttagccggaatcattctgattggtattggtgtgggttcgagcattata
atagggaatttgattggtgagggaaaagagcatgaggcgagaatgctagc
caataagttaatacgtatcagtatgatactcggaggaattgttgcttttg
cagtaatcttactacgtccaatcgctcctaactttattgaggcgtctaag
gaaacagcggatttaattcgtcagatgctatttgtttcggcttacctctt
attcttccaagccttatctgtattaactatggccggaatattacgtggtg
caggggataccctttactgtgcaacctttgatgttttgaccttatgggta
ctaaaacttggaggaggtttgcttgcaaccatagtacttcatcttccacc
tgtatgggtttactttatcttaagtagcgatgagtgtgttaaagcgctat
ttacggtaccgcgggtcttaaagggacgttggattcatgatacaacactg
cattaagatttcatatgtccagatattttgcacagtagcataattacta
gagcttattcctataatattcataggttttgatggtccattttacgttac
gatagcatatattacatcaaaaccaattctatataagatgaggttatagt
atgaacgagaaaaatataaaacacagtcaaaactttattacttcaaaaca
taatatagataaaataatgacaaatataagattaaatgaacatgataata
tctttgaaatcggctcaggaaaagggcattttacccttgaattagtacag
aggtgtaatttcgtaactgccattgaaatagaccataaattatgcaaaac
tacagaaaataaacttgttgatcacgataatttccaagttttaaacaagg
atatattgcagtttaaatttcctaaaaaccaatcctataaaatatttggt
aatataccttataacataagtacggatataatacgcaaaattgtttgata
gtatagctgatgagatttatttaatcgtggaatacgggtttgctaaaaga
ttattaaatacaaaacgctcattggcattatttttaatggcagaagttga
tatttctatattaagtatggttccaagagaatattttcatcctaaaccta
aagtgaatagctcacttatcagattaaatagaaaaaaatcaagaatatca
cacaaagataaacagaagtataattatttcgttatgaaatgggttaacaa
agaatacaagaaaatatttacaaaaaatcaatttaacaattccttaaaac
atgcaggaattgacgatttaaacaatattagctttgaacaattcttatct
cttttcaatagctataaattatttaataagaagtaataggaaataatact
cgaattattctgcaatctgttctaaaaaataaaattaagaaattactata
gcaagccaggttaaaattactagcttgctatttttgtgcatttagtacag
ttttgattattaaagaataaatttaataactattttgcaataagttattg
actatttcacaagttagtgttactatacaagtatgaaataaagatacata
aaaaaataaataatatgaaacataaattcatgacatgcggaatagaatga
aagaatattatgtcggttcctaatactaaatggatataacaatctattga
```

-continued

```
aacacttatggggtgtaagtgtggagagaatttctaaagcgccaaaagac
tctacatatgaaattctaaagcttcacacgggaataatctaatttatgta
tcttattatcataattcaggaaggtagtgtgaaaatataaaaattagttt
tcctgtttcattcaggcagtagcatttcttaaacaaatttgctatgcatt
gggtgttatctgaaaaacaaaaagcaattttctcacaacttatttctgaa
caacaatggtattaaaaatttggaggaggattttactatgaaaaaaacgg
taacattactgttggttctgaccatggtggtaagcttatttgcagcatgt
ggtaagaaaaatggatcaagcgaaaccggcacaaaagatcctgtggcaac
aagcggtgcaaaagaacctgacaaacaagatccaggcaataaagagcctg
aaaaacaagaccctgttaaaatcaagatttattactctgataatgcaacc
ttaccatttaaagaagattggttagttataaaggaagctgagaagagatt
taatgttgatttcgatttcgaagtaattccaattgcagattatcaaacaa
aagtttctttaacattaaatacaggaaataacgctccagatgtcatcctt
tatcagtcaacgcagggagagaatgcatct
```

*Cald. kristjanssonii* and *C. Stercorarium* subs *leptospartum*

To the best of our knowledge, genome sequencing of the above organisms has not occurred and if it has, it has not been made available to the public. Based on our experimental results these organisms are cellulolytic and xylanolytic. The DNA sequences of genes encoding key metabolic enzymes are needed from these organisms in order to genetically engineer them and divert carbon flow to ethanol. These include such enzymes as acetate kinase and lactate dehydrogenase. In order to obtain the sequences of these genes, the genomes of these organisms will be sequenced.

With access to genome sequences, the conserved nature of the above enzymes may be used to find the encoding genes and flanking DNA. These sequences will be used to design constructs for targeted mutagenesis employing both single and double crossover strategies. These strategies will be identical to those described above. We will also determine which antibiotics can be used as selectable markers in these organisms and which protocols for transformation work best.

Example 3

Transformation of *C. cellulolyticum*

Cells were grown in 50 mL of GS media with 4 g/l cellobiose to an OD of 0.8 in anaerobic conditions, incubated at 34 degrees C. After harvesting they were washed 3 times in equal volumes with a wash buffer containing 500 mM sucrose and 5 mM MOPS with pH adjusted to 7. After the final wash, the cell pellet was resuspended in an equal volume of wash buffer 10 μl aliquots of the cell suspension were placed in a standard electroporation cuvette with a 1 mm electrode spacing. 1 ul plasmid DNA was added. The concentration of the plasmid DNA was adjusted to ensure between a 1:1 and 10:1 molar ratio of plasmid to cells. A 5 ms pulse was applied with a field strength of 7 kV/cm (measured) across the sample. A custom pulse generator was used. The sample was immediately diluted 1000:1 with the same media used in the initial culturing and allowed to recover until growth resumed, and was determined via an increase in the OD (24-48 h). The recovered sample was diluted 50:1 and placed in selective media with either 15 ug/mL erythromycin or 15 ug/mL chloramphenicol and allowed to grow for 5-6 days. Samples exhibiting growth in selective media were tested to confirm that they were in fact *C. cellulolyticum* and that they had the plasmid.

Example 4

Constructs For Engineering Cellulolytic Strains

Cellulose is one of the main components of biomass, which can be potentially used as a substrate for generation of fuel ethanol by fermentation with *Clostridium thermocellum*. However, in this process, much energy and carbon sources are used to form by-product acetate and lactate. Engineering of the metabolic pathways of cellulose utilization in *Clostridium thermocellum* is necessary to minimize the lactate and acetate production and make energy and carbon flows favorable to ethanol formation.

Acetate kinase is an important enzyme in the metabolic pathway of cellulose utilization to form acetate in Clostridium thermocellum, which is encoded by the ack gene. Inactivation of the ack gene may interrupt acetate kinase, leading to reduction or elimination of acetate.

Lactate dehydrogenase is an important enzyme in the metabolic pathway of cellulose utilization to form lactate in *Clostridium thermocellum*, which is encoded by the ldh gene. Inactivation of the ldh gene may interrupt lactate dehydrogenase, leading to reduction or elimination of lactate generation.

Inactivation of the ack Gene In *C. thermocellum* Based On the Plasmid pIKM1

Figure 7:
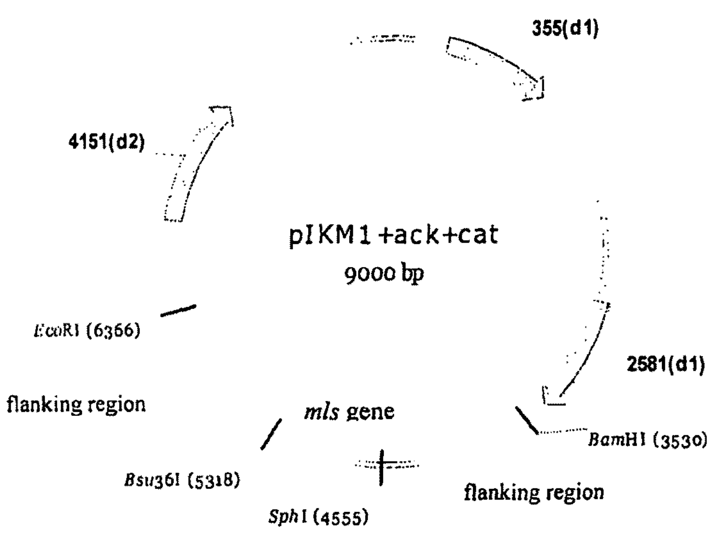
FIG. 7 shows the construction of a double crossover knockout vector for inactivation of the ack gene in *Clostridium thermocellum* based on the plasmid pIKM1.

To knock out the ack gene, a vector is constructed on the multiple cloning sites (MCS) of the plasmid pIKM1, in which the cat gene, encoding chloramphenicol acetyltransferase, is inserted into a DNA fragment of 3055 bp, involving the ack and the pta genes (encoding phosphotransacetylase), leading to knockout of 476 bp of the ack gene and 399 bp of the pta gene, and forming 1025 bp and 1048 bp flanking regions on both sides of the mLs gene respectively (FIG. 7). pNW33N contains pBC1 replicon, which is isolated from *Bacillus coagulans* and *Staphylococcus aureus*, and is anticipated to be stably replicated in Gram positive strains of bacteria, including *Clostridium thermocellum*. The sequence of the ack knockout vector constructed on plasmid pIKM1 is set forth as SEQ ID NO:1.

Figure 8:
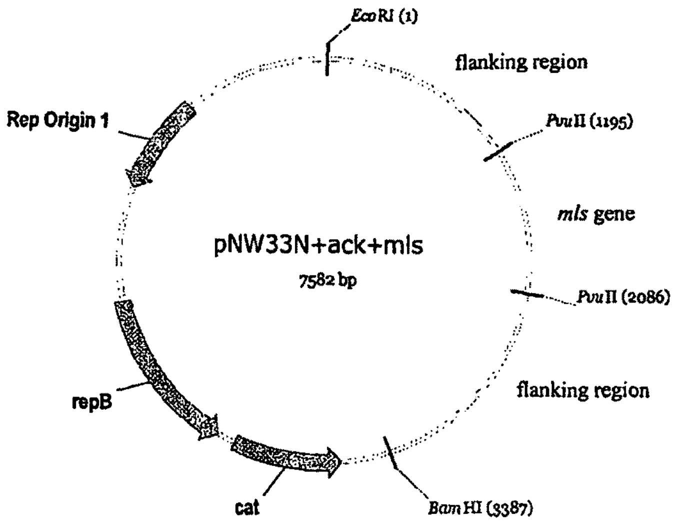
FIG. 8 shows the construction of a double crossover knockout vector for inactivation of the ack gene in *Clostridium thermocellum* based on the replicative plasmid pNW33N.

Inactivation of the ack Gene In *C. thermocellum* Based On the Replicative Plasmid pNW33N To knock out the ack gene, a vector is constructed on the multiple cloning sites (MCS) of the replicative plasmid pNW33N, in which the macrolide, lincosamide, and streptogramin B ($MLS_B$) resistant gene mLs is inserted into a DNA fragment of 3345 bp, which includes the ack gene, the pta gene (encoding phosphotransacetylase) and an unknown upstream gene, leading to knockout of 855 bp of the ack gene and formation of flanking regions of 1195 bp and 1301 bp on either side of the mLs gene (FIG. 8). pNW33N contains pBC1 replicon, which is isolated from *Bacillus coagulans* and *Staphylococcus aureus*, and is anticipated to be stably replicated in Gram positive strains of bacteria, including *Clostridium thermocellum*. The sequence of the ack knockout vector constructed on plasmid pNW33N is set forth as SEQ ID NO:2.

Inactivation of the ldh Gene In *C. thermocellum* Based on the Plasmid pIKM1

Figure 9:
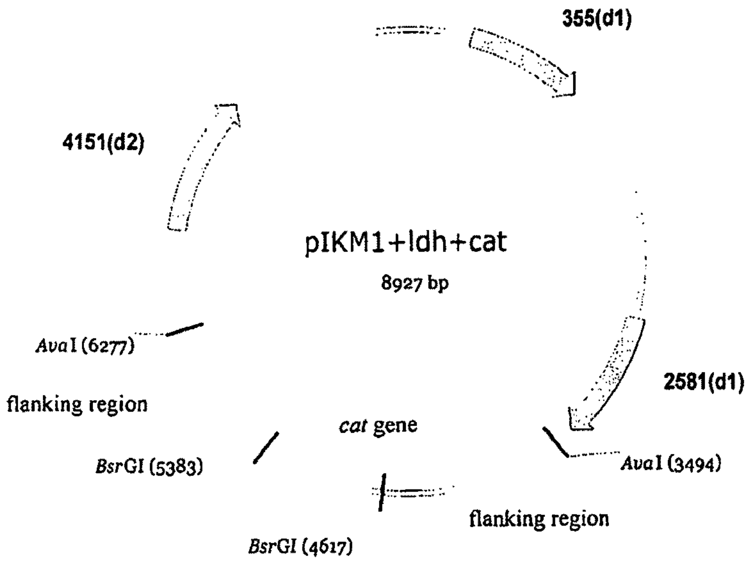
FIG. 9 shows the construction of a double crossover knockout vector for inactivation of the ldh gene in *Clostridium thermocellum* based on the plasmid pIKM1.

To knock out the ldh gene, a vector is constructed on the multiple cloning sites (MCS) of the plasmid pIKM1, in which the cat gene, encoding chloramphenicol acetyltransferase, is inserted into a DNA fragment of 3188 bp, involving the ldh and the mdh gene (encoding malate dehydrogenase), leading to knockout of a DNA fragment of 1171 bp, including part of the ldh and mdh genes, and forming 894 bp and 1123 bp flanking regions on both sides of the mLs gene, respectively (FIG. 9). The sequence of the ldh knockout vector constructed on plasmid pIKM1 is set forth as SEQ ID NO:3.

Inactivation of the ldh Gene in *C. thermocellum* Based On Plasmid pNW33N

Figure 10:
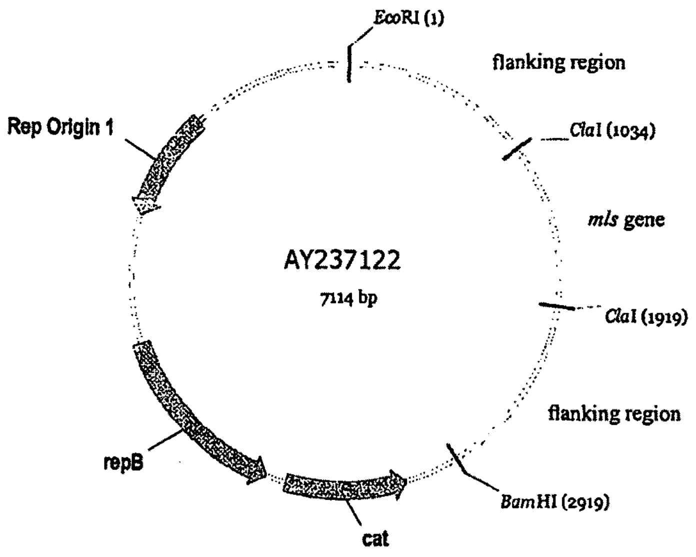
FIG. 10 shows the construction of a double crossover knockout vector for inactivation of the ldh gene in *Clostridium thermocellum* based on the replicative plasmid vector pNW33N.

To knock out the ldh gene, a vector is constructed on the multiple cloning sites (MCS) of the replicative plasmid pNW33N, in which the macrolide, lincosamide, and streptogramin B ($MLS_B$) resistant gene mLs is inserted into a DNA fragment of 2523 bp, which includes the ldh gene and the mdh gene (encoding malate dehydrogenase), leading to knocking out of a fragment of 489 bp of the ldh gene and formation of flanking regions of 1034 bp and 1000 bp on either side of the mLs gene (FIG. 10). pNW33N contains pBC1 replicon, which is isolated from *Bacillus coagulans* and *Staphylococcus aureus*, and is anticipated to be stably replicated in other Gram positive strains of bacteria, including *Clostridium thermocellum*. The sequence of the ldh knockout vector constructed on plasmid pNW33N is set forth as SEQ ID NO:4.

Inactivation of the ldh Gene In *Clostridium thermocellum* Based On Plasmid pUC19

Figure 11:
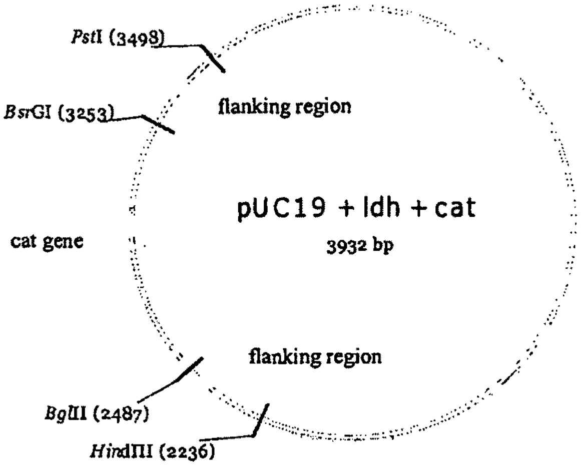
FIG. 11 shows the construction of a double crossover suicide vector for inactivation of the ldh gene in *Clostridium thermocellum* based on the plasmid pUC19.

To knock out the ldh gene, a vector is constructed on the multiple cloning sites (MCS) of the pUC19 plasmid, in which a gene encoding chloramphenicol acetyltransferase (the cat gene) is inserted into a ldh gene fragment of 717 bp, leading to a flanking region of 245 bp and 255 bp on either side of the cat gene (FIG. 11). pUC19 is an *E. coli* plasmid vector, containing pMB1 origin, which cannot be amplified in Gram positive strains of bacteria, including *Clostridium thermocellum*. A similar vector may be constructed, in which the mLs gene is flanked by the ldh gene fragments. The sequence of the ldh knockout vector constructed on plasmid pUC19 is set forth as SEQ ID NO:5.

Expression of Xylose Isomerase And Xylulose Kinase In *C. thermocellum* And *C. straminisolvens* (Prophetic Example)

Figure 35:
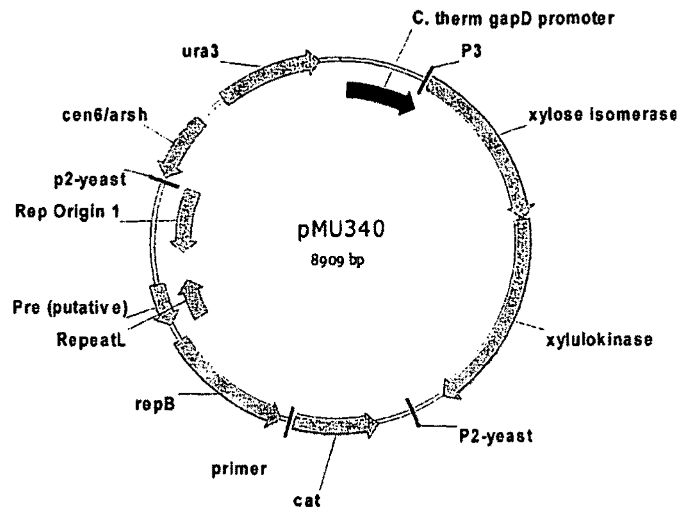
FIG. 35 shows an example of a pMU340 plasmid.

For expression of xylose isomerase and xylulose kinase in *C. thermocellum*, the xylose isomerase and xylulose kinase genes were cloned from *T. saccharolyticum* and placed under control of the *C. thermocellum* gapDH promoter. This cassette is harbored in a *C. thermocellum* replicative plasmid based on the pNW33N backbone, resulting in pMU340 (FIG. 35) SEQ ID NO:74. Upon transfer into *C. thermocellum*, the resulting transformation can be assayed for the ability to grow on xylose. Analogous constructs can be created using the *C. kristajanssonii* xylose isomerase and xylulose kinase genes. These constructs can be tested for functionality in *C. straminsolvens* as well.

Expression of Pyruvate Decarboxylase And Alcohol Dehydrogenase In *C. thermocellum* And *C. straminisolvens* (Prophetic Example)

Figure 36:
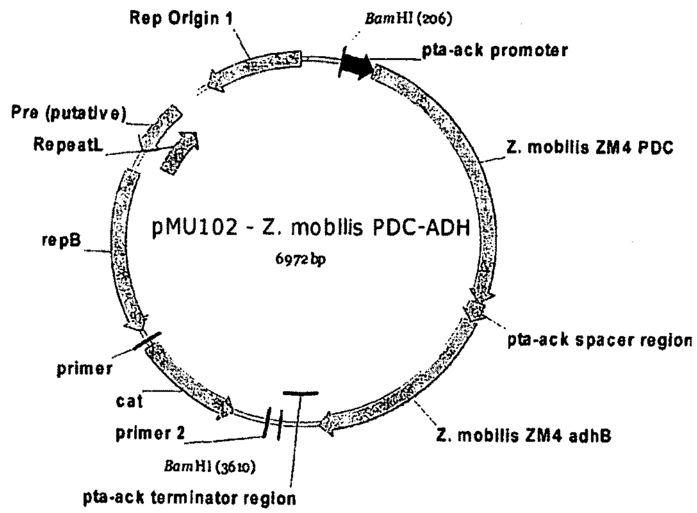
FIG. 36 shows an example of a pMU102 *Z. mobilis* PDC-ADH plasmid.
Figure 37:
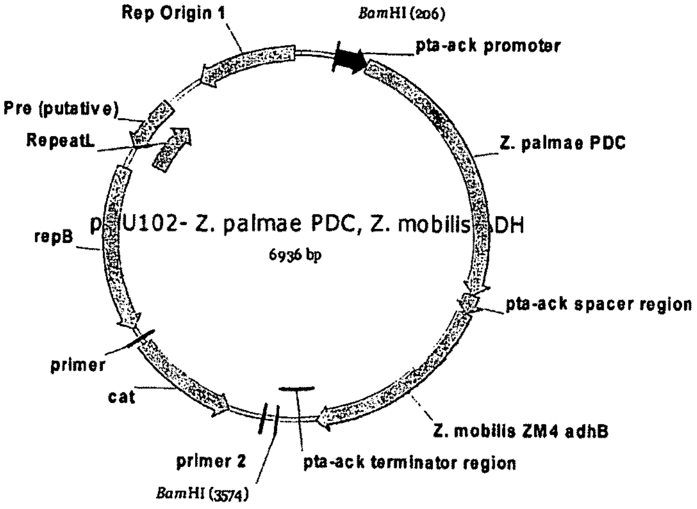
FIG. 37 shows an example of a pMU102 *Z. palmae* PDC, *Z. mobilis* ADH plasmid.

For expression of pyruvate decarboxylase and alcohol dehydrogenase in *C. thermocellum*, the pyruvate decarboxylase genes are cloned from sources *Z. mobilis* and *Z. palmae* and the alcohol dehydrogenase gene is cloned from source *Z. mobilis*. These genes (pdc and adh) will be expressed as an operon from the *C. thermocellum* pta-ack promoter. This cassette is harbored in a *C. thermocellum* replicative plasmid based on the pNW33N backbone (FIGS. 36 and 37), SEQ ID NOS:75 and 76. Upon transfer into *C. thermocellum*, the resulting transformation can be screened for enhanced ethanol production and/or aldehyde production to measure the functionality of the expressed enzymes. These constructs will be tested for functionality in *C. straminsolvens* as well.

Example 5

Fermentation of Avicel® Using *C. straminisolvens*

Figure 27:
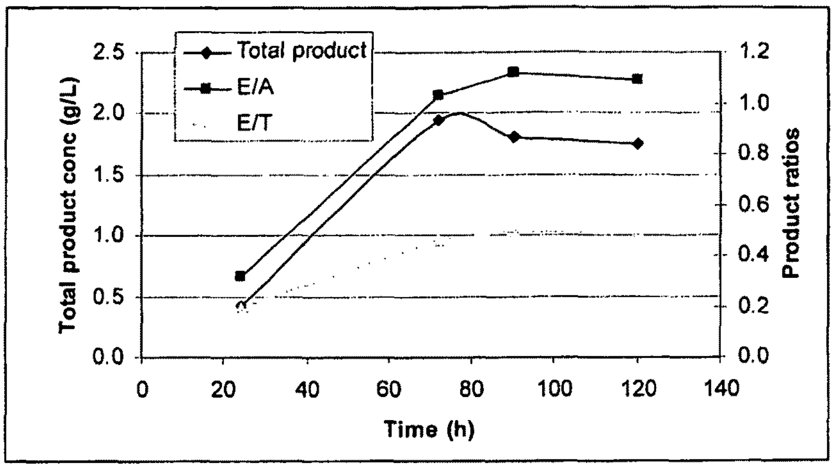
FIG. 27 shows the product concentration profiles for 1% Avicel® using *C. straminisolvens*. The ethanol-to-acetate ratio is depicted as E/A and the ratio of ethanol-to-total products is depicted as E/T.

*C. straminisolvens* was used to ferment 1% Avicel® in serum bottles containing CTFUD medium. The product concentration profile and the ratios are shown in FIG. 27. About 2 g/L of total products was generated in 3 d with ethanol constituting about 50% of the total products. FIG. 27 shows the product concentration profiles for 1% Avicel® using *C. straminisolvens*. The ethanol to acetate ratio is depicted as E/A and the ratio of ethanol to total products is depicted as E/T.

Example 6

Engineered Group II Introns For Mesophilic And Thermophilic Cellulolytic, Xylanolytic Organisms Mobile group II introns, found in many bacterial genomes, are both catalytic RNAs and retrotransposable elements. They use a mobility mechanism known as retrotransposition in which the excised intron RNA reverse splices directly into a DNA target site and is then reverse transcribed by an intron-encoded protein. The mobile *Lactococcus lactis* L1.LtrB group II intron has been developed into genetic tools known as Targetron™ vectors, which are commercially available from Sigma Aldritch (Catalog #TA0100). This product and its use are the subject of one or more of U.S. Pat. Nos. 5,698,421, 5,804,418, 5,869,634, 6,027,895, 6,001,608, and 6,306,596 and/or other pending U.S. and foreign patent applications controlled by InGex, LLC.

Targetrons cassettes (FIGS. 28 and 29) which contain all the necessary sequences for retro-transposition may be subcloned into vectors capable of replication in mesophilic or thermophilic cellulolytic organisms. The Targetron cassette may be modified by replacing the lac promoter with any host- or species-specific constitutive or inducible promoters. The cassettes may be further modified through site-directed mutagenesis of the native recognition sequences such that the Group II intron is retargeted to insert into genes of interest creating genetic knockouts. For example, the group II intron could be redesigned to knockout lactate dehydrogenase or acetate kinase in any mesophilic or thermophilic cellulolytic organism. Table 4 depicts an example of insertion location and primers to retarget Intron to *C. cellulolyticum* acetate kinase (SEQ ID NO:21). Table 5 depicts an example of insertion location and primers to retarget Intron to *C. cellulolyticum* lactate dehydrogenase (SEQ ID NO:21).

Figure 28:
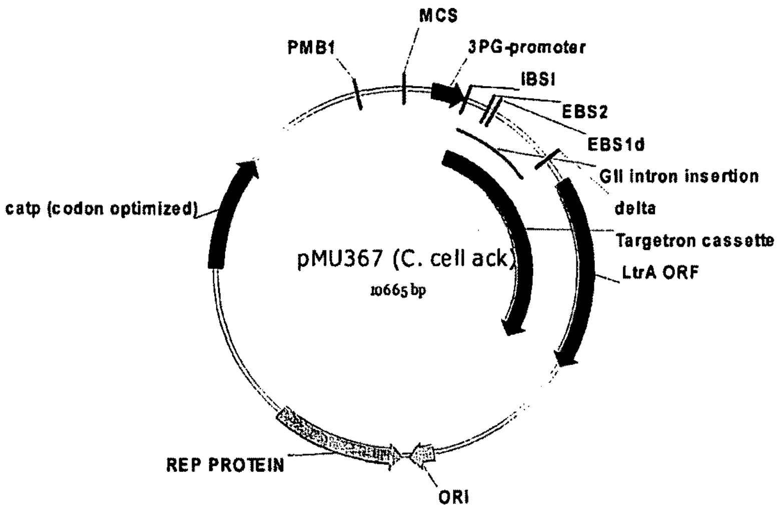
FIG. 28 shows an example of a vector for retargeting the L1.LtrB intron to insert in *C. cell*. ACK gene (SEQ ID NO:21).

An example of a vector for retargeting the L1.Ltrb intron to insert in *C. cell.* ack gene (SEQ ID NO:21) is depicted in FIG. 28. The vector sequence of pMU367 (*C. cell.* acetate kinase KO vector) is SEQ ID NO:30.

Figure 29:
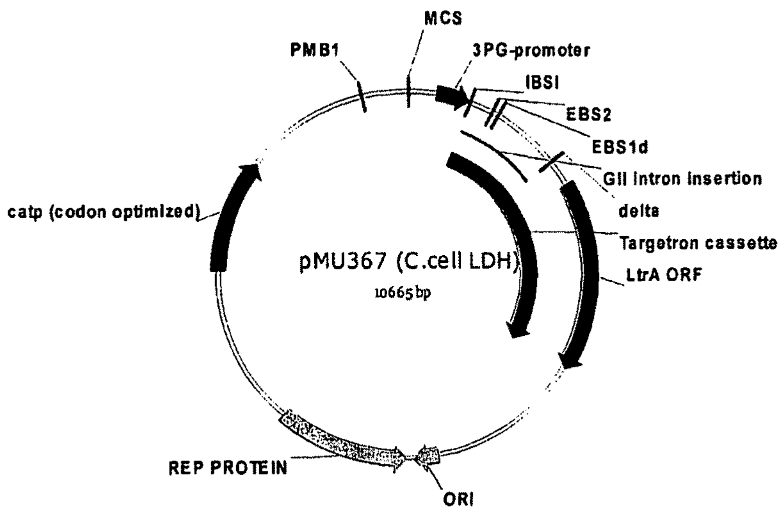
FIG. 29 shows an example of vector for retargeting the L1.LtrB intron to insert in *C. cell*. LDH2744 gene (SEQ ID NO:23).

An example of a vector for retargeting the L1.Ltrb intron to insert in *C. cell.* LDH2744 gene (SEQ ID NO:23) is depicted in FIG. 29. The vector sequence of pMU367 (*C. cell.* lactate dehydrogenase KO vector) is set for as SEQ ID NO:31.

TABLE 4

| | |
|---|---|
| Predicted Insertion location (SEQ ID NO: 62) | ATTTACCTGGCTGGGAATACTGAGACATAT-intron-GTCATTGAGGCCGTA |
| IBS1 mutagenic primer (SEQ ID NO: 63) | AAAAAAGCTTATAATTATCCTTA**ATTTCCTACTAC**GTGCGCCCAGATAGGGTG |
| EBS1d mutagenic primer (SEQ ID NO: 64) | CAGATTGTACAAATGTGGTGATAACAGATAAGTC**TACTACTG**TAACTTACCTTTCTTTGT |
| EBS2 mutagenic primer (SEQ ID NO: 65) | TGAACGCAAGTTTCTAATTTCG**GTTGAAATC**CGATAGAGGAAAGTGTCT |

TABLE 5

| | |
|---|---|
| Predicted Insertion location (SEQ ID NO: 66) | TTAAATGTTGATAAGGAAGCTCTTTTCAAT-intron-GAAGTTAAGGTAGCA |
| IBS1 mutagenic primer (SEQ ID NO: 67) | AAAAAAGCTTATAATTATCCTTA**GCTCTCTTCAAT**GTGCGCCCAGATAGGGTG |

TABLE 5-continued

| | |
|---|---|
| EBS1d mutagenic primer (SEQ ID NO 68) | CAGATTGTACAAATGTGGTGATAACAGATAAGTC**TTCAATGA**TAACTTACCTTTCTTTGT |
| EBS2 mutagenic primer (SEQ ID NO: 69) | TGAACGCAAGTTTCTAATTTCG**ATTAGAGCT**CGATAGAGGAAAGTGTCT |

Example 7

Transformation of *Thermoanaerobacter* And *Thermoanaerobacterium* Strains (Prophetic Example)

*Thermoanaerobacter pseudoethanolicus* 39E, *Thermoanaerobacterium saccharolyticum* JW/SL-YS485, *Thermoanaerobacterium saccharolyticum* B6A-RI, and *Thermoanaerobacter* sp. strain 59 will be transformed with the following protocol. Cells are grown at 55° C. in 40 mL of DSMZ M122 media with the following modifications: 5 g/L cellobiose instead of cellulose, 1.8 g/L K$_2$HPO$_4$, no glutathione, and 0.5 g/L L-cystiene-HCl until an optical density of 0.6 to 0.8. Cells are then harvested and washed twice with 40 mL 0.2 M cellobiose at room temperature. Cells are re-suspended in 0.2 M cellobiose in aquilots of 100 uL and 0.1 to 1 ug plasmid DNA is added to the sample in a 1 mm gap-width electroportation cuvette. An exponential pulse (Bio-Rad Instruments) of 1.8 kV, 25 µF, 200 Ω, ~3-6 ms is applied to the cuvette, and cells are diluted 100-200 fold in fresh M122 and incubated for 12-16 hours at 55° C. The recovered cells are then diluted 25-100 fold in petri-plates with fresh agar-containing media containing a selective agent, such as 200 µg/mL kanamycin. Once the media has solidified, plates incubated at 55° C. for 24-72 hours for colony formation. Colonies can be tested by PCR for evidence of site-specific recombination.

Example 8

Fermentation Performance of Engineered *Thermoanaerobacter* And *Thermoanaerobacterium* Strains Table 6 depicts the fermentation performance of engineered *Thermoanaerobacter* and *Thermoanaerobacterium* strains. Cultures were grown for 24 hours in M122 at 55° C. without shaking The following abbreviations are used in Table 6: Cellobiose (CB), glucose (G), lactic acid (LA), acetic acid (AA), and ethanol (Etoh). Values are in grams per liter. YS485—*Thermoanaerobacterium saccharolyticum* JW/SL-YS485, B6A-RI—*Thermoanaerobacterium saccharolyticum* B6A-RI, 39E—*Thermoanaerobacter pseudoethanolicus* 39E.

TABLE 6

| Fermentation sample | CB | G | LA | AA | Etoh |
|---|---|---|---|---|---|
| YS485 wildtype | 0 | 0 | 0.77 | 1.04 | 1.40 |
| YS485 ΔL-Idh | 0 | 0 | 0 | 0.92 | 1.73 |
| YS485 Δpta/ack | 2.51 | 0 | 0.75 | 0.06 | 0.62 |
| YS485 ΔL-Idh, Δpta/ack | 0 | 0 | 0 | 0 | 2.69 |
| B6A-RI wildtype | 0 | 0 | 0 | 1.0 | 1.76 |
| B6A-RI ΔL-Idh, Δpta/ack strain #1 | 0 | 0 | 0 | 0 | 2.72 |
| B6A-RI ΔL-Idh, Δpta/ack strain #2 | 0.45 | 0 | 0 | 0 | 2.49 |

TABLE 6-continued

| Fermentation sample | CB | G | LA | AA | Etoh |
|---|---|---|---|---|---|
| 39E wildtype | 0.51 | 0 | 1.51 | 0.15 | 1.87 |
| Media | 5.10 | 0.25 | 0 | 0 | 0 |

Example 9

Figure 38:
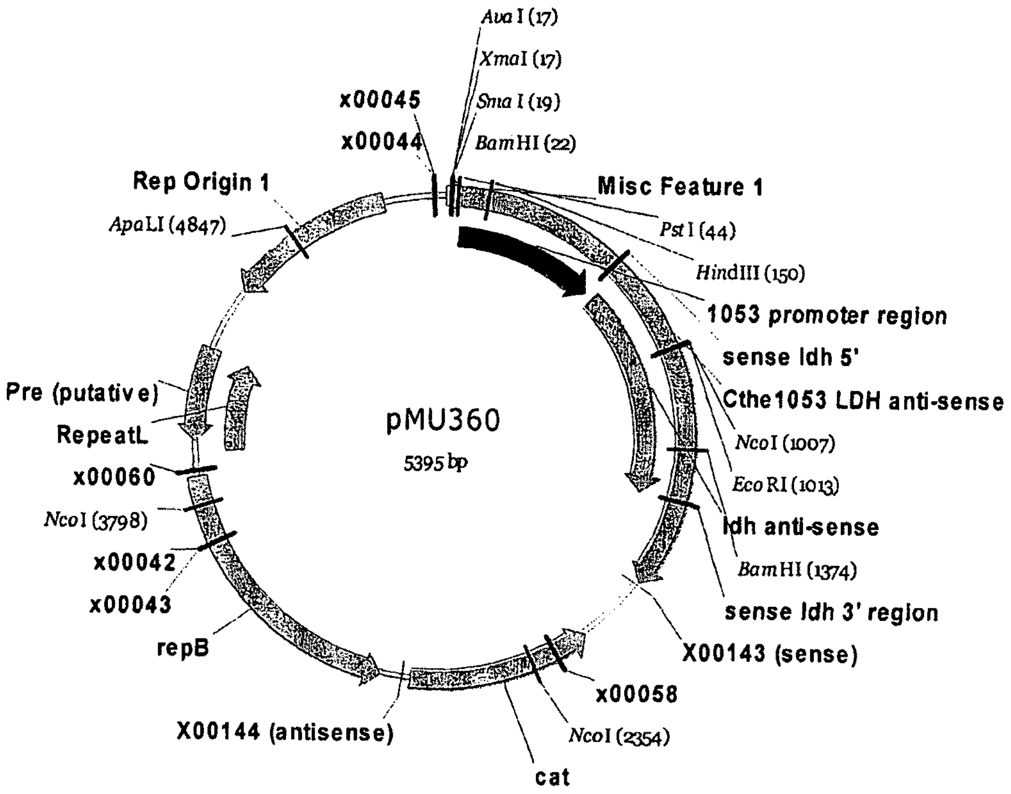
FIG. 38 shows the plasmid map of pMU360. The DNA sequence of pMU360 is set forth as SEQ ID NO:61.

Construct For Engineering Cellulolytic And Xylanolytic Strains—Antisense RNA Technology Example A replicative plasmid (FIG. 38) carrying an antisense RNA cassette targeting a *C. thermocellum* gene coding for lactate dehydrogenase (Cthe_1053) was transferred to *C. thermocellum* 1313 by electroporation and thiamphenicol selection. The transformation efficiency observed for this plasmid was equal to that of the parent vector, pMU102. The sequence of the plasmid is shown in SEQ ID NO: 61. The asRNA cassette is depicted in FIG. 38 and is organized as follows: (i) the entire 1827 bp cassette is cloned into the multicloning site of pMU102 in the orientation shown in FIG. 38, (ii) the native promoter region is contained within the first 600 bp of the cassette, (iii) the first 877 bp of the ldh open reading frame are fused to the native promoter in the antisense orientation, (iv) approximately 300 additional by are included downstream of the asRNA ldh region.

Figure 39:
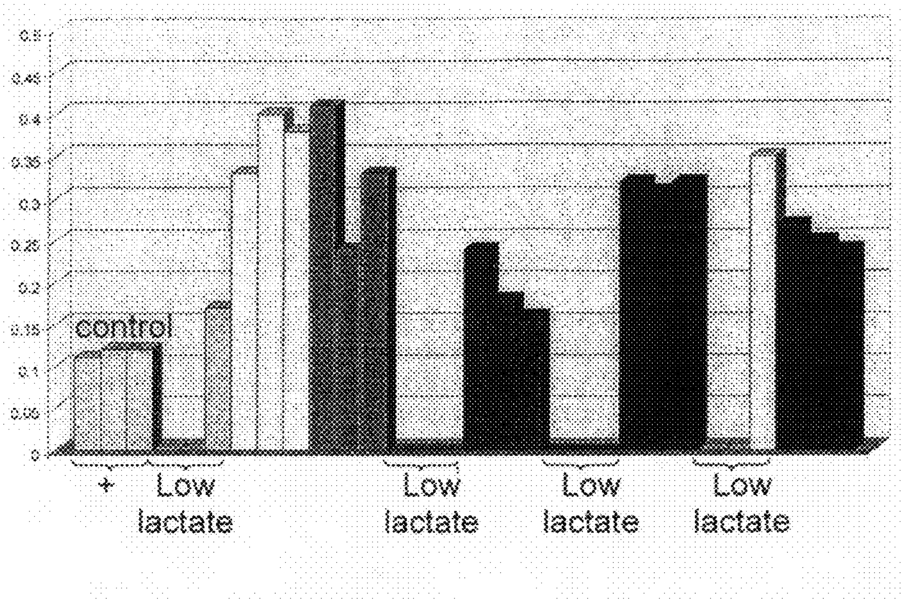
FIG. 39 shows the lactate levels in nine colonies of thiamphenicol-resistant transformants.
Figure 40:
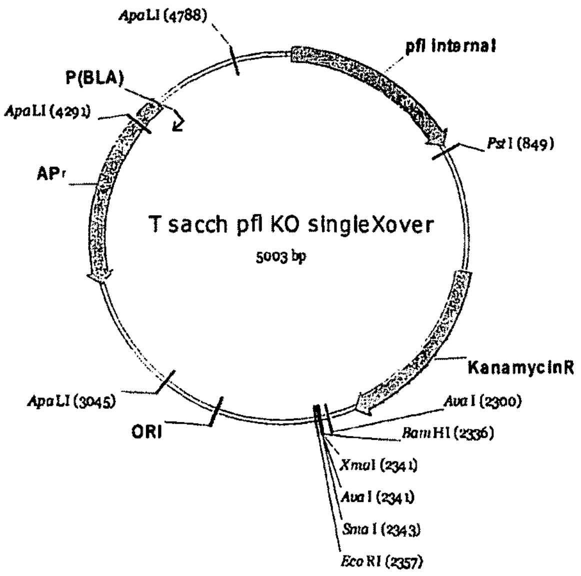
FIG. 40 shows an example of a *T. sacch.* pfl KO single crossover plasmid (SEQ ID NO:47).
Figure 41:
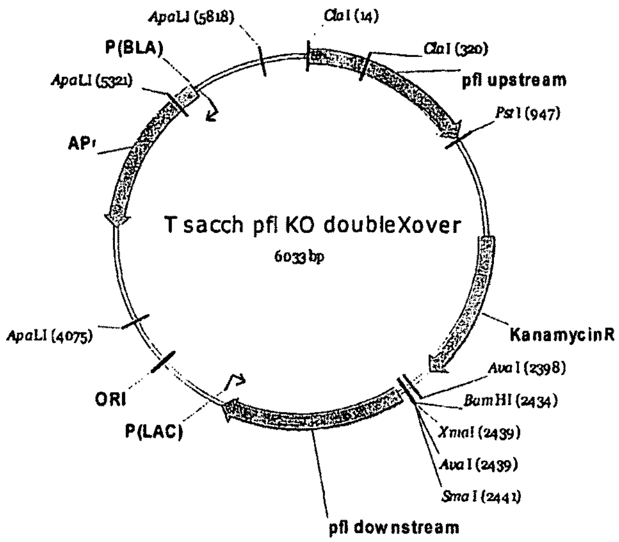
FIG. 41 shows an example of a *T. sacch.* pfl KO double crossover plasmid (SEQ ID NO:48).
Figure 42:
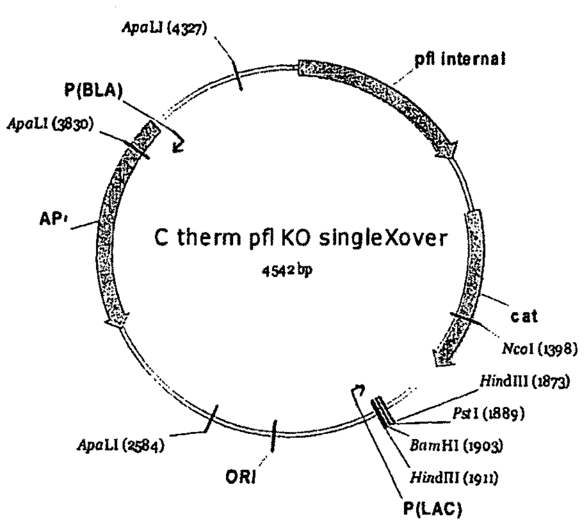
FIG. 42 shows an example of a *C. therm.* pfl KO single crossover plasmid (SEQ ID NO:49).
Figure 43:
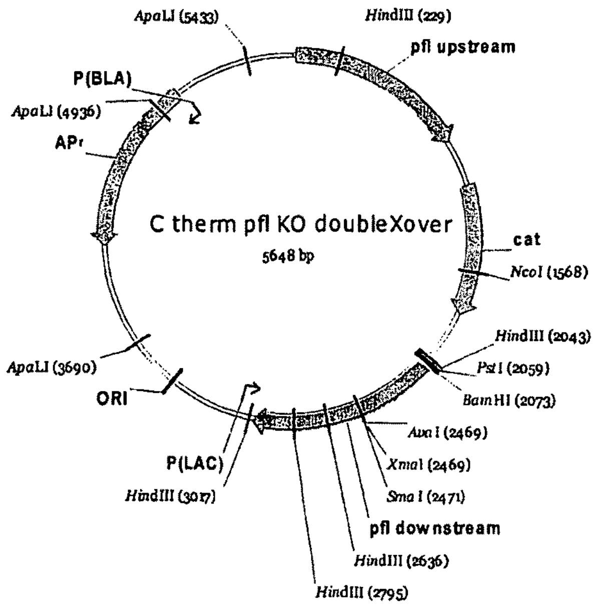
FIG. 43 shows an example of a *C. therm.* pfl KO double crossover plasmid (SEQ ID NO:50).
Figure 44:
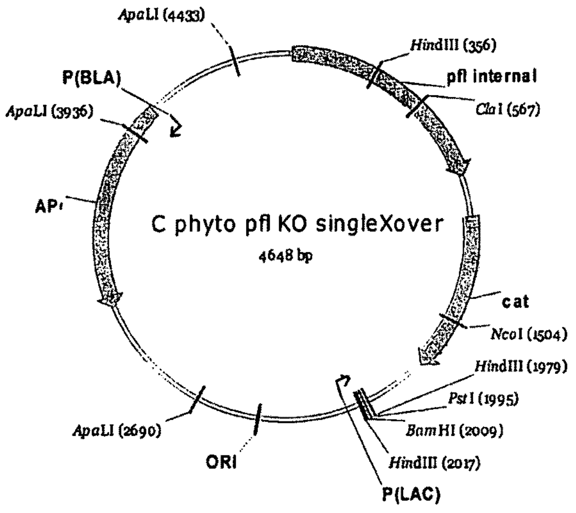
FIG. 44 shows an example of a *C. phyto.* pfl KO single crossover plasmid (SEQ ID NO:51).
Figure 45:
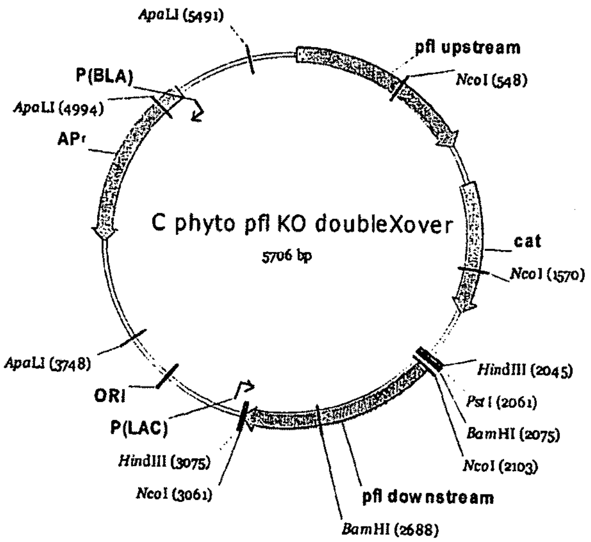
FIG. 45 shows an example of a *C. phyto.* pfl KO double crossover plasmid (SEQ ID NO:52).
Figure 46:
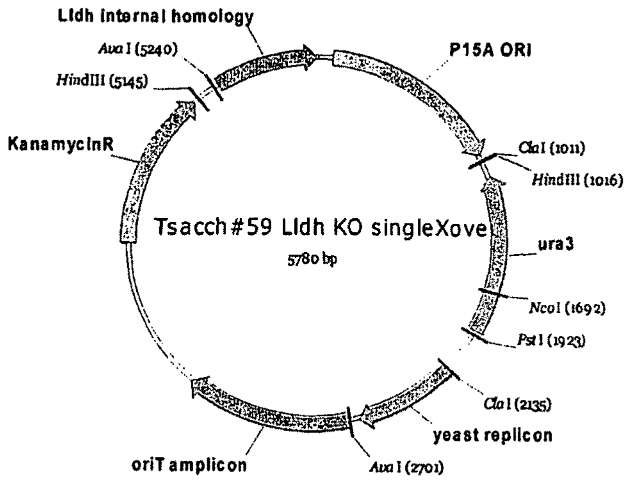
FIG. 46 shows an example of a *T. sacch.* #59 L-ldh KO single crossover plasmid (SEQ ID NO:53).
Figure 47:
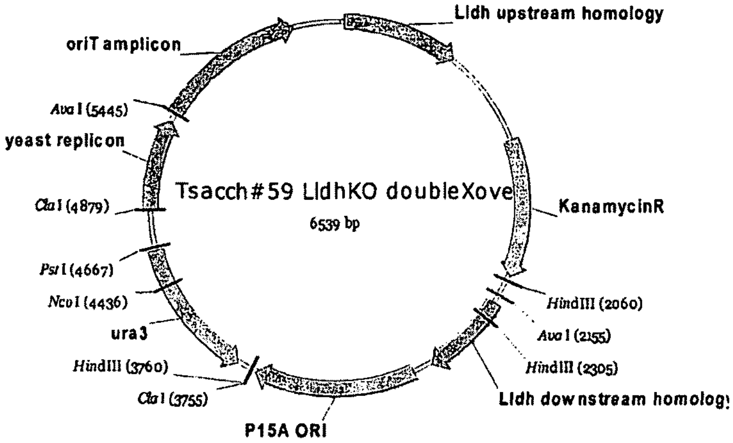
FIG. 47 shows an example of a *T. sacch.* #59 L-ldh KO double crossover plasmid (SEQ ID NO:54).
Figure 48:
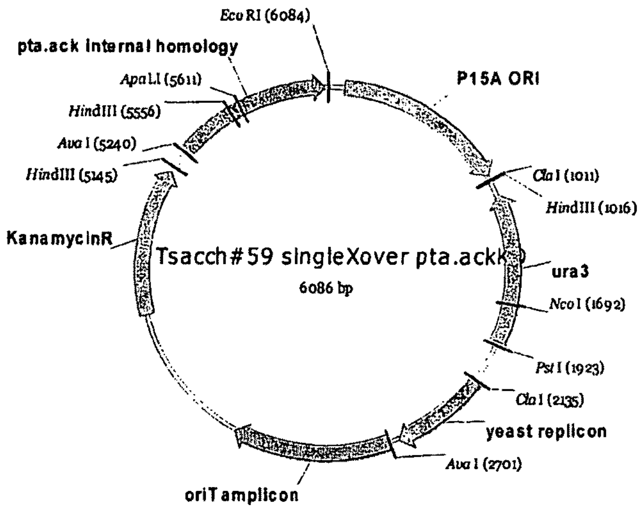
FIG. 48 shows an example of a *T. sacch.* #59 pta/ack KO single crossover plasmid (SEQ ID NO:55).
Figure 49:
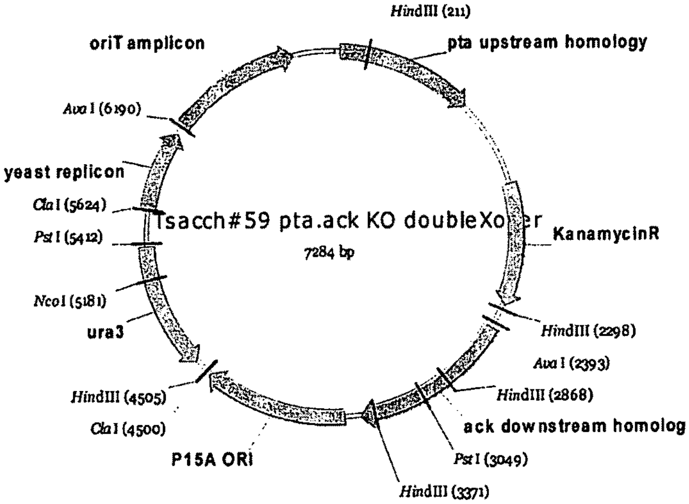
FIG. 49 shows an example of a *T. sacch.* #59 pta/ack KO double crossover plasmid (SEQ ID NO:56).
Figure 50:
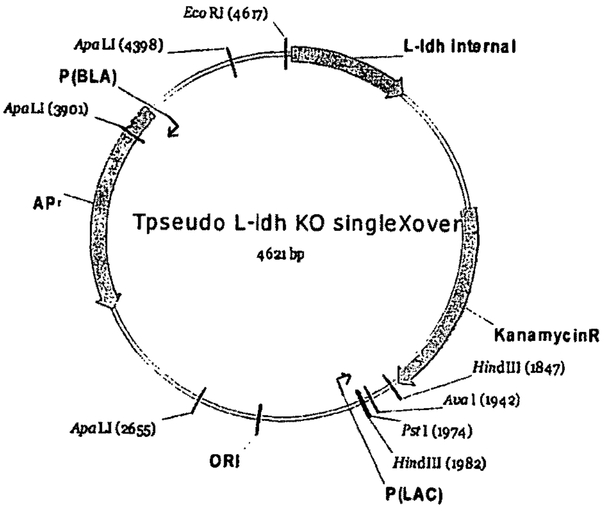
FIG. 50 shows an example of a *T. pseudo.* L-ldh KO single crossover plasmid (SEQ ID NO:57).
Figure 51:
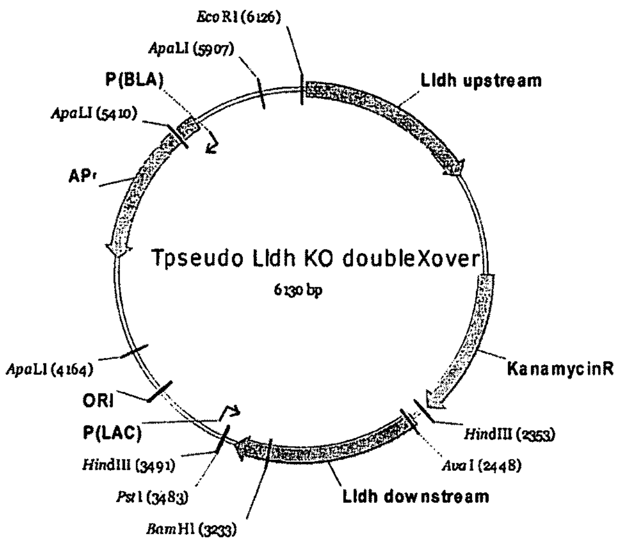
FIG. 51 shows an example of a *T. pseudo.* L-ldh KO double crossover plasmid (SEQ ID NO:58).
Figure 52:
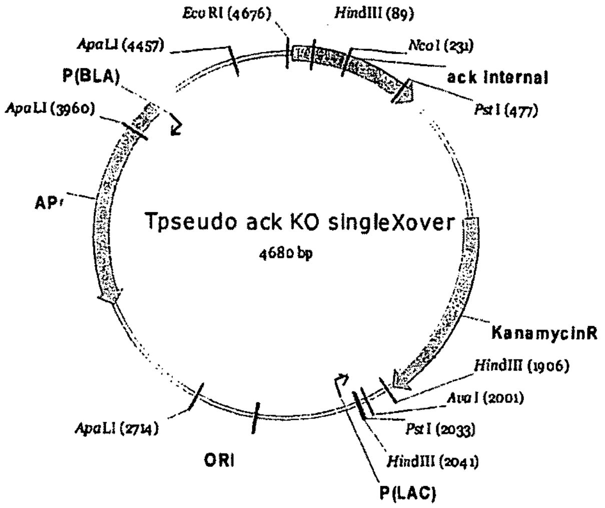
FIG. 52 shows an example of a *T. pseudo.* ack KO single crossover plasmid (SEQ ID NO:59).
Figure 53:
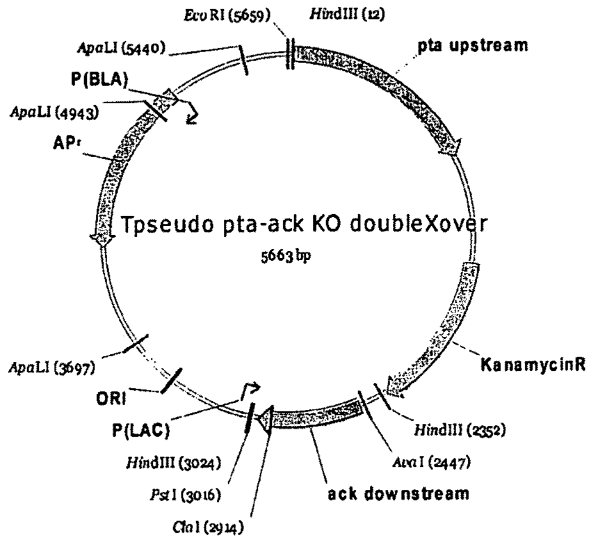
FIG. 53 shows an example of a *T. pseudo.* pta/ack KO double crossover plasmid (SEQ ID NO:60).

The resulting thiamphenicol resistant colonies were screened for altered end product formation by growing standing cultures on M122C media in the presence of 6 ug/mL thiamphenicol (to maintain the plasmid), as shown in FIG. 39. A preliminary screen of 9 randomly selected thiamphenicol-resistant transformants showed that 4 cultures exhibited low levels of lactate production relative to wild type. Additionally, a construct carrying antisense RNA directed to both ldh genes are to be constructed in order to partially, substantially, or completely delete, silence, inactivate, or down-regulate both genes simultaneously.

Example 10

Figure 34:
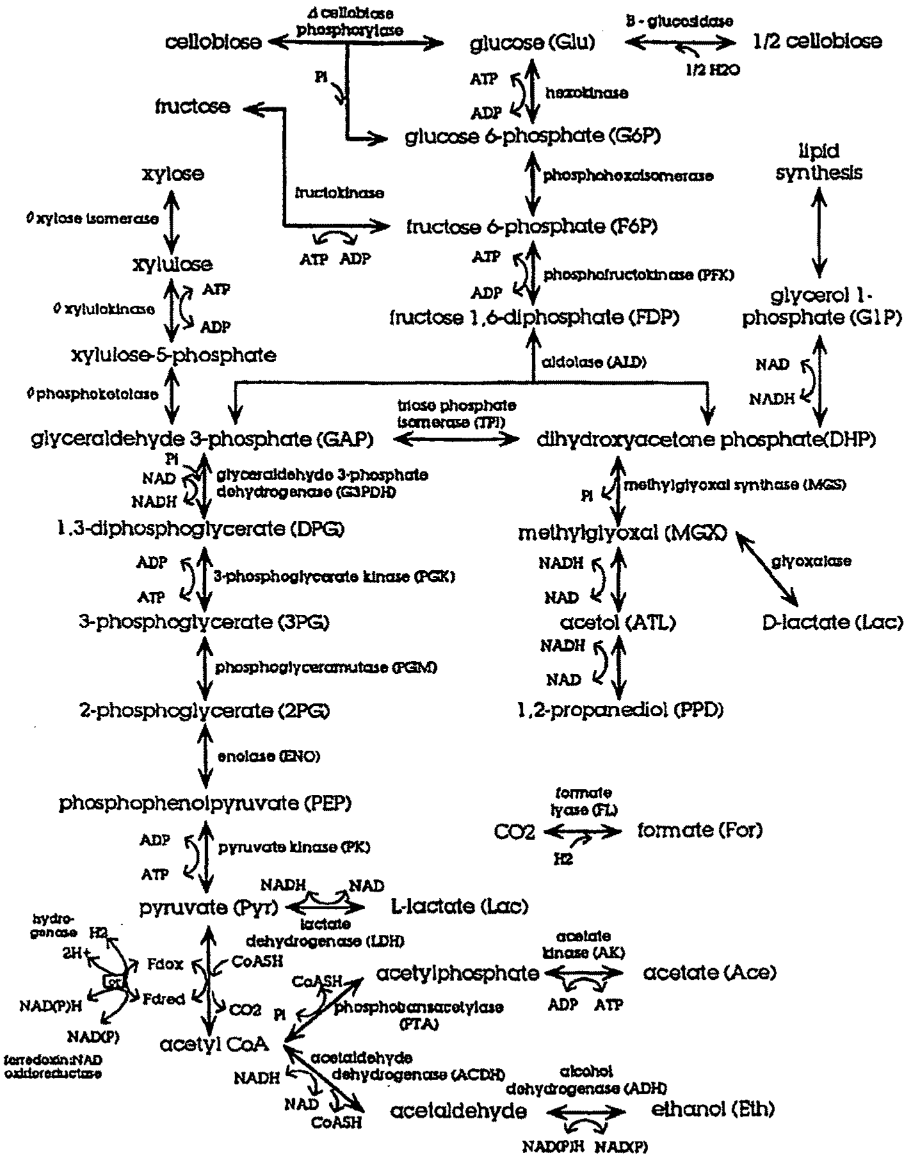
FIG. 34 shows a schematic of the glycolysis/fermentation pathway.

SEQ ID NOS:44, 45, and 46 are the pyruvate-formate-lyase (aka formate acetyltransferase, EC. 2.3.1.54, pfl) genes from *Thermoanaerobacterium saccharolyticum* YS485, *Clostridium thermocellum* ATCC 27405, and *Clostridium phytofermentans*. Pfl catalyzes the conversion of pyruvate to Acetyl-CoA and formate (FIG. 34). Deletion of pfl will result in the elimination of formate production, and could result in a decrease in acetic acid yield in some thermophilic strains, with a resulting increase in ethanol yield.

SEQ ID NOS:47-52, depicted in FIGS. 40-45, show pfl knockout plasmids, two each for the three organisms listed above. Each organism has a single crossover and double crossover plasmid designed to partially, substantially, or completely delete, silence, inactivate, or down-regulate the pfl enzyme. Single crossover plasmids are designed with a single DNA sequence (400 bp to 1000 bp) homologous to an internal section of the pfl gene, double crossover plasmids are designed with two DNA sequences (400 to 1000 bp) homologous to regions upstream (5') and downstream (3') to the pfl gene. All plasmids are designed to use the best available antibiotic markers for selection in the given organism. Plasmids can be maintained in *E. coli* and constructed through a DNA synthesis contract company, such as Codon Devices or DNA 2.0.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid molecule comprising the nucleotide sequence of SEQ ID NO:1, or a full complement thereof.

2. An isolated nucleic acid molecule comprising a nucleotide sequence which shares at least 98% identity to a nucleotide sequence of SEQ ID NO: 1, or a full complement thereof, wherein the nucleotide sequence when transformed in a host cell aids in the process of converting biomass to ethanol.

3. A genetic construct comprising SEQ ID NO:1 operably linked to a promoter expressible in a thermophilic or mesophilic bacterium.

4. A recombinant thermophilic or mesophilic bacterium comprising the genetic construct of claim 3.

5. A vector comprising the nucleic acid molecule of claim 1 or claim 2.

6. A host cell comprising the nucleic acid molecule of claim 1 or claim 2.

7. A genetically modified thermophilic or mesophilic microorganism, wherein the genetically modified microorganism has been transformed by a nucleotide sequence of SEQ ID NO:1;

thereby partially, substantially, or completely deleting, silencing, inactivating, or down-regulating a gene that encodes acetate kinase, and increasing the native ability of said thermophilic or mesophilic microorganism to produce ethanol as a fermentation product.

8. The genetically modified microorganism according to claim 7, wherein said microorganism is a species of the genera *Thermoanaerobacterium, Thermoanaerobacter, Clostridium, Geobacillus, Saccharococcus, Paenibacillus, Bacillus, Caldicellulosiruptor, Anaerocellum*, or *Anoxybacillus*.

9. The genetically modified microorganism according to claim 7, wherein said microorganism is a bacterium selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus*, and *Anaerocellum thermophilum*.

10. The genetically modified microorganism according to claim 7, wherein said microorganism is selected from the group consisting of: (a) a thermophilic or mesophilic microorganism with a native ability to metabolize a hexose sugar; (b) a thermophilic or mesophilic microorganism with a native ability to metabolize a pentose sugar; (c) a thermophilic or mesophilic microorganism with a native ability to metabolize a hexose sugar and a pentose sugar; (d) a thermophilic or mesophilic microorganism with a native ability to hydrolyze cellulose; (e) a thermophilic or mesophilic microorganism with a native ability to hydrolyze xylan; and (f) a thermophilic or mesophilic microorganism with a native ability to hydrolyze cellulose and xylan.

11. The genetically modified microorganism according to claim 7, wherein said microorganism has a native ability to metabolize a hexose sugar; and a first non-native gene is inserted, which first non-native gene encodes a first non-native enzyme that confers the ability to metabolize a pentose sugar, thereby allowing said thermophilic or mesophilic microorganism to produce ethanol as a fermentation product from a pentose sugar.

12. The genetically modified microorganism according to claim 7, wherein said microorganism has a native ability to metabolize a pentose sugar; and a first non-native gene is inserted, which first non-native gene encodes a first non-native enzyme that confers the ability to metabolize a hexose sugar, thereby allowing said thermophilic or mesophilic microorganism to produce ethanol as a fermentation product from a hexose sugar.

13. The genetically modified microorganism according to claim 7, wherein a second native gene is partially, substantially, or completely deleted, silenced, inactivated, or down-regulated, which second native gene encodes a second native enzyme involved in the metabolic production of an organic acid or a salt thereof.

14. The genetically modified microorganism according to claim 13, wherein said second native enzyme is lactate dehydrogenase or phosphotransacetylase.

15. The genetically modified microorganism according to claim 7, wherein said microorganism has a native ability to hydrolyze cellulose; and a first non-native gene is inserted, which first non-native gene encodes a first non-native enzyme that confers the ability to hydrolyze xylan.

16. The genetically modified microorganism according to claim 7, wherein said microorganism has a native ability to hydrolyze xylan; and a first non-native gene is inserted, which first non-native gene encodes a first non-native enzyme that confers the ability to hydrolyze cellulose.

17. The genetically-modified microorganism according to claim 7, wherein said microorganism is mesophilic.

18. The genetically-modified microorganism according to claim 7, wherein said microorganism is thermophilic.

19. A process for converting lignocellulosic biomass to ethanol, comprising contacting lignocellulosic biomass with a genetically modified thermophilic or mesophilic microorganism according to claim 7.

* * * * *